United States Patent [19]
Chang et al.

[11] Patent Number: 6,150,093
[45] Date of Patent: *Nov. 21, 2000

[54] UNIQUE ASSOCIATED KAPOSI'S SARCOMA VIRUS SEQUENCES AND USES THEREOF

[75] Inventors: Yuan Chang; Patrick S. Moore, both of New York, N.Y.

[73] Assignee: The Trustees of Columbia University in the City of New York, New York, N.Y.

[ * ] Notice: This patent is subject to a terminal disclaimer.

[21] Appl. No.: 08/793,624

[22] PCT Filed: Aug. 11, 1995

[86] PCT No.: PCT/US95/10194

§ 371 Date: Feb. 18, 1997

§ 102(e) Date: Feb. 18, 1997

[87] PCT Pub. No.: WO96/06159

PCT Pub. Date: Feb. 29, 1996

Related U.S. Application Data

[63] Continuation-in-part of application No. 08/420,235, Apr. 11, 1995, Pat. No. 5,801,042, which is a continuation-in-part of application No. 08/343,101, Nov. 21, 1994, Pat. No. 5,830,759, which is a continuation-in-part of application No. 08/292,365, Aug. 18, 1994, abandoned.

[51] Int. Cl.$^7$ .............................. C12Q 1/68; C12N 5/10; C12N 7/00; C12N 15/63
[52] U.S. Cl. ...................... 435/6; 435/235.1; 435/252.3; 435/320.1; 435/325; 536/23.1; 536/24.32
[58] Field of Search ........................ 435/6, 235.1, 252.3, 435/320.1, 325, 372, 372.2; 536/23.1, 23.72, 24.3, 24.32, 24.33

[56] References Cited

PUBLICATIONS

Boldogh et al. (1981) Kaposi's sarcoma. IV. Detection of CMV DNA, CMV RNA and CMNA in tumor biopsies. Int. J. Cancer 28:469–474, Oct. 1981.
Hutchinson et al. (1986) Organization and expression of the major genes from the long terminal repeat of the human cytomegalovirus genome. 155:160–171, Nov. 1986.
Baer et al (1984) DNA sequence and expression of the B95–8 Epstein–Barr virus genome, Nature 310, 207–211.
Mosca et al (1987) Herpes simplex virus type–1 can reactivate transcription of latent human immunodeficiency virus, Nature 325, 67–70.
Delli Bovi et al (1987) Isolation of a rearranged human transforming gene following transfection of Kaposi sarcoma DNA, Proc Natl Acad Sci USA 84, 5660–5664.
Gallo (1993) Aspects of the molecular pathogenesis of AIDS, J Cellular Biochem 17E, 5.
Gallo (1994) New approaches for interfering with human immunodeficiency virus replication and for Kaposi's sarcoma, J Cellular Biochem 18B, 108.
Chang et al (1994) Identification of herpesvirus–like DNA sequences in AIDS–associated Kaposi's sarcoma, Science 265, 1865–1869.
Cesarman et al (Mar. 10, 1995) Kaposi's sarcoma–associated herpes–virus–like DNA sequences are present in AIDS–related body cavity based lymphomas, The FASEB Journal 9, A973, abstract 5650.
Gompels et al (1988) Conservation of glycoprotein H (gH) in herpesviruses: nucleotide sequence of the gH gene from herpesvirus saimiri, J Gen Virol 69, 2819–2829.
Gompels et al (1991) Characterization and sequence analysis of anti–body–selected antigenic variants of herpes simplex virus show a conformationally complex epitope on glycoprotein H, J Virol 65, 2393–2401.
Forrester et al (1992) Construction and properties of a mutant of herpes simplex virus type 1 with glycoprotein H coding sequences deleted, J Virol 66, 341–348.
Roop et al (1993) A mutant herpes simplex virus type 1 unable to express glycoprotein L cannot enter cells, and its particles lack glycoprotein H, J Virol 67, 2285–2297.
Scott et al (1993) Identification and sequence analysis of the homologues of the herpes simplex virus type 1 glycoprotein H in Marek's disease virus and the herpesvirus of turkeys, J Gen Virol 74, 1185–1190.
Liu et al (1993) Human herpesvirus–6 glycoprotein H and L homologs are components of the gp100 complex and the gH external domain is the target for neutralizing monoclonal antibodies, Virology 197, 12–22.
Tewari et al (1994) Characterization of immune responses to baculovirus–expressed equine herpesvirus type 1 glycoproteins D and H in a murine model, J Gen Virol 75, 1735–1741.
McGowan et al (1994) Expression and characterization of equine herpesvirus 1 glycoprotein H using a recombinant baculovirus, Arch Virol 137, 389–395.
Pulford et al (1994) Expression of the Epstein–Barr virus envelope fusion glycoprotein gp85 gene by a recombinant baculovirus, J Gen Virol 75, 3241–3248.
Farrell et al (1994) Vaccine potential of a herpes simplex virus type 1 mutant with an essential glycoprotein deleted, J Virol 68, 927–932.
Baranowski et al (1995) Synthesis and processing of bovine herpesvirus–1 glycoprotein H, Virology 206, 651–654.
Giraldo et al (1972) Herpes–type virus particles in tissue culture of Kaposi's sarcoma from different geographic regions, Journal of the National Cancer Institute 49, 1509–1513.

(List continued on next page.)

*Primary Examiner*—Robert A. Schwartzman
*Attorney, Agent, or Firm*—John P. White; Cooper & Dunham LLP

[57] ABSTRACT

This invention provides an isolated DNA molecule which is at least 30 nucleotides in length and which uniquely defines a herpesvirus associated with Kaposi's sarcoma. This invention provides an isolated herpesvirus associated with Kaposi's sarcoma. This invention provides an antibody specific to the peptide. Antisense and triplex oligonucleotide molecules are also provided. This invention provides a method of vaccinating a subject for KS, prophylaxis diagnosing or treating a subject with KS and detecting expression of a DNA virus associated with Kaposi's sarcoma in a cell.

24 Claims, 37 Drawing Sheets

OTHER PUBLICATIONS

Giraldo et al (1984) Kaposi's sarcoma: a natural model of interrelationships between viruses, immunologic responses, genetics and oncogenesis, Antibiotics and Chemotherapeutics 32, 1–11.

Iochim et al (1992) Cytomegalovirus, angiomatosis, and Kaposi's sarcoma. new observations of a debated relationship, Modern Pathology 5, 169–178.

Jahan et al (1989) Analysis of human KS biopsies and cloned cell lines for cytomegalovirus, HIV–1, and other selected DNA virus sequences, AIDS Research and Human Retroviruses 5, 225–231.

Walter et al (1984) Kaposi's sarcoma: presence of herpes–type virus particles in a tumor specimen, Human Pathology 15, 1145–1146.

Dupin et al (Mar. 25, 1995) Herpesvirus–like DNA sequences in patients with Mediterranean Kaposi's sarcoma, The Lancet 345, 761–762.

Huang et al (Mar. 25, 1995) Human herpesvirus–like nucleic acid in various forms of Kaposi's sarcoma, The Lancet 345, 759–761.

Su et al (Mar. 18, 1995) Herpesvirus–like DNA sequence in Kaposi's sarcoma from AIDS and non–AIDS patients in Taiwan, The Lancet 345, 722–723.

Chang (Feb. 24, 1995) Letter to the editor, Science 267, 1079.

Cohen (Dec. 16, 1994) Is a new virus the cause of KS?, Science 266, 1803–1804.

Karp and Broder (Apr. 4, 1995) Molecular foundations of cancer: new targets for intervention, Nat Med 1, 309–320.

McGrath et al (Apr. 1, 1995) Identification of a clonal form of HIV in early Kaposi's sarcoma: evidence for a novel model of oncogenesis, "sequential neoplasia" J Acq Immun Def Hum Retrovirol 8, 379–385.

Relman (Feb. 16, 1995) Has trench fever returned?, New Eng J Med 332, 463–464.

Rubin (Jan. 13, 1995) Letter to the editor, Science 267, 157–158.

Schulz and Weiss (Jan. 5, 1995) A finger on the culprit, Nature 373, 17–18.

Ambroziak and Blackbourn (Apr. 28, 1995) Herpes–like sequences in HIV–infected and uninfected Kaposi's sarcoma, Science 268, 582–583 (Exhibit 2).

Cesarman et al (May 4, 1995) Kaposi's sarcoma–associated herpesvirus–like DNA sequences in AIDS–related body–cavity–based lymphomas, New Eng J Med 332, 1186–1191 (Exhibit 3).

Cohen (Jun. 30, 1995) Controversy: is KS really caused by new herpesvirus?, Science 268, 1847–1848 (Exhibit 4).

Collandre et al (Apr. 22, 1995) Kaposi's sarcoma and new herpesvirus, Lancet 345, 1043 (Exhibit 5).

Drew and Brindley (May 1995) Female–specific sequences isolated from *Schistosoma mansoni* by representational difference analysis, Mol Biochem Parasitology 71, 173–181 (Exhibit 6).

Duvic (Jul. 1995) Human immunodeficiency virus and the skin: selected controversies, J Invest Dermatol 105, S117–120S (Exhibit 7).

Farid (Jun. 15, 1995) Letter to the editor, New Eng J Med 332, 1647 (Exhibit 8).

Geddes et al (Jul. 5, 1995) Birthplace and classic Kaposi's sarcoma in Italy, J Nat Canc Inst 87, 1015–1017 (Exhibit 9).

Lebbe et al (May 6, 1995) Kaposi's sarcoma and a new herpesvirus, Lancet 345, 1180 (Exhibit 10).

Levine (Jul. 5, 1995) Viral–associated neoplasms in humans: additional clues, J Nat Canc Inst 87, 947–949 (Exhibit 11).

Newton et al (May 27, 1995) Cancer and HIV infection in Rwanda, Lancet 345, 1378–1379) (Exhibit 13).

Rady et al (May 27, 1995) Herpesvirus–like DNA sequences in non–Kaposi's sarcoma skin lesions of transplant patients, Lancet 345, 1339–1340 (Exhibit 14).

Roizman (May 4, 1995) New viral footprints in Kaposi's sarcoma, New Eng J Med 332, 1227–1228 (Exhibit 15).

Roulston et al (Jun. 1995) Regulation of human immunodeficiency virus type 1 and cytokine gene expression in myeloid cells by NF–kB/Rel transcription factors, Microbiol Res 59, 481–505 (Exhibit 16).

Schalling et al (Jul. 1995) A role for a new herpes virus (KSHV) in different forms of Kaposi's sarcoma, Nature Medicine 1, 707–708 (Exhibit 17).

Schutte et al (Jun. 20, 1995) Identification by representational difference analysis of a homozygous deletion in pancreatic carcinoma that lies within the BRCA2 region, Proc Natl Acad Sci USA 92, 5950–5954 (Exhibit 18).

FIGURE 3A-1

SEQ. ID. No. 1

```
TCGAGTCGGA GAGTTGGCAC AGGCCTTGAG CTCGCTGTGA CGTTCTCACG GTGTTGGTTG    60
GGATCAGCTG GTGACTCAGA CAAGTCTTGA GCTCTACAAC GTAACATACG GGCTGATGCC   120
CACCCGATAC CAGAATTACG CAGTCGGCAA TTCTGTGCCC TAGAGTCACC TCAAAGAATA   180
ATCTGTGGTG TCCAAGGGGA GGGTTCTGGG GCCGGCTACT TAGAAACCGC CATAGATCGG   240
GCAGGGTGGA GTACTTGAGG AGCCGGCGGT AGTGGCCAG GTGGGCCCGG TTACCTGCTC    300
TTTTGCGTGC TGCTGGAAGC CTGCTCAGGG ATTTCTTAAC CTCGGCCTCG GTTGGACGTA   360
CCATGGCAGA AGGCGGTTTT GGAGCGGACT CGGTGGGGCG CGGCGAGAA AAGGCCTCTG    420
TGACTAGGGG AGGCAGGTGG GACTTGGGGA GCTCGACGA CGAATCAAGC ACCTCCACAA    480
CCAGCACGGA TATGGACGAC CTCCCTGAGG AGAGGAAACC ACTAACGGGA AAGTCTGTAA    540
AAACCTCGTA CATATACGAC GTGCCCACCG TCCCGACCAG CAAGCCGTGG CATTTAATGC   600
ACGACAACTC CCTCTACGCA ACGCCTAGGT TTCCGCCCAG ACCTCTCATA CGGCACCCTT   660
CCGAAAAAGG CAGCATTTTT GCCAGTCGGT TGTCAGCGAC TGACGACGAC TCGGGAGACT   720
ACGCGCCAAT GGATCGCTTC GCCTTCCAGA GCCCCAGGGT GTGTGGTCGC CCTCCCCTC    780
CGCCTCCAAA TCACCCACCT CCGGCAACTA GGCCGGCAGA CGCGTCAATG GGGGACGTGG   840
GCTGGGCGGA TCTGCAGGGA CTCAAGAGAA CCCCAAAGGG ATTTTTAAAA ACATCTACCA   900
AGGGGGCAG TCTCAAAGCC CGTGGACGCG ATGTAGGTGA CCGTCTCAGG GACGGCGCT     960
TTGCCTTTAG TCCTAGGGGC CCATAGGGCA AAACATTAAA TCATGGTTGG              1020
GGATCGGAGA ATCATCGGCG ACTGCTGTCC CCGTCACCAC GCAGCTTATG GTACCGGTGC   1080
ACCTCATTAG AACGCCTGTG ACCGTGGACT ACAGGAATGT TTATTTGCTT TACTTAGAGG   1140
GGGTAATGGG TGTGGGCAAA TCAACGCTGG TCAACGCCGT GTGCGGGATC TTGCCCCAGG   1200
```

FIGURE 3A-2

```
AGAGAGTGAC AAGTTTTCCC GAGCCCATGG TGTACTGGAC GAGGGCATTT ACAGATTGTT   1260
ACAAGGAAAT TTCCCACCTG ATGAAGTCTG GTAAGGCGGG AGACCCGCTG ACGTCTGCCA   1320
AAATATACTC ATGCCAAAAC AAGTTTTCGC TCCCCTTCCG GACGAACGCC ACCGCTATCC   1380
TGCGAATGAT GCAGCCCTGG AACGTTGGGG GTGGGTCTGG GAGGGCACT CACTGGTGCG   1440
TCTTTGATAG GCATCTCCTC TCCCCAGCAG TGGTGTTCCC TCTCATGCAC CTGAAGCACG   1500
GCCGCCTATC TTTTGATCAC TTCTTTCAAT TACTTTCCAT CTTTAGAGCC ACAGAAGGCG   1560
ACGTGGTCGC CATTCTCACC CTCTCCAGCG CCGAGTCGTT GCGGCGGGTC AGGGCGAGGG   1620
GAAGAAAGAA CGACGGGACG GTGGAGCAAA ACTACATCAG AGAATTGGCG TGGGCTTATC   1680
ACGCCGTGTA CTGTTCATGG ATCATGTTGC AGTACATCAC TGTGGAGCAG ATGGTACAAC   1740
TATGCGTACA AACCACAAAT ATTCCGGAAA TCTGCTTCCG CAGCGTGCGC CTGGCACACA   1800
AGGAGGAAAC TTTGAAAAAC CTTCACGAGC AGAGCATGCT ACCTATGATC ACCGGTGTAC   1860
TGGATCCCGT GAGACATCAT CCCGTCGTGA TCGAGCTTTG CTTTTGTTTC TTCACAGAGC   1920
TGAGAAAATT ACAATTTATC GTAGCCGACG CGGATAAGTT CCACGACGAC GTATGCGGCC   1980
TGTGGACCGA AATCTACAGG CAGATCCTGT CCAATCCGGC TATTAAACCC AGGGCCATCA   2040
ACTGGCCAGC ATTAGAGAGC CAGTCTAAAG CAGTTAATCA CCTAGAGGAG ACATGCAGGG   2100
TCTAGCCTTC TTGGCGGCCC TTGCATGCTG GCGATGCATA TCGTTGACAT GTGGAGCCAC   2160
TGGCGCGTTG CCGACAACGG CGACGACAAT AACCCGCTCC GCCACGCAGC TCATCAATGG   2220
GAGAACCAAC CTCTCCATAG AACTGGAATT CAACGGCACT AGTTTTTTTC TAAATTGGCA   2280
AAATCTGTTG AATGTGATCA CGGAGCCGGC CCTGACAGAG TTGTGGACCT CCGCCGAAGT   2340
CGCCGAGGAC CTCAGGGTAA CTCTGAAAAA GAGGCAAAGT CTTTTTTTCC CCAACAAGAC   2400
```

FIGURE 3A-3

```
AGTTGTGATC TCTGGAGACG GCCATCGCTA TACGTGCGAG GTGCCGACGT CGTCGCAAAC    2460
TTATAACATC ACCAAGGGCT TTAACTATAG CGCTCTGCCC GGGCACCTTG GCGGATTTGG    2520
GATCAACGCG CGTCTGGTAC TGGGTGATAT CTTCGCATCA AAATGGTCGC TATTCGCGAG    2580
GGACACCCCA GAGTATCGGG TGTTTTACCC AATGAATGTC ATGGCCGTCA AGTTTTCCAT    2640
ATCCATTGGC AACAACGAGT CCGGCGTAGC GCTCTATGGA GTGGTGTCGG AAGATTTCGT    2700
GGTCGTCACG CTCCACAACA GGTCCAAAGA GGCTAACGAG ACGGCGTCCC ATCTTCTGTT    2760
CGGTCTCCCG GATTCACTGC CATCTCTGAA GGGCCATGCC ACCTATGATG AACTCACGTT    2820
CGCCCGAAAC GCAAAATATG CGCTAGTGGC GATCCTGCCT AAAGATTCTT ACCAGACACT    2880
CCTTACAGAG AATTACACTC GCATATTTCT GAACATGACG GAGTCGACGC CCCTCGAGTT    2940
CACGCGGACG ATCCAGACCA GGATCGTATC AATCGAGGCC AGGCGCGCCT GCGCAGCTCA    3000
AGAGGCGGCG CCGGACATAT TCTTGGTGTT GTTTCAGATG TTGGTGGCAC ACTTTCTTGT    3060
TGCGCGGGGC ATTGCCGAGC ACCGATTTGT GGAGGTGGAC TGCGTGTGTC GGCAGTATGC    3120
GGAACTGTAT TTTCTCCGCC GCATCTCGCG TCTGTGCATG CCCACGTTCA CCACTGTCGG    3180
GTATAACCAC ACCACCCTTG GCGCTGTGGC CGCCACACAA ATAGCTCGCG TGTCCGCCAC    3240
GAAGTTGGCC AGTTTGCCCC GCTCTTCCCA GGAAACAGTG CTGGCCATGG TCCAGCTTGG    3300
CGCCCGTGAT GGCGCCGTCC CTTCCTCCAT TCTGGAGGGC ATTGCTATGG TCGTCGAACA    3360
TATGTATACC GCCTACACTT ATGTGTACAC ACTCGGCGAT ACTGAAAGAA AATTAATGTT    3420
GGACATACAC ACGGTCCTCA CCGACAGCTG CCCGCCCAAA GACTCCGGAG TATCAGAAAA    3480
GCTACTGAGA ACATATTTGA TGTTCACATC AATGTGTACC AACATAGAGC TGGGCGAAAT    3540
GATCGCCCGC TTTTCCAAAC CGGACAGCCT TAACATCTAT AGGGCATTCT CCCCCTGCTT    3600
TCTAGGACTA AGGTACGATT TGCATCCAGC CAAGTTGCGC GCCGAGGCGC CGCAGTCGTC    3660
CGCTCTGACG CGGACTGCCG TTGCCAGAGG AACATCGGGA TTCGCAGAAT TGCTCCACGC    3720
GCTGCACCTC GATAGCTTAA ATTTAATTCC GGCGATTAAC TGTTCAAAGA TTACAGCCGA    3780
CAAGATAATA GCTACGGTAC CCTTGCCTCA CGTCACGTAT ATCATCAGTT CCGAAGCACT    3840
CTCGAACGCT GTTGTCTACG AGGTGTCGGA GATCTTCCTC AAGAGTGCCA TGTTTATATC    3900
TGCTATCAAA CCCGATTGCT CCGGCTTTAA CTTTTCTCAG ATTGATAGGC ACATTCCCAT    3960
AGTCTACAAC ATCAGCACAC AAGAAGAGG TTGCCCCCTT TGTGACTCTG TAATCATGAG    4020
CTACGATGAG AGCGATGGCC TGCAGTCTCT CATGTATGTC ACTAATGAAA GGGTGCAGAC    4080
CAACCTCTTT TTAGATAAGT CACCTTTCTT TGATAATAAC AACCTACACA TTCATTATTT    4140
GTGGCTGAGG GACAACGGGA CCGTAGTGGA GATAAGGGGC ATGTATAGAA GACGCGCAGC    4200
CAGTGCTTTG TTTCTAATTC TCTCTTTTAT TGGGTTCTCG GGGGTTATCT ACTTTCTTTA    4260
CAGACTGTTT TCCATCCTTT ATTAGACGGT CAATAAAGCG TAGATTTTTA AAAGGTTTCC    4320
TGTGCATTCT TTTTGTATGG GCATATACTT GGCAAGAAAT CCGAGCACCT CAGAAAGTGG    4380
ATTGCCGTCA CATATCAGTT CGACCACCCC TGCACCTAGC CATGCGGCGC TTTGACGGTC    4440
TTTGGGGCTA CACATCATAA AGTACTTTTC CATGGCTTCT ATAAGCACCT TGGAACAATC    4500
```

FIGURE 3A-4

```
TGGGGGTTGG CGAATGGGTT CCCTAAACGG GAAATCCTCT ATGGTATTCA GGCAGAAGAC    4560
CGCGTCCTCC ACCCGACGTT TGAGTCTTTC TAGCAGAGCG CCGAAGAACT CCCGCTCGTG    4620
TGTTTTCGCA GGGGCAAGTT CTGCGCCGTA CAGCGATGAG AAACACGACA CGATGTTTTC    4680
CAGCCCCATG CTGCGCAGCA ACACGTGCTT CAGGAACAGG TGTTGTAGCC GGTTCAGTTT    4740
TAGCTTGGGT AGAAAAGTTA TCGAGTTGTT AGCACGCTCC ATGATGGTAA CGGTGTTGAA    4800
GTCACAGACC GGGCTTTCTC CGAGTCTCGG CCGCCTGAGT CCAATCATGT AGAACATAGA    4860
CGCGGCCTCG TTGTCTGTGT TAAGTGACAC GATATCCCGT TCGCAAACCT GTGCGATGTT    4920
GTGTTTCAGT ATAGATCTGG TCTGACCGGC ACGGGGTGTT ATGGGGTGAC GCGGTAAAGG    4980
CGACTCTGGG TCAAACACCT TTATGCGGTT GGCGGCCTCG TCGATGACGA CACGCTTGTT    5040
CGCGGCGTGT ATGGGACGC GACGGCATCC CGCTGGCAGA TCTATAATCT TAAAGTTGGT     5100
ATAAGACTGG TCGCTCGTTA TGGCCAGCCG GCACTCCGGT AGTATCTGCG TGTCCTCGAA    5160
TTCGTGGCCG CGTACGACTG GCTTGGAGTG CAGGTAAACG CCAAGAGATG CGGTCTCTTC    5220
GCCTACGCAC AAGTGGCTTC TTAACGCGTA GGGGTGCGGT GAGAGCATGA TCCGTAGCAA    5280
CGATAGTTCC GGGTGCCTAG CCGCGTAGAG TGGCAGGGTA GACGAGTCCG GAGTCCCAAA    5340
CTTTTCGAAC AACAGTGGCA TCGGGACTTC AGGATTAGAG ACTCCCACCA TGGCCGCCAC    5400
CGCCGGAGAG GTCAAGACGT GAAACACGCG CTCGCCTGTC GACAGGCGCG CCGCGCCCTC    5460
TACTAGACTA GCCTTCACGT CCGGAACTCG TAACATAGCT TAGACCAGCG GACGGACGCA    5520
ACGTACGCGG GGATCGGCTG GCGGTGTCTG CTCGTTGGAC GCGGCCGTTC GGTGGCGCCA    5580
GTGCAGGCCT AGTTTGCGAA TGGCGTGACG GACAATTTGT GGCTTTAGAG CGGCGAACCG    5640
ATGACCCGTG GTGGCGACGA ACGAAATGAA GTTTGCATTG CGGCCCAACT CGTCTAGCCT    5700
GGTCTTCTTG TTTCGGGCAT AGATTTTCGG GATTAGGTTA CACTTTTTAT ATCCCAGTAC    5760
TGCGCACTCG TGTTTGCTTT TAGTGTGACT GATTATCTTC TTTGAGAAGT CAAACAGGCC    5820
CCGGCGGCG GCTCGCCTAA TGCAAGCCAC GTCAAGCCTG AGAAACGAAC AGCATTCCAC     5880
CAGACACTCC AGGAACCTTT TGTGTAGCGT CTGTATTTGG GAACGGTTTC TGTGCTCAAG    5940
TAGGGAGAAT ATTCTATTTT TGTTTCCGTC GATGCGCGCG TGCTGGTCCG TGAGAATGGG    6000
CGCCAGCTCG TGGCGAATCT GTTCCACAAG AGGCTGCCCG TACACTTTAG AAATCGTGGC    6060
TGTCGCGGCC TTAAACCAGG ACACGTTTAG CCCATCCTTG CTGGAGACCA CAGATGGAAA    6120
GTTTGTGGTC CAAAATACGT TTTTTCGCCC CATTCTCACC ATGTACTGGT TTTCCAGTCC    6180
GTGCAGGTCC AACGTGGAGT TCCAATTTGC TATCGATACA GGAAATATGT GCCTGATTGG    6240
CAGAAAGCAT TTCAGCGTAC CCATTGCGAA GAGAAAGTGC AGCATGTCCC CACTGATGTT    6300
GATGTTTATT GCGGTGCCTT GACACATGTT GTCGGAAAAA AACACGCTTA TGGTAAAAGA    6360
AGGTTCCTTT ACGGAGTACT TTCGTATAAC AAAATTGTTG GTCAATCTGG GGATGTTTAA    6420
AATAGTCTTT TGCAGGGTGT TAGGAACGTG GCAGCTTATC TTAGTGTTAA TCACCATGTT    6480
GGTGTTGAAT ATGGTGATCT TGAAGTTTTC CAAACTGACG TGTTTTGTGG GTTCCAGCAT    6540
GTCTGACACT GTAGAGCTGC CCAGAGTCCG CGCGTCCGTG GCCGCGTATC GTTGGAAGCA    6600
```

FIGURE 3A-5

```
CGCCTGCAAA TTTCCTTTCA TGGCTGCTCG CCGGTCTTTC GGCGCGTACC GGATTCTTGA    6660
AAGCGTCGCC GCCAGGAGAC GCGGTGTCTC GTGGGTGCCT AAAAAGTTTG CGCAGGGGTG    6720
CAGTCCGCTG CACGAGTGGC CGATGCAGTC TGCCACTGCC ATACACATGA CGAGTCTGTA    6780
GATGGCCGGT GTGCCCGGAT ACACTAGATA GTAGGTACAA TCTGGGGTAC TGACGACCAC    6840
CCTGTATGGC TTTGGTCCGG GGTCCTTGCG TTGGATTTTT ACGTGCAGAC GGGACACGAG    6900
CTGGTTTAGA GCCAGCTGAA AGCCCACCAG ATCCCGTCCG TTAACCTTGA CGTCCTGGTG    6960
CTTACTCTGT TTCGACAGGT TCTTCAGCAC GGTGGGCAGT CGCTCTACGT TGTGAGCGAT    7020
GGCACGGCGC AGCGAGACCA GCTCTCCGTG CCACCCCAC GTGGCCATGA AGCTGCTGAT     7080
GTTAAACTTT AAAAAATGTA GCTGTGCGTC TGGGGATGCG GGTGGCATTA TTGAAAACGA    7140
GAGATGCTTC AGGCTCTCCA GGAGTGCAAA ATAATTTTGA TAGATTGTGG GTTGTAGACT    7200
ATGGGCAAC ACCGCCAGAA ACGCATGAAA ACACTGTTCG AACTCCCAGA ACTCCAGGTA     7260
CCTGCACACT ATCCTGAACA TGGCTTTGTA ACATATGGTG CACGTTAGTA GCGCGGGAAG    7320
ATACAGCGAG CGTAGCTCCC TGAATTCGCA GGGTTTATCA CAATCATCGG TAAGTTCCCA   7380
TGATCCCACC GCAGGTAGGT AGTTGTCGGT GTCTATCTGT CCGCGCGTAA ACACTCCACC    7440
ACCGTCAATT ATTAAACCTT CGCCGCTGTA CCGTCGACCC ACTTTTCCCA AAAGAGTCCC    7500
TTCTTGATGT ATAAAAGGGT GGAGGCGTTC CCCCAGGAGT AGTCTGCGTA TCGCTCTGCA    7560
GGCGAAAAAG GTGGGCTCGG GCTGCATCAT CTTATCAAGA CCTTCTAAGG TCAGCTCTGC    7620
CTGCAGGTGC GAGTTGGTGG CCAGACAGCA GAATATTTCC AGCTGTGATT CCCAAGTCGC    7680
TTGATAACAC GTGGTCTGCG GACTCGTCGT CAGGGAGGCG CTCGGTGGCA GTAGTAGGGG    7740
GCCCTCGAGC GCTGCCATGG AGGCGACCTT GGAGCAACGA CCTTTCCCGT ACCTCGCCAC    7800
GGAGGCCAAC CTCCTAACGC AGATTAAGGA GTCGGCTGCC GACGGACTCT TCAAGAGCTT    7860
TCAGCTATTG CTCGGCAAGG ACGCCAGAGA AGGCAGTGTC CGTTTCGAAG CGCTACTGGG    7920
CGTATATACC AATGTGGTGG AGTTTGTTAA GTTTCTGGAG ACCGCCCTCG CCGCCGCTTG    7980
CGTCAATACC GAGTTCAAGG ACCTGCGGAG AATGATAGAT GGAAAAATAC AGTTTAAAAT    8040
TTCAATGCCC ACTATTGCCC ACGGAGACGG GAGGAGGCCC AACAAGCAGA GACAGTATAT    8100
CGTCATGAAG GCTTGCAATA AGCACCACAT CGGTGCGGAG ATTGAGCTTG CGGCCGCAGA    8160
CATCGAGCTT CTCTTCGCCG AGAAAGAGAC GCCCTTGGAC TTCACAGAGT ACGCGGGTGC    8220
CATCAAGACG ATTACGTCGG CTTTGCAGTT TGGTATGGAC GCCCTAGAAC GGGGGCTAGT    8280
GGACACGGTT CTCGCAGTTA AACTTCGGCA CGCTCCACCC GTCTTTATTT TAAAGACGCT    8340
GGGCGATCCC GTCTACTCTG AGAGGGGCCT CAAAAAGGCC GTCAAGTCTG ACATGGTATC    8400
CATGTTCAAG GCACACCTCA TAGAACATTC ATTTTTTCTA GATAAGGCCG AGCTCATGAC    8460
AAGGGGGAAG CAGTATGTCC TAACCATGCT CTCCGACATG CTGGCCGCGG TGTGCGAGGA    8520
TACCGTCTTT AAGGGTGTCA GCACGTACAC CACGGCCTCT GGGCAGCAGG TGGCCGGCGT    8580
CCTGGAGACG ACGGACAGCG TCATGAGACG GCTGATGAAC CTGCTGGGGC AAGTGGAAAG    8640
TGCCATGTCC GGGCCCGCGG CCTACGCCAG CTACGTTGTC AGGGGTGCCA ACCTCGTCAC    8700
```

FIGURE 3A-6

```
CGCCGTTAGC TACGGAAGGG CGATGAGAAA CTTTGAACAG TTTATGGCAC GCATAGTGGA    8760
CCATCCCAAC GCTCTGCCGT CTGTGGAAGG TGACAAGGCC GCTCTGGCGG ACGGACACGA    8820
CGAGATTCAG AGAACCCGCA TCGCCGCCTC TCTCGTCAAG ATAGGGGATA AGTTTGTGGC    8880
CATTGAAAGT TTGCAGCGCA TGTACAACGA GACTCAGTTT CCCTGCCCAC TGAACCGGCG    8940
CATCCAGTAC ACCTATTTCT TCCCTGTTGG CCTTCACCTT CCCGTGCCCC GCTACTCGAC    9000
ATCCGTCTCA GTCAGGGGCG TAGAATCCCC GGCCATCCAG TCGACCGAGA CGTGGGTGGT    9060
TAATAAAAAC AACGTGCCTC TTTGCTTCGG TTACCAAAAC GCCCTCAAAA GCATATGCCA    9120
CCCTCGAATG CACAACCCCA CCCAGTCAGC CCAGGCACTA AACCAAGCTT TTCCCGATCC    9180
CGACGGGGGA CATGGGTACG GTCTCAGGTA TGAGCAGACG CCAAACATGA ACCTATTCAG    9240
AACGTTCCAC CAGTATTACA TGGGGAAAAA CGTGGCATTT GTTCCCGATG TGGCCCAAAA    9300
AGCGCTCGTA ACCACGGAGG ATCTACTGCA CCCAACCTCT CACCGTCTCC TCAGATTGGA    9360
GGTCCACCCC TTCTTTGATT TTTTTGTGCA CCCCTGTCCT GGAGCGAGAG GATCGTACCG    9420
CGCCACCCAC AGAACAATGG TTGGAAATAT ACCACAACCG CTCGCTCCAA GGGAGTTTCA    9480
GGAAAGTAGA GGGGCGCAGT TCGACGCTGT GACGAATATG ACACACGTCA TAGACCAGCT    9540
AACTATTGAC GTCATACAGG AGACGGCATT TGACCCCGCG TATCCCCTGT TCTGCTATGT    9600
AATCGAAGCA ATGATTCACG GACAGGAAGA AAAATTCGTG ATGAACATGC CCCTCATTGC    9660
CCTGGTCATT CAAACCTACT GGGTCAACTC GGGAAAACTG GCGTTTGTGA ACAGTTATCA    9720
CATGGTTAGA TTCATCTGTA CGCATATTGG GAATGGAAGC ATCCCTAAGG AGGCGCACGG    9780
CCACTACCGG AAAATCTTAG GCGAGCTCAT CGCCCTTGAG CAGGCGCTTC TCAAGCTCGC    9840
GGGACACGAG ACGGTGGGTC GGACGCCGAT CACACATCTG GTTTCGGCTC TCCTCGACCC    9900
GCATCTGCTG CCTCCCTTTG CCTACCACGA TGTCTTTACG GATCTTATGC AGAAGTCATC    9960
CAGACAACCC ATAATCAAGA TCGGGGATCA AAACTACGAC AACCCTCAAA ATAGGGCGAC   10020
ATTCATCAAC CTCAGGGGTC GCATGGAGGA CCTAGTCAAT AACCTTGTTA ACATTTACCA   10080
GACAAGGGTC AATGAGGACC ATGACGAGAG ACACGTCCTG GACGTGGCGC CCCTGGACGA   10140
GAATGACTAC AACCCGGTCC TCGAGAAGCT ATTCTACTAT GTTTTAATGC CGGTGTGCAG   10200
TAACGGCCAC ATGTGCGGTA TGGGGGTCGA CTATCAAAAC GTGGCCCTGA CGCTGACTTA   10260
CAACGGCCCC GTCTTTGCGG ACGTCGTGAA CGCACAGGAT GATATTCTAC TGCACCTGGA   10320
GAACGGAACC TTGAAGGACA TTCTGCAGGC AGGCGACATA CGCCCGACGG TGGACATGAT   10380
CAGGGTGCTG TGCACCTCGT TTCTGACGTG CCCTTTCGTC ACCCAGGCCG CTCGCGTGAT   10440
CACAAAGCGG GACCCGGCCC AGAGTTTTGC CACGCACGAA TACGGAAGG ATGTGGCGCA    10500
GACCGTGCTT GTTAATGGCT TTGGTGCGTT CGCGGTGGCG GACCGCTCTC GCGAGGCGGC   10560
GGAGACTATG TTTTATCCGG TACCCTTTAA CAAGCTCTAC GCTGACCCGT TGGTGGCTGC   10620
CACACTGCAT CCGCTCCTGC CAAACTATGT CACCAGGCTC CCCAACCAGA GAAACGCGGT   10680
GGTCTTTAAC GTGCCATCCA ATCTCATGGC AGAATATGAG GAATGGCACA AGTCGCCCGT   10740
CGCGGCGTAT GCCGCGTCTT GTCAGGCCAC CCCGGGCGCC ATTAGCGCCA TGGTGAGCAT   10800
```

FIGURE 3A-7

```
GCACCAAAAA CTATCTGCCC CCAGTTTCAT TTGCCAGGCA AAACACCGCA TGCACCCTGG    10860
TTTTGCCATG ACAGTCGTCA GGACGGACGA GGTTCTAGCA GAGCACATCC TATACTGCTC    10920
CAGGGCGTCG ACATCCATGT TTGTGGGCTT GCCTTCGGTG GTACGGCGCG AGGTACGTTC    10980
GGACGCGGTG ACTTTTGAAA TTACCCACGA GATCGCTTCC CTGCACACCG CACTTGGCTA    11040
CTCATCAGTC ATCGCCCCGG CCCACGTGGC CGCCATAACT ACAGACATGG GAGTACATTG    11100
TCAGGACCTC TTTATGATTT TCCCAGGGGA CGCGTATCAG GACCGCCAGC TGCATGACTA    11160
TATCAAAATG AAAGCGGGCG TGCAAACCGG CTCACCGGGA AACAGAATGG ATCACGTGGG    11220
ATACACTGCT GGGGTTCCTC GCTGCGAGAA CCTGCCCGGT TTGAGTCATG GTCAGCTGGC    11280
AACCTGCGAG ATAATTCCCA CGCCGGTCAC ATCTGACGTT GCCTATTTCC AGACCCCAG     11340
CAACCCCCGG GGGCGTGCGG CGTCGGTCGT GTCGTGTGAT GCTTACAGTA ACGAAAGCGC    11400
AGAGCGTTTG TTCTACGACC ATTCAATACC AGACCCCGCG TACGAATGCC GGTCCACCAA    11460
CAACCCGTGG GCTTCGCAGC GTGGCTCCCT CGGCGACGTG CTATACAATA TCACCTTTCG    11520
CCAGACTGCG CTGCCGGGCA TGTACAGTCC TTGTCGGCAG TTCTTCCACA AGGAAGACAT    11580
TATGCGGTAC AATAGGGGGT TGTACACTTT GGTTAATGAG TATTCTGCCA GGCTTGCTGG    11640
GGCCCCCGCC ACCAGCACTA CAGACCTCCA GTACGTCGTG GTCAACGGTA CAGACGTGTT    11700
TTTGGACCAG CCTTGCCATA TGCTGCAGGA GGCCTATCCC ACGCTCGCCG CCAGCACAG    11760
AGTTATGCTT GCCGAGTACA TGTCAAACAA GCAGACACAC GCCCCAGTAC ACATGGGCCA    11820
GTATCTCATT GAAGAGGTGG CGCCGATGAA GAGACTATTA AAGCTCGGAA ACAAGGTGGT    11880
GTATTAGCTA ACCCTTCTAG CGTTGGCTAG TCATGGCACT CGACAAGAGT ATAGTGGTTA    11940
ACTTCACCTC CAGACTCTTC GCTGATGAAC TGGCCGCCCT TCAGTCAAAA ATAGGGAGCG    12000
TACTGCCGCT CGGAGATTGC CACCGTTTAC AAAATATACA GGCATTGGGC CTGGGGTGCG    12060
TATGCTCACG TGAGACATCT CCGGACTACA TCCAAATTAT GCAGTATCTA TCCAAGTGCA    12120
CACTCGCTGT CCTGGAGGAG GTTCGCCCGG ACAGCCTGCG CCTAACGCGG ATGGATCCCT    12180
CTGACAACCT TCAGATAAAA AACGTATATG CCCCCTTTTT TCAGTGGGAC AGCAACACCC    12240
AGCTAGCAGT GCTACCCCCA TTTTTTAGCC GAAAGGATTC CACCATTGTG CTCGAATCCA    12300
ACGGATTTGA CCCCGTGTTC CCCATGGTCG TGCCGCAGCA ACTGGGCAC GCTATTCTGC     12360
AGCAGCTGTT GGTGTACCAC ATCTACTCCA AAATATCGGC CGGGGCCCCG GATGATGTAA    12420
ATATGGCGGA ACTTGATCTA TATACCACCA ATGTGTCATT TATGGGGCGC ACATATCGTC    12480
TGGACGTAGA CAACACGGAT CCACGTACTG CCCTGCGAGT GCTTGACGAT CTGTCCATGT    12540
ACCTTTGTAT CCTATCAGCC TTGGTTCCCA GGGGTGTCT CCGTCTGCTC ACGGCGCTCG     12600
TGCGGCACGA CAGGCATCCT CTGACAGAGG TGTTTGAGGG GGTGGTGCCA GATGAGGTGA    12660
CCAGGATAGA TCTCGACCAG TTGAGCGTCC CAGATGACAT CACCAGGATG CGCGTCATGT    12720
TCTCCTATCT TCAGAGTCTC AGTTCTATAT TTAATCTTGG CCCCAGACTG CACGTGTATG    12780
CCTACTCGGC AGAGACTTTG GCGGCCTCCT GTTGGTATTC CCCACGCTAA CGATTTGAAG    12840
CGGGGGGGGT ATGGCGTCAT CTGATATTCT GTCGGTTGCA AGGACGGATG ACGGCTCCGT    12900
```

FIGURE 3A-8

```
CTGTGAAGTC TCCCTGCGTG GAGGTAGGAA AAAAACTACC GTCTACCTGC CGGACACTGA    12960
ACCCTGGGTG GTAGAGACCG ACGCCATCAA AGACGCCTTC CTCAGCGACG GGATCGTGGA    13020
TATGGCTCGA AAGCTTCATC GTGGTGCCCT GCCCTCAAAT TCTCACAACG GCTTGAGGAT    13080
GGTGCTTTTT TGTTATTGTT ACTTGCAAAA TTGTGTGTAC CTAGCCCTGT TTCTGTGCCC    13140
CCTTAATCCT TACTTGGTAA CTCCCTCAAG CATTGAGTTT GCCGAGCCCG TTGTGGCACC    13200
TGAGGTGCTC TTCCCACACC CGGCTGAGAT GTCTCGCGGT TGCGATGACG CGATTTTCTG    13260
TAAACTGCCC TATACCGTGC CTATAATCAA CACCACGTTT GGACGCATTT ACCCGAACTC    13320
TACACGCGAG CCGGACGGCA GGCCTACGGA TTACTCCATG GCCCTTAGAA GGGCTTTTGC    13380
AGTTATGGTT AACACGTCAT GTGCAGGAGT GACATTGTGC CGCGGAGAAA CTCAGACCGC    13440
ATCCCGTAAC CACACTGAGT GGGAAAATCT GCTGGCTATG TTTTCTGTGA TTATCTATGC    13500
CTTAGATCAC AACTGTCACC CGGAAGCACT GTCTATCGCG AGCGGCATCT TTGACGAGCG    13560
TGACTATGGA TTATTCATCT CTCAGCCCCG GAGCGTGCCC TCGCCTACCC CTTGCGACGT    13620
GTCGTGGGAA GATATCTACA ACGGGACTTA CCTAGCTCGG CCTGGAAACT GTGACCCCTG    13680
GCCCAATCTA TCCACCCCTC CCTTGATTCT AAATTTTAAA TAAAGGTGTG TCACTGGTTA    13740
CACCACGATT AAAAACCACT CACTGAGATG TCTTTTTAAC CGCTAAGGGA TTATACCGGG    13800
ATTTAAAACC GCCCACTGAT TTTTTTACGC TAAGAGTTGG GTGCTTGGGG GGTTTTGCAT    13860
TGCTCTGTTG TAAACTATAT ATAAGTTAAA CCAAAATTCG CAGGGAGACA AGGTGACGGT    13920
GGTGAGAACT CAGTTGAGAG TCAGAGAATA CAGTGCTAAT CAGGGTAGAT GAGCATGACT    13980
TTCCCCGTCT CCAGTCACCG GAGGAATGGT GGACGGCTCC GTCCTGGTGC GAATGGCCAC    14040
CAAGCCTCCC GTGATTGGTC TTATAACAGT GCTCTTCCTC CTAGTCATAG GCGCCTGCGT    14100
CTACTGCTGC ATTCGCGTGT TCCTGGCGGC TCGACTGTGG CGCGCCACCC CACTAGGCAG    14160
GGCCACCGTG GCGTATCAGG TCCTTCGCAC CCTGGGACCG CAGGCCGGGT CACATGCACC    14220
GCCGACGGTG GGCATAGCTA CCCAGGAGCC CTACCGTACA ATATACATGC CAGATTAGAA    14280
CGGGGTGTGT GCTATAATGG ATGGCTATGG GGGGGGGCTG TAGATAATTG AGCGCTGTGC    14340
TTTTATTGTG GGGATATGGG CTTGTACATG TGTCTATCAT CGGTAGCCAT AAAATGGGCC    14400
ATGACAACTG CCACAAGTAA GTCGTCCGAC ATGTGCTTTT GCTTGGCGCT GTATGACTGC    14460
CCTCCATCCC TAAGCGGGAC GCACTTGATC GCGCGGACCT GTTCTACCAG GTAGGTCACC    14520
GGGTCAAATG ATATTTTGAT GGTGTTGGAC ACCACGTCT  GGCTGGCGCT CAGGGTGCCG    14580
GAGTTCAGAG CGTAGATGAA TGTCTCAAAC GCGGAGGATT TCTCGCCTCC CAACATGTAA    14640
ATTGGCCACT GCAGGGCGCT GCTCTTGTCA GTATAGTGTA GAAAATGTAT GGGGAGCGGG    14700
CATATTTCGT TAAGGACGGT TGCAATGGCC ACCCCAGAAT CTTGGCTGCT GTTGCCTTCG    14760
ACCGCCGCGT TCACGCGCTC AATTGTGGTG TGGAGCACAG CGATCGCCTT AATCATCGTG    14820
CATGCGCAGG ACGCTATCTC GTAAGCAGCT GCGCCAGTGA GGTCGCGCAG AAGAAATGC    14880
TCCATGCCCA ATATGAGGCT TCTGGTGGGA GTCTGAGTAC TCGTGACAAC GGCGCCCACG    14940
CCAGTACCGG ACGCCTCCGT GTTGTTCGTA TACGCGGGGT CGATGTAAAC AAACAGCTGT    15000
```

FIGURE 3A-9

```
TTTCCAAGGC ACTTCTGAAC CTCCTGGGCG GTGGTGTCTA CCCGACACAT GTCAAACTGT   15060
GTCAGCGCTG CGTCACCCAC CACGCGGTAA AGCGTAGCAT TTGACGACGC TGCTCCCTCG   15120
CCCATTAGTT CGGTGTCGAA TGCCCCCTCC ATAAAGAGGT TGGTGGTGGT TTTGATGGAT   15180
TCGTCGATGG TGATGTACGT CGGAATGTGC AGTCTGTAAC AAGGACAGGA CACTAGTGCG   15240
TCTTGCAGGT GGAAATCTTC TCGGTGGTCC GCACACACGT AACTGACCAC ATTCAGCATC   15300
TTTTCCTGGG CGTTCCTGAG GTTAAGCAGG AAACTCGTGG AGCGGTCTGA CGAGTTCACG   15360
GATGATATAA ATATAAGCTT GGCGTCTTTC TGAAGCATGA AACCCAGAAT AGCCGGCAGT   15420
GCATCCTTTT TAATAAAATT CGCCTCGTCT ACGTAGAGCA GGTTAAAGGT CTGTCCCCGA   15480
ATGCTCTGCA GACACGGAAA GACACAAAAG AGGGGCTCAT AAGCGGCTAA CAGTAAAGGA   15540
GAGGAGGCGA ACAGTGCGTG GCTCTTGGTT CTTGGGAATA AAAGGGGGCG TGTGTGCCGA   15600
TCGATCGTAT GGGTGAGCCA GTGGATCCTG GACATGTGGT GAATGAGAAA GATTTTGAGG   15660
AGTGTGAACA ATTTTTCAGT CAACCCCTTA GGGAGCAAGT GGTCGCGGGG GTCAGGGCAC   15720
TCGACGGCCT CGGTCTCGCT GACTCTCTAT GTCACAAAAC AGAAAGACTC TGCCTGCTGA   15780
TGGACCTGGT GGGCACGGAG TGCTTTGCGA GGGTGTGCCG CCTAGACACC GGTGCGAAAT   15840
GAAGAGTGTG GCGAGTCCCT TATGTCAGTT CCACGGCGTG TTTTGCCTGT ACCAGTGTCG   15900
CCAGTGCCTG GCATACCACG TGTGTGATGG GGGCGCCGAA TGCGTTCTCC TGCATACGCC   15960
GGAGAGCGTC ATCTGCGAAC TAACGGGTAA CTGCATGCTC GGCAACATTC AAGAGGGCCA   16020
GTTTTTAGGG CCGGTACCGT ATCGGACTTT GGATAACCAG GTTGACAGGG ACGCATATCA   16080
CGGGATGCTA GCGTGTCTGA AACGGGACAT TGTGCGGTAT TTGCAGACAT GGCCGGACAC   16140
CACCGTAATC GTGCAGGAAA TAGCCCTGGG GGACGGCGTC ACCGACACCA TCTCGGCCAT   16200
TATAGATGAA ACATTCGGTG AGTGTCTTCC CGTACTGGGG GAGGCCCAAG GCGGGTACGC   16260
CCTGGTCTGT AGCATGTATC TGCACGTTAT CGTCTCCATC TATTCGACAA AAACGGTGTA   16320
CAACAGTATG CTATTTAAAT GCACAAAGAA TAAAAAGTAC GACTGCATTG CCAAGCGGGT   16380
GCGGACAAAA TGGATGCGCA TGCTATCAAC GAAAGATACG TAGGTCCTCG CTGCCACCGT   16440
TTGGCCCACG TGGTGCTGCC TAGGACCTTT CTGCTGCATC ACGCCATACC CCTGGAGCCC   16500
GAGATCATCT TTTCCACCTA CACCCGGTTC AGCCGGTCGC CAGGGTCATC CCGCCGGTTG   16560
GTGGTGTGTG GGAAACGTGT CCTGCCAGGG GAGGAAAACC AACTTGCGTC TTCACCTTCT   16620
GGTTTGGCGC TTAGCCTGCC TCTGTTTTCC CACGATGGGA ACTTTCATCC ATTTGACATC   16680
TCGGTACTGC GCATTTCCTG CCCTGGTTCT AATCTTAGTC TTACTGTCAG ATTTCTCTAT   16740
CTATCTCTGG TGGTGGCTAT GGGGGCGGGA CGGAATAATG CGCGGAGTCC GACCGTTGAC   16800
GGGGTATCGC CGCCAGAGGG CGCCGTAGCC CACCCTTTGG AGGAACTGCA GAGGCTGGCG   16860
CGTGCTACGC CGGACCCGGC ACTCACCCGT GGACCGTTGC AGGTCCTGAC CGGCCTTCTC   16920
CGCGCAGGGT CAGACGGAGA CCGCGCCACT CACCACATGG CGCTCGAGGC TCCGGGAACC   16980
GTGCGTGGAG AAAGCCTAGA CCCGCCTGTT TCACAGAAGG GGCCAGCGCG CACACGCCAC   17040
AGGCCACCCC CCGTGCGACT GAGCTTCAAC CCCGTCAATG CCGATGTACC CGCTACCTGG   17100
```

FIGURE 3A-10

```
CGAGACGCCA CTAACGTGTA CTCGGGTGCT CCCTACTATG TGTGTGTTTA CGAACGCGGT   17160
GGCCGTCAGG AAGACGACTG GCTGCCGATA CCACTGAGCT TCCCAGAAGA GCCCGTGCCC   17220
CCGCCACCGG GCTTAGTGTT CATGGACGAC TTGTTCATTA ACACGAAGCA GTGCGACTTT   17280
GTGGACACGC TAGAGGCCGC CTGTCGCACG CAAGGCTACA CGTTGAGACA GCGCGTGCCT   17340
GTCGCCATTC CTCGCGACGC GGAAATCGCA GACGCAGTTA AATCGCACTT TTTAGAGGCG   17400
TGCCTAGTGT TACGGGGGCT GGCTTCGGAG GCTAGTGCCT GGATAAGAGC TGCCACGTCC   17460
CCGCCCCTTG GCCGCCACGC CTGCTGGATG GACGTGTTAG GATTATGGGA AAGCCGCCCC   17520
CACACTCTAG GTTTGGAGTT ACGCGGCGTA AACTGTGGCG GCACGGACGG TGACTGGTTA   17580
GAGATTTTAA AACAGCCCGA TGTGCAAAAG ACAGTCAGCG GGAGTCTTGT GGCATGCGTG   17640
ATCGTCACAC CCGCATTGGA AGCCTGGCTT GTGTTACCTG GGGGTTTTGC TATTAAAGCC   17700
CGCTATAGGG CGTCGAAGGA GGATCTGGTG TTCATTCGAG GCCGCTATGG CTAGCCGGAG   17760
GCGCAAACTT CGGAATTTCC TAAACAAGGA ATGCATATGG ACTGTTAACC CAATGTCAGG   17820
GGACCATATC AAGGTCTTTA ACGCCTGCAC CTCTATCTCG CCGGTGTATG ACCCTGAGCT   17880
GGTAACCAGC TACGCACTGA GCGTGCCTGC TTACAATGTG TCTGTGGCTA TCTTGCTGCA   17940
TAAAGTCATG GGACCGTGTG TGGCTGTGGG AATTAACGGA GAAATGATCA TGTACGTCGT   18000
AAGCCAGTGT GTTTCTGTGC GGCCCGTCCC GGGGCGCGAT GGTATGGCGC TCATCTACTT   18060
TGGACAGTTT CTGGAGGAAG CATCCGGACT GAGATTTCCC TACATTGCTC CGCCGCCGTC   18120
GCGCGAACAC GTACCTGACC TGACCAGACA AGAATTAGTT CATACCTCCC AGGTGGTGCG   18180
CCGCGGCGAC CTGACCAATT GCACTATGGG TCTCGAATTC AGGAATGTGA ACCCTTTTGT   18240
TTGGCTCGGG GGCGGATCGG TGTGGCTGCT GTTCTTGGGC GTGGACTACA TGGCGTTCTG   18300
TCCGGGTGTC GACGGAATGC CGTCGTTGGC AAGAGTGGCC GCCCTGCTTA CCAGGTGCGA   18360
CCACCCAGAC TGTGTCCACT GCCATGGACT CCGTGGACAC GTTAATGTAT TTCGTGGGTA   18420
CTGTTCTGCG CAGTCGCCGG GTCTATCTAA CATCTGTCCC TGTATCAAAT CATGTGGGAC   18480
CGGGAATGGA GTGACTAGGG TCACTGGAAA CAGAAATTTT CTGGGTCTTC TGTTCGATCC   18540
CATTGTCCAG AGCAGGGTAA CAGCTCTGAA GATAACTAGC CACCCAACCC CCACGACGT    18600
CGAGAATGTG CTAACAGGAG TGCTCGACGA CGGCACCTTG GTGCCGTCCG TCCAAGGCAC   18660
CCTGGGTCCT CTTACGAATG TCTGACTACT TCAGCCGCTT GCTGATATAT GAGTGTAAAA   18720
AACTTAAGGC CCTGGGCTTA CGTTCTTATT GAAGCATGTT GCGCACATCA GCGAGCTGGA   18780
CCGTCCTCCG GGTCGCGTGT AGATTATGGT TCCGTTCTCC TTCTTGATGT TTAAATTTTT   18840
GGGGGGGAAC CACCGACAAA GCGTCTTTAT GATTTCCGCG AACACGGAGT TGGCTACGTG   18900
CTTTTGGTGG GCTACGTACC CAATGTTAAT GTTCTCTACG GATGCCAGTA GCATGCTGAT   18960
GATCGCCACC ACTATCCATG TCTTTCCGTG TCTCCTTGGT ATTAGGAATA CGCTTGCCTT   19020
TTGCTTAAAC GTCTGTAAAA CACTGTTTGG AGTTTCAAAT AAACCGAAGT ACTGCTTAAA   19080
CAATCCAAAC AACTGGTGCG TCTTTTGTGG GGCCTTGATT GAAACCAAAA AGAAAAAAGT   19140
GTGCATTACT AGCTGCTGTT GGAAGGGCTC CAGCCAGTGC ACCCCGGGAA CGTAACAGCC   19200
```

FIGURE 3A-11

```
GTTCAGAAAG GACGAAAGGT TAACCAGAAA AGCCTGAAGT TCGCGGTAGA CAGAGCAGGC    19260
GTGCAGGGAG TCGTGTGTTT TTCTGCCCGC CTGGTACTCG ACCAGTTGAT CGGCCGTGGA    19320
GACGTGCGCG TCCTCGCGCA CACACCGCAT CTGCAAGTAT GTTGATAGGG ACTCCAATAG    19380
GCGCGGCTTT GCGGGACGT  TGTCCTCGGA CGGTCTGGGG GTTCCACGT  CGGGATTTGC    19440
TGACGTGGGC GTGGCGGGAT GGTGCCGTGT GCAGTATGTT TCCAGGACCG AACTGTATGA    19500
GTTTATTCTG TGCACCACGC CAATAAAAGG GTGCGCCATC CGTGCCGTTT TGGGACAGTG    19560
TCGCGTGAAT GTCGGGCAC  TCAGTTCCCA CCTCTCTCCG GCGTCTTTGG CGGTCTCCTC    19620
CAGGTTGGCG GCAAGGCGCT CCCTGTGACG GCTGAGCAGC ATGTTTGCTT TGAGCTCGCT    19680
CGTGTCCGAG GGTGACCCGG AGGTGACCAG TAGGTACGTC AAGGGCGTAC AACTTGCCCT    19740
GGACCTTAGC GAGAACACAC CTGGACAATT TAAGTTGATA GAAACTCCCC TGAACAGCTT    19800
CCTCTTGGTT TCCAACGTGA TGCCCGAGGT CCAGCCAATC TGCAGTGGCC GGCCGGCCTT    19860
GCGGCCAGAC TTTAGTAATC TCCACTTGCC TAGACTGGAG AAGCTCCAGA GAGTCCTCGG    19920
GCAGGGTTTC GGGGCGGCGG GTGAGGAAAT CGCACTGGAC CCGTCTCACG TAGAAACACA    19980
CGAAAAGGGC CAGGTGTTCT ACAACCACTA TGCTACCGAG GAGTGGACGT GGGCTTTGAC    20040
TCTGAATAAG GATGCGCTCC TTCGGGAGGC TGTAGATGGC CTGTGTGACC CCGGAACTTG    20100
GAAGGGTCTT CTTCCTGACG ACCCCCTTCC GTTGCTATGG CTGCTGTTCA ACGGACCCGC    20160
CTCTTTTTGT CGGGCCGACT GTTGCCTGTA CAAGCAGCAC TGCGGTTACC CGGGCCCGGT    20220
GCTACTTCCA GGTCACATGT ACGCTCCCAA ACGGGATCTT TTGTCGTTCG TTAATCATGC    20280
CCTGAAGTAC ACCAAGTTTC TATACGGAGA TTTTTCCGGG ACATGGGCGG CGGCTTGCCG    20340
CCCGCCATTC GCTACTTCTC GGATACAAAG GGTAGTGAGT CAGATGAAAA TCATAGATGC    20400
TTCCGACACT TACATTTCCC ACACCTGCCT CTTGTGTCAC ATATATCAGC AAAATAGCAT    20460
AATTGCGGGT CAGGGACCC  ACGTGGGTGG AATCCTACTG TTGAGTGGAA AAGGGACCCA    20520
GTATATAACA GGCAATGTTC AGACCCAAAG GTGTCCAACT ACGGGCGACT ATCTAATCAT    20580
CCCATCGTAT GACATACCGG CGATCATCAC CATGATCAAG GAGAATGGAC TCAACCAACT    20640
CTAAAAGAGA GTTTATTAAG TCGGCTCTGG AGGCCAACAT CAACAGGAGG GCAGCTGTAT    20700
CGCTATTTGA                                                          20710
```

FIGURE 3B

SEQ. ID. No. 36

```
GGATCCCTCT GACAACCTTC AGATAAAAAA CGTATATGCC CCCTTTTTTC AGTGGGACAG    60
CAACACCCAG CTAGCAGTGC TACCCCCATT TTTTAGCCGA AAGGATTCCA CCATTGTGCT   120
CGAATCCAAC GGATTTGACC CCGTGTTCCC CATGGTCGTG CCGCAGCAAC TGGGGCACGC   180
TATTCTGCAG CAGCTGTTGG TGTACCACAT CTACTCCAAA ATATCGGCCG GGGCCCCGGA   240
TGATGTAAAT ATGGCGGAAC TTGATCTATA TACCACCAAT GTGTCATTTA TGGGGCGCAC   300
ATATCGTCTG GACGTAGACA ACACGGATCC                                    330
```

FIGURE 3C

SEQ. ID. No. 37

```
GGATCCGCTG GCAGGTGGGC GCGCACCTCG TCGGGTAGCT TGGAGACAAA CAGCTCCAGG    60
CCAGTCCGCG CCGTAGCGCC TGCAGGTGCC TCACCACCGG GGCCGGGTCA TGCGATCTGT   120
TTAGTCCGGA GAAGATAGGG CCCTTGGGAA GCCGCTGAAC CAGCTCCAGG GTCTCCAAGA   180
TGCGCACCGG TTGTCGGAGC TGTCGCGATA GAGGTTAGGG TAGGTGTCCG GTCCGTCCGT   240
GGGCTCAAAC CTGCCCAGAC ACACCACTGT CTGCTGGGGG ATCATCCTTC TCAGGGAGAT   300
GCATTCTTTG GAAGTAGTGG TAGAGATGGA GCAGACTGCC AGGGCGTTGC AGGAGTGGTG   360
GCGATGGTGC GCACCGTTTT TAAGAAACCC CCAGGGTGG GGACTCCCGC TCCCTGCAGC   420
ATCTCGGCCT GCTGTACGTC CTTGGCGAAT ATGCGACGAA ATCGGCTGTG CGCACGGGGT   480
CCCAGGGCCG GTCCGGTGGC ATACAGGCCG GTGAGGGCCC CCTGGGTCTG TCCGCCTGGA   540
AACAGGGTGC TGTGAAACAA CAGGTTGCAA GGCCGCGAAT ACCCCTCTGC ACGCTGCTGT   600
GGACGTGGGT GTATGCTCCG TGGATCC                                      627
```

FIGURE 3D

SEQ. ID. No. 38

```
AGCCGAAAGG ATTCCACCAT TGTGCTCGAA TCCAACGGAT TTGACCCCGT GTTCCCCATG      60
GTCGTGCCGC AGCAACTGGG GCACGCTATT CTGCAGCAGC TGTTGGTGTA CCACATCTAC     120
TCCAAAATAT CGGCCGGGGC CCCGGATGAT GTAAATATGG CGGAACTTGA TCTATATACC     180
ACCAATGTGT CATTTATGGG GCGCACATAT CGTCTGGACG TAGACAACAC GGA            233
```

FIGURE 3E

SEQ. ID. No. 39

```
GAAATTACCC ACGAGATCGC TTCCCTGCAC ACCGCACTTG GCTACTCATC AGTCATCGCC    60
CCGGCCCACG TGGCCGCCAT AACTACAGAC ATGGGAGTAC ATTGTCAGGA CCTCTTTATG   120
ATTTTCCCAG GGGACGCGTA TCAGGACCGC CAGCTGCATG ACTATATCAA AATGAAAGCG   180
GGCGTGCAAA CCGGCTCACC GGGAAACAGA ATGGATCACG TGGGATACAC TGCTGGGGTT   240
CCTCGCTGCG AGAACCTGCC CGGTTTGAGT CATGGTCAGC TGGCAACCTG CGAGATAATT   300
CCCACGCCGG TCACATCTGA CGTTGCCT                                      328
```

FIGURE 3F

SEQ. ID. No. 40

```
AACACGTCAT GTGCAGGAGT GACATTGTGC CGCGGAGAAA CTCAGACCGC ATCCCGTAAC    60
CACACTGAGT GGGAAAATCT GCTGGCTATG TTTTCTGTGA TTATCTATGC CTTAGATCAC   120
AACTGTCACC CG                                                       132
```

FIGURE 6

```
         1
HSVSA  MLTDKITIVS  LTSRLFADEI  TKLQKKIGSI                        50
KS     MALDKSIVVN  FTSRLFADEL  AALQSKIGSV  LPLQDPHKLQ  SLDTLGLNAV
EBV    ..MDLKVWS   LSSRLYTDEI  AKMQQRIGCI  LPLGDCHRLQ  NIQALGLGCV
                                           LPLASTHGTQ  NVGGLGLGQV

51
HSVSA  CSRDVFPDYV  HMFSYLSKCT                                    100
KS     CSRETSPDYI  QIMQYLSKCT  LAILEEVNPD  NLILTRLDPS  ETYQIKNVYE
EBV    YSLETVPDYV  SMYNYLSDCT  LAVLEEVRPD  SLRLTRMDPS  DNLQIKNVYA
                               LAVLDEVSVD  SLILTKIVPG  QTYAIKNKYQ

101
HSVSA  PMFQWDGFSN  LTVIPPMFGR  QQATVTLESN  GFDLVFPSVV  PSDLAQAIIG  150
KS     PFFQWDSNTQ  LAVLPPFFSR  KDSTIVLESN  GFDPVFPMVV  PQQLGHAILQ
EBV    PFFQWHGTGS  LSVMPPVFGR  EHATVKLESN  DVDIVFPMML  PTPIAEEVLQ

151
HSVSA  KILLYNLYSR  LVESDP.EIN  IEEVNMYTTN  VTHMGRHYVE  DINHNNANEA  200
KS     QLLVYHIYSK  ISAGAPDDVN  MAELDLYTTN  VSFMGRTYRL  DVDNTDPRTA
EBV    KILLFNVYSR  VVMQAPGNAD  MLDVHMHLGS  VSYLGHHYEL  ALPEVPGPLG

201
HSVSA  LKSLDDLAVY  TCILSALIPR  ACLRMTILM   RHDQHELLDV  FRGIVPREVY  250
KS     LRVLDDLSMY  LCILSALVPR  GCLRLLTALV  RHDRHPLTEV  FEGVVPDEVT
EBV    LALLDNLSLY  FCIMVTLLPR  ASMRLVRGLI  RHEHDLLNL   FQEMVPDEIA

251
HSVSA  EIDANALSIG  DDITRMTTFI  TYLQSLSSIF  NLGAKLHLSS  YASETQTATC  300
KS     RIDLDQLSVP  DDITRMRVMF  SYLQSLSSIF  NLGPRLHVYA  YSAETLAASC
EBV    RIDLDDLSVA  DDLSRMRVMM  TYLQSLASLF  NLGPRLATAA  YSQETLTATC

301
HSVSA  WISYC
KS     WYSPR
EBV    WLR
```

Gene Homologs

| KSHV ORF | Start | ATG | Stop | aa | TATA | polyA | HVS ORF | HVS %I,%S | EHV-2 ORF | EHV-2 %I,%S | EBV ORF | EBV %I,%S | F |
|---|---|---|---|---|---|---|---|---|---|---|---|---|---|
| ORF20* | 20090 | 20153 | | 184 | | 18684 | ORF20 | | ORF20 | | BXRF1 | | |
| ORF21 | 20436 | 20343 | 18601 | 580 | | 16414 | ORF21 | 32%,50% | ORF21 | 31%,51% | BXLF1 | 28%,50% | TK |
| ORF22 | 18631 | 18613 | 16421 | 730 | 18685 | 16422 | ORF22 | 35%,55% | ORF22 | 31%,52% | BXLF2 | 26%,48% | gH |
| ORF23 | 15206 | 15210 | 16422 | 403 | 14955 | 16422 | ORF23 | 33%,57% | ORF23 | 34%,56% | BTRF1 | 31%,51% | |
| ORF24 | 12843 | 12948 | 15206 | 752 | 11641 | 8849 | ORF24 | 45%,66% | ORF24 | 41%,58% | BCRF1 | 38%,57% | |
| ORF25 | 13021 | 12949 | 8819 | 1376 | 13256 | | ORF25 | 65%,81% | ORF25 | 63%,79% | BCLF1 | 56%,75% | MCP |
| ORF26 | 8808 | 8793 | 7876 | 305 | 13256 | 6987 | ORF26 | 58%,76% | ORF26 | 46%,70% | BDLF1 | 49%,73% | VP23 |
| ORF27 | 7870 | 7855 | 6983 | 290 | 7419 | 6987 | ORF27 | 29%,49% | ORF27 | 20%,44% | BDLF2 | 19%,43% | |
| ORF28 | 6740 | 6737 | 6367 | 120 | 6830 | 5274 | — | | — | | — | | |
| ORF29b | 5029 | | 6363 | 430 | 4507 | 6359 | ORF29b | 64%,83% | ORF29b | 68%,82% | BDRF1 | 60%,76% | SG |
| ORF30 | 5186 | 5102 | 4869 | 77 | 5340 | 4362 | ORF30 | 33%,55% | ORF30 | 38%,56% | BDLF3.5 | 30%,53% | |
| ORF31 | 4971 | 4962 | 4288 | 224 | 5340 | 4362 | ORF31 | 43%,63% | ORF31 | 38%,64% | BDLF4 | 36%,58% | |
| ORF32 | 4360 | 4319 | 2957 | 454 | 5340 | 3019 | ORF32 | 30%,52% | ORF32 | 32%,51% | BGLF1 | 27%,47% | |
| ORF33 | 3072 | 2964 | 2028 | 312 | 3020 | 1653 | ORF33 | 36%,58% | ORF33 | 33%,56% | BGLF2 | 32%,52% | |
| ORF29a | 743 | 1049 | 1987 | 312 | | | ORF29a | 53%,68% | ORF29a | 52%,68% | BGRF1 | 41%,57% | SG |
| ORF34 | 1065 | 1050 | 69 | 327 | 3020 | | ORF34 | 42%,59% | ORF34 | 29%,60% | BGLF3 | 33%,55% | |
| ORF35* | | | 138 | 45 | | 54 | ORF35 | | ORF35 | | BGLF3.5 | | |

The nomenclature used for KSHV ORFs is relative to the HVS ORF nomenclature.
*, incomplete ORFs; S, strand (C, complementary); TATA, location of upstream TATA elements (TATTAA, TATAAA, TATAAT); polyadenylation signal, (AATAAA, ATTAAA); %I, percentage of aligned amino acid identity; %S, percentage of aligned similar amino acids; F, function; TK, thymidine kinase; gH, glycoprotein H; MCP, major capsid protein; VP23, virion protein; SG, putative DNA packaging spliced gene.

FIGURE 13

| Patient no. AIDS-KS Cases | HIV Risk Group* | Non-absorbed | | P3H3-absorbed | |
|---|---|---|---|---|---|
| | | HBL-6 | P3H3 | HBL-6 | P3H3 |
| 1 | H/B | 4050 | 1350 | 4050 | 50 |
| 2 | H/B | 450 | 50 | 450 | 50 |
| 3 | H/B | 450 | 450 | 450 | 50 |
| 4 | H/B | 450 | 450 | 150 | <50 |
| 5 | H/B | 4050 | 1350 | 1350 | 150 |
| 6 | H/B | 4050 | 1350 | 450 | 50 |
| 7 | H/B | 12,150 | 450 | 12,150 | 150 |
| 8 | H/B | 1350 | 1350 | 1350 | 150 |
| 9 | H/B | 1350 | 450 | 1350 | 50 |
| 10 | H/B | 150 | 150 | 150 | <50 |
| 11 | H/B | 150 | 450 | 50 | <50 |
| 12 | H/B | 450 | 450 | 450 | 50 |
| 13 | H/B | 1350 | 450 | 1350 | 50 |
| 14 | H/B | 4050 | 1350 | 4050 | 50 |
| GMT | | 1153 | 526 | 780 | 63 |
| HIV / AIDS Controls | | | | | |
| 1 | H/B | 150 | 150 | 50 | 50 |
| 2 | H/B | 150 | 150 | 50 | 50 |
| 3 | H/B | 12,150 | 4050 | 150 | 150 |
| 4 | H/B | 1350 | 4050 | 150 | 150 |
| 5 | H/B | 4050 | 4050 | 450 | 450 |
| 6 | IVDU-F | 1350 | 1350 | 150 | 150 |
| 7 | IVDU-F | 12,150 | 12,150 | 450 | 450 |
| 8 | Hemo | 50 | 150 | <50 | <50 |
| 9 | Hemo | 50 | 50 | <50 | <50 |
| 10 | Hemo | 150 | 150 | <50 | <50 |
| 11 | Hemo | 450 | 1350 | 50 | 150 |
| 12 | Hemo | 150 | 450 | 50 | 50 |
| 13 | Hemo | 50 | 50 | <50 | <50 |
| 14 | Hemo | 50 | <50 | <50 | <50 |
| 15 | Hemo | 150 | 450 | 50 | 50 |
| 16 | Hemo | 150 | 150 | 50 | 50 |
| GMT | | 342 | 450 | 81 | 87 |
| Kruskall-Wallace H value** | | 4.3 | 0.31 | 15.4 | 1.2 |
| p value** | | 0.04 | 0.6 | 0.00009 | 0.30 |

*H/B=Homosexual/bisexual males, IVDU-F=Female intravenous drug user, Hemo=hemophiliac male.
**Comparison between log titers for case and control sera.

FIGURE 21

| | Initial Sample | Second Sample |
|---|---|---|
| AIDS-KS, n=21 | | |
| Months prior to or after AIDS-KS median (range) | -13 (-87 to -4) | +1 (-6 to +20) |
| CD4+ count, mm³ median (range) | 432 (63 to 866) | 124 (8 to 640) |
| KSHV positivity no. (%) | 9 (43%) | 12 (57%) |
| Gay/Bisexual AIDS without KS, n=23 | | |
| Months prior to AIDS diagnosis median (range) | -55 (-106 to -13) | -5 (-8 to -0) |
| CD4+ count, mm³ median (range) | 612 (333 to 1309) | 215 (11 to 598) |
| KSHV positivity no. (%) | 1 (4%) | 2 (9%) |
| Hemophilic AIDS without KS, n=19 | | |
| CD4+ count, mm³* median (range) | 344 (83 to 559) | |
| KSHV positivity no. (%) | 2 (11%) | |

*CD4+ counts available for 15 hemophilic patients at or prior to sample collection date.

FIGURE 22

PCR analysis of $KS330_{233}$ in DNA samples from patients with Kaposi's sarcoma and tumor controls

|  | No. tested | KS $KS330_{233}$ positive (%) |
|---|---|---|
| KS tissue: |  |  |
| AIDS-KS | 24 | 22 (92) |
| Endemic KS | 20 | 17 (85) |
| Total | 44 | 39 (89) |
| Control Tumors: |  |  |
| HIV seropositive | 7 | 1 (14) |
| HIV seronegative | 15 | 2 (13) |
| Total | 22 | 3 (14) |

UNIQUE ASSOCIATED KAPOSI'S SARCOMA VIRUS SEQUENCES AND USES THEREOF

This application is a 371 of PCT/US95/10194 filed Aug. 11, 1995, and continuation-in-part application of U.S. Ser. No. 08/420,235, filed on Apr. 11, 1995, U.S. Pat. No. 5,801,042, which is a continuation-in-part application of U.S. Ser. No. 08/343,101, filed on Nov. 21, 1994, U.S. Pat. No. 5,830,759, which is a continuation-in-part application of U.S. Ser. No. 08/292,365, filed on Aug. 18, 1994, abandoned, which is hereby incorporated by reference.

The invention disclosed herein was made with Government support under a co-operative agreement CCU210852 from the Centers for Disease Control and Prevention, of the Department of Health and Human Services. Accordingly, the U.S. Government has certain rights in this invention.

Throughout this application, various publications may be referenced by Arabic numerals in brackets. Full citations for these publications may be found at the end of each Experimental Details Section. The disclosures of the publications cited herein are in their entirety hereby incorporated by reference into this application to more fully describe the state of the art to which this invention pertains.

BACKGROUND OF THE INVENTION

Kaposi's sarcoma (KS) is the most common neoplasm occurring in persons with acquired immunodeficiency syndrome (AIDS). Approximately 15–20% of AIDS patients develop this neoplasm which rarely occurs in immunocompetent individuals [13, 14]. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS [6, 15, 55, 83]. KS is uncommon among adult AIDS patients infected through heterosexual or parenteral HIV transmission, or among pediatric AIDS patients infected through vertical HIV transmission [77]. Agents previously suspected of causing KS include cytomegalovirus, hepatitis B virus, human papillomavirus, Epstein-Barr virus, human herpesvirus 6, human immunodeficiency virus (HIV), and Mycoplasma penetrans [18, 23, 85, 91, 92]. Non-infectious environmental agents, such as nitrite inhalants, also have been proposed to play a role in KS tumorigenesis [33]. Extensive investigations, however, have not demonstrated an etiologic association between any of these agents and AIDS-KS [37, 44, 46, 90].

SUMMARY OF THE INVENTION

This invention provides an isolated DNA molecule which is at least 30 nucleotides in length and which uniquely defines a herpesvirus associated with Kaposi's sarcoma. This invention provides an isolated herpesvirus associated with Kaposi's sarcoma.

This invention provides a method of vaccinating a subject for KS, prophylaxis diagnosing or treating a subject with KS and detecting expression of a DNA virus associated with Kaposi's sarcoma in a cell.

KS330Bam hybridized to 11 of the 19 and KS627Bam hybridized to 12 of the 19 DNA samples from AIDS-KS lesions. Two additional cases (lanes 12 eand 13) were shown to have faint bands with both KS330Bam and KS627Bam probes after longer exposure. One negative specimen (lane 3) did not have microscopically detectable KS in the tissue specimen. Seven of 8 additional KS DIA samples also hybridized to both sequences.

FIG. 3A–3F: Nucleotide sequences of the DNA herpesvirus associated with KS (KSHV).

Figure 4A:
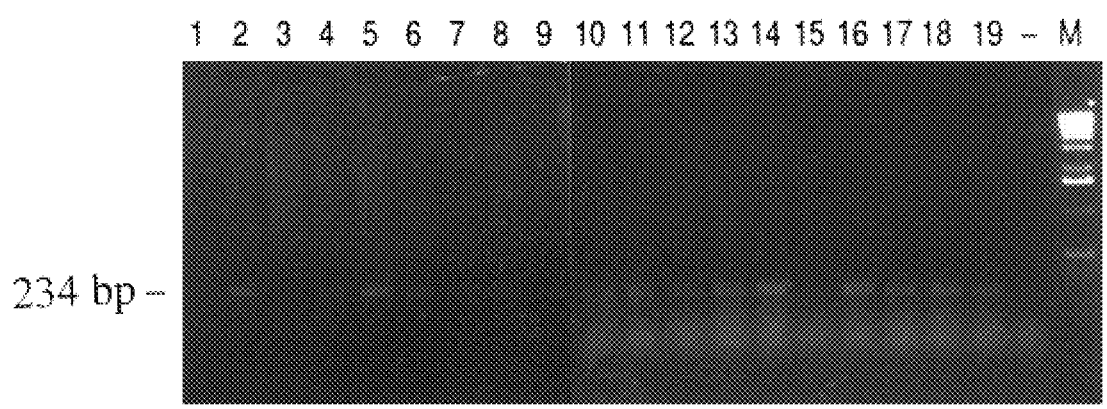
Figure 4B:

FIG. 4A–4B: PCR amplification of a representative set of KS-derived DNA samples using KS330$_{234}$ primers. FIG. 4A shows the agarose gel of the amplification products from 19 KS DNA samples (lanes 1–19) and FIG. 4B shows specific hybridization of the PCR products to a $^{32}$P end-labelled 25 bp internal oligonucleotide (FIG. 3B) after transfer of the gel to a nitrocellulose filter. Negative samples in lanes 3 and 15 respectively lacked microscopically detectable KS in the sample or did not amplify the constitutive p53 exon 6, suggesting that these samples were negative for technical reasons. An additional 8 AIDS-KS samples were amplified and all were positive for KS330$_{234}$. Lane 20 is a negative control and Lane M is a molecular weight marker.

Figure 5:
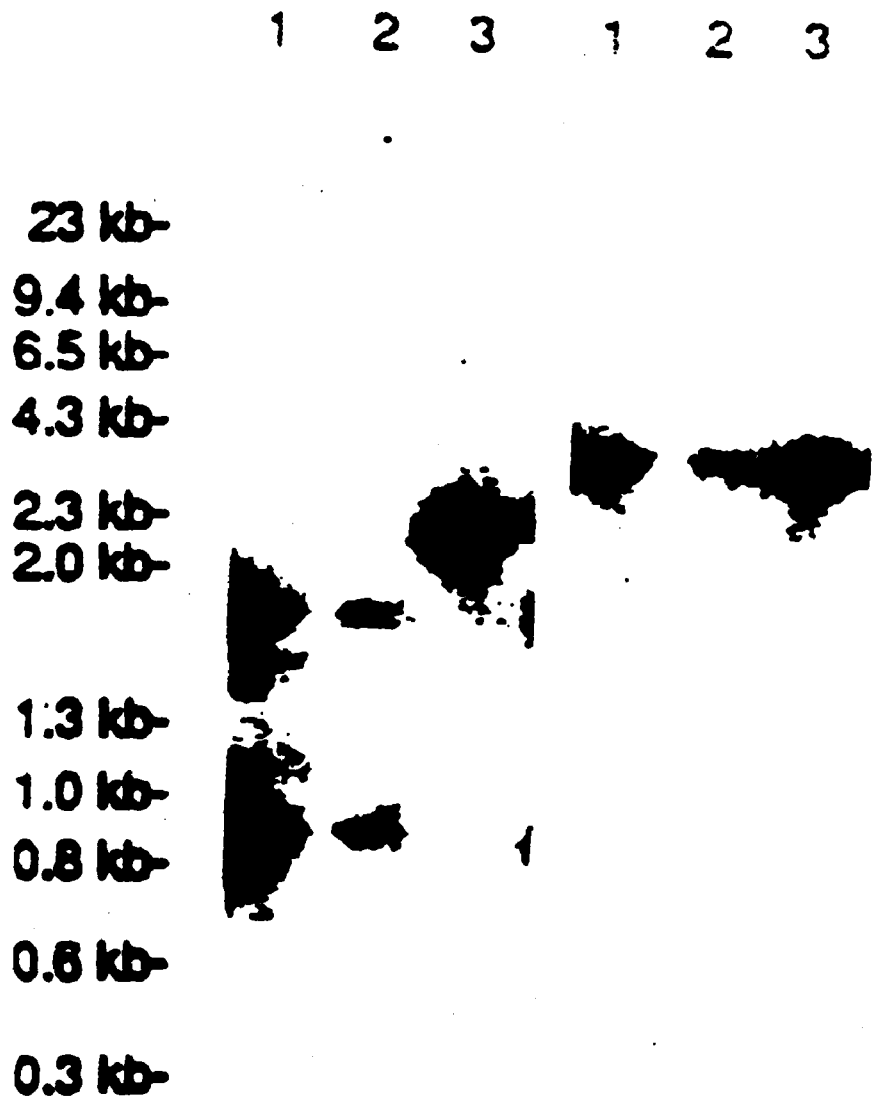

FIG. 5: Southern blot hybridization of KS330Bam and KS627Bam to AIDS-KS genomic DNA extracted from three subjects (lanes 1, 2, and 3) and digested with PvuII. Based on sequence information (FIG. 3A), restricted sites for Pvu II occur between bp 12361–12362 of the KSHV sequence (FIG. 3A, SEQ ID NO: 1), at bp 134 in KS330Bam (FIG. 3B, SEQ ID NO: 2) and bp 414 in KS627Bam (FIG. 3C, SEQ ID NO: 3). KS330Bam and KS627Bam failed to hybridize to the same fragments in the digests indicating that the two sequences are separated from each other by one or more intervening Bam HI restriction fragments. Digestion with Pvu II and hybridization to KS330Bam resulted in two distinct banding patterns (lanes 1 and 2 vs. lane 3) suggesting variation between KS samples.

FIG. 6: Comparison of amino acid homologies between EBV ORF BDLF1 (SEQ ID NO: 47), and HSVA ORF 26 (SEQ ID NO: 46) and a 918 bp reading frame of the Kaposi's sarcoma agent which includes KS330Bam. Amino acid identity is denoted by reverse lettering. In HSVSA, ORF 26 encodes a minor capsid VP23 which is a late gene product.

Figure 7:
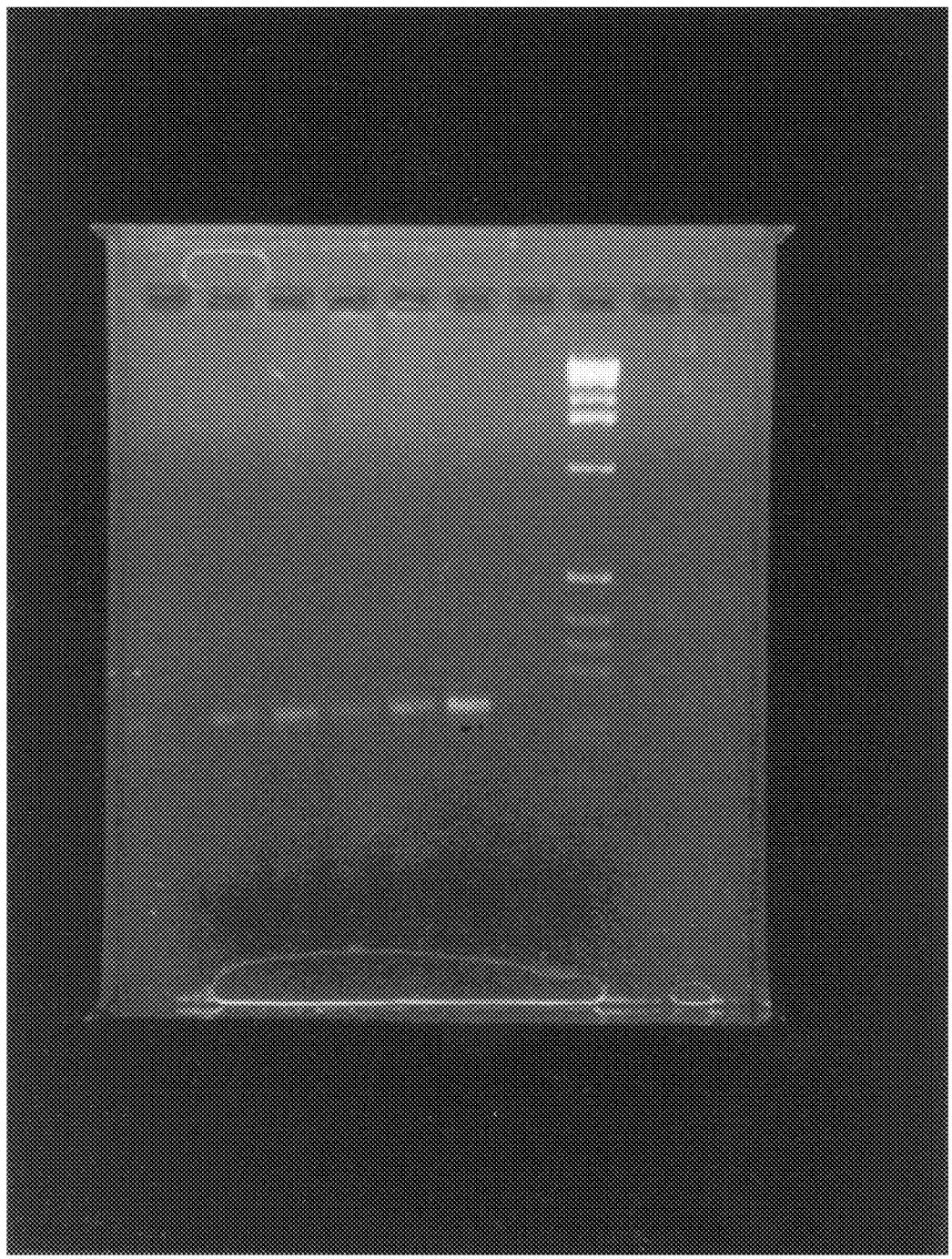

FIG. 7: Subculture of Raji cells co-cultivated with BCBL-1 cells treated with TPA for 2 days. PCR shows that Raji cells are positive for KSHV sequences and indicate that the agent is a transmissible virus.

Figure 8:
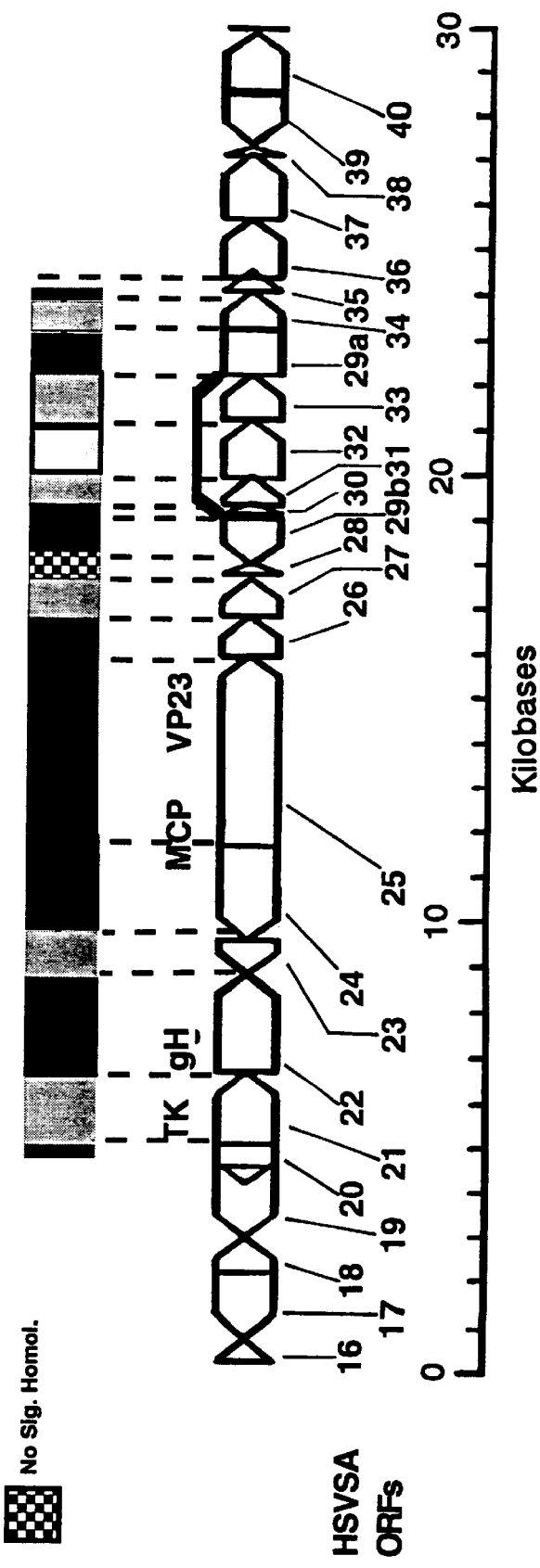

FIG. 8: A schematic diagram of the orientation of KSHV open reading frames identified on the KS5 20,710 bp DNA fragment. Homologs to each open reading frame from a corresponding region of the herpesvirus saimiri (HSVSA) genome are present in an identical orientation, except for the region corresponding to the ORF 28 of HSVSA (middle schematic section). The shading for each open reading frame corresponds to the approximate % amino acid identity for the KSHV ORF compared to this homolog in HSVSA. Noteworthy homologs that are present in this section of DNA include homologs to thymidine kinase (ORF21), gH glycoprotein (ORF22), major capsid protein (ORF25) and the VP23 protein (ORF26) which contains the original KS330Bam sequence derived by representational difference analysis.

Figure 9:
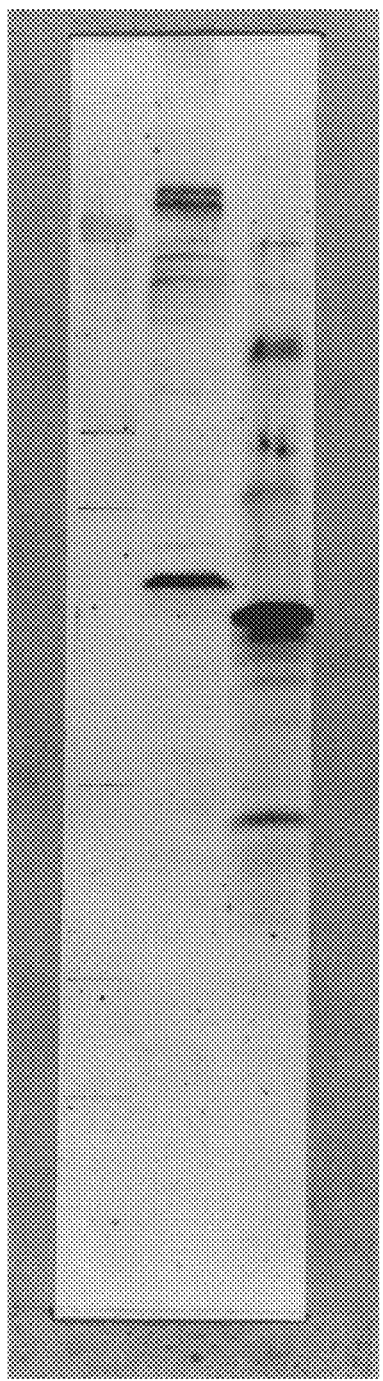

FIG. 9: The ~200 kD antigen band appearing on a Western blot of KS patient sera against BCBL1 lysate (B1) and Raji lysate (RA). M is molecular weight marker. The antigen is a doublet between ca. 210 kD and 240 kD.

Figure 10:
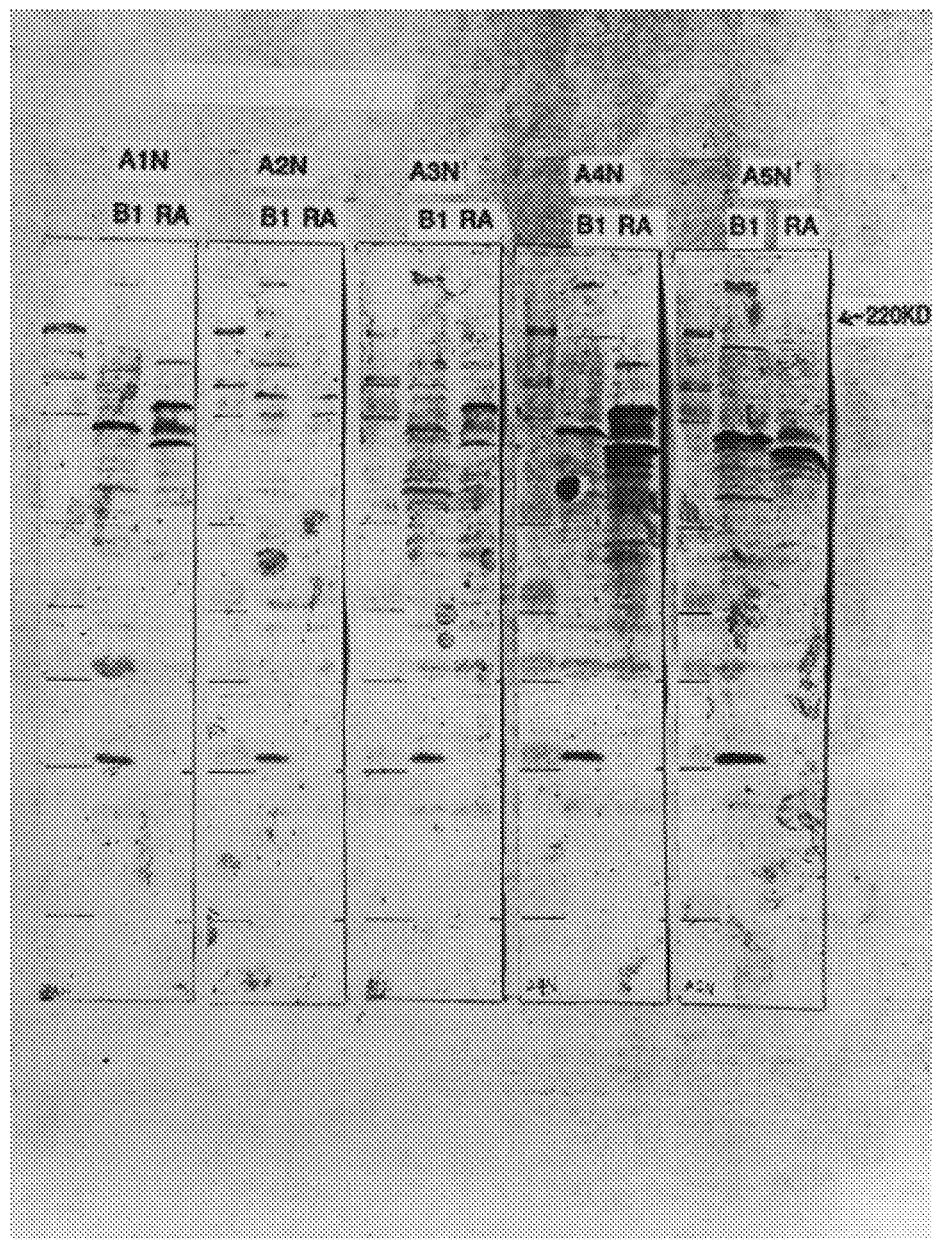

FIG. 10: 5 control patient sera without KS (A1N, A2N, A3N, A4N and A5N). B1=BCBL1 lysate, RA=Raji lysate. The 220 kD band is absent from the Western blots using patient sera without KS.

Figure 11:
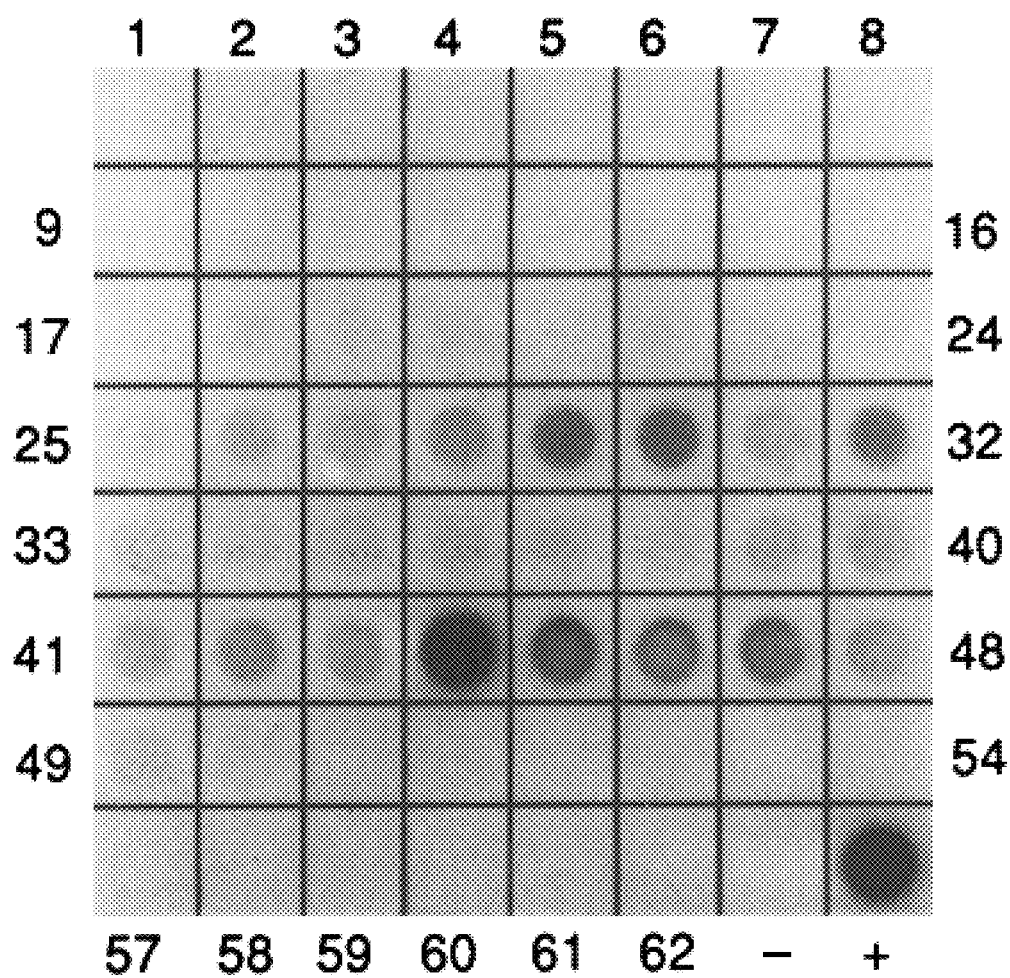

FIG. 11: In this figure, 0.5 ml aliquots of the gradient have been fractionated (fractions 1–62) with the 30% gradient fraction being at fraction No. 1 and the 10% gradient fraction being at fraction No. 62. Each fraction has been dot hybridized to a nitrocellulose membrane and then a $^{32}$P-labeled KSHV DNA fragment, KS631Bam has been hybridized to the membrane using standard techniques. The figure shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

FIG. 12: Location, feature, and relative homologies of KS5 open reading frames compared to translation products of herpesvirus saimiri (HSV), equine herpesvirus 2 (EHV2) and Epstein-Barr virus (EBV).

FIG. 13: Indirect immunofluorescence end-point and geometric mean titers (GMT) in AIDS-KS and AIDS control sera against HBL-6 and P3H3 prior to and after adsorption with P3H3.

Figure 14:
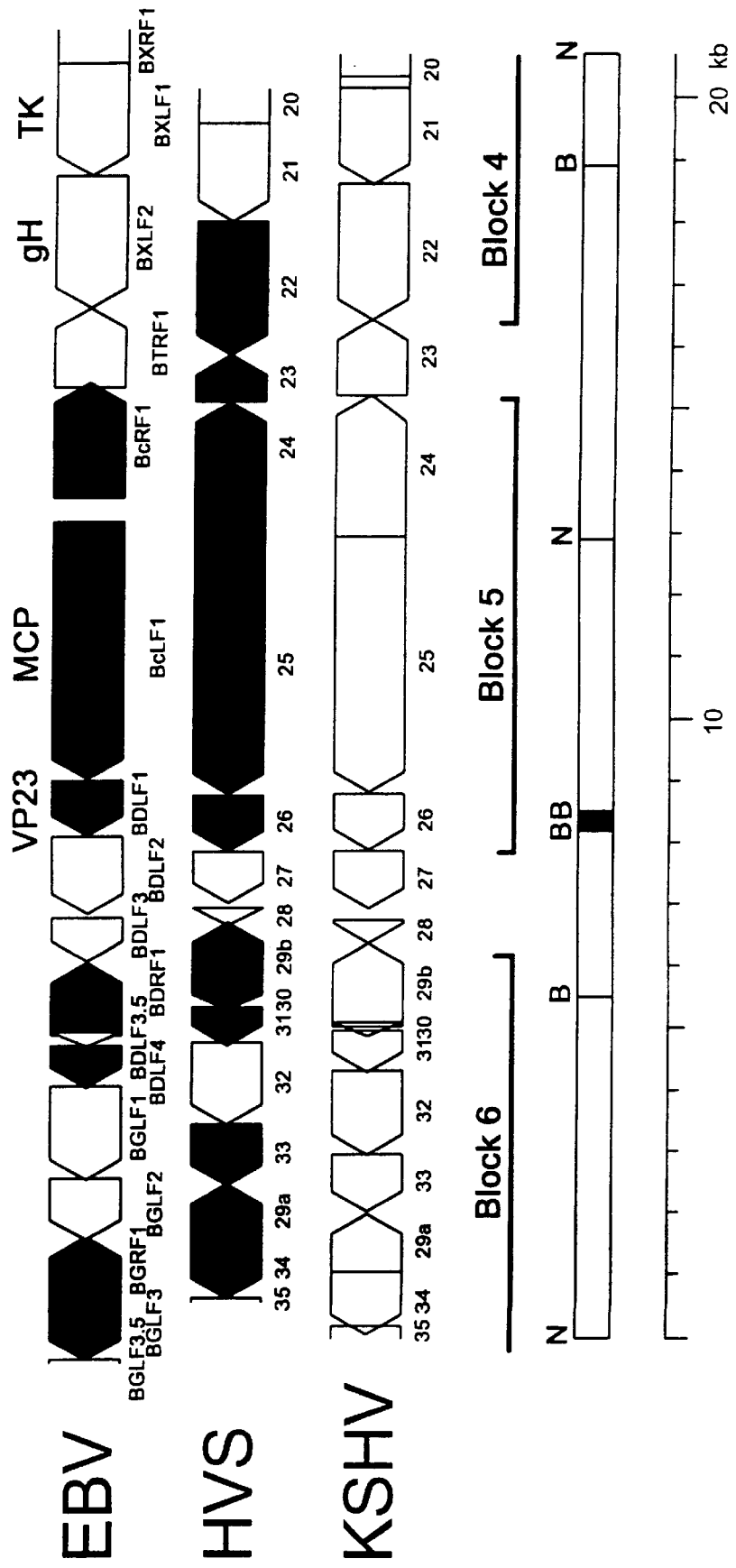

FIG. 14: Genetic map of KS5, a 20.7 kb lambda phage clone insert derived from a human genomic library prepared from an AIDS-KS lesion. Seventeen partial and complete open reading frames (ORFs) are identified with arrows denoting reading frame orientations. Comparable regions of the Epstein-Barr virus (EBV) and herpesvirus saimiri (HVS) genomes are shown for comparison. Levels of amino acid similarity between KSHV ORFs are indicated by shading of EBV and HVS ORFs (black, over 70% similarity; dark gray, 55–70% similarity; light gray, 40–54% similarity; white, no detectable homology). Domains of conserved herpesvirus sequence blocks and locations of restriction endonuclease sites used in subcloning are shown beneath the KSHV map (B, Bam HI site; N, Not I site). The small Bam HI fragment (black) in the VP23 gene homolog corresponds to the KS330Bam fragment generated by representational difference analysis which was used to identify the KS5 lambda phage clone.

Figure 15A:
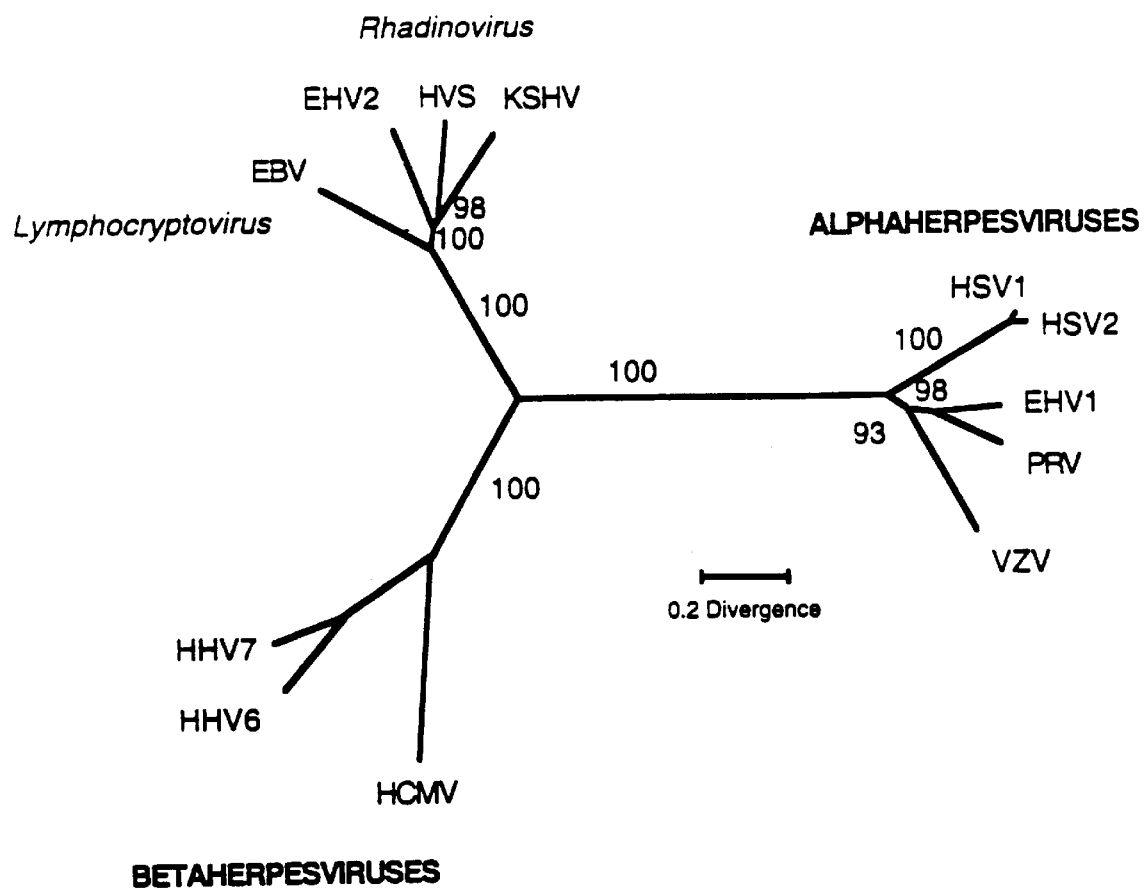
Figure 15B:
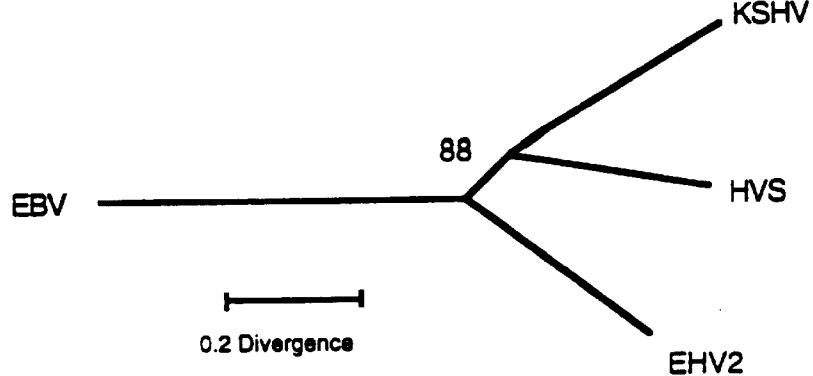

FIGS. 15A–15B: Phylogenetic trees of KSHV based on comparison of aligned amino acid sequences between herpesviruses for the MCP gene and for a concatenated nine-gene set. The comparison of MCP sequences (FIG. 15A) was obtained by the neighbor-joining method and is shown in unrooted form with branch lengths proportional to divergence (mean number of substitution events per site) between the nodes bounding each branch. Comparable results were obtained by maximum parsimony analysis. The number of times out of 100 bootstrap samplings the division indicated by each internal branch was obtained are shown next to each branch; bootstrap values below 75 are not shown. FIG. 15B is a phylogenetic tree of gammaherpesvirus sequences based on a nine-gene set CS1 (see text) and demonstrates that KSHV is most closely related to the gamma-2 herpesvirus sublineage, genus Rhadinovirus. The CS1 amino acid sequence was used to infer a tree by the Protml maximum likelihood method; comparable results, not shown were obtained with the neighbor-joining and maximum parsimony methods. The bootstrap value for the central branch is marked. On the basis of the MCP analysis, the root must lie between EBV and the other three species. Abbreviations for virus species used in the sequence comparisons are 1) Alphaherpesvirinae: HSV1 and HSV2, herpes simplex virus types 1 and 2; EHV1, equine herpesvirus 1; PRV, pseudorabies virus; and VZV, varicella-zoster virus, 2) Betaherpesvirinae: HCMV, human cytomegalovirus; HHV6 and HHV7, human herpesviruses 6 and 7, and 3) Gammaherpesvirinae: HVS, herpesvirus saimiri; EHV2, equine herpesvirus 2; EBV, Epstein-Barr virus; and Kaposi's sarcoma-associated herpesvirus.

Figure 16A:
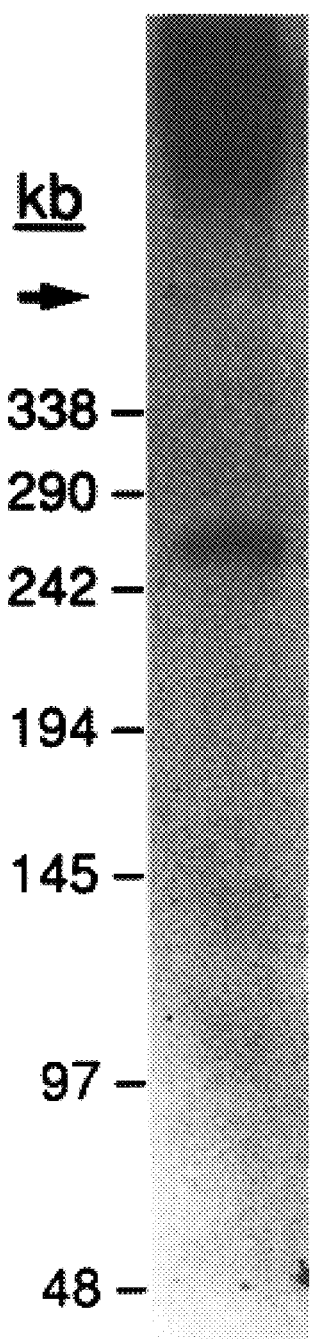
Figure 16B:
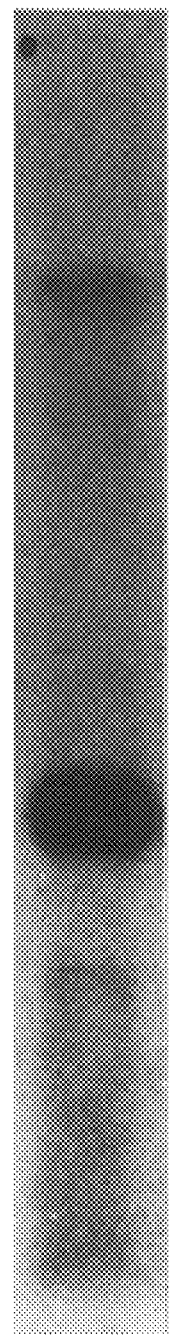

FIGS. 16A–16B: CHEF gel electrophoresis of BCBL-1 DNA hybridized to KS631Bam (FIG. 16A) and EBV terminal repeat (FIG. 16B). KS631Bam hybridizes to a band at 270 kb as well as to a diffuse band at the origin. The EBV termini sequence hybridizes to a 150–160 kb band consistent with the linear form of the genome. Both KS631Bam (dark arrow) and an EBV terminal sequence hybridize to high molecular weight bands immediately below the origin indicating possible concatemeric or circular DNA. The high molecular weight KS631Bam hybridizing band reproduces poorly but is visible on the original autoradiographs.

Figure 17:
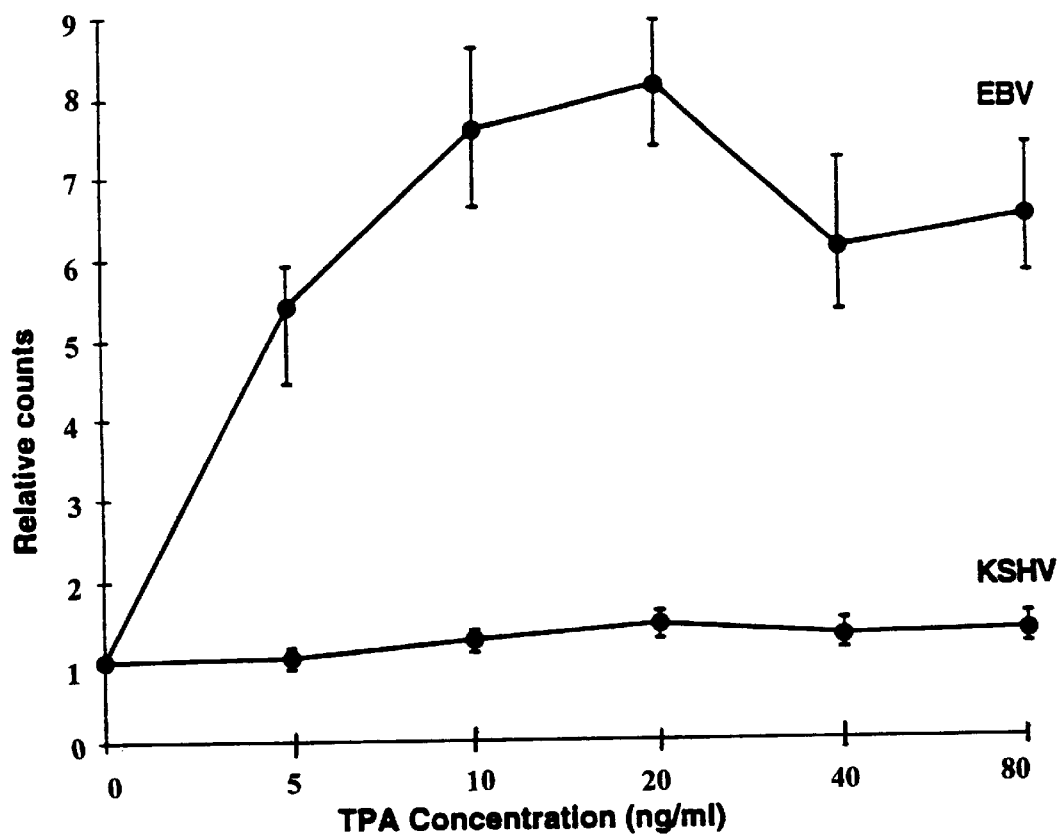

FIG. 17: Induction of KSHV and EBV replication in BCBL-1 with increasing concentrations of TPA. Each determination was made in triplicate after 48 h of TPA incubation and hybridization was standardized to the amount of cellular DNA by hybridization to beta-actin. The figure shows the mean and range of relative increase in hybridizing genome for EBV and KSHV induced by TPA compared to uninduced BCBL-1. TPA at 20 ng/ml induced an eight-fold increase in EBV genome (upper line) at 48 h compared to only a 1.4 fold increase in KSHV genome (lower line).

Despite the lower level of KSHV induction, increased replication of KSHV genome after induction with TPA concentrations over 10 ng/ml was reproducibly detected.

Figure 18A:
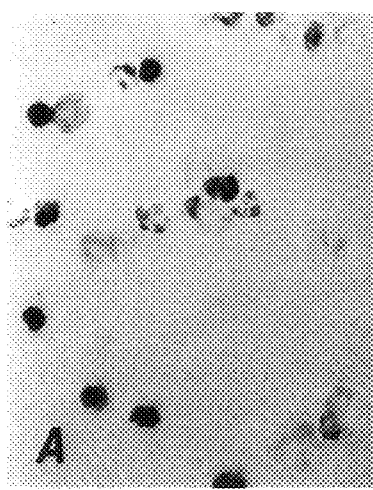
Figure 18B:
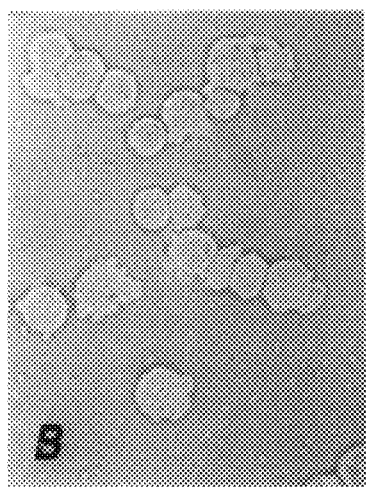
Figure 18C:
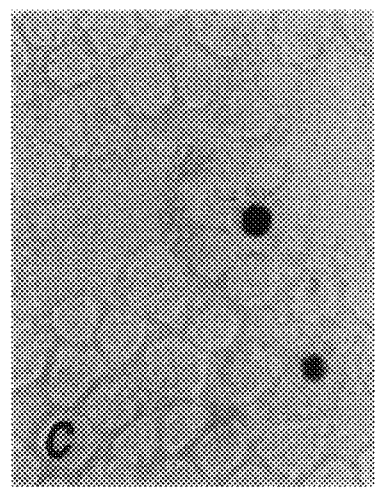

FIGS. 18A–18C: In situ hybridization with an ORF26 oligomer to BCBL-1, Raji and RCC-1 cells. Hybridization occurred to nuclei of KSHV infected BCBL-1 (FIG. 18A), but not to uninfected Raji cells (FIG. 18B). RCC-1, a Raji cell line derived by cultivation of Raji with BCBL-1 in communicating chambers separated by a 0.45μ filter, shows rare cells with positive hybridization to the KSHV ORF26 probe (FIG. 18C).

Figure 19A:
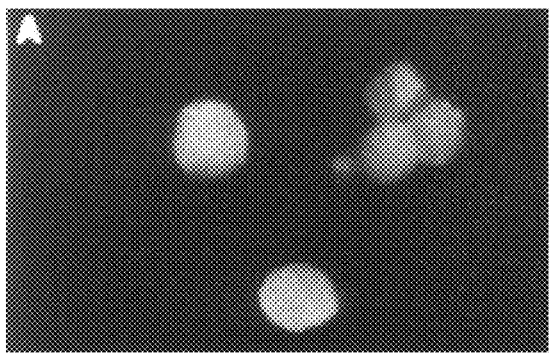
Figure 19B:
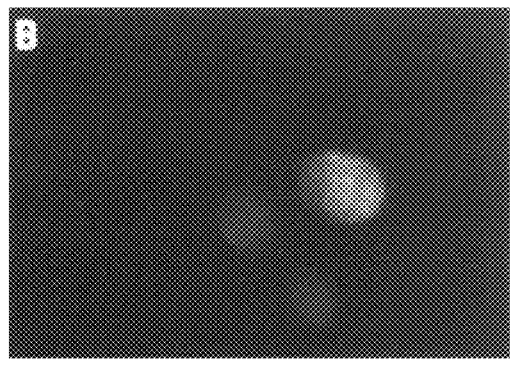
Figure 19C:
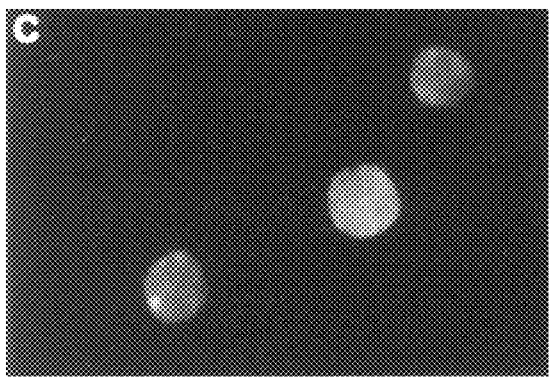
Figure 19D:
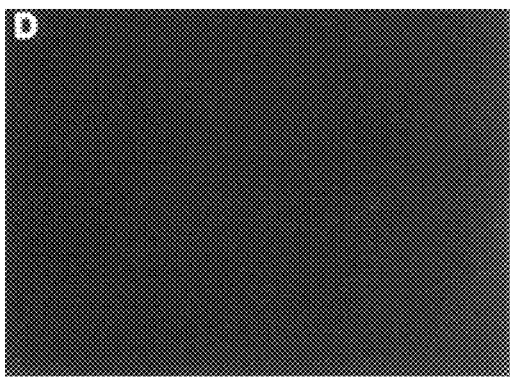

FIGS. 19A–19D: Representative example of IFA staining of HBL-6 with AIDS-KS patient sera and control sera from HIV-infected patients without KS. Both AIDS-KS (FIG. 19A) and control (FIG. 19B) sera show homogeneous staining of HBL-6 at 1:50 dilution. After adsorption with paraformaldehyde-fixed P3H3 to remove cross-reacting antibodies directed against lymphocyte and EBV antigens, antibodies from AIDS-KS sera localize to HBL-6 nuclei (FIG. 19C). P3H3 adsorption of control sera eliminates immunofluorescent staining of HBL-6 (FIG. 19D).

Figure 20A:
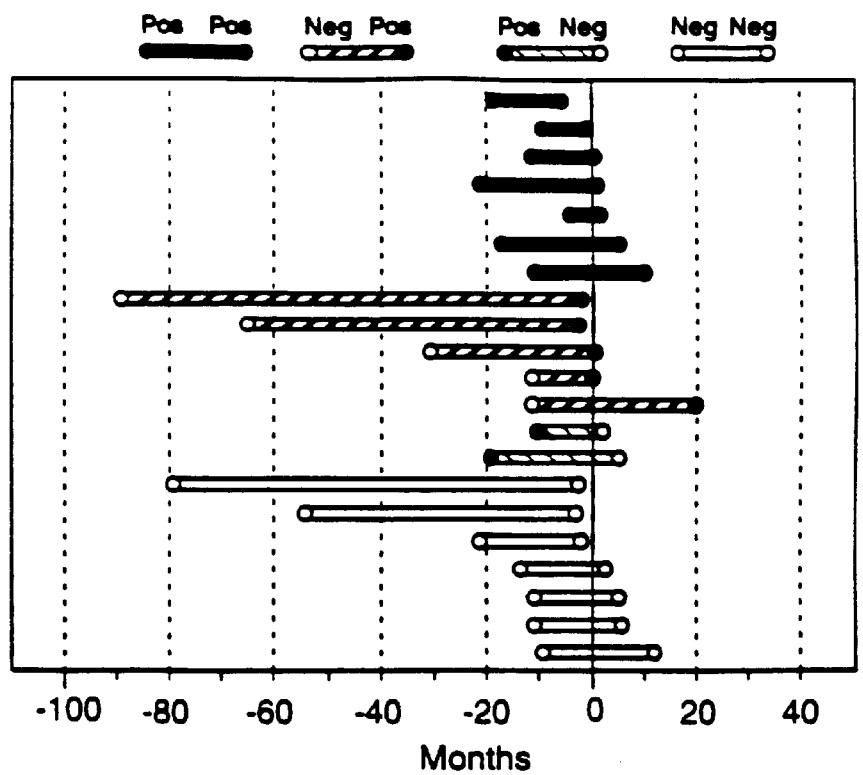
Figure 20B:
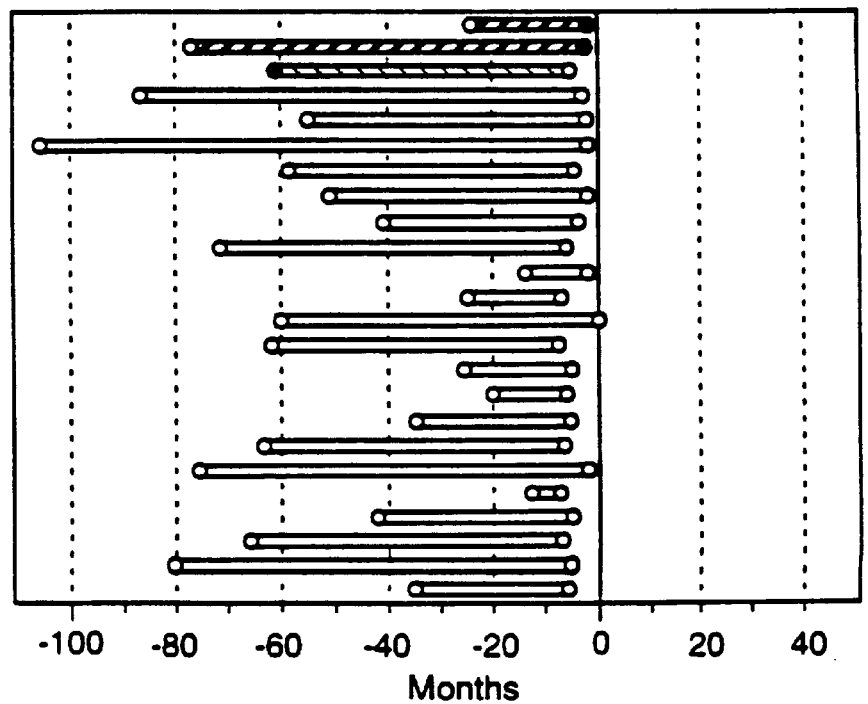

FIGS. 20A–20B: Longitudinal PCR examination for KSHV DNA of paired PBMC samples from AIDS-KS patients (A) and homosexual/bisexual AIDS patients without KS (B). Time 0 is the date of KS onset for cases; or other AIDS-defining illness for controls. All samples were randomized and examined blindly. Overall, 7 of the KS patients were KSHV positive at both examination dates (solid bars) and 5 converted from a negative to positive PBMC sample (forward striped bars) immediately prior to or after KS onset. Two previously positive KS patients were negative after KS diagnosis (reverse striped bars) and the remaining KS patients were negative at both timepoints (open bars). Two homosexual/bisexual control PBMC samples without KS converted from negative to positive and one control patient reverted from PCR positive to negative for KSHV DNA.

FIG. 21: Sample collection characteristics for AIDS-KS patients, gay/bisexual AIDS patients and hemophilic AIDS patients.

FIG. 22: PCR analysis of $KS330_{233}$ in DNA samples from patients with Kaposi's sarcoma and tumor controls.

DETAILED DESCRIPTION OF THE INVENTION

Definitions

The following standard abbreviations are used throughout the specification to indicate specific nucleotides:

C=cytosine A=adenosine

T=thymidine G=guanosine

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

By a nucleic acid sequence "homologous to" or "complementary to", it is meant a nucleic acid that selectively hybridizes, duplexes or binds to viral DNA sequences encoding proteins or portions thereof when the DNA sequences encoding the viral protein are present in a human genomic or cDNA library. A DNA sequence which is homologous to a target sequence can include sequences which are shorter or longer than the target sequence so long as they meet the functional test set forth. Hybridization conditions are specified along with the source of the CDNA library.

Typically, the hybridization is done in a Southern blot protocol using a 0.2XSSC, 0.1% SDS, 65° C. wash. The term "SSC" refers to a citrate-saline solution of 0.15 M sodium chloride and 20 Mm sodium citrate. Solutions are often expressed as multiples or fractions of this concentration. For example, 6xSSC refers to a solution having a sodium chloride and sodium citrate concentration of 6 times this amount or 0.9 M sodium chloride and 120 mM sodium citrate. 0.2xSSC refers to a solution 0.2 times the SSC concentration or 0.03 M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a herpesvirus peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the herpesvirus of the invention in the presence of a heterogeneous population of proteins and other biologics including viruses other than the herpesvirus. Thus, under designated immunoassay conditions, the specified antibodies bind to the herpesvirus antigens and do not bind in a significant amount to other antigens present in the sample. Specific binding to an antibody under such conditions may require an antibody that is selected for its specificity for a particular protein. For example, antibodies raised to the human herpesvirus immunogen described herein can be selected to obtain antibodies specifically immunoreactive with the herpesvirus proteins and not with other proteins. These antibodies recognize proteins homologous to the human herpesvirus protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane [32] for a description of immunoassay formats and conditions that can be used to determine specific immunoreactivity.

"Biological sample" as used herein refers to any sample obtained from a living organism or from an organism that has died. Examples of biological samples include body fluids and tissue specimens.

I. Kaposis's Sarcoma (KS)—Associated Herpesvirus.

This invention provides an isolated DNA molecule which is at least 30 nucleotides in length and which uniquely defines a herpesvirus associated with Kaposi's sarcoma.

In one embodiment the isolated DNA molecule comprises at least a portion of the nucleic acid sequence as shown in FIG. 3A (SEQ ID NO: 1). In another embodiment the isolated DNA molecule is a 330 base pair (bp) sequence. In another embodiment the isolated DNA molecule is a 12–50 bp sequence. In another embodiment the isolated DNA molecule is a 30–37 bp sequence.

In another embodiment the isolated DNA molecule is genomic DNA. In another embodiment the isolated DNA molecule is cDNA. In another embodiment a RNA is derived form the isolated nucleic acid molecule or is capable of hybridizing with the isolated DNA molecule. As used herein "genomic" means both coding and non-coding regions of the isolated nucleic acid molecule.

Further, the DNA molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

This invention provides an isolated nucleic acid molecule encoding an ORF20 (SEQ ID NOs: 22 and 23), ORF21 (SEQ ID NOs: 14 and 15), ORF22 (SEQ ID NOs: 16 and 17), ORF23 (SEQ ID NOs: 18 and 19), ORF24 (SEQ ID NOs: 20 and 21), ORF25 (SEQ ID NOs: 2 and 3), ORF26 (SEQ ID NOs: 24 and 25), ORF27 (SEQ ID NOs: 26 and 27), ORF28 (SEQ ID NOs: 28 and 29), ORF29A (SEQ ID NOs: 30 and 31), ORF29B (SEQ ID NOs: 4 and 5), ORF30 (SEQ ID NOs: 6 and 7), ORF31 (SEQ ID NOs: 8 and 9), ORF32 (SEQ ID NOs: 32 and 33), ORF33 (SEQ ID NOs: 10 and 11), ORF34 (SEQ ID NOs: 34 and 35), or ORF35 (SEQ ID NOs: 12 AND 13).

This invention provides an isolated polypeptide encoded by ORF20 (SEQ ID NOs: 22 and 23), ORF21 (SEQ ID NOs: 14 and 15), ORF22 (SEQ ID NOs: 16 and 17), ORF23 (SEQ ID NOs: 18 and 19), ORF24 (SEQ ID NOs: 20 and 21), ORF25 (SEQ ID NOs: 2 and 3), ORF26 (SEQ ID NOs: 24 and 25), ORF27 (SEQ ID NOs: 26 and 27), ORF28 (SEQ ID NOs: 28 and 29), ORF29A (SEQ ID NOs: 30 and 31), ORF29B (SEQ ID NOs: 4 and 5), ORF30 (SEQ ID NOs: 6 and 7), ORF31 (SEQ ID NOs: 8 and 9), ORF32 (SEQ ID NOs: 32 and 33), ORF33 (SEQ ID NOs: 10 and 11), ORF34 (SEQ ID NOs: 34 and 35), or ORF35 (SEQ ID NOs: 12 AND 13).

For Example, TK is encoded by ORF 21; glycoprotein H (gH) by ORF 22; major capsid protein (MCP) by ORF 25; virion polypeptide (VP23) by ORF 26; and minor capsid protein by ORF 27.

This invention provides for a replicable vector comprising the isolated DNA molecule of the DNA virus. The vector includes, but is not limited to: a plasmid, cosmid, λ phage or yeast artificial chromosome (YAC) which contains at least a portion of the isolated nucleic acid molecule.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

This invention provides a host cell containing the above vector. The host cell may contain the isolated DNA molecule artificially introduced into the host cell. The host cell may be a eukaryotic or bacterial cell (such as *E.coli*), yeast cells, fungal cells, insect cells and animal cells. Suitable animal cells include, but are not limited to Vero cells, HeLa cells, Cos cells, CV1 cells and various primary mammalian cells.

This invention provides an isolated herpesvirus associated with Kaposi's sarcoma. In one embodiment the herpesvirus comprises at least a portion of a nucleotide sequence as shown in FIGS. 3A (SEQ ID NO: 1).

In one embodiment the herpesvirus may be a DNA virus. In another embodiment the herpesvirus may be a Herpesviridae. In another embodiment the herpesvirus may be a gammaherpesvirinae. The classification of the herpesvirus may vary based on the phenotypic or molecular characteristics which are known to those skilled in the art.

This invention provides an isolated DNA virus wherein the viral DNA is about 270 kb in size, wherein the viral DNA encodes a thymidine kinase, and wherein the viral DNA is capable of selectively hybridizing to a nucleic acid probe selected from the group consisting of SEQ ID NOs: 38–40.

The KS-associated human herpesvirus of the invention is associated with KS and is involved in the etiology of the disease. The taxonomic classification of the virus has not yet been made and will be based on phenotypic or molecular characteristics known to those of skill in the art. However, the novel KS-associated virus is a DNA virus that appears to be related to the Herpesviridae family and the gammaherpesvirinae subfamily, on the basis of nucleic acid homology.

A. Sequence identity of the viral DNA and its proteins.

The human herpesvirus of the invention is not limited to the virus having the specific DNA sequences described herein. The KS-associated human herpesvirus DNA shows substantial sequence identity, as defined above, to the viral DNA sequences described herein. DNA from the human herpesvirus typically selectively hybridizes to one or more of the following three nucleic acid probes:

Probe 1 (SEQ ID NO:38)

AGCCGAAAGG ATTCCACCAT TGTGCTCGAA TCCAACGGAT

TTGACCCCGT GTTCCCCATG GTCGTGCCGC AGCAACTGGG

GCACGCTATT CTGCAGCAGC TGTTGGTGTA CCACATCTAC

TCCAAAATAT CGGCCGGGGC CCCGGATGAT GTAAATATGG

CGGAACTTGA TCTATATACC ACCAATGTGT CATTTATGGG

GCGCACATAT CGTCTGGACG TAGACAACAC GGA

Probe 2 (SEQ ID NO:39):

GAAATTACCC ACGAGATCGC TTCCCTGCAC ACCGCACTTG

GCTACTCATC AGTCATCGCC CCGGCCCACG TGGCCGCCAT

AACTACAGAC ATGGGAGTAC ATTGTCAGGA CCTCTTTATG

ATTTTCCCAG GGGACGCGTA TCAGGACCGC CAGCTGCATG

ACTATATCAA AATGAAAGCG GGCGTGCAAA CCGGCTCACC

GGGAAACAGA ATGGATCACG TGGGATACAC TGCTGGGGTT

CCTCGCTGCG AGAACCTGCC CGGTTTGAGT CATGGTCAGC

TGGCAACCTG CGAGATAATT CCCACGCCGG TCACATCTGA

CGTTGCCT

Probe 3 (SEQ ID NO:40):

AACACGTCAT GTGCAGGAGT GACATTGTGC CGCGGAGAAA

CTCAGACCGC ATCCCGTAAC CACACTGAGT GGGAAAATCT

GCTGGCTATG TTTTCTGTGA TTATCTATGC CTTAGATCAC

AACTGTCACC CG

Hybridization of a viral DNA to the nucleic acid probes listed above is determined by using standard nucleic acid hybridization techniques as described herein. In particular, PCR amplification of a viral genome can be carried out using the following three sets of PCR primers:

```
1)   AGCCGAAAGGATTCCACCAT;        (SEQ ID NO:41)
     TCCGTGTTGTCTACGTCCAG         (SEQ ID NO:48)

2)   GAAATTACCCACGAGATCGC;        (SEQ ID NO:42)
     AGGCAACGTCAGATGTGA           (SEQ ID NO:43)

3)   AACACGTCATGTGCAGGAGTGAC;     (SEQ ID NO:43)
     CGGGTGACAGTTGTGATCTAAGG      (SEQ ID NO:50)
```

In PCR techniques, oligonucleotide primers, as listed above, complementary to the two 3' borders of the DNA region to be amplified are synthesized. The polymerase chain reaction is then carried out using the two primers. See PCR Protocols: *A Guide to Methods and Applications* [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to the solid phase phosphoramidite triester method first described by Beaucage and Carruthers [19] using an automated synthesizer, as described in Needham-VanDevanter [69]. Purification of oligonucleotides is by either native acrylamide gel electrophoresis or by anion-exchange HPLC as described in Pearson, J. D. and Regnier, F. E. [75A]. The sequence of the synthetic oligonucleotide can be verified using the chemical degradation method of Maxam, A. M. and Gilbert, W. [63].

B. Isolation and propagation of KS-inducing strains of the Human Herpesvirus

Using conventional methods, the human herpesvirus can be propagated in vitro. For example, standard techniques for growing herpes viruses are described in Ablashi, D. V. [1]. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 µg/ml polybrene for 2 hours at 37° C. prior to infection.

Infected cells are observed by demonstrating morphological changes, as well as being positive for antigens from the human herpesvirus by using monoclonal antibodies immunoreactive with the human herpes virus in an immunofluorescence assay.

For virus isolation, the virus is either harvested directly from the culture fluid by direct centrifugation, or the infected cells are harvested, homogenized or lysed and the virus is separated from cellular debris and purified by standard methods of isopycnic sucrose density gradient centrifugation.

One skilled in the art may isolate and propagate the DNA herpesvirus associated with Kaposi's sarcoma (KSHV) employing the following protocol. Long-term establishment of a B lymphoid cell line infected with the KSHV from body-cavity based lymphomas (RCC-1 or HBL-6) is prepared extracting DNA from the Lymphoma tissue using standard techniques [27, 49, 66].

The KS associated herpesvirus may be isolated from the cell DNA in the following manner. An infected cell line (HBL-6 RCC-1), which can be lysed using standard methods such as hyposomatic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45μ filter and centrifuged again at 100,000×g for 1 hour to pellet the virus. The virus car. then be washed and centrifuged again at 100,000 ×g for 1 hour.

The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at $>1\times10^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell Line at a concentration of $>1\times10^6$ cells/ml. The media is centrifuged at 2000×g for 10 minutes and filtered through a 0.45μ filter to remove cells. The media is applied in a 1:1 volume with cells growing at $>1\times10^6$ cells/ml for 48 hours. The cells are washed and pelleted and placed in fresh culture medium, and tested after 14 days of growth.

RCC-1 and RCC-$1_2$F5 were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

HBL-6 was deposited on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

C. Immunological Identity of the Virus

The KS-associated human herpesvirus can also be described immunologically. KS-associated human herpesviruses are selectively immunoreactive to antisera generated against a defined immunogen such as the viral major capsid protein depicted in Seq. ID No. 12, herein. Immunoreactivity is determined in an immunoassay using a polyclonal antiserum which was raised to the protein which is encoded by the amino acid sequence or nucleic acid sequence of SEQ ID NOs: 18–20. This antiserum is selected to have low crossreactivity against other herpes viruses and any such crossreactivity is removed by immunoabsorbtion prior to use in the immunoassay.

In order to produce antisera for use in an immunoassay, the protein which is encoded by the amino acid sequence or nucleic acid of SEQ ID NOs: 18–20 is isolated as described herein. For example, recombinant protein can be produced in a mammalian cell line. An inbred strain of mice such as balb/c is immunized with the protein which is encoded by the amino acid sequence or nucleic acid of SEQ ID NOs: 2–37 using a standard adjuvant, such as Freund's adjuvant, and a standard mouse immunization protocol (see [32], supra). Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other viruses of the gammaherpesvirinae subfamily, particularly human herpes virus types 1–7, by using a standard immunoassay as described in [32], supra. These other gammaherpesvirinae virus can be isolated by standard techniques for isolation herpes viruses as described herein.

The ability of the above viruses to compete with the binding of the antisera to the immunogen protein is determined. The percent crossreactivity for other viruses is calculated, using standard calculations. Those antisera with less than 10% crossreactivity with each of the other viruses listed above is selected and pooled. The cross-reacting antibodies are then removed from the pooled antisera by immunoabsorption with the above-listed viruses.

The immunoabsorbed and pooled antisera are then used in a competitive binding immunoassay procedure as described above to compare an unknown virus preparation to the specific KS herpesvirus preparation described herein and containing the nucleic acid sequence described in SEQ ID NOs: 2–37. In order to make this comparison, the immunogen protein which is encoded by the amino acid sequence or nucleic acid of SEQ ID NOs: 2–37 is the labeled antigen and the virus preparations are each assayed at a wide range of concentrations. The amount of each virus preparation required to inhibit 50% of the binding of the antisera to the labeled immunogen protein is determined. Those viruses that specifically bind to an antibody generated to an immunogen consisting of the protein of SEQ ID NOs: 2–37 are those virus where the amount of virus needed to inhibit 50% of the binding to the protein does not exceed an established amount. This amount is no more than 10 times the amount of the virus that is needed for 50% inhibition for the KS-associated herpesvirus containing the DNA sequence of SEQ ID NO: 1. Thus, the KS-associated herpesviruses of the invention can be defined by immunological comparison to the specific strain of the KS-associated herpesvirus for which nucleic acid sequences are provided herein.

This invention provides, a nucleic acid molecule of at least 14 nucleotides capable of specifically hybridizing with the isolated DNA molecule. In one embodiment, the molecule is DNA. In another embodiment, the molecule is RNA. In another embodiment the nucleic acid molecule may be 14–20 nucleotides in length. In another embodiment the nucleic acid molecule may be 16 nucleotides in length.

This invention provides, a nucleic acid molecule of at least 14 nucleotides capable of specifically hybridizing with a nucleic acid molecule which is complementary to the isolated DNA molecule In one embodiment, the molecule is DNA. In another embodiment, the molecule is RNA.

The nucleic acid molecule of at least 14 nucleotides may hybridize with moderate stringency to at least a portion of a nucleic acid molecule with a sequence shown in FIGS. 3A–3F (SEQ ID NOs: 1, 10–17, and 38–40).

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6× SSC solution, washing at room temperature with 6× SSC solution, followed by washing at about 680° in a 6× SSC in a 0.6× SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing Conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the pathogenic organism or disease marker to which the relevant sequence listing relates.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

DNA virus nucleic acid rearrangements/mutations may be detected by Southern blotting, single stranded conformational polymorphism gel electrophoresis (SSCP), PCR or other DNA based techniques, or for RNA species by Northern blotting, PCR or other RNA-based techniques.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, [19], or by the triester method according to Matteucci, et al., [62], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

This invention provides for an isolated DNA molecule which encodes at least a portion of a Kaposi's sarcoma associated herpesvirus: virion polypeptide 23, major capsid protein, capsid proteins, thymidine kinase, or tegument protein.

This invention also provides a method of producing a polypeptide encoded by isolated DNA molecule, which comprises growing the above host vector system under suitable conditions permitting production of the polypeptide and recovering the polypeptide so produced.

This invention provides an isolated peptide encoded by the isolated DNA molecule associated with Kaposi's sarcoma. In one embodiment the peptide may be a polypeptide. Further, this invention provides a host cell which expresses the polypeptide of isolated DNA molecule.

In one embodiment the isolated peptide or polypeptide is encoded by at least a portion of an isolated DNA molecule. In another embodiment the isolated peptide or polypeptide is encoded by at least a portion of a nucleic acid molecule with a sequence as set forth in (SEQ ID NOs: 2–37).

Further, the isolated peptide or polypeptide encoded by the isolated DNA molecule may be linked to a second nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the peptide or polypeptide encoded by the isolated DNA molecule. In one embodiment the antibody is a monoclonal antibody. In another embodiment the antibody is a polyclonal antibody.

The antibody or DNA molecule may be labelled with a detectable marker including, but not limited to: a radioactive label, or a calorimetric, a luminescent, or a fluorescent marker, or gold. Radioactive labels include, but are not limited to: $^3$H, $^{14}$C, $^{32}$P, $^{33}$P; $^{35}$S, $^{36}$Cl, $^{51}$Or, $^{57}$Co, $^{59}$Co, $^{59}$Fe, $^{90}$Y, $^{125}$I, $^{131}$I, and $^{186}$Re. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detected by a second antibody which may be linked to an enzyme, such as alkaline phosphatase or horseradish peroxidase. Other enzymes which may be employed are well known to one of ordinary skill in the art.

This invention provides a method to select specific regions on the polypeptide encoded by the isolated DNA molecule of the DNA virus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

II. Immunoassays

The antibodies raised against the viral strain or peptides may be detectably labelled, utilizing conventional labelling techniques well-known to the art. Thus, the antibodies may be radiolabelled using, for example, radioactive isotopes such as $^3$H, $^{125}$I, $^{131}$I, and $^{35}$S.

The antibodies may also be labelled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

Once labeled, the antibody may be employed to identify and quantify immunologic counterparts (antibody or antigenic polypeptide) utilizing techniques well-known to the art.

A description of a radioimmunoassay (RIA) may be found in *Laboratory Techniques in Biochemistry and Molecular Biology* [52], with particular reference to the chapter entitled "An Introduction to Radioimmune Assay and Related Techniques" by Chard, T., incorporated by reference herein.

A description of general immunometric assays of various types can be found in the following U.S. Pat. Nos. 4,376,110 (David et al.) or 4,098,876 Piasio).

A. Assays for viral antigens

In addition to the detection of the causal agent using nucleic acid hybridization technology, one can use immunoassays to detect for the virus, specific peptides, or for antibodies to the virus or peptides. A general overview of the applicable technology is in Harlow and Lane [32], incorporated by reference herein.

In one embodiment, antibodies to the human herpesvirus can be used to detect the agent in the sample. In brief, to produce antibodies to the agent or peptides, the sequence being targeted is expressed in transfected cells, preferably bacterial cells, and purified. The product is injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane [32] at pages 567–573 and 584–589.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell (see, Kohler and Milstein [50], incorporated herein by reference). Alternative methods of immortalization include transformation with Epstein Barr Virus, oncogenes, or retroviuses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies. See for example: McCafferty, J et al. [64]; Hoogenboom, H. R. et al. [39]; and Marks, J. D. et al. [60].

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selection of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in $E.\ coli$ is also useful. Examples of such markers include genes specifying resistance to antibiotics. See [81] supra, for details concerning selection markers and promoters for use in $E.\ coli$. Suitable eukaryote hosts may include plant cells, insect cells, mammalian cells, yeast, and filamentous fungi.

Methods for characterizing naturally processed peptides bound to MHC (major histocompatibility complex) I molecules have been developed. See, Falk et al. [24], and PCT publication No. WO 92/21033 published Nov. 26, 1992, both of which are incorporated by reference herein. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey, et al. [45], incorporated by reference herein, and of the human MHC class I molecule, HLA-A2.1 type by mass spectrometry (Hunt, et al. [40], incorporated by reference herein). See also, Rotzschke and Falk [79], incorporated by reference herein for a general review of the characterization of naturally processed peptides in MHC class I. Further, Marloes, et al. [61], incorporated by reference herein, describe how class I binding motifs can be applied to the identification of potential viral immunogenic peptides in vitro.

The peptides described herein produced by recombinant technology may be purified by standard techniques well known to those of skill in the art. Recombinantly produced viral sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods, and others. See, for instance, Scopes, R. [84], incorporated herein by reference.

B. Serological tests for the presence of antibodies to the human herpesvirus.

This invention further embraces diagnostic kits for detecting the presence of a KS agent in biological samples, such as serum or solid tissue samples, comprising a container containing antibodies to the human herpesvirus, and instructional material for performing the test. Alternatively, inactivated viral particles or peptides or viral proteins derived from the human herpesvirus may be used in a diagnostic kit to detect for antibodies specific to the KS associated human herpesvirus.

Diagnostic kits for detecting the presence of a KS agent in tissue samples, such as skin samples or samples of other affected tissue, comprising a container containing a nucleic acid sequence specific for the human herpesvirus and instructional material for detecting the KS-associated herpesvirus are also included. A container containing nucleic acid primers to any one of such sequences is optionally included as are antibodies to the human herpesvirus as described herein.

Antibodies reactive with antigens of the human herpesvirus can also be measured by a variety of immunoassay methods that are similar to the procedures described above for measurement of antigens. For a review of immunological and immunoassay procedures applicable to the measurement of antibodies by immunoassay techniques, see Basic and Clinical Immunology 7th Edition [12], and [32], supra.

In brief, immunoassays to measure antibodies reactive with antigens of the KS-associated human herpesvirus can be either competitive or noncompetitive binding assays. In competitive binding assays, the sample analyte competes with a labeled analyte for specific binding sites on a capture agent bound to a solid surface. Preferably the capture agent is a purified recombinant human herpesvirus protein produced as described above. Other sources of human herpesvirus proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of the human herpesvirus antigens.

Hemagglutination Inhibition (HI) and Complement Fixation (CF) which are two laboratory tests that can be used to detect infection with human herpesvirus by testing for the presence of antibodies against the virus or antigens of the virus.

Serological methods can be also be useful when one wishes to detect antibody to a specific variant. For example, one may wish to see how well a vaccine recipient has responded to the new variant.

Alternatively, one may take serum from a patient to see which variant the patient responds to the best.

This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence as shown in FIG. 3A–3F (SEQ ID NOs: 1–37).

This invention provides an antisense molecule capable of hybridizing to the isolated DNA molecule. In one embodiment the antisense molecule is DNA. In another embodiment the antisense molecule is RNA.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein. Oligomer of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention provides a cell line containing the isolated KS associated herpesvirus of the subject invention. In one embodiment the isolated DNA molecule is artificially introduced into the cell. Cell lines include, but are not limited to: fibroblasts, such as HFF, NIH/3T3; Epithelial cells, such as 5637; lymphocytes, such as FCB; T-cells, such as CCRF-CEM (ATCC CCL 119); B-cells, such as BJAB and Raji (ATCC CCL 86); and myeloid cells such as K562 (ATCC CCL 243); Vero cells and carcinoma cells. Methods of producing such cell lines are known to those skilled in the art. In one embodiment the isolated KS associated herpesvirus is introduced into a RCC-1 cell line.

III. In vitro diagnostic assays for the detection of KS

This invention provides a method of diagnosing Kaposi's sarcoma in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the DNA molecule from the tumor lesion is amplified before step (b). In another embodiment PCR is employed to amplify the nucleic acid molecule. Methods of amplifying nucleic acid molecules are known to those skilled in the art.

A person of ordinary skill in the art will be able to obtain appropriate DNA sample for diagnosing Kaposi's sarcoma in the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One examples of such solid matrix is nitrocellulose paper.

This invention provides a method of diagnosing Kaposi's sarcoma in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

This invention provides a method of diagnosing a DNA virus in a subject, which comprises (a) obtaining a suitable bodily fluid sample from the subject, (b) contacting the suitable bodily fluid of the subject to a support having already bound thereto a Kaposi's sarcoma antibody, so as to bind the Kaposi's sarcoma antibody to a specific Kaposi's sarcoma antigen, (c) removing unbound bodily fluid from the support, and (d) determining the level of Kaposi's sarcoma antibody bound by the Kaposi's sarcoma antigen, thereby diagnosing the subject for Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto a Kaposi's sarcoma antigen, so as to bind Kaposi's sarcoma antigen to a specific Kaposi's sarcoma antibody, (c) removing unbound bodily fluid from the support, and (d) determining the level of the Kaposi's sarcoma antigen bound by the Kaposi's sarcoma antibody, thereby diagnosing Kaposi's sarcoma.

This invention provides a method of detecting expression of a DNA virus associated with Kaposi's sarcoma in a cell which comprises obtaining total cDNA obtained from the cell, contacting the cDNA so obtained with a labelled DNA molecule under hybridizing conditions, determining the presence of cDNA hybridized to the molecule, and thereby detecting the expression of the DNA virus. In one embodiment mRNA is obtained from the cell to detect expression of the DNA virus.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with a DNA virus associated with Kaposi's sarcoma may be diagnosed with the above described methods.

The detection of the human herpesvirus and the detection of virus-associated KS are essentially identical processes. The basic principle is to detect the virus using specific ligands that bind to the virus but not to other proteins or nucleic acids in a normal human cell or its environs. The ligands can either be nucleic acid or antibodies. The ligands can be naturally occurring or genetically or physically modified such as nucleic acids with non-natural or antibody derivatives, i.e., Fab or chimeric antibodies. Serological tests for detection of antibodies to the virus may also be performed by using protein antigens obtained from the human herpesvirus, and described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS is present.

A. Nucleic acid assays.

The diagnostic assays of the invention can be nucleic acid assays such as nucleic acid hybridization assays and assays which detect amplification of specific nucleic acid to detect for a nucleic acid sequence of the human herpesvirus described herein.

Accepted means for conducting hybridization assays are known and general overviews of the technology can be had from a review of: *Nucleic Acid Hybridization: A Practical Approach* [72]; *Hybridization of Nucleic Acids Immobilized on Solid Supports* [41]; *Analytical Biochemistry* [4] and Innis et al., PCR Protccols [74], supra, all of which are incorporated by reference herein.

If PCR is used in conjunction with nucleic acid hybridization, primers are designed to target a specific portion of the nucleic acid of the herpesvirus. For example, the primers set forth in SEQ ID NOs: 38–40 may be used to target detection of regions of the herpesvirus genome encoding ORF 25 homologue—ORF 32 homologue. From the information provided herein, those of skill in the art will be able to select appropriate specific primers.

Target specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of the human herpesvirus of the invention, nucleic acid probes are about 50 to about 1000 nucleotides, most preferably about 200 to about 400 nucleotides.

A sequence is "specific" for a target organism of interest if it includes a nucleic acid sequence which when detected is determinative of the presence of the organism in the presence of a heterogeneous population of proteins and other biologics. A specific nucleic acid probe is targeted to that portion of the sequence which is determinative of the organism and will not hybridize to other sequences especially those of the host where a pathogen is being detected.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

The probe must be of sufficient length to be able to form a stable duplex with its target nucleic acid in the sample, i.e., at least about 14 nucleotides, and may be longer (e.g., at least about 50 or 10) bases in length). Often the probe will be more than about 100 bases in length. For example, when probe is prepared by nick-translation of DNA in the presence of labeled nucleotides the average probe length may be about 100–600 bases.

As noted above, the probe will be capable of specific hybridization to a specific KS-associated herpes virus nucleic acid. Such "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, [81], supra, Ausubel, F., et al. [8] [hereinafter referred to as Sambrook], Methods in Enzymology [67] or *Hybridization with Nucleic Acid Probes* [42] all of which are incorporated herein by reference.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

A probe can be identified as capable of hybridizing specifically to its target nucleic acid by hybridizing the probe to a sample treated according the protocol of this invention where the sample contains both target virus and animal cells (e.g., nerve cells). A probe is specific if the probe's characteristic signal is associated with the herpesvirus DNA in the sample and not generally with the DNA of the host cells and non-biological materials (e.g., substrate) in a sample.

The following stringent hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2× SSC, and 0.1% (w/v) dextran sulfate, followed by washing in 1× SSC at 70° C. for 5 minutes; 2× SSC at 37° C. for 5 minutes; 0.2× SSC at room temperature for 5 minutes, and $H_2O$ at room temperature for 5 minutes.

Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions. To test the specificity of the virus specific probes, the probes can be tested on host cells containing the KS-associated herpesvirus and compared with the results from cells containing non-KS-associated virus.

It will be apparent to those of ordinary skill in the art that a convenient method for determining whether a probe is specific for a KS-associated viral nucleic acid utilizes a Southern blot (or Dot blot) using DNA prepared from one or more KS-associated human herpesviruses of the invention. Briefly, to identify a target specific probe DNA is isolated from the virus. Test DNA either viral or cellular is transferred to a solid (e.g., charged nylon) matrix. The probes are labelled following conventional methods. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$). For radioactively-labeled DNA or RNA probes an example of stringent hybridization conditions is hybridization in a solution containing denatured probe and 5× SSC at 65° C. for 8–24 hours followed by washes in 0.1× SSC, 0.1% SDS (sodium dodecyl sulfate) at 50–65° C. In general, the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the KS-associated viral DNA but not to the non-KS associated viral DNA, as evidenced by the presence of a signal associated with the appropriate target and the absence of a signal from the non-target nucleic acids, is identified as specific for the KS associated virus. It is further appreciated that in determining probe specificity and in utilizing the method of this invention to detect KS-associated herpesvirus, a certain amount of background signal is typical and can easily be distinguished by one of skill from a specific signal. Two fold signal over background is acceptable.

A preferred method for detecting the KS-associated herpesvirus is the use of PCR and/or dot blot hybridization. The presence or absence of an KS agent for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer may be used for the detection of message in samples of RNA or reverse transcriptase PCR and cDNA can be detected by methods described above. This procedure is also well known in the art. See [81] incorporated by reference herein.

An alternative means for determining the presence of the human herpesvirus is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in Methods Enzymol. [67] incorporated by reference herein. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above described probes are also useful for in-situ hybridization or in order to locate tissues which express this gene, or for other hybridization assays for the presence of this gene or its MRNA in various biological tissues. In-situ hybridization is a sensitive localization method which is not dependent on expression of antigens or native vs. denatured conditions.

Oligonucleotide (oligo) probes, synthetic oligonucleotide probes or riboprobes made from KSHV phagemids/plasmids, are relatively homogeneous reagents and successful hybridization conditions in tissue sections is readily transferable from one probe to another. Commercially synthesized oligonucleotide probes are prepared against the identified genes. These probes are chosen for length (45–65 mers), high G-C content (50–70%) and are screened for uniqueness against other viral sequences in GenBank.

Oligonucleotides are 3'end-labeled with [$\alpha$-$^{35}$S]dATP to specific activities in the range of $1\times10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 $\mu$m intervals and thawed onto 3-aminopropyltriethoxysilane treated slides and allowed to air dry. The slides are then be fixed in 4% freshly prepared paraformaldehyde, rinsed in water. Formalin-fixed, paraffin embedded KS tissues cut at 6 $\mu$m and baked onto glass slides can also be used. The sections are then deparaffinized in xylenes and rehydrated through graded alcohols. Prehybridization in 20 mM Tris Ph 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (Ph 7.4), 3× SSC, 1× Denhardt's solution, 100 ug/ml salmon sperm DNA, 125 ug/ml yeast tRNA and the oligo probe ($10^6$cpm/ml) at 42° C. overnight. The slides are washed twice with 2× SSC and twice with 1× SSC for 15 minutes each at room temperature and visualized by autoradiography. Briefly, sections are dehydrated through graded alcohols containing 0.3M ammonium acetate and air dried. The slides are dipped in Kodak NTB2 emulsion, exposed for days to weeks, developed, and counterstained with hematoxylin and eoxin. Alternative immunohistochemical protocols may be employed which are known to those skilled in the art.

IV. Treatment of human herpesvirus-induced KS

This invention provides a method of treating a subject with Kaposi's sarcoma, comprising administering to the subject an effective amount of the antisense molecule capable of hybridizing to the isolated DNA molecule under conditions such that the antisense molecule selectively enters a tumor cell of the subject, so as to treat the subject.

This invention provides a method for treating a subject with Kaposi's sarcoma (KS) comprising administering to the subject having a human herpesvirus-associated KS a pharmaceutically effective amount of an antiviral agent in a pharmaceutically acceptable carrier, wherein the agent is effective to treat the subject with KS-associated human herpes virus.

Further, this invention provides a method of prophylaxis or treatment for Kaposi's sarcoma (KS) by administering to a patient at risk for KS, an antibody that binds to the human herpesvirus in a pharmaceutically acceptable carrier. In one embodiment the antiviral drug is used to treat a subject with the DNA herpesvirus of the subject invention.

The use of combinations of antiviral drugs and sequential treatments are useful for treatment of herpesvirus infections and will also be useful for the treatment of herpesvirus-induced KS. For example, Snoeck et al. [88], found additive or synergistic effects against CMV when combining anti-herpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. [56].

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. [11]) describes the use of thymilydate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophalactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach, S. L., et al. [28]) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

A. Antiviral Agents.

The antiherpesvirus agents that will be useful for treating virus-induced KS can be grouped into broad classes based on their presumed modes of action. These classes include agents that act (i) by inhibition of viral DNA polymerase, (ii) by targeting other viral enzymes and proteins, (iii) by miscellaneous or incompletely understood mechanisms, or (iv) by binding a target nucleic acid (i.e., inhibitory nucleic acid therapeutics). Antiviral agents may also be used in combination (i.e. together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of viral DNA polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside aralogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al. [11]).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al. [95]) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq [22] and in other references cited supra and infra, all of which are incorporated by reference herein.

Anti-herpesvirus medications suitable for treating viral induced KS include, but are not limited to, nucleoside analogs including acyclic nucleoside phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosylcytosine (ara-C) ; HPMPC [(S)-1-[3-hydroxy-2-(phosphonylmethoxy)propyl] cytosine (e.g., GS 504 Gilead Science) and its cyclic form (cHPMPC); HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis (isopropoxy)-2-propoxymethyl)purine]; PMEA [9-(2-phosphonylmethoxyethyl)adenine]; bromovinyl-deoxyuridine (Burns and Sandford. [21]); 1-β-D- arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al. [11])]; and 5-mercutithio analogs of 2'-deoxyuridine (Holliday, J., and Williams, M. V. [38]); acyclovir [9-([2-hydroxyethoxy] methyl)guanine; e.g., Zovirax (Burroughs Wellcome)]; penciclovir (9-[4-hydroxy-2-(hydroxymethyl)butyl]-guanine); ganciclovir [(9-[1,3-dihydroxy-2 propoxymethyl]-guanine) e.g., Cymevene, Cytovene (Syntex), DHPG (Stals et al. [89]]; isopropylether derivatives of ganciclovir (see, e.g., Winkelmann et al. [94]); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(+−)-9-[1β,2α,3β)-2,3-bis (hydroxymethyl)-1-cyclobutyl]adenine], cyclobut-G [(+−)-9-[1β,2α,3β)-2,3-bis(hydroxymethyl)-1-cyclobutyl] guanine], BHCG [(R)-(1α,2β,1α)-9-(2,3-bis (hydroxymethyl)cyclobutyl]guanine], and an active isomer of racemic BHCG, SQ 34,514 [1R-1α,2β,3α)-2-amino-9-[2,3-bis(hydroxymethyl)cyclobutyl]-6H-purin-6-one (see, Braitman et al.(1991) [20]]. Certain of these antiherpesviral agents are discussed in Gorach et al. [28]; Saunders et al. [82]; Yamanaka et al., [96]; Greenspan et al. [29], all of which are incorporated by reference herein.

Triciribine and triciribine monophosphate are potent inhibitors against herpes viruses. (Ickes et al. [43], incorporated by reference herein), HIV-1 and HIV-2 (Kucera et al. [51], incorporated by reference herein) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella- Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble [73]. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK- HSV, VZV or CMV infections in animal models ([22], supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al. [5] which is incorporated by reference herein. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Agents that target viral proteins other than DNA polymerase or other viral functions.

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cycloalkylmethyl]-5-substituted -uracils and -guanines as described in, e.g., U.S. Pat. Nos. 4,863,927 and 4,782,062 (Tolman et al.; Merck)) as well as other enzymes. It will be apparent to one of ordinary skill in the art that there are additional viral proteins, both characterized and as yet to be discovered, that can serve as target for antiviral agents.

iv) Other agents and modes of antiviral action.

Kutapressin is a liver derivative available from Schwarz Parma of Milwaukee, Wis. in an injectable form of 25 mg/ml. The recommended dosage for herpesviruses is from 200 to 25 mg/ml per clay for an average adult of 150 pounds.

Poly(I) Poly($C_{12}$U), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) [see, *The Pink Sheet* 55(20) May 17, 1993].

Interferon is known inhibit replication of herpes viruses. See [73], supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and 5,175,165 (Blumenkopf et al.; Burroughs Wellcome). U.S. Pat. No. 4,880,820 (Ashton et al.; Merck) describes the antiherpes virus agent (S)-9-(2,3-dihydroxy-1-propoxymethyl)guanine.

U.S. Pat. No. 4,708,935 (Suhadolnik et al.; Research Corporation) describes a 3'-deoxyadenosine compound effective in inhibiting HSV and EBV. U.S. Pat. No. 4,386,076 (Machida et al.; Yamasa Shoyu Kabushiki Kaisha) describes use of (E)-5-(2-halogenovinyl)-arabinofuranosyluracil as an antiherpesvirus agent. U.S. Pat. No. 4,340,599 (Lieb et al.; Bayer Aktiengesellschaft) describes phosphonohydroxyacetic acid derivatives useful as antiherpes agents. U.S. Pat. Nos. 4,093,715 and 4,093,716 (Lin et al. Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al.; Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

v) Inhibitory nucleic acid therapeutics

Also contemplated here are inhibitory nucleic acid therapeutics which can inhibit the activity of herpesviruses in patients with KS. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene, C. and Toulme, J. [34], which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the Inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

This invention relates to the targeting of inhibitory nucleic acids to sequences the human herpesvirus of the invention for use in treating KS. An example of an antiherpes virus inhibitory nucleic acid is ISIS 2922 (ISIS Pharmaceuticals) which has activity against CMV [see, *Biotechnology News* 14 (14) p. 5].

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

iii) Administration

The subjects to be treated or whose tissue nay be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy.

Having identified a primary causal agent of KS in humans as a novel human herpesvirus, there are immunosuppressive therapies that can modulate the immunologic dysfunction that arises from the presence of viral infected tissue. In particular, agents that block the immunological attack of the viral infected cells will ameliorate the symptoms of KS and/or reduce the disease progress. Such therapies include antibodies that specifically block the targeting of viral infected cells. Such agents include antibodies which bind to cytokines that upregulate the immune system to target viral infected cells.

The antibody may be administered to a patient either singly or in a cocktail containing two or more antibodies, other therapeutic agents, compositions, or the like, including, but not limited to, immuno-suppressive agents, potentiators and side-effect relieving agents. Of particular interest are immuno-suppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administering to the subject in an effective amount to vaccinate a subject against Kaposi's sarcoma.

This invention provides a method of immunizing a subject against a disease caused by the DNA herpesvirus associated with Kaposi's sarcoma which comprises administering to the subject an effective immunizing dose of the isolated herpesvirus vaccine.

A. Vaccines

The invention also provides substances suitable for use as vaccines for the prevention of KS and methods for administering them. The vaccines are directed against the human herpesvirus of the invention, and most preferably comprise antigen obtained from the KS-associated human herpesvirus.

Vaccines can be made recombinantly. Typically, a vaccine will include from about 1 to about 50 micrograms of antigen or antigenic protein or peptide. More preferably, the amount of protein is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1:2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al. [30]; Hardy, I. et al. [31]; Levin, M. J. et al. [54]; Gershon, A. A. [26]. Vaccines against Herpes simplex Types 1 and 2 are also commercially available with some success in protection against primary disease, but have been less successful in preventing the establishment of latent infection in sensory ganglia (Roizman, B. [78]; Skinner, G. R. et al. [87]).

Vaccines against the human herpesvirus can be made by isolating extracellular viral particles from infected cell cultures, inactivating the virus with formaldehyde followed by ultracentrifugation to concentrate the viral particles and remove the formaldehyde, and immunizing individuals with 2 or 3 doses containing $1\times10^9$ virus particles (Skinner, G. R. et al. [86]). Alternatively, envelope glycoproteins can be expressed in *E. coli* or transfected into stable mammalian cell lines, the proteins can be purified and used for vaccination (Lasky, L. A. [53]). MHC—binding peptides from cells infected with the human herpesvirus can be identified for vaccine candidates per the methodology of [61], supra.

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacteriurn acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Michigan). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 $\mu$g of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral proteins from the human herpesvirus. For example, it is known in the protein art that certain amino acid residues can be substituted with amino acids of similar size and polarity without an undue effect upon the biological activity of the protein. The human herpesvirus proteins have significant tertiary structure and the epitopes are usually conformational. Thus, modifications should generally preserve conformation to produce a protective immune response.

B. Antibody Prophylaxis

Therapeutic, intravenous, polyclonal or nonoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring therapeutic efficacy

This invention provides a method for monitoring the therapeutic efficacy of treatment for Kaposi's sarcoma, which comprises determining in a first sample from a subject with Kaposi's sarcoma the presence of the isolated DNA molecule, administering to the subject a therapeutic amount of an agent such that the agent is contacted to the cell in a sample, determining after a suitable period of time the amount of the isolated DNA molecule in the second sample from the treated subject, and comparing the amount of isolated DNA molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays For Pharmaceutical Agents of Interest in Alleviating the Symptoms of KS.

Since an agent involved in the causation or progression of KS has been identified and described here, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus proteins or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada, H. et al. [7]; Kikuta et al. [48] both incorporated by reference herein). Infected cultures and their supernatants can be assayed for the total amount of virus including the presence of the viral genome by quantitative PCR, by dot blot assays, or by using immunologic methods. For example, a culture of susceptible cells could be infected with the human herpesvirus in the presence of various concentrations of drug, fixed on slides after a period of days, and examined for viral antigen by indirect immunofluorescence with monoclonal antibodies to viral peptides ([48], supra. Alternatively, chemically adhered MT-4 cell monolayers can be used for an infectious agent assay using indirect immunofluorescent antibody staining to search for focus reduction (Higashi, K. et al. [36], incorporated by reference herein).

As an alternative to whole cell in vitro assays, purified enzymes isolated from the human herpesvirus can be used as targets for rational drug design to determine the effect of the potential drug on enzyme activity, such as thymidine phosphotransferase or DNA polymerase. The genes for these two enzymes are provided herein. A measure of enzyme activity indicates effect on the agent itself.

Drug screens using herpes viral products are known and have been previously described in EP 0514830 (herpes proteases) and WO 94/04920 ($U_L13$ gene product).

This invention provides an assay for screening anti-KS chemotherapeutics. Infected cells can be incubated in the presence of a chemical agent that is a potential chemotherapeutic against KS (e.g. acyclo-guanosine). The level of virus in the cells is then determined after several days by IFA for antigens or Southern blotting for viral genome or Northern blotting for MRNA and compared to control cells. This assay can quickly screen large numbers of chemical compounds that may be useful against KS.

Further, this invention provides an assay system that is employed to identify drugs or other molecules capable of binding to the DNA molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention is further illustrated in the Experimental Details section which follows. This section is set forth to aid in an understanding of the invention but is not intended to, and should not be construed to, limit in any way the invention as set forth in the claims which follow thereafter

EXPERIMENTAL DETAILS SECTION I

Experiment 1

Representational difference analysis (RDA) to identify and characterize unique DNA sequences in KS tissue To search for foreign DNA sequences belonging to an infectious agent in AIDS-KS, representational difference analysis (RDA) was employed to identify and characterize unique DNA sequences in KS tissue that are either absent or present in low copy number in non-diseased tissue obtained from the same patient [58]. This method can detect adenovirus genome added in single copy to human DNA but has not been used to identify previously uncultured infectious agents. RDA is performed by making simplified "representations" of genomes from diseased and normal tissues from the same individual through PCR amplification of short restriction fragments. The DNA representation from the diseased tissue is then ligated to a priming sequence and hybridized to an excess of unligated, normal tissue DNA representation. Only unique sequences found in the diseased tissue have priming sequences on both DNA strands and are preferentially amplified during subsequent rounds of PCR amplification. This process can be repeated using different ligated priming sequences to enrich the sample for unique DNA sequences that are only found in the tissue of interest.

Figure 1:
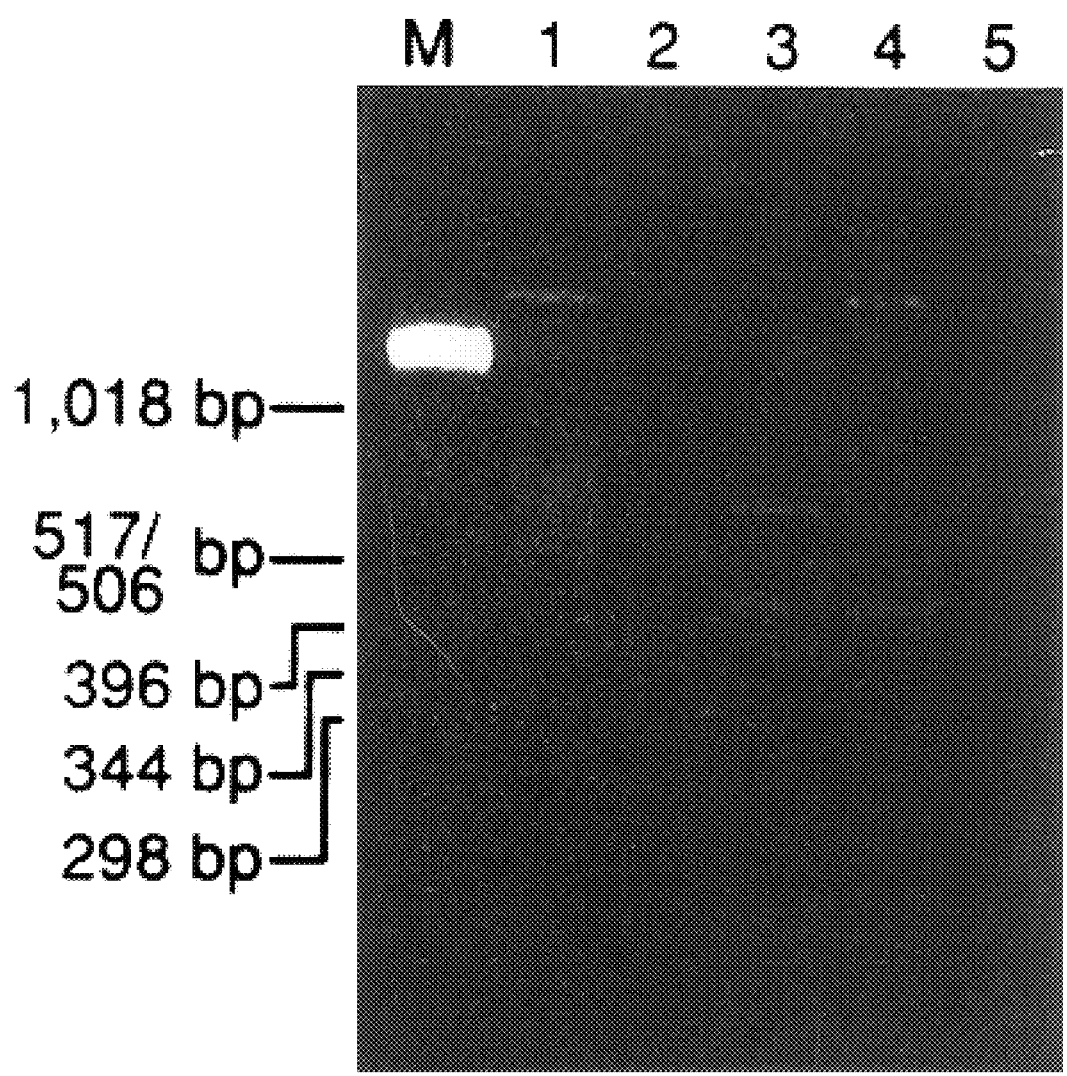
FIG. 1: Agarose gel electrophoresis of RDA products from AIDS-KS tissue and uninvolved tissue. RDA was performed on DNA extracted from KS skin tissue and uninvolved normal skin tissue obtained at autopsy from a homosexual man with AIDS-KS. Lane 1 shows the initial PCR amplified genomic representation of the AIDS-KS DNA after Bam HI digestion. Lanes 2–4 show that subsequent cycles of ligation, amplification, hybridization and digestion of the RDA products resulted in amplification of discrete bands at 380, 450, 540 and 680 bp. RDA of the extracted AIDS-KS DNA performed against itself resulted in a single band at 540 bp (lane 5). Bands at 380 bp and 680 bp correspond to KS330Bam and KS627Bam respectively after removal of 28 bp priming sequences. Bands at 450 and 540 bp hybridized nonspecifically to both KS and non-KS human DNA. Lane M is a molecular weight marker.

DNA (10 $\mu$g) extracted from both the KS lesion and unaffected tissue were separately digested to completion with Bam HI (20 units/$\mu$g) at 37° C. for 2 hours and 2 $\mu$g of digestion fragments were ligated to NBam12 and NBam24 priming sequences [primer sequences described in 58]. Thirty cycles of PCR amplification were performed to amplify "representations" of both genomes. After construction of the genomic representations, KS tester amplicons between 150 and 1500 bp were isolated from an agarose gel and NBam priming sequences were removed by digestion with Bam HI. To search for unique DNA sequences not found in non-KS driver DNA, a second set of priming sequences (JBam12 and JBam24) was ligated onto only the KS tester DNA amplicons (FIG. 1, lane 1). 0.2 μg of ligated KS lesion amplicons were hybridized to 20 μg of unligated, normal tissue representational amplicons. An aliquot of the hybridization product was then subjected to 10 cycles of PCR amplification using JBam24, followed by mung bean nuclease digestion. An aliquot of the mung bean-treated difference product was then subjected to 15 more cycles of PCR with the JBam24 primer (FIG. 1, lane 2). Amplification products were redigested with Bam HI and 200 ng of the digested product was ligated to RBam12 and RBam24 primer sets for a second round of hybridization and PCR amplification (FIG. 1, lane 3). This enrichment procedure was repeated a third time using the JBam primer set (FIG. 1, lane 4). Both the original driver and the tester DNA samples (Table 2, Patient A) were subsequently found to contain the AIDS-KS specific sequences KS330Bam and KS631Bam (previously identified as KS627Bam) indicating that RDA can be successfully employed when the target sequences are present in unequal copy number in both tissues.

The initial round of DNA amplification-hybridization from KS and normal tissue resulted in a diffuse banding pattern (FIG. 1, lane 2), but four bands at approximately 380, 450, 540 and 680 bp were identifiable after the second amplification-hybridization (FIG. 1, lane 3). These bands became discrete after a third round of amplification-hybridization (FIG. 1, lane 4). Control RDA, performed by hybridizing DNA extracted from AIDS-KS tissue against itself, produced a single band at approximately 540 bp (FIG. 1, lane 5). The four KS-associated bands (designated KS330Bam, KS390Bam, KS480Bam, KS627Bam after digestion of the two flanking 28 bp ligated priming sequences with Bam HI) were gel purified and cloned by insertion into the pCRII vector. PCR products were cloned in the pCRII vector using the TA cloning system (Invitrogen Corporation, San Diego, Calif.).

Experiment 2

Determination of the specificity of AIDS-KS unique sequences.

To determine the specificity of these sequences for AIDS-KS, random-primed $^{32}$P-labeled inserts were hybridized to Southern blots of DNA extracted from cryopreserved tissues obtained from patients with and without AIDS. All AIDS-KS specimens were examined microscopically for morphologic confirmation of KS and immunohistochemically for Factor VIII, Ulex europaeus and CD34 antigen expression. One of the AIDS-KS specimens was apparently mislabeled since KS tissue was not detected on microscopic examination but was included in the KS specimen group for purposes of statistical analysis. Control tissues used for comparison to the KS lesions included 56 lymphomas from patients with and without AIDS, 19 hyperplastic lymph nodes from patients with and without AIDS, 5 vascular tumors from nonAIDS patients and 13 tissues infected with opportunistic infections that commonly occur in AIDS patients. Control DNA was also extracted from a consecutive series of 49 surgical biopsy specimens from patients without AIDS. Additional clinical and demographic information on the specimens was not collected to preserve patient confidentiality.

The tissues, listed in Table 1, were collected from diagnostic biopsies and autopsies between 1983 and 1993 and stored at −70° C. Each tissue sample was from a different patient, except as noted in Table 1. Most of the 27 KS specimens were from lymph nodes dissected under surgical conditions which diminishes possible contamination with normal skin flora. All specimens were digested with Bam HI prior to hybridization. KS390Bam and KS480Bam hybridized nonspecifically to both KS and non-KS tissues and were not further characterized. 20 of 27 (74%) AIDS-KS DNAs hybridized with variable intensity to both KS330Bam and KS627Bam, and one additional KS specimen hybridized only to KS627Bam by Southern blotting (FIG. 2 and Table 1). In contrast to AIDS-KS lesions, only 6 of 39 (15%) non-KS tissues from patients with AIDS hybridized to the KS330Bam and KS627Bam inserts (Table 1).

Specific hybridization did not occur with lymphoma or lymph node DNA from 36 persons without AIDS or with control DNA from 49 tissue biopsy specimens obtained from a consecutive series of patients. DNA extracted from several vascular tumors, including a hemangiopericytoma, two angiosarcomas and a lymphangioma, were also negative by Southern blot hybridization. DNA extracted from tissues with opportunistic infections common to AIDS patients, including 7 acid-fast bacillus (undetermined species), 1 cytomegalovirus, 1 cat-scratch bacillus, 2 cryptococcus and 1 toxoplasmosis infected tissues, were negative by Southern blot hybridization to KS330Bam and KS627Bam (Table 1).

TABLE 1

Southern blot hybridization for KS330Bam and KS627Bam and PCR amplification for KS330$_{234}$ in human tissues from individual patients

| Tissue | n | KS330Bam Southern hybridization n (%) | KS627Bam Southern hybridization n (%) | KS330$_{234}$ PCR positive |
|---|---|---|---|---|
| AIDS-KS | 27* | 20 (74) | 21 (78) | 25 (93) |
| AIDS lymphomas | 27† | 3 (11) | 3 (11) | 3 (11) |
| AIDS lymph nodes | 12 | 3 (25) | 3 (25) | 3 (25) |
| Non-AIDS Lymphomas | 29 | 0 (0) | 0 (0) | 0 (0) |
| Non-AIDS lymph nodes | 7 | 0 (0) | 0 (0) | 0 (0) |
| Vascular tumors | 4§ | 0 (0) | 0 (0) | 0 (0) |
| Opportunistic infections | 13Π | 0 (0) | 0 (0) | 0 (0) |
| Consecutive surgical biopsies | 49¶** | 0 (0) | 0 (0) | 0 (0) |

Legend to Table 1:
* Includes one AIDS-KS specimen unamplifiable for p53 exon 6 and one tissue which on microscopic examination did not have any detectable KS tissue present. Both of these samples were negative by Southern blot hybridization to KS330Bam and KS627Bam and by PCR amplification for the KS330$_{234}$ amplicon.
† Includes 7 small non-cleaved cell lymphomas, 20 diffuse large cell and immunoblastic lymphomas. Three of the lymphomas with immunoblastic morphology were positive for KS330Bam and KS627Bam.

‡ Includes 13 anaplastic large cell lymphomas, 4 diffuse large cell lymphomas, 4 small lymphocytic lymphomas/chronic lymphocytic leukemias, 3 hairy cell leukemias, 2 monocytoid B-cell lymphomas, 1 follicular small cleaved cell lymphoma, 1 Burkitt's lymphoma, 1 plasmacytoma.

§ Includes 2 angiosarcomas, 1 hemangiopericytoma and 1 lymphangioma.

II Includes 2 cryptococcus, 1 toxoplasmosis, 1 cat-scratch bacillus, 1 cytomegalovirus, 1 Epstein-Barr virus, and 7 acid-fast bacillus infected tissues. In addition, pure cultures of Mycobacterium avium-complex were negative by Southern hybridization and PCR, and pure cultures of Mycoplasma penetrans were negative by PCR.

¶ Tissues included skin, appendix, kidney, prostate, hernia sac, lung, fibrous tissue, gallbladder, colon, foreskin, thyroid, small bowel, adenoid, vein, axillary tissue, lipoma, heart, mouth, hemorrhoid, pseudoaneurysm and fistula track. Tissues were collected from a consecutive series of biopsies on patients without AIDS but with unknown HIV serostatus.

** Apparent nonspecific hybridization at approximately 20 Kb occurred in 4 consecutive surgical biopsy DNA samples: one colon and one hernia sac DNA sample hybridized to KS330Bam alone, another hernia sac DNA sample hybridized to KS627Bam alone and one appendix DNA sample hybridized to both KS330Bam and KS627Bam. These samples did not hybridize in the 330–630 bp range expected for these sequences and were PCR negative for $KS330_{234}$.

In addition, DNA from Epstein-Barr virus-infected peripheral blood lymphocytes and pure cultures of Mycobacterium avium-complex were also negative by Southern hybridization. Overall, 20 of 27 (74%) AIDS-KS specimens hybridized to KS330Bam and 21 of 27 (78%) AIDS-KS specimens hybridized to KS627Bam, compared to only 6 of 142 (4%) non-KS human DNA control specimens ($\chi^2$=85.02, p<10−7 and $\chi^2$=92.4, p<10−7 respectively).

Figure 2A:
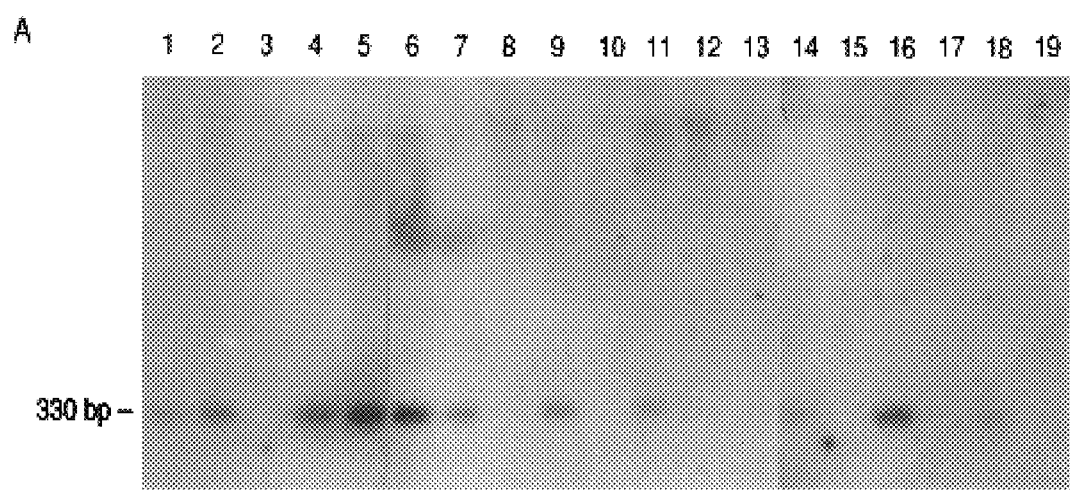
FIGS. 2A–2B: Hybridization of $^{32}$P-labelled KS330Bam (FIG. 2A) and KS627Bam (FIG. 2B) sequences to a representative panel of 19 DNA samples extracted from KS lesions and digested with Bam HI.
Figure 2B:
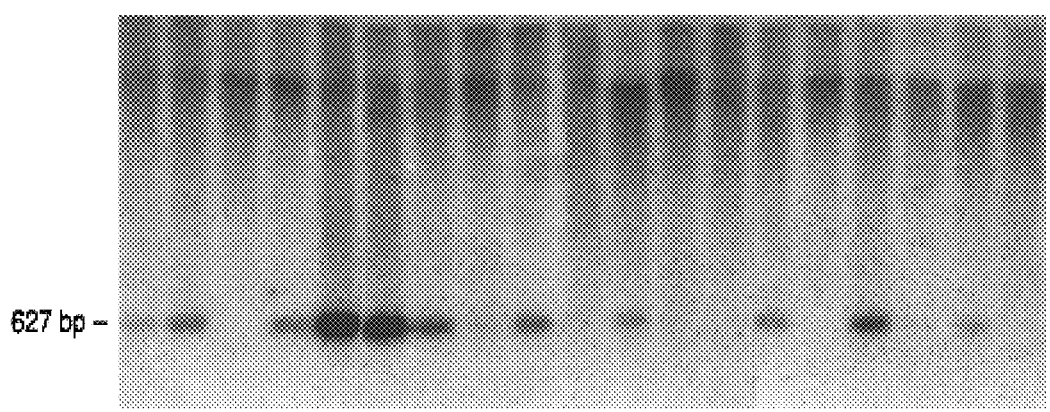

The sequence copy number in the AIDS-KS tissues was estimated by simultaneous hybridization with KS330Bam and a 440 bp probe for the constant region of the T cell receptor β gene [76]. Samples in lanes 5 and 6 of FIGS. 2A–2B showed similar intensities for the two probes indicating an average copy number of approximately two KS330Bam sequences per cell, while remaining tissues had weaker hybridization signals for the KS330Bam probe.

Experiment 3

Characterization of KS330Bam and KS627Bam

To further characterize KS330Bam and KS627Bam, six clones for each insert were sequenced. The Sequenase version 2.0 (United States Biochemical, Cleveland, Ohio) system was used and sequencing was performed according to manufacturer's instructions. Nucleotides sequences were confirmed with an Applied Biosystems 373A Sequencer in the DNA Sequencing Facilities at Columbia University.

KS330Bam is a 330 bp sequence with 51% G:C content (FIG. 3B) and KS627Bam is a 627 bp sequence with a 63% G:C content (FIG. 3C). KS330Bam has 54% nucleotide identity to the BDLF1 open reading frame (ORF) of Epstein-Barr virus (EBV). Further analysis revealed that both KS330Bam and KS627Bam code for amino acid sequences with homology to polypeptides of viral origin. SwissProt and PIR protein databases were searched for homologous ORF using BLASTX [3].

KS330Bam is 51% identical by amino acid homology to a portion of the ORF26 open reading frame encoding the capsid protein VP23 (NCBI g.i. 60348, bp 46024–46935) of herpesvirus saimiri [2], a gammaherpesvirus which causes fulminant lymphoma in New world monkeys. This fragment also has a 39% identical amino acid sequence to the theoretical protein encoded by the homologous open reading frame BDLF1 in EBV (NCBI g.i. 59140, bp 132403–133307) [9]. The amino acid sequence encoded by KS627Bam is homologous with weaker identity (31%) to the tegument protein, gp140 (ORF 29, NCBI g.i. 60396, bp108782–112681) of herpesvirus saimiri.

Sequence data from KS330Bam was used to construct PCR primers to amplify a 234 bp fragment designated $KS330_{234}$ (FIG. 3B). The conditions for PCR analyses were as follows: 94° C. for 2 min (1 cycle); 94° C. for 1 min, 58° C. for 1 min, 72° C. for 1 min (35 cycles) ; 72° C. extension for 5 min (1 cycle). Each PCR reaction used 0.1 µg of genomic DNA, 50 pmoles of each primer, 1 unit of Taq polymerase, 100 µM of each deoxynucleotide triphosphate, 50 mM KCl, 10 mM Tris-HCl (pH 9.0), and 0.1% Triton-X-100 in a final volume of 25 µl. Amplifications were carried out in a Perkin-Elmer 480 Thermocycler with 1-s ramp times between steps.

Although Southern blot hybridization detected the KS330Bam sequence in only 20 of 27 KS tissues, 25 of the 27 tissues were positive by PCR amplification for $KS330_{234}$ (FIGS. 4A–4B) demonstrating that KS330Bam is present in some KS lesions at levels below the threshold for detection by Southern blot hybridization. All $KS330_{234}$ PCR products hybridized to a $^{32}P$ end-labelled 25 bp internal oligomer, confirming the specificity of the PCR (FIG. 4B). Of the two AIDS-KS specimens negative for $KS330_{234}$, both specimens appeared to be negative for technical reasons: one had no microscopically detectable KS tissue in the frozen sample (FIGS. 4A–4B, lane 3), and the other (FIGS. 4A–4B, lane 15) was negative in the control PCR amplification for the p53 gene indicating either DNA degradation or the presence of PCR inhibitors in the sample. PCR amplification of the p53 tumor suppressor gene was used as a control for DNA quality. Sequences of p53 primers from PE-5, 5'-ACAGGGCTGGTTGCCCAGGGT-3' (SEQ ID No: 44); and P6–3. 5'-AGTTGCAAACCAGACCTCAG-3' (SEQ ID NO: 45) [25].

Except for the 6 control samples from AIDS patients that were also positive by Southern blot hybridization, none of the other 136 control specimens were positive by PCR for $KS330_{234}$. All of these specimens were amplifiable for the p53 gene, indicating that inadequate PCR amplification was not the reason for lack of detection of $KS330_{234}$ in the control tissues. Samples containing DNA from two candidate KS agents, EBV and Mycoplasma penetrans (ATCC Accession No. 55252), a pathogen commonly found in the genital tract of patients with AIDS-KS [59] were also negative for amplification of $KS330_{234}$. In addition, several KS specimens were tested using commercial PCR primers (Stratagene, La Jolla, Calif.) specific for mycoplasmata and primers specific for the EBNA-2, EBNA-3C and EBER regions of EBV and were negative [57].

Overall, DNA from 25 (93%) of 27 AIDS-KS tissues were positive by PCR compared with DNA from 6 (4%) of 142 control tissues, including 6 (15%) of 39 non-KS lymph nodes and lymphomas from AIDS patients ($\chi^2$=38.2, p<10−6), 0 of 36 lymph nodes and lymphomas from nonAIDS patients ($\chi^2$=55.2, p<10−7) and 0 of 49 consecutive biopsy specimens ($\chi^2$=67.7, p<10−7). Thus, $KS330_{234}$ was found in all 25 amplifiable tissues with microscopically detectable AIDS-KS, but rarely occurred in non-KS tissues, including tissues from AIDS patients.

Of the six control tissues from AIDS patients that were positive by both PCR and Southern hybridization, two patients had KS elsewhere, two did not develop KS and complete clinical histories for the remaining two patients were unobtainable. Three of the six positive non-KS tissues were lymph nodes with follicular hyperplasia taken from patients with AIDS. Given the high prevalence of KS among patients with AIDS, it is possible that undetected microscopic foci of KS were present in these lymph nodes. The other three positive tissue specimens were B cell immunoblastic lymphomas from AIDS patients. It is possible that the putative KS agent is also a cofactor for a subset of AIDS-associated lymphomas [16, 17, 80].

To determine whether KS330Bam and KS627Bam are portions of a larger genome and to determine the proximity of the two sequences to each other, samples of KS DNA were digested with Pvu II restriction enzymes. Digested genomic DNA from three AIDS-KS samples were hybridized to KS330Bam and KS627Bam by Southern blotting (FIG. 5). These sequences hybridized to various sized fragments of the digested KS DNA indicating that both sequences are fragments of larger genomes. Differences in the KS330Bam hybridization pattern to Pvu II digests of the three AIDS-KS specimens indicate that polymorphisms may occur in the larger genome. Individual fragments from the digests failed to simultaneously hybridize with both KS330Bam and KS627Bam, demonstrating that these two Bam HI restriction fragments are not adjacent to one another.

If KS330Bam and KS627Bam are heritable polymorphic DNA markers for KS, these sequences should be uniformly detected at non-KS tissue sites in patients with AIDS-KS. Alternatively, if KS330Bam and KS627Bam are sequences specific for an exogenous infectious agent, it is likely that some tissues are uninfected and lack detectable KS330Bam and KS627Bam sequences. DNA extracted from multiple uninvolved tissues from three patients with AIDS-KS were hybridized to $^{32}$P-labelled KS330Bam and KS627Bam probes as well as analyzed by PCR using the KS330$_{234}$ primers (Table 2). While KS lesion DNA samples were positive for both bands, unaffected tissues were frequently negative for these sequences. KS lesions from patients A, B and C, and uninvolved skin and muscle from patient A were positive for KS330Bam and KS627Bam, but muscle and brain tissue from patient B and muscle, brain, colon, heart and hilar lymph node tissues from patient C were negative for these sequences. Uninvolved stomach lining adjacent to the KS lesion in patient C was positive by PCR, but negative by Southern blotting which suggests the presence of the sequences in this tissue at levels below the detection threshold for Southern blotting.

TABLE 2

Differential detection of KS330Bam, KS627Bam and KS330$_{234}$ sequences in KS-involved and non-involved tissues from three patients with AIDS-KS

|  | KS330Bam | KS627Bam | KS330$_{234}$ |
| --- | --- | --- | --- |
| Patient A |  |  |  |
| KS, skin | + | + | + |
| nl skin | + | + | + |
| nl muscle | + | + | + |

TABLE 2-continued

Differential detection of KS330Bam, KS627Bam and KS330$_{234}$ sequences in KS-involved and non-involved tissues from three patients with AIDS-KS

|  | KS330Bam | KS627Bam | KS330$_{234}$ |
| --- | --- | --- | --- |
| Patient B |  |  |  |
| KS, skin | + | + | + |
| nl muscle | − | − | − |
| nl brain | − | − | − |
| Patient C |  |  |  |
| KS, stomach | + | + | + |
| nl stomach adjacent to KS | − | − | + |
| nl muscle | − | − | − |
| nl brain | − | − | − |
| nl colon | − | − | − |
| nl heart | − | − | − |
| nl hilar lymph nodes | − | − | − |

Experiment 4

Subcloning and sequencing of KSHV

KS330Bam and KS627Bam are genomic fragments of a novel 5 infectious agent associated with AIDS-KS. A genomic library from a KS lesion was made and a phage clone with a 20 kb insert containing the KS330Bam sequence was identified. The 20 kb clone digested with PvuII (which cuts in the middle of the KS330Bam sequence) produced 1.1 kb and 3 kb fragments that hybridized to KS330Bam. The 1.1 kb subcloned insert and ~900 bp from the 3 kb subcloned insert resulting in 9404 bp of contiguous sequence was entirely sequenced. This sequence contains partial and complete open reading frames homologous to regions in gamma herpesviruses.

The KS330Bam sequence is an internal portion of an 918 bp ORF with 55–56% nucleotide identity to the ORF26 and BDLF1 genes of HSVSA and EBV respectively. The EBV and HSVSA translated amino acid sequences for these ORFs demonstrate extensive homology with the amino acid sequence encoded by the KS-associated 918 bp ORF (FIG. 6). In HSVSA, the VP23 protein is a late structural protein involved in capsid construction. Reverse transcriptase (RT)-P(R of mRNA from a KS lesion is positive for transcribed KS330Bam mRNA and that indicates that this ORF is transcribed in KS lesions. Additional evidence for homology between the KS agent and herpesviruses comes from a comparison of the genomic organization of other potential ORFs on the 9404 bp sequence (FIG. 3A) The 5' terminus of the sequence is composed nucleotides having 66–67% nucleotide identity and 68–71% amino acid identity to corresponding regions of the major capsid protein (MCP) ORFs for both EBV and HSVSA. This putative MCP ORF of the KS agent lies immediately 5' to the BDLF1/ORF26 homolog which is a conserved orientation among herpesvirus subfamilies for these two genes. At the 3' end of this sequence, the reading frame has strong amino acid and nucleotide homology to HSVSA ORF 27. Thus, KS-associated DNA sequences at four loci in two separate regions with homologies to gamma herpesviral genomes have been identified.

In addition to fragments obtained from Pvu II digest of the 21 Kb phage insert described above, fragments obtained from a BamHI/NotI digest were also subcloned into pBluescript (Stratagene, La Jolla, Calif.). The termini of these subcloned fragments were sequenced and were also found to be homologous to nucleic acid sequence EBV and HSVSA genes. These homologs have been used to develop a preliminary map of subcloned fragments (FIG. 9). Thus, sequencing has revealed that the KS agent maintains co-linear homology to gamma herpesviruses over the length of the 21 Kb phage insert.

Experiment 5

Determination of the phylogeny of KSHV

Regions flanking KS330Bam were sequenced and characterized by directional walking. This was performed by the following strategy: 1) KS genomic libraries were made and screened using the KS330Bam fragment as a hybridization probe, 2) DNA inserts from phage clones positive for the KS330Bam probe were isolated and digested with suitable restriction enzyme(s), 3) the digested fragments were subcloned into pBluescript (Stratagene, La Jolla, Calif.), and 4) the subclones were sequenced. Using this strategy, the major capsid protein (MCP) ORF homolog was the first important gene locus identified. Using sequenced unique 3' and 5' end-fragments from positive phage clones as probes, and following the strategy above a KS genomic library are screened by standard methods for additional contiguous sequences.

For sequencing purposes, restriction fragments are subcloned into phagemid pBluescript KS+, pBluescript KS−, pBS+, or pBS− (Stratagene) or into plasmid pUC18 or pUC19. Recombinant DNA was purified through CsCl density gradients or by anion-exchange chromatography (Qiagen).

Nucleotide sequenced by standard screening methods of cloned fragments of KSHV were done by direct sequencing of double- stranded DNA using oligonucleotide primers synthesized commercially to "walk" along the fragments by the dideoxy-nucleotide chain termination method. Junctions between clones are confirmed by sequencing overlapping clones.

Targeted homologous genes in regions flanking KS330Bam include, but are not limited to: Il-10 homolog, thymidine kinase (TK), g85 g35, gH, capsid proteins and MCP. TK is an early protein of the herpesviruses functionally linked to DNA replication an a target enzyme for anti-herpesviral nucleosides. TK phosphorylates acyclic nucleosides such as acyclovir which in turn inhibit viral DNA polymerase chain extension. Determining the sequence of this gene will aid in the prediction of chemotherapeutic agents useful against KSHV. TK is encoded by the EBV BXLF1 ORF located ~9700 bp rightward of BDLF1 and by the HSVSA ORF 21 ~9200 bp rightward of the ORF 26. A subcloned fragment of KS5 was identified with strong homology to the EBV and HSVSA TK open reading frames.

g85 is a late glycoprotein involved in membrane fusion homologous to gH in HSV1. In EBV, this protein is encoded by BLXF2 ORF located ~7600 bp rightward of BDLF1, and in HSVSA it is encoded by ORF 22 located ~7100 bp rightward of ORF26.

g35 is a late EBV glycoprotein found in virion and plasma membrane. It is encoded by BDLF3 ORF which is 1300 bp leftward of BDLF1 in EBV. There is no BDLF3 homolog in HSVSA. A subcloned fragment has already been identified with strong homology to the EBV gp35 open reading frame.

Major capsid protein (MCP) is a conserved 150 KDa protein which is the major component of herpesvirus capsid. Antibodies are generated against the MCP during natural infection with most herpesviruses. The terminal 1026 bp of this major capsid gene homolog in KSHV have been sequenced.

Targeted homologous genes/loci in regions flanking KS627Bam include, but are not limited to: terminal reiterated repeats, LMPI, EBERs and Ori P. Terminal reiterated sequences are present in all herpesviruses. In EBV, tandomly reiterated 0.5 Kb long terminal repeats flank the ends of the linear genome and become joined in the circular form. The terminal repeat region is immediately adjacent to BNRF1 in EBV and ORF 75 in HSVSA. Since the number of terminal repeats varies between viral strains, identification of terminal repeat regions may allow typing and clonality studies of KSHV in KS legions. Sequencing through the terminal repeat region may determine whether this virus is integrated into human genome in KS.

LMPI is an latent protein important in the transforming effects of EBV in Burkitt's lymphoma. This gene is encoded by the EBV BNRF1 ORF located ~2000 bp rightward of tegument protein ORF BNRF1 in the circularized genome. There is no LMP1 homolog in HSVSA.

EBERs are the most abundant RNA in latently EBV infected cells and Ori-P is the origin of replication for latent EBV genome. This region is located between ~4000–9000 bp leftward of the BNRF1 ORF in EBV; there are no corresponding regions in HSVSA.

The data indicates that the KS agent is a new human herpesvirus related to gamma herpesviruses EBV and HSVSA. The results are not due to contamination or to incidental co-infection with a known herpesvirus since the sequences are distinct from all sequenced herpesviral genomes (including EBV, CMV, HHV6 and HSVSA) and are associated specifically with KS in three separate comparative studies. Furthermore, POR testing of KS DNA with primers specific for EBV-1 and EBV-2 failed to demonstrate these viral genomes in these tissues. Al though KSHV is homologous to EBV regions, the sequence does not match any other known sequence and thus provides evidence for a new viral genome, related to but distinct from known members of the herpesvirus family.

Experiment 6

Serological studies

Indirect immunofluorescence assay (IFA)

Virus-containing cells are coated to a microscope slide. The slides are treated with organic fixatives, dried and then incubated with patient sera. Antibodies in the sera bind to the cells, and then excess nonspecific antibodies are washed off. An antihuman immunoglobulin linked to a fluorochrome, such as fluorescein, is then incubated with the slides, and then excess fluorescent immunoglobulin is washed off. The slides are then examined under a microscope and if the cells fluoresce, then this indicates that the sera contains antibodies directed against the antigens present in the cells, such as the virus.

An indirect immunofluorescence assay (IFA) was performed on the Body Cavity-Based Lymphoma cell line (BCBL-1), which is a naturally transformed EBV infected (nonproducing) B cell line, using 4 KS patient sera and 4 control sera (from AIDS patients without KS). Initially, both sets of sera showed similar levels of antibody binding. To remove nonspecific antibodies directed against EBV and lymphocyte antigens, sera at 1:25 dilution were pre-adsorbed using $3 \times 10^6$ 1% paraformaldehyde-fixed Raji cells per ml of sera. BCBL1 cells were fixed with ethanol/ acetone, incubated with dilutions of patient sera, washed and incubated with fluorescein-conjugated goat anti-human IgG. Indirect immunofluorescent staining was determined.

Table 3 shows that unabsorbed case and control sera have similar end-point dilution indirect immunofluorescence assay (IFA) titers against the BCBL1 cell line. After Raji adsorption, case sera have four-fold higher IFA titers against BCBL1 cells than control sera. Results indicated that pre-adsorption against paraformaldehyde-fixed Raji cells reduces fluorescent antibody binding in control sera but do not eliminate antibody binding to KS case sera. These results indicate that subjects with KS have specific antibodies directed against the KS agent that can be detected in serological assays such as IFA, Western blot and Enzyme immunoassays (Table 3).

TABLE 3

Indirect immunofluorescence end-point titers for KS case and non-KS control sera against the BCBL-1 cell line

| Sera No. | Status* | Pre-adsorption | Post-adsorption** |
|---|---|---|---|
| 1 | KS | ≧1:400 | ≧1:400 |
| 2 | KS | 1:100 | 1:100 |
| 3 | KS | 1:200 | 1:100 |
| 4 | KS | ≧1:400 | 1:200 |
| 5 | Control | ≧1:400 | 1:50 |
| 6 | Control | 1:50 | 1:50 |
| 7 | Control | 1:100 | 1:50 |
| 8 | Control | 1:200 | 1:50 |

Legend Table 3:
*KS = autopsy-confirmed male, AIDS patient
Control = autopsy-confirmed female, AIDS patient, no KS
**Adsorbed against RAJI cells treated with 1% paraformaldehyde Immunoblotting ("Western blot")

Virus-containing cells or purified virus (or a portion of the virus, such as a fusion protein) is electrophoresed on a polyacrylamide gel to separate the protein antigens by molecular weight. The proteins are blotted onto a nitrocellulose or nylon membrane, then the membrane is incubated in patient sera. Antibodies directed against specific antigens are developed by incubating with a anti-human immunoglobulin attached to a reporter enzyme, such as a peroxidase. After developing the membrane, each antigen reacting against antibodies in patient sera shows up as a band on the membrane at the corresponding molecular weight region.

Enzyme immunoassay ("EIA or ELISA")

Virus-containing cells or purified virus (or a portion of the virus, such as a fusion protein) is coated to the bottom of a 96-well plate by various means (generally incubating in alkaline carbonate buffer). The plates are washed, then the wells are incubated with patient sera. Antibodies in the sera directed against specific antigens stick on the plate. The wells are washed again to remove nonspecific antibody, then they are incubated with a antihuman immunoglobulin attached to a reporter enzyme, such as a peroxidase. The plate is washed again to remove nonspecific antibody and then developed. Wells containing antigen that is specifically recognized by antibodies in the patients sera change color and can be detected by an ELISA plate reader (a spectrophotomer).

All three of these methods can be made more specific by pre-incubating patient sera with uninfected cells to adsorb out cross-reacting antibodies against the cells or against other viruses that may be present in the cell line, such as EBV. Cross-reacting antibodies can potentially give a falsely positive test result (i.e. the patient is actually not infected with the virus but has a positive test result because of cross-reacting antibodies directed against cell antigens in the preparation). The importance of the infection experiments with Raji is that if Raji cells, or another well-defined cell line, can be infected, then the patient's sera can be pre-adsorbed against the uninfected parental cell line and then tested in one of the assays. The only antibodies left in the sera after pre-adsorption that bind to antigens in the preparation should be directed against the virus.

Experiment 7

BCBL 1, from lymphomatous tissues belonging to a rare infiltrating, anaplastic body cavity lymphoma occurring in AIDS patients has been placed in continuous cell culture and shown to be continuously infected with the KS agent. This cell line is also naturally infected with Epstein-Barr Virus (EBV). The BCBL cell line was used as an antigen substrate to detect specific KS antibodies in persons infected with the putative virus by Western-blotting. Three lymphoid B cell lines were used as controls. These included the EBV genome positive cell line P3H3, the EBV genome defective cell line Raji and the EBV genome negative cell line Bjab.

Cells from late-log phase culture were washed 3 time with PBS by centrifugation at 500 g for 10 min. and suspended in sample buffer containing 50 mM Tris-HCl pH 6.8, 2% SDS (w/v), 15% glycerol (v/v), 5% β-mercaptoethanol (v/v) and 0.001% bromophenol (w/v) with protease inhibitor, 100 $\mu$M phenylmethylsulfonyl fluoride (PMSF). The sample was boiled at 100° C. for 5 min and centrifuged at 14,000 g for 10 min. The proteins in the supernatant was then fractionated by sodium, dodecyl sulfate-polyacrylamide gel electrophoresis (SDS-PAGE) under reducing conditions with a separation gel of 15% and a stacking gel of 5% (3). Prestained protein standards were included: myosin, 200 kDa; β-galactosidase, 118 kDA; BSA, 78 kDa; ovalbumin, 47.1 kDa; carbonic anhydrase, 31.4 kDa; soybean trypsin inhibitor, 25.5 kDa, lysozyme, 18.8 kDa and aprotinin, 8.3 kDa (Bio-Rad). Immunoblotting experiments were performed according to the method of Towbin et al. (4). Briefly, the proteins were electrophorectically transferred to Hybon-C extra membranes (Pharmacia) at 24 V for 70 min. The membranes were then dried at 37° C. for 30 min, saturated with 5% skim milk in Tris-buffered saline, pH 7.4 (TBS) containing 50 mM Tris-HCl and 200 mM NaCl, at room temperature for 1 h. The membranes were subsequently incubated with human sera at dilution 1:200 in 1% skim milk overnight at room temperature, washed 3 times with a solution containing TBS, 0.2% Triton X-100 and 0.05% skim milk and then 2 times with TBS. The membranes were then incubated for 2 h at room temperature with alkaline phosphatase conjugated goat anti-mouse IgG+IgM+ IgA (Sigma) diluted at 1:5000 in 1% skim milk. After repeating the washing, the membranes were stained with nitroblue tetranolium chloride and 5-bromo-4-chloro-3-indolylphosphate p-toluidine salt (Gibco BRL).

Two bands of approximately 226 kDa and 234 kDa were identified to be specifically present on the Wester-blot of BCBL cell lysate in 5 sera from AIDS gay man patients infected with KS. These 2 bands were absent from the lysates of P3H3, Raji and Bjab cell lysates. 5 sera from AIDS gay man patients without KS and 2 sera from AIDS woman patients without KS as well as 1 sera from nasopharyncel carcinoma patient were not able to detect these 2 bands in BCBL 1, P3H3, Raji and Bjab cell lysates. In a blinded experiment, using the 226 kDa and 234 kDa markers, 15 out of 16 sera from KS patients were correctly identified. In total, the 226 kDa and 234 kDa markers were detected in 20 out of 21 sera from KS patients.

The antigen is enriched in the nuclei fraction of BCBL1. Enriched antigen with low background can be obtained by preparing nucleic from BCBC as the starting antigen preparation using standard, widely available protocols. For example, 500–750 ml of BCBL at $5\times10^5$ cells/ml can be pelleted at low speed. The pellet is placed in 10 mM NaCl, 10 mM Tris pH 7.8, 1.5 mM $MgCl_2$ (equi volume)+1.0% NP-40 on ice for 20 min to lyse cells. The lysate is then spun at 1500 rpm for 10 min. to pellet nucleic. The pellet is used as the starting fraction for the antigen preparation for the Western blot. This will reduce cross- reactive cytoplasmic antigens.

Experiment 8

Transmission studies
Co-infection experiments

BCBL1 cells were co-cultivated with Raji cell lines separated by a $0.45\mu$ tissue filter insert. Approximately, $1–2\times10^6$ BCBL1 and $2\times10^6$ Raji cells were co-cultivated for 2–20 days in supplemented RPMI alone, in 10 $\mu$g/ml 5'-bromodeoxyuridine (BUdR) and 0.6 $\mu$g/ml 5'-flourodeoxyuridine or 20 ng/ml 12-O-tetradecanoylphorbol-13-acetate (TPA). After 2,8,12 or 20 days co-cultivation, Raji cells were removed, washed and placed in supplemented RPMI 1640 media. A Raji culture co-cultivated with BCBL1 in 20 ng/ml TPA for 2 days survived and has been kept in continuous suspension culture for >10 weeks. This cell line, designated RCC1 (Raji Co-Culture, No. 1) remains PCR positive for the $KS330_{234}$ sequence after multiple passages. This cell line is identical to its parental Raji cell line by flow cytometry using EMA, B1, B4 and BerH2 lymphocyte-flow cytometry (approximately 2%). RCC1 periodically undergo rapid cytolysis suggestive of lytic reproduction of the agent. Thus, RCC1 is a Raji cell line newly infected with KSHV.

The results indicate the presence of a new human virus, specifically a herpesvirus in KS lesions. The high degree of association between this agent and AIDS-KS (>90%), and the low prevalence of the agent in non-KS tissues from immunocompromised AIDS patients, indicates that this agent has a causal role in AIDS-KS [47, 68].

Experiment 10

Isolation of KSHV

Crude virus preparations are made from either the supernatant or low speed pelleted cell fraction of BCBL1 cultures. Approximately 650 ml or more of log phase cells should be used ($>5\times10^6$ cells/ml).

For bonding whole virion from supernatant, the cell free supernatant is spun at 10,000 rpm in a GSA rotor for 10 min to remove debris. PEG-8000 is added to 7%, dissolved and placed on ice for >2.5 hours. The PEG-supernatant is then spun at 10,000×g for 30 min. supernatant is poured off and the pellet is dried and scraped together from the centrifuge bottles. The pellet is then resuspended in a small volume (1–2 ml) of virus buffer (VB, 0.1 M NaCl, 0.01 M Tris, pH 7.5). This procedure will precipitate both naked genome and whole virion. The virion are then isolated by centrifugation at 25,000 rpm in a 10–50% sucrose gradient made with VB. One ml fractions of the gradient are then obtained by standard techniques (e.g. using a fractionator) and each fraction is then tested by dot blotting using specific hybridizing primer sequences to determine the gradient fraction containing the purified virus (preparation of the fraction maybe needed in order to detect the presence of the virus, such as standard DNA extraction).

To obtain the episomal DNA from the virus, the pellet of cells is washed and pelleted in PBS, then lysed using hypotonic shock and/or repeated cycles of freezing and thawing in a small volume (<3 ml). Nuclei and other cytoplasmic debris are removed by centrifugation at 10,000 g for 10 min, filtration through a 0.45 m filter and then repeat centrifugation at 10,000 g for 10 min. This crude preparation contains viral genome and soluble cell components. The genome preparation can then be gently chloroform-phenol extracted to remove associated proteins or can be placed in neutral DNA buffer (1 M NaCl, 50 mM Tris, 10 mM EDTA, pH 7.2–7.6) with 2% sodium dodecylsulfate (SDS) and 1% sarcosyl. The genome is then banded by centrifugation through 10–30% sucrose gradient in neutral DNA buffer containing 0.15% sarcosyl at 20,000 rpm in a SW 27.1 rotor for 12 hours (for 40,000 rpm for 2–3 hours in an SW41 rotor). The band is detected as described above.

An example of the method for isolating KSHV genome from KSHV infect ed cell cultures (97 and 98). Approximately 800 ml of BCBL1 cells are pelleted, washed with saline, and pelleted by low speed centrifugation. The cell pellet is lysed with an equal volume of RSB (10 mM NaCl, 10 mM Tris-HCl, 1.5 mM MgCl2, pH 7.8) with 1% NP-40 on ice for 10 minutes. The lysate is centrifuged at 900×g for 10 minutes to pellet nuclei. This step is repeated. To the supernatant is added 0.4% sodium dodecylsulfate and EDTA to a final concentration of 10 mM. The supernatant is loaded on a 10–30% sucrose gradient in 1.0 M NaCl, 1 mM EDTA, 50 mM Tris-HCl, pH 7.5. The gradients are centrifuged at 20,000 rpm on a SW 27.1 rotor for 12 hours. In FIG. 11, 0.5 ml aliquots of the gradient have been fractionated (fractions 1–62) with the 30% gradient fraction being at fraction No. 1 and the 10%. gradient fraction being at fraction No. 62. Each fraction has been dot hybridized to a nitrocellulose membrane and then a $^{32}$P-labeled KSHV DNA fragment, KS631Bam has been hybridized to the membrane using standard techniques. FIG. 11 shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

EXPERIMENT 11

Purification of KSHV

DNA is extracted using standard techniques from the RCC-1 or RCC-$1_{2F5}$ cell line [27, 49, 66]. The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at $>1\times10^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of $>1\times10^6$ cells/ml. The media is centrifuged at 2000×g for 10 minutes and filtered through a $0.45\mu$ filter to remove cells. The media is applied in a 1:1 volume with cells growing at $>1\times10^6$ cells/ml for 48 hours. The cells are washed and pelleted and placed in fresh culture medium, and tested after 14 days of growth.

The herpesvirus may be isolated from the cell DNA in the following manner. An infected cell line, which can be lysed using standard methods such as hyposmotic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45μ filter and centrifuged again at 100,000×g for 1 hour to pellet the virus. The virus can then be washed and centrifuged again at 100,000×g for 1 hour.

REFERENCES

1. Ablashi, D. V., et al. *Virology* 184:545–552.
2. Albrecht, J. C., et al. (1992) *J. Virol.* 66:5047.
3. Altshul, S. F., et al. (1990) *J. Molec. Biol.* 215:403.
4. *Analytical Biochemistry* (1984) 238:267–284.
5. Andrei, et al. (1992) *Eur. J. Clin. Microbiol. Infect. Dis.* 11(2):143–51.
6. Archibald, C. P., et al. (1992) *Epidemiol.* 3:203.
7. Asada, H., et al (1989) *J. Clin. Microbiol.* 27(10):2204.
8. Ausubel, F., et al. (1987) *Current Protocols in Molecular Biology*, New York.
9. Baer, R. J., et al. (1984) *Nature* 310:207.
10. Bagasra, et al. (1992) *J. New England Journal of Medicine* 326(21):1385–1391.
11. Balzarini, et al. (1990) *Mol. Pharm.* 37,402–7.
12. *Basic and Clinical Immunology* 7th Edition D. Stites and A. Terr ed.
13. Beral, V., et al. (1990) *Lancet* 335:123.
14. Beral, V., et al. (1991) *Brit. Med. J.* 302:624.
15. Beral, V., et al. (1992) *Lancet* 339:632.
16. Bendsöe, N., et al. (1990) *Eur. J. Cancer* 26:699.
17. Biggar, R. J., et al. (1994) *Am. J. Epidemiol.* 139:362.
18. Bovenzi, P., et al. (1993) *Lancet* 341:1288.
19. Beaucage and Carruthers (1981) *Tetrahedron Lett.* 22:1859–1862.
20. Braitman, et al. (1991) *Antimicrob. Agents and Chemotherapy* 35(7):1464–8.
21. Burns and Sanford, (1990) *J. Infect. Dis.* 162(3):634–7.
22. De Clercq, (1993) *Antimicrobial Chemotherapy* 32, Suppl. A, 121–132.
23. Drew, W. L., et al. (1982) *Lancet* ii:125.
24. Falk, et al. (1991) *Nature* 351:290.
25. Gaidano, G., et al. (1991) *Proc. Natl. Acad. Sci. USA* 88:5413.
26. Gershon, A. A., (1992) *J. Inf. Des.* 166(Suppl):563.
27. Glick, J. L., (1980) *Fundamentals of Human Lymphoid Culture*, Marcel Dokker, New York.
28. Gorbach, S. L., et al. (1992) *Infectious Disease* Ch.35:289, W. B. Saunders, Philadelphia, Pa.
29. Greenspan, et al. (1990) *J. Acquir. Immune Defic. Syndr.* 3 (6):571.
30. Hardy, I., et al. (1990) *Inf. Dis. Clin. N. Amer.* 4(1):159.
31. Hardy, I., et al. (1991) *New Engl. J. Med.* 325 (22):1545.
31A. Harel-Bellan, A., et al. (1988) *Exp. Med.* 168:2309–2318
32. Harlow and Lane, (1988) *Antibodies, A Laboratory Manual*, Cold Spring Harbor Publication, New York.
33. Haverkos, H. W., et al. (1985) *Sexually Transm. Dis.* 12:203.
34. Helene, C. and Toulme, J. (1990) *Biochim. Biophys. Acta.* 1049:99–125.
35. Heniford, et al. (1993) *Nucleic Acids Research* 21(14):3159–3166.
36. Higashi, K., et al. (1989) *J. Clin. Micro.* 27(10):2204.
37. Holmberg, S. D., et al. (1990) *Cancer Detection and Prevention* 14:331.
38. Holliday, J., and Williams, M. V., (1992) *Antimicrob. Agents Chemother.* 36(9):1935.
39. Hoogenboom, H. R., et al. (1991) *Nuc. Acids Res.* 19:4133.
40. Hunt, et al. (1991) *Eur. J. Immunol.* 21:2963–2970.
41. *Hybridization of Nucleic Acids Immobilized on Solid Supports* Meinkoth, J. and Wahl, G.
42. *Hybridization with Nucleic Acid Probes* pp. 495–524, (1993) Elsevier, Amsterdam.
43. Ickes, et al. (1994) *Antiviral Research* 23, Seventh International Conf. on Antiviral Research, Abstract No. 122, Supp. 1.
44. Jahan, N., et al. (1989) *AIDS Research and Human Retroviruses* 5:225.
45. Jardetzkey, et al. (1991) *Nature* 353:326.
46. Johnston, G. S., et al. (1990) *Cancer Detection and Prevention* 14:337.
47. Jung, J. U., et al. (1991) *Proc. Natl. Acad. Sci. USA* 88:7051.
48. Kikuta, et al. (1989) *Lancet* Oct. 7:861.
49. Knowles, D. M., et al. (1989) *Blood* 73:792–798.
50. Kohler and Milstein, (1976) *Eur. J. Immunol.* 6:511–519.
51. Kucera, et al. (1993) *AIDS Res. Human Retroviruses* 9:307–314.
52. *Laboratory Techniques in Biochemistry and Molecular Biology* (1978) North Holland Publishing Company, New York.
53. Lasky, L. A., (1990) *J. Med. Virol.* 31(1):59.
54. Levin, M. J., et al. (1992) *J. Inf. Dis.* 166(2):253.
55. Lifson, A. R., et al. (1990) *Am. J. Epidemiol.* 131:221.
56. Lin, et al. (1991) *Antimicrob Agents Chemother* 35(11):2440–3.
57. Lin, J. C., et al. (1993) *Blood* 81:3372.
58. Lisitsyn, N., et al. (1993) *Science* 259:946.
59. Lo, S -C., et al. (1992) *Internat. J. Systematic Bacteriol.* 42:357.
60. Marks, J. D., et al. (1991) J. Mol Biol. 222:581–597.
61. Marloes, et al. (1991) *Eur. J. Immunol.* 21:2963–2970.
62. Matteucci, et al. (1981) *Am. Chem. Soc.* 103:3185.
63. Maxam, A. M. and Gilbert, W. *Methods in Enzymology* (1980) Grossman, L. and Moldave, D., eds., Academic Press, New York, 65:499–560.
64. McCafferty, J., et al. (1990) *Nature* 348:552.
65. Means and Feeney, (1990) *Bioconjugate Chem.* A recent reveiw of protein modification techniques, 1:2–12.
66. Metcalf, D. (1984) *Clonal Culture of Hematopoeitic Cells:Techniques and Applications*, Elvier, New York.
67. *Methods in Enzymology* Vol. 152, (1987) Berger, S. and Kimmel, A. ed., Academic Press, New York
68. Miller, G., *Virology* (1990) B. N. Fields, D. M. Knipe eds., Raven Press, New York, 2:1921.
69. Needham-VanDevanter, D. R., et al., (1984) *Nucelic Acids Res.* 12:6159–6168.
70. Needleman and Wunsch, (1970) *J. Mol. Biol.* 48:443.
71. Neuvo, et al. (1993) *American Journal of Surgical Pathology* 17(7), 683–690.
72. *Nucleic Acid Hybridization: A Practical Approach* (1985) Ed. Hames, B. D. and Higgins, S. J., IRL Press.
73. Oren and Soble, (1991) *Clinical Infectious Diseases* 14:741–6.
74. *PCR Protocols: A Guide to Methods and Applications.* (1990) Innis, M., Gelfand D., Sninsky, J. and White, T., eds., Academic Press, San Diego.
75. Pearson and Lipman, (1988) *Proc. Natl. Acad. Sci.* (*USA*) 85:2444.
75A. Pearson, J. D., and Regnier, F. E., (1983) *J. Chrom.* 255:137–14976.

76. Pellici, P. G., et al. (1985) *J. Exp. Med.* 162:1015.
77. Peterman, T. A., et al. (1991) *Cancer Surveys Imperial Cancer Research Fund*, London, 10:23–37.
78. Roizman, B. (1991) *Rev. Inf. Disease* 13 Suppl. 11:S892.
79. Rötzschke and Falk, (1991) *Immunol. Today* 12:447.
80. Safai, B., et al. (1980) *Cancer* 45:147:2.
81. Sambrook, et al. (1989) *Molecular Cloning: A Laboratory Manual* (2nd ed.), Cold Spring Harbor Laboratory, Vols. 1–3.
82. Saunders, et al. (1990) *J. Acquir. Immune Defic. Syndr.* 3 (6):571.
83. Schecter, M. T., et al. (1991) *Am. J. Epidemiol.* 134:485.
84. Scopes, R., (1982) *Protein Purification: Principles and Practice* Springer-Verlag, New York.
85. Siddiqui, A., et al. (1983) *Proc. Natl. Acad. Sci. USA* 80:4861.
86. Skinner, G. R., et al. (1991) *Comp. Immuno. Microbiol. Inf. Dis.* 14(2):13.
87. Skinner, G. R., et al. (1992) *Med. Microbiol. Immunol.* 180(6):305. Smith and Waterman (1981) *Adv. Appl. Math.* 2:482.
88. Snoeck, et al. (1992) *Eur. J. Clin. Micro. Infect. Dis.* 11(12):1144–55.
89. Stals, et al. (1993) *Antimicrobial Agents Chemother.* 37(2):218–23.
90. van den Berg, F. et al. (1989) *J. Clin. Pathol.* 42:128.
91. Vogel, J., et al. (1988) *Nature* 335:606.
92. Wang, R. H. -Y., et al. (1993) *Clin. Infect. Dis.* 17:724.
93. Wickstrom, E. L., et al. (1988) *PNAS (USA)* 85:1028–1032.
94. Winkelmann, et al. (1988) *Drug Res.* 38, 1545–48.
95. Winkler, et al. (1990) *Antiviral Research* 14:61–74.
96. Yamandaka, et al. (1991) *Mol. Pharmacol.* 40(3):446.
97. Pellicer, A. et al. (1978) *Cell* 14:133–141.
98. Gibson, W. and Roizmann B. (1972) *J. Virol.* 10:1044–52.

EXPERIMENTAL DETAILS SECTION II

Sequencing Studies:

A lambda phage (KS5) from a KS lesion genomic library identified by positive hybridization with KS330Bam was digested with BamHI and Not I (Boehringer-Mannheim, Indianapolis Ind.); five fragments were gel isolated and subcloned into Bluescript II KS (Stratagene, La Jolla Calif.). The entire sequence was determined by bidirectional sequencing at a seven fold average redundancy by primer walking and nested deletions.

DNA sequence data were compiled and aligned using ALIGN (IBI-Kodak, Rochester N.Y.) and analyzed using the Wisconsin Sequence Analysis Package Version 8-UNIX (Genetics Computer Group, Madison Wis.) and the GRAIL Sequence Analysis, Gene Assembly and Sequence Comparison System v. 1.2 (Informatics Group, Oak Ridge Tenn.). Protein site motifs were identified using Motif (Genetics Computer Group, Madison Wis.).

Sources of Herpesvirus Gene Sequence Comparisons:

Complete genomic sequences of three gammaherpesviruses were available: Epstein-Barr virus (EBV), a herpesvirus of humans [4]; herpesvirus saimiri (HVS), a herpesvirus of the New World monkey *Saimiri sciureus* [1]; and equine herpesvirus 2 (EHV2 [49]). Additional thymidine kinase gene sequences were obtained for alcelaphine herpesvirus 1 (AHV1 [22]) and bovine herpesvirus 4 (BHV4 [31]). Sequences for the major capsid protein genes of human herpesvirus 6B and human herpesvirus 7 (HHV7) were from Mukai et al. [34]. The sources of all other sequences used are listed previously in McGeoch and Cook [31] and McGeoch et al. [32].

Phylogenetic Inference:

Predicted amino acid sequences used for tree construction were based on previous experience with herpesviral phylogenetic analyses [31]. Alignments of homologous sets of amino acid sequences were made with the AMPS [5] and Pileup [16] programs. Regions of alignments that showed extreme divergence with marked length heterogeneity, typically terminal sections, were excised. Generally, positions in alignments that contained inserted gaps in one or more sequences were removed before use for tree construction. Phylogenetic inference programs were from the Phylip set, version 3.5c [14] and from the GCG set [16]. Trees were built with the maximum parsimony (MP), neighbor joining (NJ) methods. For the NJ method, which utilizes estimates of pairwise distances between sequences, distances were estimated as mean numbers of substitution events per site with Protdist using the PAM 250 substitution probability matrix of Schwartz & Dayhoff [46]. Bootstrap analysis [15] was carried out for MP and NJ trees, with 100 sub-replicates of each alignment, and consensus trees obtained with the program Consense. In addition the program Protml was used to infer trees by the maximum likelihood (ML) method. Protml was obtained form J. Adachi, Department of Statistical Science, The Graduate University for Advanced Study, Tokyo 106, Japan. Because of computational constraints, Protml was used only with the 4-species CS1 alignment.

Clamped Homogeneous Electric Field (CHEF) Gel Electrophoresis:

Agarose plugs were prepared by resuspending BCBL-1 cells in 1% LMP agarose (Biorad, Hercules Calif.) and 0.9% NaCl at 42° C. to a final concentration of $2.5 \times 10^7$ cells/ml. Solidified agarose plugs were transferred into lysis buffer (0.5M EDTA pH 8.0, 1% sarcosyl, proteinase K at 1 mg/ml final concentration) and incubated for 24 hours. Approximately $10^7$ BCBL-1 cells were loaded in each lane. Gels were run at a gradient of 6.0 V/cm with a run time of 28 h 28 min. on a CHEF Mapper XA pulsed field gel electrophoresis apparatus (Biorad, Hercules Calif.), Southern blotted and hybridized to KS627Bam, KS330Bam and an EBV terminal repeat sequence [40].

TPA Induction of Genome Replication:

Late Log phase BCBL-1 cells (5×10 cells per ml) were incubated with varying amounts of 12-O-tetradecanoylphorbol-13-acetate (TPA, Sigma Chemical Co., St. Louis Mo.) for 48 h, cells were then harvested and washed with phosphate-buffered saline (PBS) and DNA was isolated by chloroform-phenol extraction. DNA concentrations were determined by UV absorbance; 5 µg of whole cell DNA was quantitatively dot blot hybridized in triplicate (Manifold I, Schleicher and Schuell, Keene NH). KS631Bam, EBV terminal repeat and beta-actin sequences were random-primer labeled with $^{32}P$ [13]. Specific hybridization was quantitated on a Molecular Dynamics PhosphorImager 425E.

Cell Cultures and Transmission Studies:

Cells were maintained at $5 \times 10^5$ cells per ml in RPMI 1640 with 20% fetal calf serum (FCS, Gibco-BRL, Gaithersburg Md.) and periodically examined for continued KSHV infection by PCR and dot hybridization. The T cell line Molt-3 (a gift from Dr. Jodi Black, Centers for Disease Control and Prevention), Raji cells (American Type Culture Collection, Rockville Md.) and RCC-1 cells were cultured in RPMI 1640 with 10% FCS. Owl monkey kidney cells (American Type Culture Collection, Rockville Md.) were cultured in MEM with 10% FCS and 1% nonessential amino acids (Gibco-BRL, Gaithersburg Md.).

To produce the RCC-1 cell line, 2×10⁶ Raji cells were cultivated with 1.4×10⁶ BCBL-1 cells in the presence of 20 ng/ml TPA for 2 days in chambers separated by Falcon 0.45 µg filter tissue culture inserts to prevent contamination of Raji with BCBL-1. Demonstration that RCC-1 was not contaminated with BCBL-1 was obtained by PCR typing of HLA-DR alleles [27] (Raji and RCC-1: DRβ1*0310, DRβ3*02, BCBL-1: DRβ104,*07, Drβ4*01) and confirmed by flow cytometry to determine the presence (Raji, RCC1) or absence (BCBL-1) of EMA membrane antigen. Clonal sublines of RCC-1 were obtained by dilution in 96 well plates to 0.1 cells/well in RPMI 1640, 20% FCS and 30% T-STIM culture supplement (Collaborative Biomedical Products, Bedford Mass.). Subcultures were examined to ensure that each was derived from a single cluster of growing cells.

In situ hybridization was performed with a previously described 25 bp oligomer located in ORF26 which was 5' labeled with fluorescein (Operon, Alameda Calif.) and hybridized to cytospin preparations of BCBL-1, RCC-1 and Raji cells using the methods of Lungu et al. [29]. Slides were both directly visualized by UV microscopy and by incubating slides with anti-fluorescein-alkaline phosphatase (AP)-conjugated antibody (Boehringer-Mannheim, Indianapolis Ind.), allowing immunohistochemical detection of bound probe. Positive control hybridization was performed using a 26 bp TET-labeled EBV DNA polymerase gene oligomer (Applied Biosystems, Alameda Calif.) which was visualized by UV microscopy only and negative control hybridization was performed using a 25 bp 5' fluorescein-labeled HSV1 α47 gene oligomer (Operon, Alameda Calif.) which was visualized in a similar manner as the KSHV ORF26 probe. All nuclei of BCBL-1, RCC-1 and Raji appropriately stained with the EBV hybridization probe whereas no specific staining of the cells occurred after hybridization with the HSV1 probe.

The remaining suspension cell lines used in transmission experiments were pelleted, and resuspended in 5 ml of 0.22 or 0.45µ filtered BCBL-1 tissue culture supernatant for 16 h. BCBL-1 supernatants were either from unstimulated cultures or from cultures stimulated with 20 ng/ml TPA. No difference in transmission to recipient cell lines was noted using various filtration or stimulation conditions. Fetal cord blood lymphocytes (FCBL) were obtained from heparinized fresh post-partum umbilical cord blood after separation on Ficoll-Paque (Pharmacia LKB, Uppsala Sweden) gradients and cultured in RPMI 1640 with 10% fetal calf serum. Adherent recipient cells were washed with sterile Hank's Buffered Salt Solution (HBSS, Gibco-BRL, Gaithersburg Md.) and overlaid with 5 ml of BCBL-1 media supernatant. After incubation with BCBL-1 media supernatant, cells were washed three times with sterile HBSS, and suspended in fresh media. Cells were subsequently rewashed three times every other day for six days and grown for at least two weeks prior to DNA extraction and testing. PCR to detect KSHV infection was performed using nested and unnested primers from ORF 26 and ORF 25 as previously described [10, 35].

Indirect Immunofluorescence Assay:

AIDS-KS sera were obtained from ongoing cohort studies (provided by Drs. Scott Holmberg, Thomas Spira and Harold Jaffe, Centers for Disease Control, and Prevention, and Isaac Weisfuse, New York City Department of Health). Sera from AIDS-KS patients were drawn between 1 and 31 months after initial KS diagnosis, sera from intravenous drug user and homosexual/bisexual controls were drawn after non-KS AIDS diagnosis, and sera from HIV-infected hemophiliac controls were drawn at various times after HIV infection. Immunofluorescence assays were performed using an equal volume mixture of goat anti-human IgG-FITC conjugate (Molecular Probes, Eugene Oreg.) and goat anti-human IgM-FITC conjugate (Sigma Chemical Co., St. Louis Mo.) diluted 1:100 and serial dilutions of patient sera. End-point titers were read blindly and specific immunoglobulin binding was assessed by the presence or absence of a specular fluorescence pattern in the nuclei of the plated cells. To adsorb cross-reacting antibodies, 20 µl serum diluted 1:10 in phosphate-buffer saline (PBS), pH 7.4, were adsorbed with 1–3×10⁷ paraformaldehyde-fixed P3H3 cells for 4–10 h at 25° C. and removed by low speed centrifugation. P3H3 were induced prior to fixation with 20 ng/ml TPA for 48 h, fixed with 1% paraformaldehyde in PBS for 2 h at 4° C., and washed three times in PBS prior to adsorption.

RESULTS

Sequence Analysis of a 20.7 kb KSHV DNA Sequence:

To demonstrate that KS330Bam and KS631Bam are genomic fragments from a new and previously uncharacterized herpesvirus, a lambda phase clone (KS5) derived from an AIDS-KS genomic DNA library was identified by hybridization to the KS330Bam sequence. The KS5 insert was subcloned after NotI/BamHI digestion into five subfragments and both strands of each fragment were sequenced by primer walking or nested deletion with a 7-fold average redundancy. The KS5 sequence is 20,705 bp in length and has a G+C content of 54.0%. The observed/expected CpG dinucleotide ratio is 0.92 indicating no overall CpG suppression in this region.

Open reading frame (ORF) analysis identified 15 complete ORFs with coding regions ranging from 231 bp to 4128 bp in length, and two incomplete ORFs at the termini of the KS5 clone which were 135 and 552 bp in length (FIG. 12). The coding probability of each ORF was analyzed using GRAIL 2 and CodonPreference which identified 17 regions having excellent to good protein coding probabilities. Each region is within an ORF encoding a homolog to a known herpesvirus gene with the exception of one ORF located at the genome position corresponding to ORF28 in herpesvirus saimiri (HVS). Codon preference values for all of the ORFs were higher across predicted ORFs than in non-coding regions when using a codon table composed of KS5 homologs to the conserved herpesvirus major capsid (MCP), glycoprotein H (gH), thymidine kinase (TK), and the putative DNA packaging protein (ORF29a/ORF29b) genes.

The translated sequence of each ORF was used to search GenBank/EMBL databases with BLASTX and FastA algorithms [2, 38]. All of the putative KS5 ORFs, except one, have sequence and collinear positional homology to ORFs from gamma-2 herpesviruses, especially HVS and equine herpesvirus 2 (EHV2). Because of the high degree of collinearity and amino acid sequence similarity between KSHV and HVS, KSHV ORFs have been named according to their HVS positional homologs (i.e. KSHV ORF25 is named after HVS ORF 25).

The KS5 sequence spans a region which includes three of the seven conserved herpesvirus gene blocks (FIG. 14) [10]. ORFs present in these blocks include genes which encode herpesvirus virion structural proteins and enzymes involved in DNA metabolism and replication. Amino acid identities between KS5 ORFs and HVS ORFs range from 30% to 60%, with the conserved MCP ORF25 and ORF29b genes having the highest percentage amino acid identity to homologs in other gammaherpesviruses. KSHV ORF28, which has no detectable sequence homology to HVS or EBV genes, has positional homology to HVS ORF28 and EBV BDLF3. ORF28 lies at the junction of two gene blocks (FIG. 14); these junctions tend to exhibit greater sequence divergence than intrablock regions among herpesviral genomes [17]. Two ORFs were identified with sequence homology to the putative spliced protein packaging genes of HVS (ORF29a/ORF29b) and herpes simplex virus type 1 (UL15). The KS330Bam sequence is located within KSHV ORF26, whose HSV-1 counterpart, VP23, is a minor virion structural component.

For every KSHV homolog, the HVS amino acid similarity spans the entire gene product, with the exception of ORF21, the TK gene. The KSHV TK homolog contains a proline-rich domain at its amino terminus (nt 20343-19636; aa 1-236) that is not conserved in other herpesvirus TK sequences, while the carboxyl terminus (nt 19637-18601; aa 237-565) is highly similar to the corresponding regions of HVS, EHV2, and bovine herpesvirus 4 (BHV4) TK. A purine binding motif with a glycine-rich region found in herpesviral TK genes, as well as other TK genes, is present in the KSHV TK homolog (GVMGVGKS; aa 260-267).

The KS5 translated amino acid sequences were searched against the PROSITE Dictionary of Protein Sites and Patterns (Dr. Amos Bairoch, University of Geneva, Switzerland) using the computer program Motifs. Four sequence motif matches were identified among KSHV hypothetical protein sequences. These matches included: (i) a cytochrome c family heme-binding motif in ORF33 (CVHCHG; aa 209-214 (SEQ ID NO:11)) and ORF34 (CLLCHI; aa 257-261 (SEQ ID NO:35)), (ii) an immunoglobulin and major histocompatibility complex protein signature in ORF25 (FICQAKH; aa 1024-1030 (SEQ ID NO:3)), (iii) a mitochondrial energy transfer protein motif in ORF26 (PDDITRMRV; aa 260-268 (SEQ ID NO:25)), and (iv) the purine nucleotide binding site identified in ORF21. The purine binding motif is the only motif with obvious functional significance. A cytosine-specific methylase motif present in HVS ORF27 is not present in KSHV ORF27. This motif may play a role in the methylation of episomal DNA in cells persistently infected with HVS [1].

Phylogenetic Analysis of KSHV:

Amino acid sequences translated from the KS5 sequence were aligned with corresponding sequences from other herpesviruses. On the basis of the level of conserved aligned residues and the low incidence of introduced gaps, the amino acid alignments for ORFs 21, 22, 23, 24, 25, 26, 29a, 29b, 31 and 34 were suitable for phylogenetic analyses.

To demonstrate the phylogenetic relationship of KSHV to other herpesviruses, a single-gene comparison was made for ORF25 (MCP) homologs from KS5 and twelve members of Herpesviridae (FIGS. 15A–15B). The thirteen available MCP amino acid sequences are large (1376 a.a. residues for the KSHV homolog) and alignment required only a low level of gapping; however, the overall similarity between viruses is relatively low [33]. The MCP set gave stable trees with high bootstrap scores and assigned the KSHV homolog to the gamma-2 sublineage (genus Rhadinovirus), containing HVS, EHV2 and BVH4 [20, 33, 43]. KSHV was most closely associated with HVS. Similar results were obtained for single-gene alignments of TK and UL15/ORF29 sets but with lower bootstrap scores so that among gamma-2 herpesvirus members branching orders for EHV2, HVS and KSHV were not resolved.

To determine the relative divergence between KSHV and other gammaherpesviruses, alignments for the nine genes listed above were concatenated to produce a combined gammaherpesvirus gene set (CS1) containing EBV, EHV2, HVS and KSHV amino acid sequences. The total length of CS1 was 4247 residues after removal of positions containing gaps introduced by the alignment process in one or more of the sequences. The CS1 alignment was analyzed by the ML method, giving the tree shown in FIG. 15B and by the MP and NJ methods used with the aligned herpesvirus MCP sequences. All three methods identified KSHV and HVS as sister groups, confirming that KSHV belongs in the gamma-2 sublineage with HVS as its closest known relative. It was previously estimated that divergence of the HVS and EHV2 lineages may have been contemporary with divergence of the primate and ungulate host lineages [33]. The results for the CS1 set suggest that HVS and KSHV represent a lineage of primate herpesviruses and, based on the distance between KSHV and HVS relative to the position of EHV2, divergence between HVS and KSHV lines is ancient.

Genomic Studies of KSHV:

CHEF electrophoresis performed on BCBL-1 cells embedded in agarose plugs demonstrated the presence of a nonintegrated KSHV genome as well as a high molecular weight species (FIGS. 16A–16B). KS631Bam (FIG. 16A) and KS330Bam specifically hybridized to a single CHEF gel band comigrating with 270 kilobase (kb) linear DNA standards. The majority of hybridizing DNA was present in a diffuse band at the well origin; a low intensity high molecular weight (HMW) band was also present immediately below the origin (FIG. 16A. arrow). The same filter was stripped and probed with an EBV terminal repeat sequence [40] yielding a 150–160 kb band (FIG. 16B) corresponding to linear EBV DNA [24]. The HMW EBV band may correspond to either circular or concatemeric EBV DNA [24].

The phorbol ester TPA induces replication-competent EBV to enter a lytic replication cycle [49]. To determine if TPA induces replication of KSHV and EBV in BCBL-1 cells, these cells were incubated with varying concentrations of TPA for 48 h (FIG. 17). Maximum stimulation of EBV occurred at 20 ng/ml TPA which resulted in an eight-fold increase in hybridizing EBV genome. Only a 1.3–1.4 fold increase in KSHV genome abundance occurred after 20–80 ng/ml TPA incubation for 48 h.

Transmission Studies:

Prior to determining that the agent was likely to be a member of Herpesviridae by sequence analysis, BCBL-1 cells were cultured with Raji cells, a nonlytic EBV transformed B cell line, in chambers separated by a 0.45μ tissue culture filter. Recipient Raji cells generally demonstrated rapid cytolysis suggesting transmission of a cytotoxic component from the BCBL-1 cell line. One Raji line cultured in 10 ng/ml TPA for 2 days, underwent an initial period of cytolysis before recovery and resumption of logarithmic growth. This cell line (RCC-1) is a monoculture derived from Raji uncontaminated by BCBL-1 as determined by PCR amplification of HLA-DR sequences.

RCC-1 has remained positive for the $KS330_{233}$ PCR product for >6 months in continuous culture (approximately 70 passages), but KSHV was not detectable by dot or Southern hybridization at any time. In situ hybridization, however, with a 25 bp KSHV ORF26-derived oligomer was used to demonstrate persistent localization of KSHV DNA to RCC-1 nuclei. As indicated in FIGS. 18A–18C, nuclei of BCBL-1 and RCC-1 (from passage ~65) cells had detectable hybridization with the ORF26 oligomer, whereas no specific hybridization occurred with parental Raji cells (FIG. 18B). KSHV sequences were detectable in 65% of BCBL-1 and 2.6% of RCC-1 cells under these conditions. In addition, forty-five monoclonal cultures were subcultured by serial dilution from RCC-1 at passage 50, of which eight (18%) clones were PCR positive by $KS330_{233}$. While PCR detection using unnested $KS330_{233}$ primer pairs was lost by passage 15 in each of the clonal cultures, persistent KSHV genome was detected in 5 clones using two more sensitive nonoverlapping nested PCR primer sets [33] suggesting that KSHV genome is lost over time in RCC-1 and its clones.

Low but persistent levels of $KS330_{233}$ PCR positivity were found for one of four Raji, one of four Bjab, two of three Molt-3, one of one owl monkey kidney cell lines and three of eight human fetal cord blood lymphocyte (FCBL) cultures after inoculation with 0.2–0.45µ filtered BCBL-1 supernatants. Among the PCR positive cultures, PCR detectable genome was lost after 2–6 weeks and multiple washings. Five FCBL cultures developed cell clusters characteristic of EBV immortalized lymphocytes and were positive for EBV by PCR using EBER primers [23]; three of these cultures were also initially $KS330_{233}$ positive. None of the recipient cell lines had detectable KSHV genome by dot blot hybridization.

Serologic Studies:

Indirect immunofluorescence antibody assays (IFA) were used to assess the presence of specific antibodies against the KSHV- and EBV-infected cell line HBL-6 in the sera from AIDS-KS patients and control patients with HIV infection or AIDS. HBL-6 was substituted for BCBL-1 for reasons of convenience; preliminary studies showed no significant differences in IFA results between HBL-6 and BCBL-1. HBL-6 have diffuse immunofluorescent cell staining with most KS patient and control unabsorbed sera suggesting nonspecific antibody binding (FIGS. 19A–19D). After adsorption with paraformaldehyde-fixed, TPA-induced P3H3 (an EBV producer subline of P3J-HR1, a gift of Dr. George Miller) to remove cross-reacting antibodies against EBV and lymphocyte antigens, patient sera generally showed specular nuclear staining at high titers while this staining pattern was absent from control patient sera (FIGS. 19B and 19D). Staining was localized primarily to the nucleus but weak cytoplasmic staining was also present at low sera dilutions.

With unadsorbed sera, the initial endpoint geometric mean titers (GMT) against HBL-6 cell antigens for the sera from AIDS-KS patients (GMT=1:1153, range: 1:150 to 1:12,150) were higher than for sera from control, non-KS patients (GMT=1:342; range 1:50 to 1:12,150: p=0.04) (FIG. 13). While AIDS-KS patients and HIV-infected gay/bisexual and intravenous drug user control patients had similar endpoint titers to HBL-6 antigens (GMT=1:1265 and GMT=1:1578, respectively), hemophilic AIDS patient titers were lower (GMT=1:104). Both case and control patient groups had elevated IFA titers against the EBV infected cell line P3H3.

The difference in endpoint GMT between case and control titers against HBL-6 antigens increased after adsorption with P3H3. After adsorption, case GMT declined to 1:780 and control GMT declined to 1:81 (p=0.00009). Similar results were obtained by using BCBL-1 instead of HBL-6 cells, by pre-adsorbing with EBV-infected nonproducer Raji cells instead of P3H3 and by using sera from a homosexual male KS patient without HIV infection, in complete remission for KS for 9 months (HBL-6 titer 1:450, P3H3 titer 1:150). Paired sera taken 8–14 months prior to KS onset and after KS onset were available for three KS patients: KS patients 8 and 13 had eight-fold rises and patient 8 had a three-fold fall in P3H3-adsorbed BCBL-1 titers from pre-onset sera to post-KS sera.

DISCUSSION

These studies demonstrate that specific DNA sequences found in KS lesions by representational difference analysis belong to a newly identified human herpesvirus. The current studies define this agent as a human gamma-2 herpesvirus that can be continuously cultured in naturally-transformed, EBV-coinfected lymphocytes from AIDS-related body-cavity based lymphomas.

Sequence analysis of the KS5 lambda phage insert provides clear evidence that the KS330Bam sequence is part of a larger herpesvirus genome. KS5 has a 54.0% G+C content which is considerably higher than the corresponding HVS region (34.3% G+C) . While there is no CpG dinucleotide suppression in the KS5 sequence, the corresponding HVS region has a 0.33 expected:observed CpG dinucleotide ratio [1]. The CpG dinucleotide frequency in herpesviruses varies from global CpG suppression among gammaherpesviruses to local CpG suppression in the betaherpesviruses, which may result from deamination of 5'-methylcytosine residues at CpG sites resulting in TpG substitutions [21]. CpG suppression among herpesviruses [21, 30, 44] has been hypothesized to reflect co-replication of latent genome in actively dividing host cells, but it is unknown whether or not KSHV is primarily maintained by a lytic replication cycle in vivo.

The 20,705 bp KS5 fragment has 17 protein-coding regions, 15 of which are complete ORFs with appropriately located TATA and polyadenylation signals, and two incomplete ORFs located at the phage insert termini. Sixteen of these ORFs correspond by sequence and collinear positional homology to 15 previously identified herpesviral genes including the highly conserved spliced gene. The conserved positional and sequence homology for KSHV genes in this region are consistent with the possibility that the biological behavior of the virus is similar to that of other gammaherpesviruses. For example, identification of a thymidine kinase-like gene on KS5 implies that the agent is potentially susceptible to TK-activated DNA polymerase inhibitors and like other herpesviruses possesses viral genes involved in nucleotide metabolism and DNA replication [41]. The presence of major capsid protein and glycoprotein H gene homologs suggest that replication competent virus would produce a capsid structure similar to other herpesviruses.

Phylogenetic analyses of molecular sequences show that KSHV belongs to the gamma-2 sublineage of the Gammaherpesvirinae subfamily, and is thus the first human gamma-2 herpesvirus identified. Its closest known relative based on available sequence comparisons is HVS, a squirrel monkey gamma-2 herpesvirus that causes fulminant polyclonal T cell lymphoproliferative disorders in some New World monkey species. Data for the gamma-2 sublineage are sparse: only three viruses (KSHV, HVS and EHV2) can at present be placed on the phylogenetic tree with precision (the sublineage also contains murine herpesvirus 68 and BHV4 [33]. Given the limitation in resolution imposed by this thin background, KSHV and HVS appear to represent a lineage of primate gamma-2 viruses. Previously, McGeoch et al.[33] proposed that lines of gamma-2 herpesviruses may have originated by cospeciation with the ancestors of their host species. Extrapolation of this view to KSHV and HVS suggests that these viruses diverged at an ancient time, possibly contemporaneously with the divergence of the Old World and New World primate host lineages. Gammaherpesviruses are distinguished as a subfamily by their lymphotrophism [41] and this grouping is supported by phylogenetic analysis based or sequence data [33]. The biologic behavior of KSHV is consistent with its phylogenetic designation in that KSHV can be found in in vitro lymphocyte cultures and in in vivo samples of lymphocytes [3].

This band appears to be a linear form of the genome because other "high molecular weight" bands are present for both EBV and KSHV in BCBL-1 which may represent circular forms of their genomes. The linear form of the EBV genome, associated with replicating and packaged DNA [41] migrates substantially faster than the closed circular form associated with latent viral replication [24]. While the 270 kb band appears to be a linear form, it is also consistent with a replicating dimer plasmid since the genome size of HVS is approximately 135 kb. The true size of the genome may only be resolved by ongoing mapping and sequencing studies.

Replication deficient EBV mutants are common among EBV strains passaged through prolonged tissue culture [23]. The EBV strain infecting Raji, for example, is an BALF-2 deficient mutant [19]; virus replication is not inducibile with TPA and its genome is maintained only as a latent circular form [23, 33]. The EBV strain coinfecting BCBL-1 does not appear to be replication deficient because TPA induces eight-fold increases in DNA content and has an apparent linear form on CHEF electrophoresis. KSHV replication, however, is only marginally induced by comparable TPA treatment indicating either insensitivity to TPA induction or that the genome has undergone loss of genetic elements required for TPA induction. Additional experiments, however, indicate that KSHV DNA can be pelleted by high speed centrifugation of filtered organelle-free, DNase I-protected BCBL-1 cell extracts, which is consistent with KSHV encapsidation.

Transmission of KSHV DNA from BCBL-1 to a variety of recipient cell lines is possible and KSHV DNA can be maintained at low levels in recipient cells for up to 70 passages. However, detection of virus genome in recipient cell lines by PCR may be due to physical association of KSHV DNA fragments rather than true infection. This appears to be unlikely given evidence for specific nuclear localization of the ORF26 sequence in RCC-1. If transmission of infectious virus from BCBL-1 occurs, it is apparent that the viral genome declines in abundance with subsequent passages of recipient cells. This is consistent with studies of spindle cell lines derived from KS lesions. Spindle cell cultures generally have PCR detectable KSHV genome when first explanted, but rapidly lose viral genome after initial passages and established spindle cell cultures generally do not have detectable KSHV sequences [3].

Infections with the human herpesviruses are generally ubiquitous in that nearly all humans are infected by early adulthood with six of the seven previously identified human herpesviruses [42]. Universal infection with EBV, for example, is the primary reason for the difficulty in clearly establishing a causal role for this virus in EBV-associated human tumors. The serologic studies identified nuclear antigen in BCBL-1 and HBL-6 which is recognized by sera from AIDS-KS patients but generally not by sera from control AIDS patients without KS after removal of EBV-reactive antibodies. These data are consistent with PCR studies of KS and control patient lymphocytes suggesting that KSHV is not ubiquitous among adult humans, but is specifically associated with persons who develop Kaposi's sarcoma. In this respect, it appears to be epidemiologically similar to HSV2 rather than the other known human herpesviruses. An alternative possibility is that elevated IFA titers against BCBL-1 reflect disease status rather than infection with the virus.

REFERENCES

1. Albrecht, J.-C., J. Nicholas, D. Biller, K. R. Cameron, B. Biesinger, C. Newamn, S. Wittmann, M. A. Craxton, H. Coleman, B. Fleckenstein, and R. W. Honess. 1992. Primary structure of the Herpesvirus saimiri genome. J Virol. 66:5047–5058.
2. Altschul, S. F., W. Gish, W. Miller, E. W. Myers, and D. J. Lipman. 1990. Basic local alignment search tool. J Mol Biol. 215:403–410.
3. Ambroziak, J. A., D. J. Blackbourn, B. G. Herndier, R. G. Glogau, J. H. Gullett, A. R. McDonald, E. T. Lennette, and J. A. Levy. 1995. Herpes-like sequences in HIV-infected and uninfected Kaposi's sarcoma patients. Science. 268:582–583.
4. Baer, R., A. T. Bankier, P. L. Biggin, P. L. Deininger, P. J. Farrell, T. J. Gibson, G. Hatfull, G. S. Hudson, S. C. Satchwell, C. Séguin, P. S. Tuffnell, and B. G. Barrell. 1984. DNA sequence and expression of the B95-8 Epstein-Barr virus genome. Nature. 310:207–211.
5. Barton, G. J., and M. J. E. Sternberg. 1987. A strategy for the rapid multiple alignment of protein sequences. Confidence levels from tertiary structure comparisons. J Mol Biol. 198:327–37.
6. Beral, V., T. A. Peterman, R. L. Berkelman, and H. W. Jaffe. 1990. Kaposi's sarcoma among persons with AIDS: a sexually transmitted infection? Lancet. 335:123–128.
7. Boshoff, C., D. Whitby, T. Hatziionnou, C. Fisher, J. van der Walt, A. Hatzakis, R. Weiss, and T. Schulz. 1995. Kaposi's sarcoma-associated herpesvirus in HIV-negative Kaposi's sarcoma. Lancet. 345:1043–44.
8. Cesarman, E., Y. Chang, P. S. Moore, J. W. Said, and D. M. Knowles. 1995. Kaposi's sarcoma-associated herpesvirus-like DNA sequences are present in AIDS-related body cavity based lymphomas. New England J Med. 332:1186–1191.
9. Chang, Y., E. Cesarman, M. S. Pessin, F. Lee, J. Culpepper, D. M. Knowles, and P. S. Moore. 1994. Identification of herpesvirus-like DNA sequences in AIDS-associated Kaposi's sarcoma. Science. 265:1865–69.
10. Chee, M. S., S. B. Bankier, C. M. Bohni, R. C. Brown, T. Horsnell, C. A. Hutchison, T. Kouzarides, J. A. Martignetti, E. Preddie, S. C. Satchwell, P. Tomlinson, K. M. Weston, and B. G. Barrell. 1990. Analysis of the protein coding content of the sequence of cytomegalovirus strain AD169. Curr Top Microbiol Immunol. 154:125–69.
11. Collandre, H., S. Ferris, O. Grau, L. Montagnier, and A. Blanchard. 1995. Kaposi's sarcoma and new herpesvirus. Lancet. 345:1043.
12. Dupin, N., M. Grandadam, V. Calvez, I. Gorin, J. T. Aubin, S. Harvard, F. Lamy, M. Leibowitch, J. M. Huraux, J. P. Escande, and H. Agut. 1995. Herpesvirus-like DNA in patients with Mediterranean Kaposi's sarcoma. Lancet. 345:761–2.
13. Feinberg, A. P., and B. Vogelstein. 1983. A technique for radiolabeling DNA restriction endonuclease fragments to high specific activity. Anal Biochem. 132:6.
14. Felsenstein, J. 1989. PHYLIP-phylogeny inference package (ver 3.2). Cladistics. 5:164–6.

15. Felsenstein, J. 1988. Phylogenies from molecular sequences: inferences and reliability. Annual Rev Microbiol. 22:521–65.
16. Genetics Computer Group. 1994. Program manual for the GCG package, version 8, Madison, Wis.
17. Gompels, U. A., J. Nicholas, G. Lawrence, M. Jones, B. J. Thomson, M. E. D. Martin, S. Efstathiou, M. Craxton, and H. A. Macaulay. 1995. The DNA sequence of human herpesvirus-6: Structure, coding content and genome evolution. Virology. 209:29–51.
18. Hatfull, G., A. T. Bankier, B. G. Barrell, and P. J. Farrell. 1988. Sequence analysis of Raji Epstein-Barr virus DNA. Virol. 164:334–40.
19. Holmberg, S. D. 1990. Possible cofactors for the development of AIDS-related neoplasms. Cancer Detection and Prevention. 14:331–336.
20. Honess, R. W. 1984. Herpes simplex and 'the herpes complex': diverse observations and a unifying hypothesis. J Gen Virol. 65:2077–2107.
21. Honess, R. W., U. A. Gompels, B. G. Barrell, M. Craxton, K. R. Cameron, R. Staden, Y.-N. Chang, and G. S. Hayward. 1989. Deviations from expected frequencies of CpG dinucleotides in herpesvirus DNAs; may be diagnostic of differences in the states of their latent genomes. J Gen Virol. 70:837–55.
22. Hsu, D., L. M. Shih, and Y. C. Zee. 1990. Nucleotide sequence of a 3.5 nucleotide fragment of malignant catarrhal fever virus strain WC11. Arch Virol. 113:53–60.
23. Kieff, E., and D. Liebowitz. 1990. Epstein-Barr virus and its replication, p. 1889–1920. In B. N. Fields and D. M. Knipe (ed.), Virology, vol. 2. Raven Press, New York.
24. Kolman, J. L., C. J. Kolman, and G. Miller. 1992. Marked variation in the size of genomic plasmids among members of the family of related Epstein-Barr viruses. Proc Natl Acad Sci, USA. 89:7772–7776.
25. Lebbé, C., P. de Crémoux, M. Rybojad, C. Costa da Cunha, P. Morel, and F. Calvo. 1995. Kaposi's sarcoma and new herpesvirus. Lancet. 345:1180.
26. Lin, J. C., S. C. Lin, B. K. De, W. P. Chan, and B. L. Evatt. 1993. Precision of genotyping of Epstein-Barr virus by polymerase chain reaction using three gene loci (EBNA-2, EBNA-3C and EBER): predominance of type A virus associated with Hodgkin's disease. Blood. 81:3372–81.
27. Liu, Z., S. Yu-Kai, Y.-P. Xi, P. Harris, and N. Suciu-Foca. 1992. T cell recognition of self-human histocompatibility leukocyte antigens (HLA)-DR peptides in the context of syngeneic HLA-DR molecules. J Exp. Med. 175:1663–8.
28. Lomonte, P., M. Bublot, P—P. Pastoret, and E. Thiry. 1992. Location and characterization of the bovine herpesvirus type 4 thymidine kinase gene; comparison with thymidine kinase of other herpesviruses. Arch. Virol. 127:327–337.
29. Martin, M. E. D., J. Nicholas, B. J. Thomson, C. Newman, and R. W. Honess. 1991. Identification of a transactivating function mapping to the putative immediate-early locus of human herpesvirus 6. J Virol. 65:5381–5390.
30. McGeoch, D. J., and S. Cook. 1994. Molecular phylogeny of the Alphaherpesvirinae subfamily and a proposed evolutionary timescale. J Mol Biol. 238:9–22.
31. McGeoch, D. J., S. Cook, A. Dolar., F. E. Jamieson, and E. A. R. Telford. 1995. Molecular phylogeny and evolutionary timescale for the family of mammalian herpesviruses. J Molec Biol. 247:443–58.
32. Miller, G. 1990. Epstein-Barr virus: Biology, pathogenesis and medical aspects, p. 1921–1957. In B. N. Fields and D. M. Knipe (ed.), Virology, 2nd ed, vol. 2. Raven Press, New York.
33. Moore, P. S., and Y. Chang. 1995. Detection of herpesvirus-like DNA sequences in Kaposi's sarcoma lesions from persons with and without HIV infection. New England J Med. 332:1181–1185.
34. Mukai, T., Y. Isegawa, and K. Yamanishi. 1995. Identification of the major capsid protein gene of human herpesvirus 7. Virus Res. 37:55–62.
35. Oettle, A. G. 1962. Geographic and racial differences in the frequency of Kaposi's sarcoma as evidence of environmental or genetic causes, vol. 18. Symposium on Kaposi's sarcoma: Unio Internationalis Contra Cancrum, Karger, Basel.
36. Pearson, W. R., and D. J. Lipman. 1988. Improved tools for biological sequence analysis. Proc Natl Acad Sci, USA. 85:2444–8.
37. Peterman, T. A., H. W. Jaffe, A. E. Friedman-Kien, and R. A. Weiss. 1991. The aetiology of Kaposi's sarcoma, p. 23–37, Cancer, HIV, and AIDS, vol. 10. Imperial Cancer Research Fund. London.
38. Raab-Traub, N., and K. Flynn. 1986. The structure of the termini of the Epstein-Barr virus as a marker of clonal cellular proliferation. Cell. 47:883–889.
39. Roizman, B. 1993. The family Herpesviridae, p. 1–9. In B. Roizman and R. J. Whitley and C. Lopez (ed.), The Human Herpeviruses. Raven Press, Ltd., New York.
40. Roizman, B. 1995. New viral footprints in Kaposi's sarcoma. N Engl J Med. 332:1227–1228.
41. Roizman, B., R. C. Desrosiers, B. Fleckenstein, C. Lopez, A. C. Minson, and M. J. Studdert. 1992. The family Herpesviridae: an update. Arch Virol. 123:425–449.
42. Sandford, G. R., K. Ho, and W. H. Burns. 1993. Characterization of the major locus of immediate-early genes of rat cytomegalovirus. J Virol. 67:4093–4103.
43. Schalling, M., M. Ekman, E. E. Kaaya, A. Linde, and P. Bieberfeld. 1995. A role for a new herpesvirus (KSHV) in different forms of Kaposi's sarcoma. Nature Med. 1:707–8.
44. Schwartz, R. M., and M. O. Dayhoff. 1978. Matrices for detecting distant relationships, p. 353–8. In M. O. Dayhoff (ed.), Atlas of protein sequence and structure, vol. 5, supple 3. National Biomedical Research Foundation, Washington.
45. Su, I.-J., Y.-S. Hsu, Y.-C. Chang, and I.-W. Wang. 1995. Herpesvirus-like DNA sequence in Kaposi's sarcoma from AIDS and non-AIDS patients in Taiwan. Lancet. 345:722–23.
46. Telford, E. A. R., M. S. Watson, H. C. Aird, J. Perry, and A. J. Davison. 1995. The DNA sequence of equine herpesvirus 2. J Molec Biol. 249:520–8.
47. zur Hausen, H., F. J. O'Neill, and U. K. Freese. 1978. Persisting oncogenic herpesvirus induced by the tumor promoter TPA. Nature. 272:373–375.

EXPERIMENTAL DETAILS SECTION III

KS Patient Enrollment:

Cases and controls were selected from ongoing cohort studies based on the availability of clinical information and appropriate PBMC samples. 21 homosexual or bisexual men with AIDS who developed KS during their participation in prospective cohort studies were identified [14–16]. Fourteen of these patients had paired PBMC samples collected after KS diagnosis (median+4 months) and at least four months prior to KS diagnosis (median−13 months), while the remaining 7 had paired PBMC taken at the study visit immediately prior to KS diagnosis (median–3 months) and at entry into their cohort study (median–51 months prior to KS diagnosis).

Hemophilic and Homosexual/Bisexual Male AIDS Patient Control Enrollment:

Two control groups of AIDS patients were examined: 23 homosexual/bisexual men with AIDS followed until death who did not develop KS ("high risk" control group) from the Multicenter AIDS Cohort Study [16]), and 19 hemophilic men ("low risk" control group) enrolled from joint projects of the National Hemophilia Foundation and the Centers for Disease Control and Prevention. Of the 16 hemophilic controls with available follow-up information, none are known to have developed KS and <2% of hemophilic AIDS patients historically develop KS [2]. For homosexual/bisexual AIDS control patients who did not develop KS, paired PBMC specimens were available at entry into their cohort study (median–35 months prior to AIDS onset) and at the study visit immediately prior to nonKS AIDS diagnosis (median (HBL-6 months prior to AIDS onset).

DNA Extraction and Analyses:

DNA from $10^6$–$10^7$ PBMC in each specimen was extracted and quantitated by spectrophotometry. Samples were prepared in physically isolated laboratories from the laboratory where polymerase chain reaction (PCR) analyses were performed. All samples were tested for amplifiability using primers specific for either the HLA-DQ locus (GH26/GH27) or b-globin [18]. PCR detection of KSHV DNA was performed as previously described [7] with the following nested primer sets: No. 1 outer 5'-AGCACTCGCAGGGCAGTACG-3' (SEQ ID NO:51) 5'-GACTCTTCGCTGATGAACTGG-3'; No. 1 inner 5'-TCCGTGTTGTCTACGTCCAG-3' (SEQ ID NO:52), 5'-AGCCGAAAGGATTCCACCAT-3' (SEQ ID NO:53); No. 2 outer 5'-AGGCAACGTCAGATGTGAC-3' (SEQ ID NO:41), 5'-GAAATTACCCACGAGATCGC-3' (SEQ ID NO:54); No. 2 inner 5'-CATGGGAGTACATTGTCAGGACCTC-3' (SEQ ID NO:42), 5'-GGAATTATCTCGCAGGTTGCC-3' (SEQ ID NO:55); No. 3 outer 5'-GGCGACATTCATCAACCTCAGGG-3' (SEQ ID NO:56), 5'-ATATCATCCTGTGCGTTCACGAC-3' (SEQ ID NO:57); No. 3 inner 5'-CATGGGAGTACATTGTCAGGACCTC-3' (SEQ ID NO:58); 5'-GGAATTATCTCGCAGGTTGCC-3' (SEQ ID NO:56). The outer primer set was amplified for 35 cycles at 94° C. for 30 seconds, 60° C. for 1 minute and 72° C. for 1 minute with a 5 minute final extension cycle at 72° C. One to three ml of the PCR product was added to the inner PCR reaction mixture and amplified for 25 additional cycles with a 5 minute final extension cycle. Primary determination of sample positivity was made with primer set No. 1 and confirmed with either primer sets 2 or 3 which amplify nonoverlapping regions of the KSHV hypothetical major capsid gene. Sampling two portions of the KSHV genome decreased the likelihood of intraexperimental PCR contamination. These nested primer sets are 2–3 logs more sensitive for detecting KSHV sequences than the previously published $KS330_{233}$ primers [6] and are estimated to be able to detect <10 copies of KSHV genome under optimal conditions. Sample preparations were prealiquoted and amplified with alternating negative control samples without DNA to monitor and control possible contamination. All samples were tested in a blinded fashion and a determination of the positivity/negativity made before code breaking. Significance testing was performed with Mantel-Haenszel chi-squared estimates and exact confidence intervals using Epi-Info ver. 6 (USD Inc., Stone Mt. Ga.).

RESULTS

KSHV Positivity of Case and Control PBMC Samples:

Paired PBMC samples were available from each KS patient and homosexual/bisexual control patient; a single sample was available from each hemophilic control patient.

To determine the KSHV positivity rate for each group of AIDS patients, a single specimen from each participant taken closest to KS or other AIDS-defining illness ("second sample") was analyzed. Overall, 12 of 21 (57%) of PBMC specimens from KS patients taken from 6 months prior to KS diagnosis to 20 months after KS diagnosis were KSHV positive. There was no apparent difference in positivity rate between immediate pre-diagnosis and post-diagnosis visit specimens (4 of 7 (57%) vs. 8 of 14 (57%) respectively).

The number of KSHV positive control PBMC specimens from both homosexual/bisexual (second visit) and hemophilic patient controls was significantly lower. Only 2 of 19 (11%) hemophilic PBMC samples were positive (odds ratio 11.3, 95 % confidence interval 1.8 to 118) and only 2 of 23 (9%) PBMC samples from homosexual/bisexual men who did not develop KS were positive (odds ratio 14.0, 95% confidence interval 2.3 to 144). If all KS patient PBMC samples taken immediately prior to or after diagnosis were truly infected, the PCR assay was at least 57% sensitive in detecting KSHV infection among PBMC samples. No significant differences in CD4+ counts were found for KS patients and homosexual/bisexual patients without KS at the second sample evaluation (Kruskall-Wallis p=0.15) (FIG. 21). CD4+ counts from the single sample from hemophilic AIDS patients were higher than CD4+ counts from KS patients (Kruskall-Wallis p=0.004), although both groups showed evidence of HIV-related immunosuppression.

Longitudinal Studies:

Paired specimens were available from all 21 KS patients and 23 homosexual/bisexual male AIDS control patients who did not develop KS. For the KS group, initial PBMC samples were taken four to 87 months (median 13 months) prior to the onset of KS. Initial PBMC samples from the control group were drawn 13 to 106 months (median 55 months) prior to onset of first nonKS AIDS-defining illness (1987 CDC surveillance definition). 11 of 21 (52%) of KS patients had detectable KSHV DNA in PBMC samples taken prior to KS onset compared to 2 of 19 (11%, p=0.005) hemophilic control samples, and 1 (4%, p=0.0004) and 2 (9%, p=0.002) of 23 homosexual/bisexual control samples taken at the first and second visits respectively (FIGS. 20A–20B). The figure shows that 7 of the paired KS patient samples were positive at both visits, 5 KS patients and 2 control patients converted from negative to positive and two KS patients and one control patient reverted from positive to negative between visits. The remaining 7 KS patients and 20 control patients were negative at both visits.

For the 5 KS patients that converted from an initial negative PBMC result to a positive result at or near to KS diagnosis, the median length of time between the first sample and the KS diagnosis was 19 months. Three of the 6 KS patients that were negative at both visits had their last PBMC sample drawn 2–3 months prior to onset of illness. It is unknown whether these patients became infected between their last study visit and the KS diagnosis date.

DISCUSSION

Ambroziak and coworkers have found evidence that KSHV preferentially infects CD19+ B cells by PBMC subset examination of three patients [19]. Other gammaherpesviruses, such as Epstein-Barr virus (EBV) and herpesvirus saimiri are also lymphotrophic herpesviruses and can cause lymphoproliferative disorders in primates [11, 20].

It is possible that KSHV, like most human herpesviruses, is a ubiquitous infection of adults [21]. EBV, for example, is detectable by PCR in CD19+ B lymphocytes from virtually all seropositive persons [22] and approximately 98% MACS study participants had EBV VCA antibodies at entry into the cohort study [23]. The findings, however, are most consistent with control patients having lower KSHV infection rates than cases and that KSHV is specifically associated with the subsequent development of KS. While it is possible that control patients are infected but have an undetectably low KSHV viral PBMC load, the inability to find evidence of infection in control patients under a variety of PCR conditions suggests that the majority of control patients are not infected. Nonetheless, approximately 10% of these patients were KSHV infected and did not develop KS. It is unknown whether or not this is similar to the KSHV infection rate for the general human population.

This study demonstrates that KSHV infection is both strongly associated with KS and precedes onset of disease in the majority of patients. 57% of KS patients had detectable KSHV infection at their second follow-up visit (52% prior to the onset of KS) compared to only 9% of homosexual/bisexual (p=0.002) and 11% of hemophilic control patients (p=0.005). Despite similar CD4+ levels between homosexual/bisexual KS cases and controls, KSHV DNA positivity rates were significantly higher for cases at both the first (p=0.005) and second sample visits indicating that immunosuppression alone was not responsible for these elevated detection rates. It is also unlikely that KSHV simply colonizes existing KS lesions in AIDS patients since neither patient group had KS at the time the initial sample was obtained. Five KS patients and two homosexual/bisexual control patients converted from a negative to a positive, possibly due to new infection acquired during the study period.

The findings are in contrast to PCR detection of KSHV DNA in all 10 PBMC samples from KS patients by Ambroziak et al. [19]. It is possible that the assay was not sensitive enough to detect virus in all samples since it was required that each positive sample to bus repeatedly positive by two independent primers in blinded PCR assays. This appears unlikely, however, given the sensitivity of the PCR nested primer sets. The 7 KS patients who were persistently negative on both paired samples may represent an aviremic or low viral load subpopulation of KS patients. The PCR conditions test a DNA amount equivalent to approximately $2 \times 10^3$ lymphocytes; an average viral load less than 1 copy per $2 \times 10^3$ cells may be negative in the assay. Two KS patients and a homosexual/bisexual control patient initially positive for KSHV PCR amplification reverted to negative in samples drawn after diagnosis. These results probably reflect inability to detect KSHV DNA in peripheral blood rather than true loss of infection although more detailed studies of the natural history of infection are needed.

The study was designed to answer the fundamental question of whether or not infection with KSHV precedes development of the KS phenotype. The findings indicate that there is a strong antecedent association between KSHV infection and KS. This temporal relationship is an absolute requirement for establishing that KSHV is central to the causal pathway for developing KS. This study contributes additional evidence for a possible causal role for this virus in the development of KS.

REFERENCES

1. Katz MH, Hessol NA, Buchbinder SP, Hirozawa A, O'Malley P, Holmberg SD. Temporal trends of opportunistic infections and malignancies in homosexual men with AIDS. *J Infect Dis.* 1994;170:198–202.
2. Beral V, Peterman TA, Berkelman RL, Jaffe HW. Kaposi's sarcoma among persons with AIDS: a sexually transmitted infection? *Lancet.* 1990;335:123–128.
3. Archibald CP, Schechter MT, Le TN, Craib KJP, Montaner JSG, O'Shaughnessy MV. Evidence for a sexually transmitted cofactor for AIDS-related Kaposi's sarcoma in a cohort of homosexual men. *Epidemiol.* 1992;3:203–209.
4. Beral V, Bull D, Jaffe H, Evans B, Gill N, Tillett H et al. Is risk of Kaposi's sarcoma in AIDS patients in Britain increased if sexual partners came from United States or Africa? *BMJ.* 1991;302:624–5.
5. Beral V. Epidemiology of Kaposi's sarcoma. *Cancer, HIV and AIDS.* London: Imperial Cancer Research Fund; 1991:5–22.
6. Chang Y, Cesarman E, Pessin MS, Lee F, Culpepper J, Knowles DM, et al. Identification of herpesvirus-like DNA sequences in AIDS-associated Kaposi's sarcoma. *Science.* 1994;265:1865–69.
7. Moore PS, Chang Y. Detection of herpesvirus-like DNA sequences in Kaposi's sarcoma lesions from persons with and without HIV infection. *New England J Med.* 1995;332:1181–1185.
8. Boshoff C, Whitby D, Hatziionnou T, Fisher C, van der Walt J, Hatzakis A et al. Kaposi's sarcoma-associated herpesvirus in HIV-negative Kaposi's sarcoma. *Lancet.* 1995;345:1043–44.
9. Su I-J, Hsu Y-S, Chang Y-C, Wang I-W. Herpesvirus-like DNA sequence in Kaposi's sarcoma from AIDS and non-AIDS patients in Taiwan. *Lancet.* 1995;345:722–23.
10. Dupin N, Grandadam M, Calvez V, Gorin I, Aubin JT, Harvard S, et al. Herpesvirus-like DNA in patients with Mediterranean Kaposi's sarcoma. *Lancet.* 1995;345:761–2.
11. Miller G. Oncogenicity of Epstein-Barr virus. J Infect Dis. 1974;130:187–205.
12. Hill AB. Environment and disease: association or causation? Proc Roy Soc Med. 1965;58:295–300.
13. Susser M. Judgment and causal inference: criteria in epidemiologic studies. Am J Epid. 1977;105:1–15.
14. Fishbein DB, Kaplan JE, Spira TJ, Miller B, Schonberger LB, Pinsky PF, et al. Unexplained lymphadenopathy in homosexual men: a longitudinal study. JAMA. 1985;254:930–5.
15. Holmberg SD. Possible cofactors for the development of AIDS-related neoplasms. Cancer Detection and Prevention. 1990;14:331–336.
16. Kaslow RA, Ostrow DG, Detels R, Phair JP, Polk BF, Rinaldo CR. The Multicenter AIDS Cohort Study: rationale, organization and selected characteristics of the participants. Am J Epidemiol. 1987;126:310–318.
17. Wolinsky S, Rinaldo C, Kwok S, Sinsky J, Gupta P, Imagawa D, et al. Human immunodeficiency virus type 1 (HIV-1) infection a median of 18 months before a diagnostic Western blot. Ann Internal Med. 1989;111:961.
18. Bauer HM, Ting Y, Greer CE, Chambers JC, Tashiro CJ, Chimera J, et al. Genital papillomavirus infection in female university students as determined by a PCR-based method. JAMA. 1991;265:2809–10.
19. Ambroziak JA, Blackbourn DJ, Herndier BG, Glogau RG, Gullett JH, McDonald AR, et al. Herpes-like sequences in HIV-infected and uninfected Kaposi's sarcoma patients. Science. 1995;268:582–583.

20. Roizman B. The family Herpesviridae. In: Roizman B, Whitley RJ, Lopez C, eds. The Human Herpeviruses. New York: Raven Press, Ltd.; 1993:1–9.
21. Roizman B. New viral footprints in Kaposi's sarcoma. N Engl J Med. 1995;332:1227–1228.
22. Miyashita EM, Yang B, Lam KMC, Crawford DH, Thorley-Lawson DA. A novel form of Epstein-Barr virus latency in normal B cells in vivo. Cell. 1995;80:593–601.
23. Rinaldo CR, Kingsley LA, Lyter DW, Rabin BS, Atchison RW, Bodner AJ, et al. Association of HTLV-III with Epstein-Barr virus infection and abnormalities of T lymphocytes in homosexual men. J Infect Dis. 1986;154:556–61.

EXPERIMENTAL DETAILS SECTION IV

To determine if the KHV-KS virus is also present in both endemic and HIV-associated KS lesions from African patients, formalin-fixed, paraffin-embedded tissues from both HIV seropositive and HIV seropositive Ugandan KS patients were compared to cancer tissues from patients without KS in a blinded case-control study.

Patient Enrollment:

Archival KS biopsy specimens were selected from approximately equal numbers of HIV-associated and endemic HIV-negative KS patients enrolled in an ongoing case-control study of cancer and HIV infection at Makerere University, Kampala Uganda. Control tissues were consecutive archival biopsies from patients with various malignancies enrolled in the same study, chosen without prior knowledge of HIV serostatus. All patients were tested for HIV antibody (measured by Cambridge Bioscience Recombigen Elisa assay).

Tissue preparation:

Each sample examined was from an individual patient. Approximately ten tissue sections were cut (10 micron) from each paraffin block using a cleaned knife blade for each specimen. Tissue sections were deparaffinized by extracting the sections twice with 1 ml xylene for 15 min. followed by two extractions with 100% ethanol for 15 min. The remaining pellet was then resuspended and incubated overnight at 50° C. in 0.5 ml of lysis buffer (25 mM KCl, 10 mM Tris-HCl, pH 8.3, 1.4 mM MgCl2, 0.01% gelatin, 1 mg/ml proteinase K). DNA was extracted with phenol/chloroform, ethanol precipitated and resuspended in 10 mM Tris-HCl, 0.1 mM EDTA, pH 8.3.

PCR Amplification:

0.2–0.4 ug of DNA was used in PCR reactions with $KS330_{233}$ primers as previously described [7]. The samples which were negative were retested by nested PCR amplification, which is approximately $10^2$–$10^3$ fold more sensitive in detecting $KS330_{233}$ sequence than the previously published $KS330_{233}$ primer set [7]. These samples were tested twice and samples showing discordant results were retested a third time. 51 of 74 samples initially examined were available for independent extraction and testing at Chester Beatty Laboratories, London using identical nested PCR primers and conditions to ensure fidelity of the PCR results. Results from eight samples were discordant between laboratories and were removed from the analysis as uninterpretable (four positive samples from each laboratory). Statistical comparisons were made using EPI-INFO ver. 5 (USD, Stone Mt. Ga., USA) with exact confidence intervals.

RESULTS

Of 66 tissues examined, 24 were from AIDS-KS cases, 20 were from endemic HIV seronegative KS cases, and 22 were from cancer control patients without KS. Seven of the cancer control patients were HIV seropositive and 15 were HIV seronegative (FIG. 22). Tumors examined in the control group included carcinomas of the breast, ovaries, rectum, stomach, and colon, fibrosarcoma, lymphocytic lymphomas, Hodgkin's lymphomas, choriocarcinoma and anaplastic carcinoma of unknown primary site. The median age of AIDS-KS patients was 29 years (range 3–50) compared to 36 years (range 3–79) for endemic KS patients and 38 years (range 21–73) for cancer controls.

Among KS lesions, 39 of 44 (89%) were positive for $KS330_{233}$ PCR product, including KS tissues from 22 of 24 (92%) HIV seropositive and 17 of 20 (85%) HIV seronegative patients. In comparison, 3 of 22 (14%) nonKS cancer control tissues were positive, including 1 of 7 (14%) HIV seropositive and 2 of 15 (13%) HIV seronegative control patients (FIG. 19). These control patients included a 73 year old HIV seronegative male and a 29 year old HIV seronegative female with breast carcinomas, and a 36 year old HIV seropositive female with ovarian carcinoma. The odds ratios for detecting the sequences in tissues from HIV seropositive and HIV seronegative cases and controls wag 66 (95% confidence interval (95% C.I.) 3.8–3161) and 36.8 (95% C.I. 4.3–428) respectively. The overall weighted Mantel-Haenzel odds ratio stratified by HIV serostatus was 49.2 (95% C.I. 9.1–335). KS tissues from four HIV seropositive children (ages 3, 5, 6, and 7 years) and four HIV seronegative children (ages 3, 4, 4, and 12 years) were all positive for $KS330_{233}$.

All discordant results (i.e. KSHV negative KS or KSHV positive nonKS cancers) were reviewed microscopically. All $KS330_{233}$ PCR negative KS samples were confirmed to be KS. Likewise, all $KS330_{233}$ PCR positive nonKS cancers were found not to have occult KS histopathologically.

DISCUSSION

These results indicate that KSHV DNA sequences are found not only in AIDS-KS [5], classical KS [6] and transplant KS [7] but also in African KS from both HIV seropositive and seronegative patients. Despite differences in clinical and epidemiological features, KSHV DNA sequences are present in all major clinical subtypes of KS from widely dispersed geographic settings.

This study was performed on banked, formalin-fixed tissues which prevented the use of specific detection assays such as Southern hybridization. DNA extracted after such treatment is often fragmented which reduces the detection sensitivity of PCR and may account for the 5 PCR negative KS samples found in the study. The results, however, are unlikely to be due to PCR contamination or nonspecific amplification. Specimens were tested blindly and a subset of samples were independently extracted and tested at a physically separate laboratory. Specimen blinding is essential to ensure the integrity of results based solely on PCR analyses. A subset of amplicons was sequenced and found to be more than 98% identical to the published $KS330_{233}$ sequence confirming their specific nature and, because of minor sequence variation, making the possibility of contamination unlikely.

In contrast to previous studies in North American and European populations, it was found 3 of 22 control tissues to have evidence of KSHV infection. Since these cancers represent a variety of tissue types, it is unlikely that KSHV has an etiologic role in these tumors. One possible explanation for the findings is that these results reflect the rate of KSHV infection in the nonKS population in Uganda. Four independent controlled studies from North America [5 and 9] Europe [7] and Asia [8] have failed to detect evidence of KSHV infection in over 200 cancer control tissues, with the exception of an unusual AIDS-associated, body-cavity-based lymphoma [9]. Taken together, these studies indicate that DNA-based detection of KSHV infection is rare in most nonKS cancer tissues from developed countries. KSHV infection has been reported in post-transplant skin tumors, although well-controlled studies are needed to confirm that these findings are not due to PCR contamination [10]. Since the rate of HIV-negative KS is much more frequent in Uganda than the United States, detection of KSHV in control tissues from cancer patients in the study may reflect a relatively high prevalence infection in the general Ugandan population.

While KS is extremely rare among children in developed countries [2], the rate of KS in Ugandan children has risen dramatically over the past 3 decades: age-standardized rates (per 100,000) for boys age 0–14 years were 0.25 in 1964–68 and 10.1 in 1992–93. Detection of KSHV genome in KS lesions from prepubertal children suggests that the virus has a nonsexual mode of transmission among Ugandan children. That five of these children were 5 years old or less raises the possibility that the agent can be transmitted perinatally. Whether or not immune tolerance due to perinatal transmission accounts for the more fulminant form of KS occurring in African children remains to be investigated.

REFERENCES

1. Oettle A. G. Geographic and racial differences in the frequency of Kaposi's sarcoma as evidence of environmental or genetic causes. Acta Un Int Cancer 1962;18:330–363.
2. Beral V. Epidemiology of Kaposi's sarcoma. In: Cancer, HIV and AIDS. London: Imperial Cancer Research Fund, 1991: 5–22.
3. Wabinga H. R., Parkin D. M., Wabwire-Mangen F., Mugerwa J. Cancer in Kampala, Uganda, in 1989–91: changes in incidence in the era of AIDS. Int J Cancer 1993;54:26–36.
4. Kestens L. et al. Endemic Kaposi's sarcoma is not associated with immunodeficiency. Int. J. Cancer 1985;36:49–54.
5. Chang Y. et al. Identification of herpesvirus-like DNA sequences in AIDS-associated Kaposi's sarcoma. Science 1994; 266:1865–9.
6. Moore P.S. and Chang Y. Detection of herpesvirus-like DNA sequences in Kaposi's sarcoma lesions from persons with and without HIV infection. New England J Med 1995; 332:1181–85.
7. Boshoff C. et al. Kaposi's sarcoma-associated herpesvirus in HIV negative Kaposi's sarcoma (letter). Lancet 1995; 345:1043–44.
8. Su, I.-J., Hsu, Y.-S., Chang, Y.-C., Wang, I.-W. Herpevirus-like DNA sequence in Kaposi's sarcoma from AIDS and non-AIDS patients in Taiwan. Lancet 1995;345: 722–3.
9. Cesarman E., Chang Y., Moore P. S., Said J. W., Knowles D. M. Kaposi's sarcoma-associated herpesvirus-like DNA sequences are present in AIDS-related body cavity based lymphomas. New England J Med 1995; 332:1186–1191.
10. Rady P. L., et al. Herpesvirus-like DNA sequences in nonKaposi's sarcoma skin lesions of transplant patients. Lancet 1995;345:1339–40.

What is claimed is:

1. An isolated nucleic acid which is at least 30 nucleotides in length and has a sequence which uniquely defines a herpesvirus associated with kaposi's sarcoma, which herpesvirus is present in and recoverable from the HBL-6 cell line (ATCC Accession No CRL 11762).

2. The isolated nucleic acid of claim 1, wherein the isolated nucleic acid is cDNA.

3. The isolated nucleic acid of claim 1, wherein the isolated nucleic acid is genomic DNA.

4. The isolated nucleic acid of claim 1, wherein the isolated nucleic acid is RNA.

5. The isolated nucleic acid of claim 1 wherein the isolated nucleic acid is labeled with a detectable marker.

6. A replicable vector comprising the isolated nucleic acid of claim 1.

7. A nucleic acid of at least 14 nucleotides which specifically hybridizes with the isolated nucleic acid of claim 1.

8. A nucleic acid of at least 14 nucleotides which specifically hybridizes with a nucleic acid which is complementary to the isolated nucleic acid of claim 1.

9. The isolated nucleic acid of claim 5, wherein the marker is a radioactive label, or a calorimetric, a luminescent, or a fluorescent marker.

10. A host cell containing the vector of claim 6.

11. The vector of claim 6, wherein the vector is a plasmid.

12. The vector of claim 6, wherein the vector is a cosmid.

13. The vector of claim 6, wherein the vector is a λ phage.

14. The vector of claim 6, wherein she vector is a YAC.

15. The nucleic acid of claim 7, wherein the nucleic acid is DNA.

16. The nucleic acid of claim 7, wherein the nucleic acid is labeled with a detectable marker.

17. The cell of claim 10 which is a eucaryotic cell.

18. The cell of claim 10 which is a bacterial cell.

19. The nucleic acid of claim 16, wherein the detectable marker is a radioactive label, or a calorimetric, a luminescent, or a fluorescent marker.

20. A method of diagnosing Kaposi's sarcoma which comprises: (a) obtaining nucleic acids from a tumor lesion of a subject; (b) contacting the nucleic acids from the tumor lesion with the labeled nucleic acid of claim 16 under hybridizing conditions; and (c) determining the presence of hybridized nucleic acids from the tumor lesion, the presence of which is indicative of Kaposi's sarcoma in the subject, thereby diagnosing Kaposi's sarcoma.

21. A method of diagnosing Kaposi's sarcoma which comprises: (a) obtaining nucleic acids from a suitable bodily fluid of a subject; (b) contacting said nucleic acids from the suitable bodily fluid with the labeled nucleic acid of claim 16 under hybridizing conditions; and (c) determining the presence of hybridized nucleic acids from the suitable bodily fluid, the presence of which is indicative of Kaposi's sarcoma in the subject, thereby diagnosing Kaposi's sarcoma.

22. The method of claim 20 wherein the nucleic acids from the tumor lesion are amplified before step (b).

23. An isolated herpesvirus associated with kaposi's sarcoma which is present in and recoverable from the HBL-6 cell line (ATCC Accession No CRL 11762).

24. A nucleic acid of at least 14 nucleotides which hybridizes under high stringency conditions to at least a portion of a nucleotide sequence as shown in FIG. 3A (SEQ ID NO:1).

* * * * *

SEQUENCE LISTING

<160> NUMBER OF SEQ ID NOS: 58

<210> SEQ ID NO 1
<211> LENGTH: 20710
<212> TYPE: DNA
<213> ORGANISM: Kaposi's sarcoma-associated herpesvirus

<400> SEQUENCE: 1

```
tcgagtcgga gagttggcac aggccttgag ctcgctgtga cgttctcacg gtgttggttg      60
ggatcagctg gtgactcaga caagtcttga gctctacaac gtaacatacg ggctgatgcc     120
cacccgatac cagaattacg cagtcggcaa ttctgtgccc tagagtcacc tcaaagaata    180
atctgtggtg tccaagggga gggttctggg gccggctact tagaaaccgc catagatcgg    240
gcagggtgga gtacttgagg agccggcggt aggtggccag gtgggcccgg ttacctgctc    300
ttttgcgtgc tgctggaagc ctgctcaggg atttcttaac ctcggcctcg gttggacgta    360
ccatggcaga aggcggtttt ggagcggact cggtggggcg cggcggagaa aaggcctctg    420
tgactagggg aggcaggtgg gacttgggga gctcggacga cgaatcaagc acctccacaa    480
ccagcacgga tatggacgac ctccctgagg agaggaaacc actaacggga aagtctgtaa    540
aaacctcgta catatacgac gtgcccaccg tcccgaccag caagccgtgg catttaatgc    600
acgacaactc cctctacgca acgcctaggt ttccgcccag acctctcata cggcacccct    660
ccgaaaaagg cagcattttt gccagtcggt tgtcagcgac tgacgacgac tcgggagact    720
```

-continued

```
acgcgccaat ggatcgcttc gccttccaga gccccagggt gtgtggtcgc cctcccttc    780 cgcctccaaa tcacccacct ccggcaacta ggccggcaga cgcgtcaatg ggggacgtgg    840
gctgggcgga tctgcaggga ctcaagagga ccccaaaggg attttaaaa acatctacca    900 agggggcag tctcaaagcc cgtggacgcg atgtaggtga ccgtctcagg gacggcggct     960
ttgcctttag tcctagggc gtgaaatctg ccatagggca aaacattaaa tcatggttgg    1020
ggatcggaga atcatcggcg actgctgtcc ccgtcaccac gcagcttatg gtaccggtgc   1080
acctcattag aacgcctgtg accgtggact acaggaatgt ttatttgctt tacttagagg   1140
gggtaatggg tgtgggcaaa tcaacgctgg tcaacgccgt gtgcgggatc ttgccccagg   1200
agagagtgac aagttttccc gagcccatgg tgtactggac gagggcattt acagattgtt   1260
acaaggaaat ttcccacctg atgaagtctg gtaaggcggg agacccgctg acgtctgcca   1320
aaatatactc atgccaaaac aagttttcgc tccccttccg gacgaacgcc accgctatcc   1380
tgcgaatgat gcagccctgg aacgttgggg gtgggtctgg gagggcact cactggtgcg    1440 tctttgatag gcatctcctc tccccagcag tggtgttccc tctcatgcac ctgaagcacg   1500
gccgcctatc ttttgatcac ttctttcaat tactttccat ctttagagcc acagaaggcg   1560
acgtggtcgc cattctcacc ctctccagcc ccgagtcgtt gcggcgggtc agggcgaggg   1620
gaagaaagaa cgacgggacg gtggagcaaa actacatcag agaattggcg tgggcttatc   1680
acgccgtgta ctgttcatgg atcatgttgc agtacatcac tgtggagcag atggtacaac   1740
tatgcgtaca aaccacaaat attccggaaa tctgcttccg cagcgtgcgc ctggcacaca   1800
aggaggaaac tttgaaaaac cttcacgagc agagcatgct acctatgatc accggtgtac   1860
tggatcccgt gagacatcat cccgtcgtga tcgagctttg cttttgtttc ttcacagagc   1920
tgagaaaatt acaatttatc gtagccgacg cggataagtt ccacgacgac gtatgcggcc   1980
tgtggaccga atctacagg cagatcctgt ccaatccggc tattaaaccc agggccatca    2040
actggccagc attagagagc cagtctaaag cagttaatca cctagaggag acatgcaggg   2100
tctagccttc ttggcggccc ttgcatgctg gcgatgcata tcgttgacat gtggagccac   2160
tggcgcgttg ccgacaacgg cgacgacaat aacccgctcc gccacgcagc tcatcaatgg   2220
gagaaccaac ctctccatag aactggaatt caacggcact agttttttc taaattggca    2280 aaatctgttg aatgtgatca cggagccggc cctgacagag ttgtggacct ccgccgaagt   2340
cgccgaggac ctcagggtaa ctctgaaaaa gaggcaaagt ctttttttcc ccaacaagac   2400
agttgtgatc tctggagacg gccatcgcta tacgtgcgag gtgccgacgt cgtcgcaaac   2460
ttataacatc accaagggct ttaactatag cgctctgccc gggcaccttg gcggatttgg   2520
gatcaacgcg cgtctggtac tgggtgatat cttcgcatca aaatggtcgc tattcgcgag   2580 ggacaccca gagtatcggg tgttttaccc aatgaatgtc atggccgtca agttttccat    2640
atccattggc aacaacgagt ccggcgtagc gctctatgga gtggtgtcgg aagatttcgt   2700
ggtcgtcacg ctccacaaca ggtccaaaga ggctaacgag acggcgtccc atcttctgtt   2760
cggtctcccg gattcactgc catctctgaa gggccatgcc acctatgatg aactcacgtt   2820
cgcccgaaac gcaaaatatg cgctagtggc gatcctgcct aaagattctt accagacact   2880
ccttacagag aattacactc gcatatttct gaacatgacg gagtcgacgc cctcgagtt    2940 cacgcggacg atccagacca ggatcgtatc aatcgaggcc aggcgcgcct gcgcagctca   3000
agaggcggcg ccgacatat tcttggtgtt gtttcagatg ttggtggcac actttcttgt    3060
tgcgcggggc attgccgagc accgatttgt ggaggtggac tgcgtgtgtc ggcagtatgc   3120
```

```
ggaactgtat tttctccgcc gcatctcgcg tctgtgcatg cccacgttca ccactgtcgg    3180
gtataaccac accacccttg gcgctgtggc cgccacacaa atagctcgcg tgtccgccac    3240
gaagttggcc agtttgcccc gctcttccca ggaaacagtg ctggccatgg tccagcttgg    3300
cgcccgtgat ggcgccgtcc cttcctccat tctggagggc attgctatgg tcgtcgaaca    3360
tatgtatacc gcctacactt atgtgtacac actcggcgat actgaaagaa aattaatgtt    3420
ggacatacac acggtcctca ccgacagctg cccgcccaaa gactccggag tatcagaaaa    3480
gctactgaga acatatttga tgttcacatc aatgtgtacc aacatagagc tgggcgaaat    3540
gatcgcccgc tttccaaac cggacagcct taacatctat agggcattct ccccctgctt    3600
tctaggacta aggtacgatt tgcatccagc caagttgcgc gccgaggcgc cgcagtcgtc    3660
cgctctgacg cggactgccg ttgccagagg aacatcggga ttcgcagaat tgctccacgc    3720
gctgcacctc gatagcttaa atttaattcc ggcgattaac tgttcaaaga ttacagccga    3780
caagataata gctacggtac ccttgcctca cgtcacgtat atcatcagtt ccgaagcact    3840
ctcgaacgct gttgtctacg aggtgtcgga gatcttcctc aagagtgcca tgtttatatc    3900
tgctatcaaa cccgattgct ccggctttaa cttttctcag attgataggc acattcccat    3960
agtctacaac atcagcacac caagaagagg ttgccccctt tgtgactctg taatcatgag    4020
ctacgatgag agcgatggcc tgcagtctct catgtatgtc actaatgaaa gggtgcagac    4080
caacctcttt ttagataagt cacctttctt tgataataac aacctacaca ttcattattt    4140
gtggctgagg gacaacggga ccgtagtgga gataaggggc atgtatagaa gacgcgcagc    4200
cagtgctttg tttctaattc tctcttttat tgggttctcg ggggttatct actttcttta    4260
cagactgttt tccatccttt attagacggt caataaagcg tagattttta aaaggtttcc    4320
tgtgcattct ttttgtatgg gcatatactt ggcaagaaat ccgagcacct cagaaagtgg    4380
attgccgtca catatcagtt cgaccacccc tgcacctagc catgcggcgc tttgacggtc    4440

tttgggcta cacatcataa agtacttttc catggcttct ataagcacct tggaacaatc    4500
tgggggttgg cgaatgggtt ccctaaacgg gaaatcctct atggtattca ggcagaagac    4560
cgcgtcctcc acccgacgtt tgagtctttc tagcagagcg ccgaagaact cccgctcgtg    4620
tgttttcgca ggggcaagtt ctgcgccgta cagcgatgag aaacacgaca cgatgttttc    4680
cagccccatg ctgcgcagca acacgtgctt caggaacagg tgttgtagcc ggttcagttt    4740
tagcttgggt agaaaagtta tcgagttgtt agcacgctcc atgatggtaa cggtgttgaa    4800
gtcacagacc gggctttctc cgagtctcgg ccgcctgagt ccaatcatgt agaacataga    4860
cgcggcctcg ttgtctgtgt taagtgacac gatatcccgt tcgcaaacct gtgcgatgtt    4920
gtgtttcagt atagatctgg tctgaccggc acgggtgttt atgggtgac gcggtaaagg    4980 cgactctggg tcaaacacct ttatgcggtt ggcggcctcg tcgatgacga cacgcttgtt    5040
cgcggcgtgt atgggacgc gacggcatcc cgctggcaga tctataatct taaagttggt    5100
ataagactgg tcgctcgtta tggccagccg gcactccggt agtatctgcg tgtcctcgaa    5160

ttcgtggccg cgtacgactg gcttggagtg caggtaaacg ccaagagatg cggtctcttc    5220
gcctacgcac aagtggcttc ttaacgcgta gggtgcggt gagagcatga tccgtagcaa    5280
cgatagttcc gggtgcctag ccgcgtagag tggcaggta gacgagtccg gagtcccaaa    5340
cttttcgaac aacagtggca tcgggacttc aggattagag actccacca tggccgccac    5400 cgccggagag gtcaagacgt gaaacacgcg ctcgcctgtc gacaggcgcg ccgcgccctc    5460
```

-continued

```
tactagacta gccttcacgt ccggaactcg taacatagct tagaccagcg gacggacgca    5520
acgtacgcgg ggatcggctg gcggtgtctg ctcgttggac gcggccgttc ggtggcgcca    5580
gtgcaggcct agtttgcgaa tggcgtgacg gacaatttgt ggctttagag cggcgaaccg    5640
atgacccgtg gtggcgacga acgaaatgaa gtttgcattg cggcccaact cgtctagcct    5700
ggtcttcttt tttcgggcat agattttcgg gattaggtta cacttttttat atcccagtac    5760 tgcgcactcg tgtttgcttt tagtgtgact gattatcttc tttgagaagt caaacaggcc    5820
ccgggcggcg gctcgcctaa tgcaagccac gtcaagcctg agaaacgaac agcattccac    5880
cagacactcc aggaaccttt tgtgtagcgt ctgtatttgg gaacggtttc tgtgctcaag    5940
tagggagaat attctatttt tgtttccgtc gatgcgcgcg tgctggtccg tgagaatggg    6000
cgccagctcg tggcgaatct gttccacaag aggctgcccg tacactttag aaatcgtggc    6060
tgtcgcggcc ttaaaccagg acacgtttag cccatccttg ctggagacca cagatggaaa    6120
gtttgtggtc caaaatacgt tttttcgccc cattctcacc atgtactggt tttccagtcc    6180
gtgcaggtcc aacgtggagt tccaatttgc tatcgataca ggaaatatgt gcctgattgg    6240
cagaaagcat ttcagcgtac ccattgcgaa gagaaagtgc agcatgtccc cactgatgtt    6300
gatgtttatt gcggtgcctt gacacatgtt gtcggaaaaa aacacgctta tggtaaaaga    6360
aggttccttt acggagtact ttcgtataac aaaattgttg gtcaatctgg ggatgtttaa    6420
aatagtcttt tgcaggggtgt taggaacgtg gcagcttatc ttagtgttaa tcaccatgtt    6480
ggtgttgaat atggtgatct tgaagttttc caaactgacg tgttttgtgg gttccagcat    6540
gtctgacact gtagagctgc ccagagtccg cgcgtccgtg gccgcgtatc gttggaagca    6600
cgcctgcaaa tttcctttca tggctgctcg ccggtctttc ggcgcgtacc ggattcttga    6660
aagcgtcgcc gccaggagac gcggtgtctc gtgggtgcct aaaaagtttg cgcaggggtg    6720
cagtccgctg cacgagtggc cgatgcagtc tgccactgcc atacacatga cgagtctgta    6780
gatggccggt gtgcccggat acactagata gtaggtacaa tctgggtac tgacgaccac    6840 cctgtatggc tttggtccgg ggtccttgcg ttggattttt acgtgcagac gggacacgag    6900
ctggtttaga gccagctgaa agcccaccag atcccgtccg ttaaccttga cgtcctggtg    6960
cttactctgt ttcgacaggt tcttcagcac ggtgggcagt cgctctacgt tgtgagcgat    7020
ggcacggcgc agcgagacca gctctccgtg ccacccccac gtggccatga agctgctgat    7080
gttaaacttt aaaaaatgta gctgtgcgtc tggggatgcg ggtggcatta ttgaaaacga    7140
gagatgcttc aggctctcca ggagtgcaaa ataattttga tagattgtgg gttgtagact    7200
atggggcaac accgccagaa acgcatgaaa acactgttcg aactcccaga actccaggta    7260
cctgcacact atcctgaaca tggctttgta acatatggtg cacgttagta gcgcgggaag    7320
atacagcgag cgtagctccc tgaattcgca gggtttatca caatcatcgg taagttccca    7380
tgatcccacc gcaggtaggt agttgtcggt gtctatctgt ccgcgcgtaa acactccacc    7440
accgtcaatt attaaacctt cgccgctgta ccgtcgaccc acttttccca aaagagtccc    7500
ttcttgatgt ataaagggt ggaggcgttc ccccaggagt agtctgcgta tcgctctgca    7560
ggcgaaaaag gtgggctcgg gctgcatcat cttatcaaga ccttctaagg tcagctctgc    7620
ctgcaggtgc gagttggtgg ccagacagca gaatatttcc agctgtgatt cccaagtcgc    7680
ttgataacac gtggtctgcg gactcgtcgt cagggaggcg ctcggtggca gtagtagggg    7740
gccctcgagc gctgccatgg aggcgacctt ggagcaacga cctttcccgt acctcgccac    7800
ggaggccaac ctcctaacgc agattaagga gtcggctgcc gacggactct tcaagagctt    7860
```

```
tcagctattg ctcggcaagg acgccagaga aggcagtgtc cgtttcgaag cgctactggg    7920
cgtatatacc aatgtggtgg agtttgttaa gtttctggag accgccctcg ccgccgcttg    7980
cgtcaatacc gagttcaagg acctgcggag aatgatagat ggaaaaatac agtttaaaat    8040
ttcaatgccc actattgccc acggagacgg gaggaggccc aacaagcaga gacagtatat    8100
cgtcatgaag gcttgcaata agcaccacat cggtgcggag attgagcttg cggccgcaga    8160
catcgagctt ctcttcgccg agaaagagac gcccttggac ttcacagagt acgcgggtgc    8220
catcaagacg attacgtcgg ctttgcagtt tggtatggac gccctagaac gggggctagt    8280
ggacacggtt ctcgcagtta aacttcggca cgctccaccc gtctttattt taaagacgct    8340
gggcgatccc gtctactctg agagggcct caaaaaggcc gtcaagtctg acatggtatc    8400
catgttcaag gcacacctca tagaacattc attttttcta gataaggccg agctcatgac    8460
aagggggaag cagtatgtcc taaccatgct ctccgacatg ctggccgcgg tgtgcgagga    8520
taccgtcttt aagggtgtca gcacgtacac cacggcctct gggcagcagg tggccggcgt    8580
cctggagacg acgacagcg tcatgagacg gctgatgaac ctgctggggc aagtggaaag    8640
tgccatgtcc gggcccgcgg cctacgccag ctacgttgtc aggggtgcca acctcgtcac    8700
cgccgttagc tacggaaggg cgatgagaaa ctttgaacag tttatggcac gcatagtgga    8760
ccatcccaac gctctgccgt ctgtggaagg tgacaaggcc gctctggcgg acggacacga    8820
cgagattcag agaacccgca tcgccgcctc tctcgtcaag ataggggata gtttgtggc    8880 cattgaaagt ttgcagcgca tgtacaacga gactcagttt ccctgcccac tgaaccggcg    8940
catccagtac acctatttct tccctgttgg ccttcacctt cccgtgcccc gctactcgac    9000
atccgtctca gtcaggggcg tagaatcccc ggccatccag tcgaccgaga cgtgggtggt    9060
taataaaaac aacgtgcctc tttgcttcgg ttaccaaaac gccctcaaaa gcatatgcca    9120
ccctcgaatg cacaacccca cccagtcagc ccaggcacta aaccaagctt ttcccgatcc    9180
cgacggggga catgggtacg gtctcaggta tgagcagacg ccaaacatga acctattcag    9240
aacgttccac cagtattaca tggggaaaaa cgtggcattt gttcccgatg tggcccaaaa    9300
agcgctcgta accacggagg atctactgca cccaacctct caccgtctcc tcagattgga    9360
ggtccacccc ttctttgatt tttttgtgca ccctgtcct ggagcgagag gatcgtaccg    9420
cgccacccac agaacaatgg ttggaaatat accacaaccg ctcgctccaa gggagtttca    9480
ggaaagtaga ggggcgcagt tcgacgctgt gacgaatatg acacacgtca tagaccagct    9540
aactattgac gtcatacagg agacggcatt tgaccccgcg tatcccctgt tctgctatgt    9600
aatcgaagca atgattcacg gacaggaaga aaaattcgtg atgaacatgc ccctcattgc    9660
cctggtcatt caaacctact gggtcaactc gggaaaactg gcgtttgtga acagttatca    9720
catggttaga ttcatctgta cgcatattgg gaatggaagc atccctaagg aggcgcacgg    9780
ccactaccgg aaaatcttag gcgagctcat cgcccttgag caggcgcttc tcaagctcgc    9840
gggacacgag acggtgggtc ggacgccgat cacacatctg gtttcggctc tcctcgaccc    9900
gcatctgctg cctcccttttg cctaccacga tgtctttacg gatcttatgc agaagtcatc    9960
cagacaaccc ataatcaaga tcggggatca aaactacgac aaccctcaaa ataggggcgac    10020 attcatcaac ctcagggtgc gcatggagga cctagtcaat aaccttgtta acatttacca    10080
gacaagggtc aatgaggacc atgacagaga acacgtcctg gacgtggcgc ccctggacga    10140
gaatgactac aacccggtcc tcgagaagct attctactat gttttaatgc cggtgtgcag    10200
```

-continued

```
taacggccac atgtgcggta tgggggtcga ctatcaaaac gtggccctga cgctgactta    10260
caacggcccc gtctttgcgg acgtcgtgaa cgcacaggat gatattctac tgcacctgga    10320
gaacggaacc ttgaaggaca ttctgcaggc aggcgacata cgcccgacgg tggacatgat    10380
cagggtgctg tgcacctcgt ttctgacgtg cccttcgtc acccaggccg ctcgcgtgat     10440
cacaaagcgg gacccggccc agagttttgc cacgcacgaa tacgggaagg atgtggcgca    10500
gaccgtgctt gttaatggct ttggtgcgtt cgcggtggcg gaccgctctc gcgaggcggc    10560
ggagactatg ttttatccgg tacccttta caagctctac gctgacccgt tggtggctgc     10620
cacactgcat ccgctcctgc caaactatgt caccaggctc cccaaccaga gaaacgcggt    10680 ggtcttttaac gtgccatcca atctcatggc agaatatgag gaatggcaca gtcgcccgt    10740 cgcggcgtat gccgcgtctt gtcaggccac cccgggcgcc attagcgcca tggtgagcat    10800
gcaccaaaaa ctatctgccc ccagtttcat ttgccaggca aaacaccgca tgcaccctgg    10860
ttttgccatg acagtcgtca ggacggacga ggttctagca gagcacatcc tatactgctc    10920
cagggcgtcg acatccatgt ttgtgggctt gccttcggtg gtacgcgcg aggtacgttc      10980 ggacgcggtg acttttgaaa ttacccacga gatcgcttcc ctgcacaccg cacttggcta    11040
ctcatcagtc atcgcccccgg cccacgtggc cgccataact acagacatgg gagtacattg    11100
tcaggacctc tttatgattt tcccagggga cgcgtatcag gaccgccagc tgcatgacta    11160
tatcaaaatg aaagcggggc tgcaaaccgg ctcaccggga aacagaatgg atcacgtggg    11220
atacactgct ggggttcctc gctgcgagaa cctgcccggt ttgagtcatg gtcagctggc    11280
aacctgcgag ataattccca cgccggtcac atctgacgtt gcctatttcc agacccccag    11340 caaccccgg gggcgtgcgg cgtcggtcgt gtcgtgtgat gcttacagta acgaaagcgc     11400
agagcgtttg ttctacgacc attcaatacc agaccccgcg tacgaatgcc ggtccaccaa    11460
caacccgtgg gcttcgcagc gtggctccct cggcgacgtg ctatacaata tcacctttcg    11520
ccagactgcg ctgccgggca tgtacagtcc ttgtcggcag ttcttccaca aggaagacat    11580
tatgcggtac aataggggt tgtacacttt ggttaatgag tattctgcca ggcttgctgg     11640 ggccccccgcc accagcacta cagacctcca gtacgtcgtg gtcaacggta cagacgtgtt    11700
tttggaccag ccttgccata tgctgcagga ggcctatccc acgctcgccg ccagccacag    11760
agttatgctt gccgagtaca tgtcaaacaa gcagacacac gccccagtac acatgggcca    11820
gtatctcatt gaagaggtgg cgccgatgaa gagactatta aagctcggaa acaaggtggt    11880
gtattagcta acccttctag cgttggctag tcatggcact cgacaagagt atagtggtta    11940
acttcacctc cagactcttc gctgatgaac tggccgccct tcagtcaaaa ataggagcg     12000 tactgccgct cggagattgc caccgtttac aaaatataca ggcattgggc ctggggtgcg    12060
tatgctcacg tgagacatct ccggactaca tccaaattat gcagtatcta tccaagtgca    12120
cactcgctgt cctggaggag gttcgcccgg acagcctgcg cctaacgcgg atggatccct    12180
ctgcaaacct tcagataaaa aacgtatatg cccccttttt tcagtgggac agcaacaccc    12240
agctagcagt gctaccccca ttttttagcc gaaaggattc caccattgtg ctcgaatcca    12300
acggatttga ccccgtgttc cccatggtcg tgccgcagca actggggcac gctattctgc    12360
agcagctgtt ggtgtaccac atctactcca aaatatcggc cggggccccg gatgatgtaa    12420
atatggcgga acttgatcta tataccacca atgtgtcatt tatggggcgc acatatcgtc    12480
tggacgtaga caacacggat ccacgtactg ccctgcgagt gcttgacgat ctgtccatgt    12540
acctttgtat cctatcagcc ttggttccca ggggtgtct ccgtctgctc acggcgctcg     12600
```

-continued

```
tgcggcacga caggcatcct ctgacagagg tgtttgaggg ggtggtgcca gatgaggtga    12660
ccaggataga tctcgaccag ttgagcgtcc cagatgacat caccaggatg cgcgtcatgt    12720
tctcctatct tcagagtctc agttctatat ttaatcttgg ccccagactg cacgtgtatg    12780
cctactcggc agagactttg gcggcctcct gttggtattc cccacgctaa cgatttgaag    12840 cgggggggt atggcgtcat ctgatattct gtcggttgca aggacggatg acggctccgt     12900
ctgtgaagtc tccctgcgtg gaggtaggaa aaaaactacc gtctacctgc cggacactga    12960
accctgggtg gtagagaccg acgccatcaa agacgccttc ctcagcgacg ggatcgtgga    13020
tatggctcga aagcttcatc gtggtgccct gccctcaaat tctcacaacg gcttgaggat    13080
ggtgcttttt tgttattgtt acttgcaaaa ttgtgtgtac ctagccctgt ttctgtgccc    13140
ccttaatcct tacttggtaa ctccctcaag cattgagttt gccgagcccg ttgtggcacc    13200
tgaggtgctc ttcccacacc cggctgagat gtctcgcggt tgcgatgacg cgattttctg    13260
taaactgccc tataccgtgc ctataatcaa caccacgttt ggacgcattt acccgaactc    13320
tacacgcgag ccggacggca ggcctacgga ttactccatg gcccttagaa gggcttttgc    13380
agttatggtt aacacgtcat gtgcaggagt gacattgtgc cgcggagaaa ctcagaccgc    13440
atcccgtaac cacactgagt gggaaaatct gctggctatg ttttctgtga ttatctatgc    13500
cttagatcac aactgtcacc cggaagcact gtctatcgcg agcggcatct ttgacgagcg    13560
tgactatgga ttattcatct ctcagccccg gagcgtgccc tcgcctaccc cttgcgacgt    13620
gtcgtgggaa gatatctaca acgggactta cctagctcgg cctggaaact gtgacccctg    13680
gcccaatcta tccaccccctc ccttgattct aaatttttaaa taaaggtgtg tcactggtta    13740
caccacgatt aaaaaccact cactgagatg tcttttttaac cgctaaggga ttataccggg    13800
atttaaaacc gcccactgat ttttttacgc taagagttgg gtgcttgggg ggttttgcat    13860
tgctctgttg taaactatat ataagttaaa ccaaaattcg cagggagaca aggtgacggt    13920
ggtgagaact cagttgagag tcagagaata cagtgctaat cagggtagat gagcatgact    13980 ttcccccgtct ccagtcaccg gaggaatggt ggacggctcc gtcctggtgc gaatggccac    14040
caagcctccc gtgattggtc ttataacagt gctcttcctc ctagtcatag gcgcctgcgt    14100
ctactgctgc attcgcgtgt tcctggcggc tcgactgtgg cgcgccaccc cactaggcag    14160
ggccaccgtg gcgtatcagg tccttcgcac cctgggaccg caggccgggt cacatgcacc    14220
gccgacggtg ggcatagcta cccaggagcc ctaccgtaca atatacatgc cagattagaa    14280
cggggtgtgt gctataatgg atggctatgg gggggggctg tagataattg agcgctgtgc    14340
ttttattgtg gggatatggg cttgtacatg tgtctatcat cggtagccat aaaatgggcc    14400
atgacaactg ccacaagtaa gtcgtccgac atgtgctttt gcttggcgct gtatgactgc    14460
cctccatccc taagcgggac gcacttgatc gcgcggacct gttctaccag gtaggtcacc    14520
gggtcaaatg atattttgat ggtgttggac accaccgtct ggctggcgct cagggtgccg    14580 gagttcgag cgtagatgaa tgtctcaaac gcggaggatt tctcgcctcc caacatgtaa    14640
attggccact gcagggcgct gctcttgtca gtatagtgta gaaatgtat ggggagcggg      14700 catatttcgt taaggacggt tgcaatggcc acccagaat cttggctgct gttgccttcg     14760
accgccgcgt tcacgcgctc aattgtggtg tggagcacag cgatcgcctt aatcatcgtg    14820
catgcgcagg acgctatctc gtaagcagct gcgcagtga ggtcgcgcag gaagaaatgc     14880
tccatgccca atatgaggct tctggtggga gtctgagtac tcgtgacaac ggcgcccacg    14940
```

-continued

```
ccagtaccgg acgcctccgt gttgttcgta tacgcgggt cgatgtaaac aaacagctgt    15000
tttccaaggc acttctgaac ctcctgggcg gtggtgtcta cccgacacat gtcaaactgt    15060
gtcagcgctg cgtcacccac cacgcggtaa agcgtagcat ttgacgacgc tgctccctcg    15120
cccattagtt cggtgtcgaa tgcccctcc ataaagaggt tggtggtggt tttgatggat     15180
tcgtcgatgg tgatgtacgt cggaatgtgc agtctgtaac aaggacagga cactagtgcg    15240
tcttgcaggt ggaaatcttc tcggtggtcc gcacacacgt aactgaccac attcagcatc    15300
ttttcctggg cgttcctgag gttaagcagg aaactcgtgg agcggtctga cgagttcacg    15360
gatgatataa atataagctt ggcgtctttc tgaagcatga aacccagaat agccggcagt    15420
gcatccttt taataaaatt cgcctcgtct acgtagagca ggttaaaggt ctgtccccga     15480
atgctctgca gacacggaaa gacacaaaag agggctcat aagcggctaa cagtaaagga     15540
gaggaggcga acagtgcgtg gctcttggtt cttgggaata aaaggggcg tgtgtgccga     15600
tcgatcgtat gggtgagcca gtggatcctg gacatgtggt gaatgagaaa gattttgagg    15660
agtgtgaaca attttcagt caaccccta gggagcaagt ggtcgcgggg gtcagggcac      15720
tcgacggcct cggtctcgct gactctctat gtcacaaaac agaaagactc tgcctgctga    15780
tggacctggt gggcacggag tgctttgcga gggtgtgccg cctagacacc ggtgcgaaat    15840
gaagagtgtg gcgagtccct tatgtcagtt ccacggcgtg ttttgcctgt accagtgtcg    15900
ccagtgcctg gcataccacg tgtgtgatgg gggcgccgaa tgcgttctcc tgcatacgcc    15960
ggagagcgtc atctgcgaac taacgggtaa ctgcatgctc ggcaacattc aagagggcca    16020
gtttttaggg ccggtaccgt atcggacttt ggataaccag gttgacaggg acgcatatca    16080
cgggatgcta gcgtgtctga aacgggacat tgtgcggtat ttgcagacat ggccggacac    16140
caccgtaatc gtgcaggaaa tagccctggg ggacggcgtc accgacacca tctcggccat    16200
tatagatgaa acattcggtg agtgtcttcc cgtactgggg gaggcccaag gcgggtacgc    16260
cctggtctgt agcatgtatc tgcacgttat cgtctccatc tattcgacaa aaacggtgta    16320
caacagtatg ctatttaaat gcacaaagaa taaaaagtac gactgcattg ccaagcgggt    16380
gcggacaaaa tggatgcgca tgctatcaac gaaagatacg taggtcctcg ctgccaccgt    16440
ttggcccacg tggtgctgcc taggacctttt ctgctgcatc acgccatacc cctggagccc    16500
gagatcatct tttccaccta cacccggttc agccggtcgc cagggtcatc ccgccggttg     16560
gtggtgtgtg ggaaacgtgt cctgccaggg gaggaaaacc aacttgcgtc ttcaccttct    16620
ggtttggcgc ttagcctgcc tctgtttttcc cacgatggga actttcatcc atttgacatc    16680
tcggtactgc gcatttcctg ccctggttct aatcttagtc ttactgtcag atttctctat     16740
ctatctctgg tggtggctat ggggcgga cggaataatg cgcggagtcc gaccgttgac      16800
ggggtatcgc cgccagaggg cgccgtagcc caccctttgg aggaactgca gaggctggcg    16860
cgtgctacgc cggacccggc actcacccgt ggaccgttgc aggtcctgac cggccttctc    16920
cgcgcagggt cagacggaga ccgcgccact caccacatgg cgctcgaggc tccgggaacc    16980
gtgcgtggag aaagcctaga cccgcctgtt tcacagaagg ggccagcgcg cacacgccac    17040
aggccacccc ccgtgcgact gagcttcaac cccgtcaatg ccgatgtacc cgctacctgg    17100
cgagacgcca ctaacgtgta ctcgggtgct ccctactatg tgtgtgttta cgaacgcggt    17160
ggccgtcagg aagacgactg gctgccgata ccactgagct tcccagaaga gcccgtgccc    17220
ccgccaccgg gcttagtgtt catggacgac ttgttcatta acacgaagca gtgcgacttt    17280
gtggacacgc tagaggccgc ctgtcgcacg caaggctaca cgttgagaca gcgcgtgcct    17340
```

-continued

```
gtcgccattc ctcgcgacgc ggaaatcgca gacgcagtta aatcgcactt tttagaggcg    17400
tgcctagtgt tacggggggct ggcttcggag gctagtgcct ggataagagc tgccacgtcc    17460
ccgccccttg gccgccacgc ctgctggatg gacgtgttag gattatggga aagccgcccc    17520
cacactctag gtttggagtt acgcggcgta aactgtggcg gcacggacgg tgactggtta    17580
gagattttaa aacagcccga tgtgcaaaag acagtcagcg ggagtcttgt ggcatgcgtg    17640
atcgtcacac ccgcattgga agcctggctt gtgttacctg ggggttttgc tattaaagcc    17700
cgctataggg cgtcgaagga ggatctggtg ttcattcgag gccgctatgg ctagccggag    17760
gcgcaaactt cggaatttcc taaacaagga atgcatatgg actgttaacc caatgtcagg    17820
ggaccatatc aaggtctta acgcctgcac ctctatctcg ccggtgtatg accctgagct    17880
ggtaaccagc tacgcactga gcgtgcctgc ttacaatgtg tctgtggcta tcttgctgca    17940
taaagtcatg ggaccgtgtg tggctgtggg aattaacgga gaaatgatca tgtacgtcgt    18000
aagccagtgt gtttctgtgc ggcccgtccc ggggcgcgat ggtatggcgc tcatctactt    18060
tggacagttt ctggaggaag catccggact gagatttccc tacattgctc cgccgccgtc    18120
gcgcgaacac gtacctgacc tgaccagaca agaattagtt catacctccc aggtggtgcg    18180
ccgcggcgac ctgaccaatt gcactatggg tctcgaattc aggaatgtga acccttttgt    18240
ttggctcggg ggcggatcgg tgtggctgct gttcttgggc gtggactaca tggcgttctg    18300
tccgggtgtc gacggaatgc cgtcgttggc aagagtggcc gccctgctta ccaggtgcga    18360
ccacccagac tgtgtccact gccatggact ccgtggacac gttaatgtat ttcgtgggta    18420
ctgttctgcg cagtcgccgg gtctatctaa catctgtccc tgtatcaaat catgtgggac    18480
cgggaatgga gtgactaggg tcactggaaa cagaaatttt ctgggtcttc tgttcgatcc    18540
cattgtccag agcagggtaa cagctctgaa gataactagc cacccaaccc ccacgcacgt    18600
cgagaatgtg ctaacaggag tgctcgacga cggcaccttg gtgccgtccg tccaaggcac    18660
cctgggtcct cttacgaatg tctgactact tcagccgctt gctgatatat gagtgtaaaa    18720
aacttaaggc cctgggctta cgttcttatt gaagcatgtt gcgcacatca gcgagctgga    18780
ccgtcctccg ggtcgcgtgt agattatggt tccgttctcc ttcttgatgt ttaaattttt    18840 ggggggggaac caccgacaaa gcgtctttat gatttccgcg aacacggagt tggctacgtg    18900
cttttggtgg gctacgtacc caatgttaat gttctctacg gatgccagta gcatgctgat    18960
gatcgccacc actatccatg tctttccgtg tctccttggt attaggaata cgcttgcctt    19020
ttgcttaaac gtctgtaaaa cactgtttgg agtttcaaat aaaccgaagt actgcttaaa    19080
caatccaaac aactggtgcg tcttttgtgg ggccttgatt gaaaccaaaa agaaaaaagt    19140
gtgcattact agctgctgtt ggaagggctc cagccagtgc accccgggaa cgtaacagcc    19200
gttcagaaag gacgaaaggt taaccagaaa agcctgaagt tcgcggtaga cagagcaggc    19260
gtgcagggag tcgtgtgttt ttctgcccgc ctggtactcg accagttgat cggccgtgga    19320
gacgtgcgcg tcctcgcgca cacaccgcat ctgcaagtat gttgataggg actccaatag    19380
gcgcggcttt gcggggacgt tgtcctcgga cggtctgggg gttccacgt cgggatttgc    19440 tgacgtgggc gtgcgggat ggtgccgtgt gcagtatgtt tccaggaccg aactgtatga    19500
gtttattctg tgcaccacgc caataaaagg gtgcgccatc cgtgccgttt gggacagtg    19560 tcgcgtgaat gtcgggggcac tcagttccca cctctctccg gcgtctttgg cggtctcctc    19620
caggttggcg gcaaggcgct ccctgtgacg gctgagcagc atgtttgctt tgagctcgct    19680
```

-continued

```
cgtgtccgag ggtgacccgg aggtgaccag taggtacgtc aagggcgtac aacttgccct      19740
ggaccttagc gagaacacac ctggacaatt taagttgata gaaactcccc tgaacagctt      19800
cctcttggtt tccaacgtga tgcccgaggt ccagccaatc tgcagtggcc ggccggcctt      19860
gcggccagac tttagtaatc tccacttgcc tagactggag aagctccaga gagtcctcgg      19920
gcagggtttc ggggcggcgg gtgaggaaat cgcactggac ccgtctcacg tagaaacaca      19980
cgaaaagggc caggtgttct acaaccacta tgctaccgag gagtggacgt gggctttgac      20040
tctgaataag gatcgctcc ttcgggaggc tgtagatggc ctgtgtgacc ccggaacttg       20100
gaagggtctt cttcctgacg acccccttcc gttgctatgg ctgctgttca acggacccgc      20160 ctcttttgt cgggccgact gttgcctgta caagcagcac tgcggttacc cgggcccggt       20220
gctacttcca ggtcacatgt acgctcccaa acgggatctt ttgtcgttcg ttaatcatgc      20280
cctgaagtac accaagtttc tatacggaga tttttccggg acatgggcgg cggcttgccg      20340
cccgccattc gctacttctc ggatacaaag ggtagtgagt cagatgaaaa tcatagatgc      20400
ttccgacact tacatttccc acacctgcct cttgtgtcac atatatcagc aaaatagcat      20460
aattgcgggt caggggaccc acgtgggtgg aatcctactg ttgagtggaa aagggaccca      20520
gtatataaca ggcaatgttc agacccaaag gtgtccaact acgggcgact atctaatcat      20580
cccatcgtat gacataccgg cgatcatcac catgatcaag gagaatggac tcaaccaact      20640
ctaaaagaga gtttattaag tcggctctgg aggccaacat caacaggagg gcagctgtat      20700
cgctatttga                                                             20710
```

<210> SEQ ID NO 2
<211> LENGTH: 4128
<212> TYPE: DNA
<213> ORGANISM: Kaposi's sarcoma-associated herpesvirus

<400> SEQUENCE: 2

```
atggaggcga ccttggagca acgacctttc ccgtacctcg ccacggaggc caacctccta       60
acgcagatta aggagtcggc tgccgacgga ctcttcaaga gctttcagct attgctcggc      120
aaggacgcca gagaaggcag tgtccgtttc gaagcgctac tgggcgtata taccaatgtg      180
gtggagtttg ttaagtttct ggagaccgcc ctcgccgccg cttgcgtcaa taccgagttc      240
aaggacctgc ggagaatgat agatggaaaa atacagttta aatttcaat gcccactatt       300 gcccacggag acgggaggag gcccaacaag cagagacagt atatcgtcat gaaggcttgc      360
aataagcacc acatcggtgc ggagattgag cttgcggccg cagacatcga gcttctcttc      420
gccgagaaag agacgcccct tggacttcaca gagtacgcgg gtgccatcaa gacgattacg      480
tcggctttgc agtttggtat ggacgcccta gaacggggc tagtggacac ggttctcgca      540
gttaaacttc ggcacgctcc accgtctttt attttaaaga cgctgggcga tcccgtctac      600
tctgagaggg gcctcaaaaa ggccgtcaag tctgacatgg tatccatgtt caaggcacac      660
ctcatagaac attcattttt tctagataag gccgagctca tgacaagggg gaagcagtat      720
gtcctaacca tgctctccga catgctggcc gcggtgtgcg aggataccgt ctttaagggt      780
gtcagcacgt acaccacggc ctctgggcag caggtggccg gcgtcctgga cgacggac        840 agcgtcatga cggctgat gaacctgctg gggcaagtgg aaagtgccat gtccgggccc        900
gcggcctacg ccagctacgt tgtcaggggt gccaacctcg tcaccgccgt tagctacgga      960
agggcgatga gaaactttga acagtttatg gcacgcatag tggaccatcc caacgctctg     1020
ccgtctgtgg aagtgacaa ggccgctctg gcggacggac acgacgagat tcagagaacc      1080
```

```
cgcatcgccg cctctctcgt caagataggg gataagtttg tggccattga aagtttgcag   1140
cgcatgtaca acgagactca gtttccctgc ccactgaacc ggcgcatcca gtacacctat   1200
ttcttccctg ttggccttca ccttcccgtg ccccgctact cgacatccgt ctcagtcagg   1260
ggcgtagaat ccccggccat ccagtcgacc gagacgtggg tggttaataa aaacaacgtg   1320
cctctttgct tcggttacca aaacgccctc aaaagcatat gccaccctcg aatgcacaac   1380
cccacccagt cagcccaggc actaaaccaa gctttcccg atcccgacgg gggacatggg   1440
tacggtctca ggtatgagca gacgccaaac atgaacctat tcagaacgtt ccaccagtat   1500
tacatgggga aaaacgtggc atttgttccc gatgtggccc aaaaagcgct cgtaaccacg   1560
gaggatctac tgcacccaac ctctcaccgt ctcctcagat ggaggtcca ccccttcttt    1620 gatttttttg tgcaccctg tcctggagcg agaggatcgt accgcgccac ccacagaaca   1680
atggttggaa atataccaca accgctcgct ccaagggagt tcaggaaag tagaggggcg    1740 cagttcgacg ctgtgacgaa tatgacacac gtcatagacc agctaactat tgacgtcata   1800
caggagacgg catttgaccc cgcgtatccc ctgttctgct atgtaatcga agcaatgatt   1860
cacggacagg aagaaaaatt cgtgatgaac atgcccctca ttgccctggt cattcaaacc   1920
tactgggtca actcgggaaa actggcgttt gtgaacagtt atcacatggt tagattcatc   1980
tgtacgcata ttgggaatgg aagcatccct aaggaggcgc acggccacta ccggaaaatc   2040
ttaggcgagc tcatcgccct tgagcaggcg cttctcaagc tcgcgggaca cgagacggtg   2100
ggtcggacgc cgatcacaca tctggtttcg gctctcctcg acccgcatct gctgcctccc   2160
tttgcctacc acgatgtctt tacgatctt atgcagaagt catccagaca acccataatc    2220
aagatcgggg atcaaaacta cgacaaccct caaaataggg cgacattcat caacctcagg   2280
ggtcgcatgg aggacctagt caataaccct tgttaacattt accagacaag ggtcaatgag   2340
gaccatgacg agagacacgt cctggacgtg gcgcccctgg acgagaatga ctacaacccg   2400
gtcctcgaga agctattcta ctatgtttta atgccggtgt gcagtaacgg ccacatgtgc   2460
ggtatggggg tcgactatca aaacgtggcc ctgacgctga cttacaacgg ccccgtcttt   2520
gcggacgtcg tgaacgcaca ggatgatatt ctactgcacc tggagaacgg aaccttgaag   2580
gacattctgc aggcaggcga catacgcccg acggtggaca tgatcagggt gctgtgcacc   2640
tcgtttctga cgtgcccttt cgtcacccag gccgctcgcg tgatcacaaa gcgggacccg   2700
gcccagagtt ttgccacgca cgaatacggg aaggatgtgg cgcagaccgt gcttgttaat   2760
ggctttggtg cgttcgcggt ggcggaccgc tctcgcgagg cggcggagac tatgttttat   2820
ccggtaccct ttaacaagct ctacgctgac ccgttggtgg ctgccacact gcatccgctc   2880
ctgccaaact atgtcaccag gctccccaac cagagaaacg cggtggtctt taacgtgcca   2940
tccaatctca tggcagaata tgaggaatgg cacaagtcgc ccgtcgcggc gtatgccgcg   3000
tcttgtcagg ccaccccggg cgccattagc gccatggtga gcatgcacca aaaactatct   3060
gcccccagtt tcatttgcca ggcaaaacac cgcatgcacc ctggttttgc catgacagtc   3120
gtcaggacgg acgaggttct agcagagcac atcctatact gctccagggc gtcgacatcc   3180
atgtttgtgg gcttgccttc ggtggtacgg cgcgaggtac gttcggacgc ggtgactttt   3240
gaaattaccc acgagatcgc ttccctgcac accgcacttg gctactcatc agtcatcgcc   3300
ccggcccacg tggccgccat aactacagac atggagtac attgtcagga cctctttatg    3360
attttcccag gggacgcgta tcaggaccgc cagctgcatg actatatcaa aatgaaagcg   3420
```

-continued

| | |
|---|---|
| ggcgtgcaaa ccggctcacc gggaaacaga atggatcacg tgggatacac tgctggggtt | 3480 |
| cctcgctgcg agaacctgcc cggtttgagt catggtcagc tggcaacctg cgagataatt | 3540 |
| cccacgccgg tcacatctga cgttgcctat ttccagaccc ccagcaaccc ccgggggcgt | 3600 |
| gcggcgtcgg tcgtgtcgtg tgatgcttac agtaacgaaa gcgcagagcg tttgttctac | 3660 |
| gaccattcaa taccagaccc cgcgtacgaa tgccggtcca ccaacaaccc gtgggcttcg | 3720 |
| cagcgtggct ccctcggcga cgtgctatac aatatcacct ttcgccagac tgcgctgccg | 3780 |
| ggcatgtaca gtccttgtcg gcagttcttc cacaaggaag acattatgcg gtacaatagg | 3840 |
| gggttgtaca ctttggttaa tgagtattct gccaggcttg ctggggcccc cgccaccagc | 3900 |
| actacagacc tccagtacgt cgtggtcaac ggtacagacg tgttttttgga ccagccttgc | 3960 |
| catatgctgc aggaggccta tcccacgctc gccgccagcc acagagttat gcttgccgag | 4020 |
| tacatgtcaa acaagcagac acacgcccca gtacacatgg gccagtatct cattgaagag | 4080 |
| gtggcgccga tgaagagact attaaagctc ggaaacaagg tggtgtat | 4128 |

<210> SEQ ID NO 3
<211> LENGTH: 1376
<212> TYPE: PRT
<213> ORGANISM: Kaposi's sarcoma-associated herpesvirus

<400> SEQUENCE: 3

```
Met Glu Ala Thr Leu Glu Gln Arg Pro Phe Pro Tyr Leu Ala Thr Glu
  1               5                  10                  15

Ala Asn Leu Leu Thr Gln Ile Lys Glu Ser Ala Ala Asp Gly Leu Phe
             20                  25                  30

Lys Ser Phe Gln Leu Leu Leu Gly Lys Asp Ala Arg Glu Gly Ser Val
         35                  40                  45

Arg Phe Glu Ala Leu Leu Gly Val Tyr Thr Asn Val Val Glu Phe Val
     50                  55                  60

Lys Phe Leu Glu Thr Ala Leu Ala Ala Cys Val Asn Thr Glu Phe
 65                  70                  75                  80

Lys Asp Leu Arg Arg Met Ile Asp Gly Lys Ile Gln Phe Lys Ile Ser
                 85                  90                  95

Met Pro Thr Ile Ala His Gly Asp Gly Arg Arg Pro Asn Lys Gln Arg
            100                 105                 110

Gln Tyr Ile Val Met Lys Ala Cys Asn Lys His His Ile Gly Ala Glu
        115                 120                 125

Ile Glu Leu Ala Ala Ala Asp Ile Glu Leu Leu Phe Ala Glu Lys Glu
    130                 135                 140

Thr Pro Leu Asp Phe Thr Glu Tyr Ala Gly Ala Ile Lys Thr Ile Thr
145                 150                 155                 160

Ser Ala Leu Gln Phe Gly Met Asp Ala Leu Glu Arg Gly Leu Val Asp
                165                 170                 175

Thr Val Leu Ala Val Lys Leu Arg His Ala Pro Pro Val Phe Ile Leu
            180                 185                 190

Lys Thr Leu Gly Asp Pro Val Tyr Ser Glu Arg Gly Leu Lys Lys Ala
        195                 200                 205

Val Lys Ser Asp Met Val Ser Met Phe Lys Ala His Leu Ile Glu His
    210                 215                 220

Ser Phe Phe Leu Asp Lys Ala Glu Leu Met Thr Arg Gly Lys Gln Tyr
225                 230                 235                 240

Val Leu Thr Met Leu Ser Asp Met Leu Ala Ala Val Cys Glu Asp Thr
                245                 250                 255
```

```
Val Phe Lys Gly Val Ser Thr Tyr Thr Thr Ala Ser Gly Gln Gln Val
            260                 265                 270

Ala Gly Val Leu Glu Thr Thr Asp Ser Val Met Arg Arg Leu Met Asn
            275                 280                 285

Leu Leu Gly Gln Val Glu Ser Ala Met Ser Gly Pro Ala Ala Tyr Ala
            290                 295                 300

Ser Tyr Val Val Arg Gly Ala Asn Leu Val Thr Ala Val Ser Tyr Gly
305                 310                 315                 320

Arg Ala Met Arg Asn Phe Glu Gln Phe Met Ala Arg Ile Val Asp His
                325                 330                 335

Pro Asn Ala Leu Pro Ser Val Glu Gly Asp Lys Ala Ala Leu Ala Asp
            340                 345                 350

Gly His Asp Glu Ile Gln Arg Thr Arg Ile Ala Ala Ser Leu Val Lys
            355                 360                 365

Ile Gly Asp Lys Phe Val Ala Ile Glu Ser Leu Gln Arg Met Tyr Asn
            370                 375                 380

Glu Thr Gln Phe Pro Cys Pro Leu Asn Arg Arg Ile Gln Tyr Thr Tyr
385                 390                 395                 400

Phe Phe Pro Val Gly Leu His Leu Pro Val Pro Arg Tyr Ser Thr Ser
            405                 410                 415

Val Ser Val Arg Gly Val Glu Ser Pro Ala Ile Gln Ser Thr Glu Thr
            420                 425                 430

Trp Val Val Asn Lys Asn Asn Val Pro Leu Cys Phe Gly Tyr Gln Asn
            435                 440                 445

Ala Leu Lys Ser Ile Cys His Pro Arg Met His Asn Pro Thr Gln Ser
450                 455                 460

Ala Gln Ala Leu Asn Gln Ala Phe Pro Asp Pro Asp Gly Gly His Gly
465                 470                 475                 480

Tyr Gly Leu Arg Tyr Glu Gln Thr Pro Asn Met Asn Leu Phe Arg Thr
                485                 490                 495

Phe His Gln Tyr Tyr Met Gly Lys Asn Val Ala Phe Val Pro Asp Val
            500                 505                 510

Ala Gln Lys Ala Leu Val Thr Thr Glu Asp Leu Leu His Pro Thr Ser
            515                 520                 525

His Arg Leu Leu Arg Leu Glu Val His Pro Phe Phe Asp Phe Phe Val
530                 535                 540

His Pro Cys Pro Gly Ala Arg Gly Ser Tyr Arg Ala Thr His Arg Thr
545                 550                 555                 560

Met Val Gly Asn Ile Pro Gln Pro Leu Ala Pro Arg Glu Phe Gln Glu
            565                 570                 575

Ser Arg Gly Ala Gln Phe Asp Ala Val Thr Asn Met Thr His Val Ile
            580                 585                 590

Asp Gln Leu Thr Ile Asp Val Ile Gln Glu Thr Ala Phe Asp Pro Ala
            595                 600                 605

Tyr Pro Leu Phe Cys Tyr Val Ile Glu Ala Met Ile His Gly Gln Glu
            610                 615                 620

Glu Lys Phe Val Met Asn Met Pro Leu Ile Ala Leu Val Ile Gln Thr
625                 630                 635                 640

Tyr Trp Val Asn Ser Gly Lys Leu Ala Phe Val Asn Ser Tyr His Met
                645                 650                 655

Val Arg Phe Ile Cys Thr His Ile Gly Asn Gly Ser Ile Pro Lys Glu
            660                 665                 670
```

```
Ala His Gly His Tyr Arg Lys Ile Leu Gly Glu Leu Ile Ala Leu Glu
            675                 680                 685

Gln Ala Leu Leu Lys Leu Ala Gly His Glu Thr Val Gly Arg Thr Pro
        690                 695                 700

Ile Thr His Leu Val Ser Ala Leu Leu Asp Pro His Leu Leu Pro Pro
705                 710                 715                 720

Phe Ala Tyr His Asp Val Phe Thr Asp Leu Met Gln Lys Ser Ser Arg
            725                 730                 735

Gln Pro Ile Ile Lys Ile Gly Asp Gln Asn Tyr Asp Asn Pro Gln Asn
        740                 745                 750

Arg Ala Thr Phe Ile Asn Leu Arg Gly Arg Met Glu Asp Leu Val Asn
            755                 760                 765

Asn Leu Val Asn Ile Tyr Gln Thr Arg Val Asn Glu Asp His Asp Glu
        770                 775                 780

Arg His Val Leu Asp Val Ala Pro Leu Asp Glu Asn Asp Tyr Asn Pro
785                 790                 795                 800

Val Leu Glu Lys Leu Phe Tyr Tyr Val Leu Met Pro Val Cys Ser Asn
            805                 810                 815

Gly His Met Cys Gly Met Gly Val Asp Tyr Gln Asn Val Ala Leu Thr
        820                 825                 830

Leu Thr Tyr Asn Gly Pro Val Phe Ala Asp Val Val Asn Ala Gln Asp
            835                 840                 845

Asp Ile Leu Leu His Leu Glu Asn Gly Thr Leu Lys Asp Ile Leu Gln
850                 855                 860

Ala Gly Asp Ile Arg Pro Thr Val Asp Met Ile Arg Val Leu Cys Thr
865                 870                 875                 880

Ser Phe Leu Thr Cys Pro Phe Val Thr Gln Ala Ala Arg Val Ile Thr
            885                 890                 895

Lys Arg Asp Pro Ala Gln Ser Phe Ala Thr His Glu Tyr Gly Lys Asp
        900                 905                 910

Val Ala Gln Thr Val Leu Val Asn Gly Phe Gly Ala Phe Ala Val Ala
            915                 920                 925

Asp Arg Ser Arg Glu Ala Ala Glu Thr Met Phe Tyr Pro Val Pro Phe
        930                 935                 940

Asn Lys Leu Tyr Ala Asp Pro Leu Val Ala Ala Thr Leu His Pro Leu
945                 950                 955                 960

Leu Pro Asn Tyr Val Thr Arg Leu Pro Asn Gln Arg Asn Ala Val Val
            965                 970                 975

Phe Asn Val Pro Ser Asn Leu Met Ala Glu Tyr Glu Glu Trp His Lys
        980                 985                 990

Ser Pro Val Ala Ala Tyr Ala Ala Ser Cys Gln Ala Thr Pro Gly Ala
            995                1000                1005

Ile Ser Ala Met Val Ser Met His Gln Lys Leu Ser Ala Pro Ser Phe
       1010                1015                1020

Ile Cys Gln Ala Lys His Arg Met His Pro Gly Phe Ala Met Thr Val
1025                1030                1035                1040

Val Arg Thr Asp Glu Val Leu Ala Glu His Ile Leu Tyr Cys Ser Arg
            1045                1050                1055

Ala Ser Thr Ser Met Phe Val Gly Leu Pro Ser Val Val Arg Arg Glu
        1060                1065                1070

Val Arg Ser Asp Ala Val Thr Phe Glu Ile Thr His Glu Ile Ala Ser
       1075                1080                1085

Leu His Thr Ala Leu Gly Tyr Ser Ser Val Ile Ala Pro Ala His Val
```

```
              1090              1095              1100
Ala Ala Ile Thr Thr Asp Met Gly Val His Cys Gln Asp Leu Phe Met
1105                1110              1115              1120

Ile Phe Pro Gly Asp Ala Tyr Gln Asp Arg Gln Leu His Asp Tyr Ile
            1125              1130              1135

Lys Met Lys Ala Gly Val Gln Thr Gly Ser Pro Gly Asn Arg Met Asp
        1140              1145              1150

His Val Gly Tyr Thr Ala Gly Val Pro Arg Cys Glu Asn Leu Pro Gly
    1155              1160              1165

Leu Ser His Gly Gln Leu Ala Thr Cys Glu Ile Ile Pro Thr Pro Val
1170              1175              1180

Thr Ser Asp Val Ala Tyr Phe Gln Thr Pro Ser Asn Pro Arg Gly Arg
1185              1190              1195              1200

Ala Ala Ser Val Val Ser Cys Asp Ala Tyr Ser Asn Glu Ser Ala Glu
            1205              1210              1215

Arg Leu Phe Tyr Asp His Ser Ile Pro Asp Pro Ala Tyr Glu Cys Arg
        1220              1225              1230

Ser Thr Asn Asn Pro Trp Ala Ser Gln Arg Gly Ser Leu Gly Asp Val
    1235              1240              1245

Leu Tyr Asn Ile Thr Phe Arg Gln Thr Ala Leu Pro Gly Met Tyr Ser
1250              1255              1260

Pro Cys Arg Gln Phe Phe His Lys Glu Asp Ile Met Arg Tyr Asn Arg
1265              1270              1275              1280

Gly Leu Tyr Thr Leu Val Asn Glu Tyr Ser Ala Arg Leu Ala Gly Ala
            1285              1290              1295

Pro Ala Thr Ser Thr Thr Asp Leu Gln Tyr Val Val Val Asn Gly Thr
        1300              1305              1310

Asp Val Phe Leu Asp Gln Pro Cys His Met Leu Gln Glu Ala Tyr Pro
    1315              1320              1325

Thr Leu Ala Ala Ser His Arg Val Met Leu Ala Glu Tyr Met Ser Asn
1330              1335              1340

Lys Gln Thr His Ala Pro Val His Met Gly Gln Tyr Leu Ile Glu Glu
1345              1350              1355              1360

Val Ala Pro Met Lys Arg Leu Leu Lys Leu Gly Asn Lys Val Val Tyr
            1365              1370              1375

<210> SEQ ID NO 4
<211> LENGTH: 1143
<212> TYPE: DNA
<213> ORGANISM: Kaposi's sarcoma-associated herpesvirus

<400> SEQUENCE: 4
agcattcggg gacagacctt taacctgctc tacgtagacg aggcgaattt tattaaaaag      60
gatgcactgc cggctattct gggtttcatg cttcagaaag acgccaagct tatatttata    120
tcatccgtga actcgtcaga ccgctccacg agtttcctgc ttaacctcag gaacgcccag    180
gaaaagatgc tgaatgtggt cagttacgtg tgtgcggacc accgagaaga tttccacctg    240
caagacgcac tagtgtcctg tccttgttac agactgcaca ttccgacgta catcaccatc    300
gacgaatcca tcaaaaccac caccaacctc tttatggagg gggcattcga caccgaacta    360
atgggcgagg gagcagcgtc gtcaaatgct acgctttacc gcgtggtggg tgacgcagcg    420
ctgacacagt ttgacatgtg tcgggtagac accaccgccc aggaggttca gaagtgcctt    480
ggaaaacagc tgtttgttta catcgacccc gcgtatacga acaacacgga ggcgtccggt    540
```

-continued

```
actggcgtgg gcgccgttgt cacgagtact cagactccca ccagaagcct catattgggc    600
atggagcatt tcttcctgcg cgacctcact ggcgcagctg cttacgagat agcgtcctgc    660
gcatgcacga tgattaaggc gatcgctgtg ctccacacca caattgagcg cgtgaacgcg    720
gcggtcgaag caacagcag ccaagattct ggggtggcca ttgcaaccgt ccttaacgaa     780
atatgcccgc tccccataca ttttctacac tatactgaca agagcagcgc cctgcagtgg    840
ccaatttaca tgttgggagg cgagaaatcc tccgcgtttg agacattcat ctacgctctg    900
aactccggca ccctgagcgc cagccagacg gtggtgtcca acaccatcaa atatcattt     960 gacccggtga cctacctggt agaacaggtc cgcgcgatca agtgcgtccc gcttagggat   1020
ggagggcagt catacagcgc caagcaaaag cacatgtcgg acgacttact tgtggcagtt   1080
gtcatggccc attttatggc taccgatgat agacacatgt acaagcccat atccccacaa   1140
taa                                                                1143
```

<210> SEQ ID NO 5
<211> LENGTH: 380
<212> TYPE: PRT
<213> ORGANISM: Kaposi's sarcoma-associated herpesvirus

<400> SEQUENCE: 5

```
Ser Ile Arg Gly Gln Thr Phe Asn Leu Leu Tyr Val Asp Glu Ala Asn
  1               5                  10                  15

Phe Ile Lys Lys Asp Ala Leu Pro Ala Ile Leu Gly Phe Met Leu Gln
                 20                  25                  30

Lys Asp Ala Lys Leu Ile Phe Ile Ser Ser Val Asn Ser Ser Asp Arg
             35                  40                  45

Ser Thr Ser Phe Leu Leu Asn Leu Arg Asn Ala Gln Glu Lys Met Leu
         50                  55                  60

Asn Val Val Ser Tyr Val Cys Ala Asp His Arg Glu Asp Phe His Leu
 65                  70                  75                  80

Gln Asp Ala Leu Val Ser Cys Pro Cys Tyr Arg Leu His Ile Pro Thr
                 85                  90                  95

Tyr Ile Thr Ile Asp Glu Ser Ile Lys Thr Thr Asn Leu Phe Met
                100                 105                 110

Glu Gly Ala Phe Asp Thr Glu Leu Met Gly Gly Ala Ala Ser Ser
            115                 120                 125

Asn Ala Thr Leu Tyr Arg Val Val Gly Asp Ala Ala Leu Thr Gln Phe
        130                 135                 140

Asp Met Cys Arg Val Asp Thr Ala Gln Glu Val Gln Lys Cys Leu
145                 150                 155                 160

Gly Lys Gln Leu Phe Val Tyr Ile Asp Pro Ala Tyr Thr Asn Asn Thr
                165                 170                 175

Glu Ala Ser Gly Thr Gly Val Gly Ala Val Val Thr Ser Thr Gln Thr
            180                 185                 190

Pro Thr Arg Ser Leu Ile Leu Gly Met Glu His Phe Phe Leu Arg Asp
        195                 200                 205

Leu Thr Gly Ala Ala Ala Tyr Glu Ile Ala Ser Cys Ala Cys Thr Met
    210                 215                 220

Ile Lys Ala Ile Ala Val Leu His Thr Thr Ile Glu Arg Val Asn Ala
225                 230                 235                 240

Ala Val Glu Gly Asn Ser Ser Gln Asp Ser Gly Val Ala Ile Ala Thr
                245                 250                 255

Val Leu Asn Glu Ile Cys Pro Leu Pro Ile His Phe Leu His Tyr Thr
```

-continued

```
                    260                 265                 270

Asp Lys Ser Ser Ala Leu Gln Trp Pro Ile Tyr Met Leu Gly Gly Glu
            275                 280                 285

Lys Ser Ser Ala Phe Glu Thr Phe Ile Tyr Ala Leu Asn Ser Gly Thr
        290                 295                 300

Leu Ser Ala Ser Gln Thr Val Val Ser Asn Thr Ile Lys Ile Ser Phe
305                 310                 315                 320

Asp Pro Val Thr Tyr Leu Val Glu Gln Val Arg Ala Ile Lys Cys Val
                325                 330                 335

Pro Leu Arg Asp Gly Gly Gln Ser Tyr Ser Ala Lys Gln Lys His Met
            340                 345                 350

Ser Asp Asp Leu Leu Val Ala Val Val Met Ala His Phe Met Ala Thr
            355                 360                 365

Asp Asp Arg His Met Tyr Lys Pro Ile Ser Pro Gln
    370                 375                 380

<210> SEQ ID NO 6
<211> LENGTH: 234
<212> TYPE: DNA
<213> ORGANISM: Kaposi's sarcoma-associated herpesvirus

<400> SEQUENCE: 6
atgggtgagc cagtggatcc tggacatgtg gtgaatgaga aagattttga ggagtgtgaa      60 caattttca gtcaacccct tagggagcaa gtggtcgcgg gggtcagggc actcgacggc     120
ctcggtctcg ctgactctct atgtcacaaa acagaaagac tctgcctgct gatggacctg     180
gtgggcacgg agtgctttgc gagggtgtgc cgcctagaca ccggtgcgaa atga          234

<210> SEQ ID NO 7
<211> LENGTH: 77
<212> TYPE: PRT
<213> ORGANISM: Kaposi's sarcoma-associated herpesvirus

<400> SEQUENCE: 7

Met Gly Glu Pro Val Asp Pro Gly His Val Val Asn Glu Lys Asp Phe
1               5                   10                  15

Glu Glu Cys Glu Gln Phe Phe Ser Gln Pro Leu Arg Glu Gln Val Val
            20                  25                  30

Ala Gly Val Arg Ala Leu Asp Gly Leu Gly Leu Ala Asp Ser Leu Cys
        35                  40                  45

His Lys Thr Glu Arg Leu Cys Leu Leu Met Asp Leu Val Gly Thr Glu
    50                  55                  60

Cys Phe Ala Arg Val Cys Arg Leu Asp Thr Gly Ala Lys
65                  70                  75

<210> SEQ ID NO 8
<211> LENGTH: 585
<212> TYPE: DNA
<213> ORGANISM: Kaposi's sarcoma-associated herpesvirus

<400> SEQUENCE: 8
atgaagagtg tggcgagtcc cttatgtcag ttccacggcg tgttttgcct gtaccagtgt      60
cgccagtgcc tggcatacca cgtgtgtgat gggggcgccg aatgcgttct cctgcatacg     120
ccggagagcg tcatctgcga actaacgggt aactgcatgc tcggcaacat tcaagagggc     180 cagttttag ggccggtacc gtatcggact ttggataacc aggttgacag ggacgcatat     240
cacgggatgc tagcgtgtct gaaacgggac attgtgcggt atttgcagac atggccggac     300
```

-continued

```
accaccgtaa tcgtgcagga aatagccctg ggggacggcg tcaccgacac catctcggcc    360
attatagatg aaacattcgg tgagtgtctt cccgtactgg gggaggccca aggcgggtac    420
gccctggtct gtagcatgta tctgcacgtt atcgtctcca tctattcgac aaaaacggtg    480
tacaacagta tgctatttaa atgcacaaag aataaaaagt acgactgcat tgccaagcgg    540
gtgcggacaa aatggatgcg catgctatca acgaaagata cgtag                   585
```

<210> SEQ ID NO 9
<211> LENGTH: 194
<212> TYPE: PRT
<213> ORGANISM: Kaposi's sarcoma-associated herpesvirus

<400> SEQUENCE: 9

```
Met Lys Ser Val Ala Ser Pro Leu Cys Gln Phe His Gly Val Phe Cys
 1               5                  10                  15
Leu Tyr Gln Cys Arg Gln Cys Leu Ala Tyr His Val Cys Asp Gly Gly
            20                  25                  30
Ala Glu Cys Val Leu Leu His Thr Pro Glu Ser Val Ile Cys Glu Leu
        35                  40                  45
Thr Gly Asn Cys Met Leu Gly Asn Ile Gln Glu Gly Gln Phe Leu Gly
    50                  55                  60
Pro Val Pro Tyr Arg Thr Leu Asp Asn Gln Val Asp Arg Asp Ala Tyr
65                  70                  75                  80
His Gly Met Leu Ala Cys Leu Lys Arg Asp Ile Val Arg Tyr Leu Gln
                85                  90                  95
Thr Trp Pro Asp Thr Thr Val Ile Val Gln Glu Ile Ala Leu Gly Asp
            100                 105                 110
Gly Val Thr Asp Thr Ile Ser Ala Ile Ile Asp Glu Thr Phe Gly Glu
        115                 120                 125
Cys Leu Pro Val Leu Gly Glu Ala Gln Gly Gly Tyr Ala Leu Val Cys
    130                 135                 140
Ser Met Tyr Leu His Val Ile Val Ser Ile Tyr Ser Thr Lys Thr Val
145                 150                 155                 160
Tyr Asn Ser Met Leu Phe Lys Cys Thr Lys Asn Lys Lys Tyr Asp Cys
                165                 170                 175
Ile Ala Lys Arg Val Arg Thr Lys Trp Met Arg Met Leu Ser Thr Lys
            180                 185                 190
Asp Thr
```

<210> SEQ ID NO 10
<211> LENGTH: 939
<212> TYPE: DNA
<213> ORGANISM: Kaposi's sarcoma-associated herpesvirus

<400> SEQUENCE: 10

```
atggctagcc ggaggcgcaa acttcggaat ttcctaaaca aggaatgcat atggactgtt    60
aacccaatgt cagggaccca tatcaaggtc tttaacgcct gcacctctat ctcgccggtg    120
tatgaccctg agctggtaac cagctacgca ctgagcgtgc ctgcttacaa tgtgtctgtg    180
gctatcttgc tgcataaagt catgggaccg tgtgtggctg tgggaattaa cggagaaatg    240
atcatgtacg tcgtaagcca gtgtgtttct gtgcggcccg tcccggggcg cgatggtatg    300
gcgctcatct acttggaca gtttctggag aagcatccg gactgagatt tccctacatt    360
gctccgccgc cgtcgcgcga acacgtacct gacctgacca gacaagaatt agttcatacc    420
```

```
tcccaggtgg tgcgccgcgg cgacctgacc aattgcacta tgggtctcga attcaggaat    480
gtgaaccctt ttgtttggct cggggcgga tcggtgtggc tgctgttctt gggcgtggac    540
tacatggcgt tctgtccggg tgtcgacgga atgccgtcgt tggcaagagt ggccgccctg    600
cttaccaggt gcgaccaccc agactgtgtc cactgccatg gactccgtgg acacgttaat    660
gtatttcgtg ggtactgttc tgcgcagtcg ccgggtctat ctaacatctg tccctgtatc    720
aaatcatgtg ggaccgggaa tggagtgact agggtcactg gaaacagaaa ttttctgggt    780
cttctgttcg atcccattgt ccagagcagg gtaacagctc tgaagataac tagccaccca    840 accccacgc acgtcgagaa tgtgctaaca ggagtgctcg acgacggcac cttggtgccg    900
tccgtccaag gcaccctggg tcctcttacg aatgtctga                          939
```

<210> SEQ ID NO 11
<211> LENGTH: 312
<212> TYPE: PRT
<213> ORGANISM: Kaposi's sarcoma-associated herpesvirus

<400> SEQUENCE: 11

```
Met Ala Ser Arg Arg Lys Leu Arg Asn Phe Leu Asn Lys Glu Cys
  1               5                  10                  15

Ile Trp Thr Val Asn Pro Met Ser Gly Asp His Ile Lys Val Phe Asn
                 20                  25                  30

Ala Cys Thr Ser Ile Ser Pro Val Tyr Asp Pro Glu Leu Val Thr Ser
             35                  40                  45

Tyr Ala Leu Ser Val Pro Ala Tyr Asn Val Ser Val Ala Ile Leu Leu
         50                  55                  60

His Lys Val Met Gly Pro Cys Val Ala Val Gly Ile Asn Gly Glu Met
 65                  70                  75                  80

Ile Met Tyr Val Val Ser Gln Cys Val Ser Val Arg Pro Val Pro Gly
                 85                  90                  95

Arg Asp Gly Met Ala Leu Ile Tyr Phe Gly Gln Phe Leu Glu Glu Ala
            100                 105                 110

Ser Gly Leu Arg Phe Pro Tyr Ile Ala Pro Pro Ser Arg Glu His
        115                 120                 125

Val Pro Asp Leu Thr Arg Gln Glu Leu Val His Thr Ser Gln Val Val
    130                 135                 140

Arg Arg Gly Asp Leu Thr Asn Cys Thr Met Gly Leu Glu Phe Arg Asn
145                 150                 155                 160

Val Asn Pro Phe Val Trp Leu Gly Gly Ser Val Trp Leu Leu Phe
                165                 170                 175

Leu Gly Val Asp Tyr Met Ala Phe Cys Pro Gly Val Asp Gly Met Pro
            180                 185                 190

Ser Leu Ala Arg Val Ala Ala Leu Leu Thr Arg Cys Asp His Pro Asp
        195                 200                 205

Cys Val His Cys His Gly Leu Arg Gly His Val Asn Val Phe Arg Gly
    210                 215                 220

Tyr Cys Ser Ala Gln Ser Pro Gly Leu Ser Asn Ile Cys Pro Cys Ile
225                 230                 235                 240

Lys Ser Cys Gly Thr Gly Asn Gly Val Thr Arg Val Thr Gly Asn Arg
                245                 250                 255

Asn Phe Leu Gly Leu Leu Phe Asp Pro Ile Val Gln Ser Arg Val Thr
            260                 265                 270

Ala Leu Lys Ile Thr Ser His Pro Thr Pro Thr His Val Glu Asn Val
        275                 280                 285
```

```
Leu Thr Gly Val Leu Asp Asp Gly Thr Leu Val Pro Ser Val Gln Gly
    290                 295                 300

Thr Leu Gly Pro Leu Thr Asn Val
305                 310

<210> SEQ ID NO 12
<211> LENGTH: 86
<212> TYPE: DNA
<213> ORGANISM: Kaposi's sarcoma-associated herpesvirus

<400> SEQUENCE: 12
atggactcaa ccaactctaa aagagagttt attaagtcgg ctctggaggc caacatcaac      60
aggagggcag ctgtatcgct atttga                                          86

<210> SEQ ID NO 13
<211> LENGTH: 28
<212> TYPE: PRT
<213> ORGANISM: Kaposi's sarcoma-associated herpesvirus

<400> SEQUENCE: 13

Met Asp Ser Thr Asn Ser Lys Arg Glu Phe Ile Lys Ser Ala Leu Glu
1               5                   10                  15

Ala Asn Ile Asn Arg Arg Ala Ala Val Ser Leu Phe
            20                  25

<210> SEQ ID NO 14
<211> LENGTH: 1743
<212> TYPE: DNA
<213> ORGANISM: Kaposi's sarcoma-associated herpesvirus

<400> SEQUENCE: 14
atggcagaag gcggttttgg agcggactcg gtggggcgcg gcggagaaaa ggcctctgtg      60
actaggggag gcaggtggga cttggggagc tcggacgacg aatcaagcac ctccacaacc     120
agcacggata tggacgacct ccctgaggag aggaaaccac taacgggaaa gtctgtaaaa     180
acctcgtaca tatacgacgt gcccaccgtc ccgaccagca agccgtggca tttaatgcac     240
gacaactccc tctacgcaac gcctaggttt ccgcccagac ctctcatacg gcaccctttcc    300 gaaaaaggca gcattttttgc cagtcggttg tcagcgactg acgacgactc gggagactac    360
gcgccaatgg atcgcttcgc cttccagagc cccagggtgt gtggtcgccc tccccttccg    420
cctccaaatc acccacctcc ggcaactagg ccggcagacg cgtcaatggg ggacgtgggc    480
tgggcggatc tgcagggact caagaggacc ccaaagggat ttttaaaaac atctaccaag    540
gggggcagtc tcaaagcccg tggacgcgat gtaggtgacc gtctcaggga cggcggcttt    600
gcctttagtc ctaggggcgt gaaatctgcc atagggcaaa acattaaatc atggttgggg    660
atcggagaat catcggcgac tgctgtcccc gtcaccacgc agcttatggt accggtgcac    720
ctcattagaa cgcctgtgac cgtggactac aggaatgttt atttgcttta cttagagggg    780
gtaatgggtg tgggcaaatc aacgctggtc aacgccgtgt gcgggatctt gccccaggag    840
agagtgacaa gttttcccga gcccatggtg tactggacga gggcattttac agattgttac    900 aaggaaatttt cccacctgat gaagtctggt aaggcgggag acccgctgac gtctgccaaa    960
atatactcat gccaaaacaa gttttcgctc cccttccgga cgaacgccac cgctatcctg   1020
cgaatgatgc agccctggaa cgttgggggt gggtctggga ggggcactca ctggtgcgtc   1080
tttgataggc atctcctctc cccagcagtg gtgttccctc tcatgcacct gaagcacggc   1140
```

-continued

```
cgcctatctt ttgatcactt ctttcaatta ctttccatct ttagagccac agaaggcgac    1200
gtggtcgcca ttctcaccct ctccagcgcc gagtcgttgc ggcgggtcag ggcgagggga    1260
agaaagaacg acgggacggt ggagcaaaac tacatcagag aattggcgtg ggcttatcac    1320
gccgtgtact gttcatggat catgttgcag tacatcactg tggagcagat ggtacaacta    1380
tgcgtacaaa ccacaaatat tccggaaatc tgcttccgca gcgtgcgcct ggcacacaag    1440
gaggaaactt tgaaaaacct tcacgagcag agcatgctac ctatgatcac cggtgtactg    1500
gatcccgtga acatcatcc cgtcgtgatc gagctttgct tttgtttctt cacagagctg    1560
agaaaattac aatttatcgt agccgacgcg gataagttcc acgacgacgt atgcggcctg    1620
tggaccgaaa tctacaggca gatcctgtcc aatccggcta ttaaacccag ggccatcaac    1680
tggccagcat tagagagcca gtctaaagca gttaatcacc tagaggagac atgcagggtc    1740
tag                                                                 1743
```

<210> SEQ ID NO 15
<211> LENGTH: 580
<212> TYPE: PRT
<213> ORGANISM: Kaposi's sarcoma-associated herpesvirus

<400> SEQUENCE: 15

```
Met Ala Glu Gly Gly Phe Gly Ala Asp Ser Val Gly Arg Gly Gly Glu
  1               5                  10                  15

Lys Ala Ser Val Thr Arg Gly Gly Arg Trp Asp Leu Gly Ser Ser Asp
             20                  25                  30

Asp Glu Ser Ser Thr Ser Thr Thr Ser Thr Asp Met Asp Asp Leu Pro
         35                  40                  45

Glu Glu Arg Lys Pro Leu Thr Gly Lys Ser Val Lys Thr Ser Tyr Ile
     50                  55                  60

Tyr Asp Val Pro Thr Val Pro Thr Ser Lys Pro Trp His Leu Met His
 65                  70                  75                  80

Asp Asn Ser Leu Tyr Ala Thr Pro Arg Phe Pro Pro Arg Pro Leu Ile
                 85                  90                  95

Arg His Pro Ser Glu Lys Gly Ser Ile Phe Ala Ser Arg Leu Ser Ala
            100                 105                 110

Thr Asp Asp Ser Gly Asp Tyr Ala Pro Met Asp Arg Phe Ala Phe
        115                 120                 125

Gln Ser Pro Arg Val Cys Gly Arg Pro Pro Leu Pro Pro Pro Asn His
    130                 135                 140

Pro Pro Pro Ala Thr Arg Pro Asp Ala Ser Met Gly Asp Val Gly
145                 150                 155                 160

Trp Ala Asp Leu Gln Gly Leu Lys Arg Thr Pro Lys Gly Phe Leu Lys
                165                 170                 175

Thr Ser Lys Gly Gly Ser Leu Lys Ala Arg Gly Arg Asp Val Gly
            180                 185                 190

Asp Arg Leu Arg Asp Gly Gly Phe Ala Phe Ser Pro Arg Gly Val Lys
        195                 200                 205

Ser Ala Ile Gly Gln Asn Ile Lys Ser Trp Leu Gly Ile Gly Glu Ser
    210                 215                 220

Ser Ala Thr Ala Val Pro Val Thr Thr Gln Leu Met Val Pro Val His
225                 230                 235                 240

Leu Ile Arg Thr Pro Val Thr Val Asp Tyr Arg Asn Val Tyr Leu Leu
                245                 250                 255

Tyr Leu Glu Gly Val Met Gly Val Gly Lys Ser Thr Leu Val Asn Ala
```

```
            260               265                270
Val Cys Gly Ile Leu Pro Gln Glu Arg Val Thr Ser Phe Pro Glu Pro
            275               280                285
Met Val Tyr Trp Thr Arg Ala Phe Thr Asp Cys Tyr Lys Glu Ile Ser
            290               295                300
His Leu Met Lys Ser Gly Lys Ala Gly Asp Pro Leu Thr Ser Ala Lys
305             310               315                    320
Ile Tyr Ser Cys Gln Asn Lys Phe Ser Leu Pro Phe Arg Thr Asn Ala
                325               330                335
Thr Ala Ile Leu Arg Met Met Gln Pro Trp Asn Val Gly Gly Gly Ser
                340               345                350
Gly Arg Gly Thr His Trp Cys Val Phe Asp Arg His Leu Leu Ser Pro
            355               360                365
Ala Val Val Phe Pro Leu Met His Leu Lys His Gly Arg Leu Ser Phe
            370               375                380
Asp His Phe Phe Gln Leu Leu Ser Ile Phe Arg Ala Thr Glu Gly Asp
385             390               395                    400
Val Val Ala Ile Leu Thr Leu Ser Ser Ala Glu Ser Leu Arg Arg Val
                405               410                415
Arg Ala Arg Gly Arg Lys Asn Asp Gly Thr Val Glu Gln Asn Tyr Ile
                420               425                430
Arg Glu Leu Ala Trp Ala Tyr His Ala Val Tyr Cys Ser Trp Ile Met
                435               440                445
Leu Gln Tyr Ile Thr Val Glu Gln Met Val Gln Leu Cys Val Gln Thr
            450               455                460
Thr Asn Ile Pro Glu Ile Cys Phe Arg Ser Val Arg Leu Ala His Lys
465             470               475                    480
Glu Glu Thr Leu Lys Asn Leu His Glu Gln Ser Met Leu Pro Met Ile
                485               490                495
Thr Gly Val Leu Asp Pro Val Arg His His Pro Val Val Ile Glu Leu
            500               505                510
Cys Phe Cys Phe Phe Thr Glu Leu Arg Lys Leu Gln Phe Ile Val Ala
            515               520                525
Asp Ala Asp Lys Phe His Asp Asp Val Cys Gly Leu Trp Thr Glu Ile
            530               535                540
Tyr Arg Gln Ile Leu Ser Asn Pro Ala Ile Lys Pro Arg Ala Ile Asn
545             550               555                    560
Trp Pro Ala Leu Glu Ser Gln Ser Lys Ala Val Asn His Leu Glu Glu
                565               570                575
Thr Cys Arg Val
            580

<210> SEQ ID NO 16
<211> LENGTH: 2193
<212> TYPE: DNA
<213> ORGANISM: Kaposi's sarcoma-associated herpesvirus

<400> SEQUENCE: 16
atgcagggtc tagccttctt ggcggcccct gcatgctggc gatgcatatc gttgacatgt    60
ggagccactg gcgcgttgcc gacaacggcg acgacaataa cccgctccgc cacgcagctc   120
atcaatggga gaaccaacct ctccatagaa ctggaattca acggcactag ttttttttcta   180 aattggcaaa atctgttgaa tgtgatcacg gagccggccc tgacagagtt gtggacctcc   240
gccgaagtcg ccgaggacct cagggtaact ctgaaaaaga ggcaaagtct ttttttcccc   300
```

-continued

```
aacaagacag ttgtgatctc tggagacggc catcgctata cgtgcgaggt gccgacgtcg    360
tcgcaaactt ataacatcac caagggcttt aactatagcg ctctgcccgg gcaccttggc    420
ggatttggga tcaacgcgcg tctggtactg ggtgatatct tcgcatcaaa atggtcgcta    480
ttcgcgaggg acaccccaga gtatcgggtg ttttacccaa tgaatgtcat ggccgtcaag    540
ttttccatat ccattggcaa caacgagtcc ggcgtagcgc tctatggagt ggtgtcggaa    600
gatttcgtgg tcgtcacgct ccacaacagg tccaaagagg ctaacgagac ggcgtcccat    660
cttctgttcg gtctcccgga ttcactgcca tctctgaagg gccatgccac ctatgatgaa    720
ctcacgttcg cccgaaacgc aaaatatgcg ctagtggcga tcctgcctaa agattcttac    780
cagacactcc ttacagagaa ttacactcgc atatttctga acatgacgga gtcgacgccc    840
ctcgagttca cgcggacgat ccagaccagg atcgtatcaa tcgaggccag gcgcgcctgc    900
gcagctcaag aggcggcgcc ggacatattc ttggtgttgt tcagatgtt ggtggcacac    960
tttcttgttg cgcggggcat tgccgagcac cgatttgtgg aggtggactg cgtgtgtcgg   1020
cagtatgcgg aactgtattt tctccgccgc atctcgcgtc tgtgcatgcc cacgttcacc   1080
actgtcgggt ataaccacac caccttggc gctgtggccg ccacacaaat agctcgcgtg   1140
tccgccacga agttggccag tttgccccgc tcttcccagg aaacagtgct ggccatggtc   1200
cagcttggcg cccgtgatgg cgccgtccct tcctccattc tggagggcat tgctatggtc   1260
gtcgaacata tgtataccgc ctacacttat gtgtacacac tcggcgatac tgaaagaaaa   1320
ttaatgttgg acatacacac ggtcctcacc gacagctgcc cgcccaaaga ctccggagta   1380
tcagaaaagc tactgagaac atatttgatg ttcacatcaa tgtgtaccaa catagagctg   1440
ggcgaaatga tcgcccgctt ttccaaaccg gacagcctta acatctatag gcattctcc    1500
ccctgctttc taggactaag gtacgatttg catccagcca agttgcgcgc cgaggcgccg   1560
cagtcgtccg ctctgacgcg gactgccgtt gccagaggaa catcgggatt cgcagaattg   1620
ctccacgcgc tgcacctcga tagcttaaat ttaattccgg cgattaactg ttcaaagatt   1680
acagccgaca agataatagc tacggtaccc ttgcctcacg tcacgtatat catcagttcc   1740
gaagcactct cgaacgctgt tgtctacgag gtgtcggaga tcttcctcaa gagtgccatg   1800
tttatatctg ctatcaaacc cgattgctcc ggctttaact tttctcagat tgataggcac   1860
attcccatag tctacaacat cagcacacca agaagaggtt gccccctttg tgactctgta   1920
atcatgagct acgatgagag cgatggcctg cagtctctca tgtatgtcac taatgaaagg   1980
gtgcagacca acctctttt agataagtca ccttttcttg ataataacaa cctacacatt   2040
cattatttgt ggctgaggga caacgggacc gtagtggaga taagggggcat gtatagaaga   2100
cgcgcagcca gtgctttgtt tctaattctc tcttttattg ggttctcggg ggttatctac   2160
tttctttaca gactgttttc catcctttat tag                                 2193
```

<210> SEQ ID NO 17
<211> LENGTH: 730
<212> TYPE: PRT
<213> ORGANISM: Kaposi's sarcoma-associated herpesvirus

<400> SEQUENCE: 17

```
Met Gln Gly Leu Ala Phe Leu Ala Ala Leu Ala Cys Trp Arg Cys Ile
 1               5                  10                  15
Ser Leu Thr Cys Gly Ala Thr Gly Ala Leu Pro Thr Thr Ala Thr Thr
            20                  25                  30
```

-continued

```
Ile Thr Arg Ser Ala Thr Gln Leu Ile Asn Gly Arg Thr Asn Leu Ser
         35                  40                  45

Ile Glu Leu Glu Phe Asn Gly Thr Ser Phe Phe Leu Asn Trp Gln Asn
 50                  55                  60

Leu Leu Asn Val Ile Thr Glu Pro Ala Leu Thr Glu Leu Trp Thr Ser
 65                  70                  75                  80

Ala Glu Val Ala Glu Asp Leu Arg Val Thr Leu Lys Lys Arg Gln Ser
                 85                  90                  95

Leu Phe Phe Pro Asn Lys Thr Val Val Ile Ser Gly Asp Gly His Arg
                100                 105                 110

Tyr Thr Cys Glu Val Pro Thr Ser Ser Gln Thr Tyr Asn Ile Thr Lys
            115                 120                 125

Gly Phe Asn Tyr Ser Ala Leu Pro Gly His Leu Gly Phe Gly Ile
            130                 135                 140

Asn Ala Arg Leu Val Leu Gly Asp Ile Phe Ala Ser Lys Trp Ser Leu
145                 150                 155                 160

Phe Ala Arg Asp Thr Pro Glu Tyr Arg Val Phe Tyr Pro Met Asn Val
                165                 170                 175

Met Ala Val Lys Phe Ser Ile Ser Ile Gly Asn Asn Glu Ser Gly Val
                180                 185                 190

Ala Leu Tyr Gly Val Val Ser Glu Asp Phe Val Val Thr Leu His
            195                 200                 205

Asn Arg Ser Lys Glu Ala Asn Glu Thr Ala Ser His Leu Leu Phe Gly
            210                 215                 220

Leu Pro Asp Ser Leu Pro Ser Leu Lys Gly His Ala Thr Tyr Asp Glu
225                 230                 235                 240

Leu Thr Phe Ala Arg Asn Ala Lys Tyr Ala Leu Val Ala Ile Leu Pro
                245                 250                 255

Lys Asp Ser Tyr Gln Thr Leu Leu Thr Glu Asn Tyr Thr Arg Ile Phe
                260                 265                 270

Leu Asn Met Thr Glu Ser Thr Pro Leu Glu Phe Thr Arg Thr Ile Gln
            275                 280                 285

Thr Arg Ile Val Ser Ile Glu Ala Arg Arg Ala Cys Ala Ala Gln Glu
290                 295                 300

Ala Ala Pro Asp Ile Phe Leu Val Leu Phe Gln Met Leu Val Ala His
305                 310                 315                 320

Phe Leu Val Ala Arg Gly Ile Ala Glu His Arg Phe Val Glu Val Asp
                325                 330                 335

Cys Val Cys Arg Gln Tyr Ala Glu Leu Tyr Phe Leu Arg Arg Ile Ser
            340                 345                 350

Arg Leu Cys Met Pro Thr Phe Thr Thr Val Gly Tyr Asn His Thr Thr
            355                 360                 365

Leu Gly Ala Val Ala Ala Thr Gln Ile Ala Arg Val Ser Ala Thr Lys
            370                 375                 380

Leu Ala Ser Leu Pro Arg Ser Ser Gln Glu Thr Val Leu Ala Met Val
385                 390                 395                 400

Gln Leu Gly Ala Arg Asp Gly Ala Val Pro Ser Ser Ile Leu Glu Gly
                405                 410                 415

Ile Ala Met Val Val Glu His Met Tyr Thr Ala Tyr Thr Tyr Val Tyr
                420                 425                 430

Thr Leu Gly Asp Thr Glu Arg Lys Leu Met Leu Asp Ile His Thr Val
            435                 440                 445

Leu Thr Asp Ser Cys Pro Pro Lys Asp Ser Gly Val Ser Glu Lys Leu
```

450                 455                 460
Leu Arg Thr Tyr Leu Met Phe Thr Ser Met Cys Thr Asn Ile Glu Leu
465                 470                 475                 480

Gly Glu Met Ile Ala Arg Phe Ser Lys Pro Asp Ser Leu Asn Ile Tyr
                485                 490                 495

Arg Ala Phe Ser Pro Cys Phe Leu Gly Leu Arg Tyr Asp Leu His Pro
            500                 505                 510

Ala Lys Leu Arg Ala Glu Ala Pro Gln Ser Ser Ala Leu Thr Arg Thr
        515                 520                 525

Ala Val Ala Arg Gly Thr Ser Gly Phe Ala Glu Leu Leu His Ala Leu
    530                 535                 540

His Leu Asp Ser Leu Asn Leu Ile Pro Ala Ile Asn Cys Ser Lys Ile
545                 550                 555                 560

Thr Ala Asp Lys Ile Ile Ala Thr Val Pro Leu Pro His Val Thr Tyr
                565                 570                 575

Ile Ile Ser Ser Glu Ala Leu Ser Asn Ala Val Val Tyr Glu Val Ser
            580                 585                 590

Glu Ile Phe Leu Lys Ser Ala Met Phe Ile Ser Ala Ile Lys Pro Asp
        595                 600                 605

Cys Ser Gly Phe Asn Phe Ser Gln Ile Asp Arg His Ile Pro Ile Val
    610                 615                 620

Tyr Asn Ile Ser Thr Pro Arg Arg Gly Cys Pro Leu Cys Asp Ser Val
625                 630                 635                 640

Ile Met Ser Tyr Asp Glu Ser Asp Gly Leu Gln Ser Leu Met Tyr Val
                645                 650                 655

Thr Asn Glu Arg Val Gln Thr Asn Leu Phe Leu Asp Lys Ser Pro Phe
            660                 665                 670

Phe Asp Asn Asn Asn Leu His Ile His Tyr Leu Trp Leu Arg Asp Asn
        675                 680                 685

Gly Thr Val Val Glu Ile Arg Gly Met Tyr Arg Arg Arg Ala Ala Ser
    690                 695                 700

Ala Leu Phe Leu Ile Leu Ser Phe Ile Gly Phe Ser Gly Val Ile Tyr
705                 710                 715                 720

Phe Leu Tyr Arg Leu Phe Ser Ile Leu Tyr
                725                 730

<210> SEQ ID NO 18
<211> LENGTH: 1215
<212> TYPE: DNA
<213> ORGANISM: Kaposi's sarcoma-associated herpesvirus

<400> SEQUENCE: 18
atgttacgag ttccggacgt gaaggctagt ctagtagagg gcgcggcgcg cctgtcgaca      60
ggcgagcgcg tgtttcacgt cttgacctct ccggcggtgg cggccatggt gggagtctct     120
aatcctgaag tcccgatgcc actgttgttc gaaaagtttg ggactccgga ctcgtctacc     180
ctgccactct acgcggctag gcacccggaa ctatcgttgc tacggatcat gctctcaccg     240 caccctacg cgttaagaag ccacttgtgc gtaggcgaag agaccgcatc tcttggcgtt      300
tacctgcact ccaagccagt cgtacgcggc acgaattcg aggacacgca gatactaccg      360
gagtgccggc tggccataac gagcgaccag tcttatacca actttaagat tatagatctg     420
ccagcgggat gccgtcgcgt ccccatacac gccgcgaaca gcgtgtcgt catcgacgag      480 gccgccaacc gcataaaggt gtttgaccca gagtcgcctt taccgcgtca ccccataaca     540

```
cccccgtgccg gtcagaccag atctatactg aaacacaaca tcgcacaggt ttgcgaacgg    600
gatatcgtgt cacttaacac agacaacgag gccgcgtcta tgttctacat gattggactc    660
aggcggccga gactcggaga aagcccggtc tgtgacttca acaccgttac catcatggag    720
cgtgctaaca actcgataac ttttctaccc aagctaaaac tgaaccggct acaacacctg    780
ttcctgaagc acgtgttgct gcgcagcatg gggctggaaa acatcgtgtc gtgtttctca    840
tcgctgtacg gcgcagaact tgcccctgcg aaaacacacg agcgggagtt cttcggcgct    900
ctgctagaaa gactcaaacg tcgggtggag gacgcggtct tctgcctgaa taccatagag    960
gatttcccgt ttagggaacc cattcgccaa cccccagatt gttccaaggt gcttatagaa   1020
gccatggaaa agtactttat gatgtgtagc cccaaagacc gtcaaagcgc cgcatggcta   1080
ggtgcagggg tggtcgaact gatatgtgac ggcaatccac tttctgaggt gctcggatttt  1140 cttgccaagt atatgcccat acaaaaagaa tgcacaggaa accttttaaa aatctacgct   1200
ttattgaccg tctaa                                                     1215
```

<210> SEQ ID NO 19
<211> LENGTH: 404
<212> TYPE: PRT
<213> ORGANISM: Kaposi's sarcoma-associated herpesvirus

<400> SEQUENCE: 19

```
Met Leu Arg Val Pro Asp Val Lys Ala Ser Leu Val Glu Gly Ala Ala
  1               5                  10                  15

Arg Leu Ser Thr Gly Glu Arg Val Phe His Val Leu Thr Ser Pro Ala
             20                  25                  30

Val Ala Ala Met Val Gly Val Ser Asn Pro Glu Val Pro Met Pro Leu
         35                  40                  45

Leu Phe Glu Lys Phe Gly Thr Pro Asp Ser Ser Thr Leu Pro Leu Tyr
     50                  55                  60

Ala Ala Arg His Pro Glu Leu Ser Leu Leu Arg Ile Met Leu Ser Pro
 65                  70                  75                  80

His Pro Tyr Ala Leu Arg Ser His Leu Cys Val Gly Glu Glu Thr Ala
                 85                  90                  95

Ser Leu Gly Val Tyr Leu His Ser Lys Pro Val Arg Gly His Glu
            100                 105                 110

Phe Glu Asp Thr Gln Ile Leu Pro Glu Cys Arg Leu Ala Ile Thr Ser
        115                 120                 125

Asp Gln Ser Tyr Thr Asn Phe Lys Ile Ile Asp Leu Pro Ala Gly Cys
    130                 135                 140

Arg Arg Val Pro Ile His Ala Ala Asn Lys Arg Val Val Ile Asp Glu
145                 150                 155                 160

Ala Ala Asn Arg Ile Lys Val Phe Asp Pro Glu Ser Pro Leu Pro Arg
                165                 170                 175

His Pro Ile Thr Pro Arg Ala Gly Gln Thr Arg Ser Ile Leu Lys His
            180                 185                 190

Asn Ile Ala Gln Val Cys Glu Arg Asp Ile Val Ser Leu Asn Thr Asp
        195                 200                 205

Asn Glu Ala Ala Ser Met Phe Tyr Met Ile Gly Leu Arg Arg Pro Arg
    210                 215                 220

Leu Gly Glu Ser Pro Val Cys Asp Phe Asn Thr Val Thr Ile Met Glu
225                 230                 235                 240

Arg Ala Asn Asn Ser Ile Thr Phe Leu Pro Lys Leu Lys Leu Asn Arg
                245                 250                 255
```

```
Leu Gln His Leu Phe Leu Lys His Val Leu Leu Arg Ser Met Gly Leu
                260                 265                 270
Glu Asn Ile Val Ser Cys Phe Ser Ser Leu Tyr Gly Ala Glu Leu Ala
            275                 280                 285
Pro Ala Lys Thr His Glu Arg Glu Phe Phe Gly Ala Leu Leu Glu Arg
        290                 295                 300
Leu Lys Arg Arg Val Glu Asp Ala Val Phe Cys Leu Asn Thr Ile Glu
305                 310                 315                 320
Asp Phe Pro Phe Arg Glu Pro Ile Arg Gln Pro Pro Asp Cys Ser Lys
                325                 330                 335
Val Leu Ile Glu Ala Met Glu Lys Tyr Phe Met Met Cys Ser Pro Lys
            340                 345                 350
Asp Arg Gln Ser Ala Ala Trp Leu Gly Ala Gly Val Val Glu Leu Ile
        355                 360                 365
Cys Asp Gly Asn Pro Leu Ser Glu Val Leu Gly Phe Leu Ala Lys Tyr
        370                 375                 380
Met Pro Ile Gln Lys Glu Cys Thr Gly Asn Leu Leu Lys Ile Tyr Ala
385                 390                 395                 400
Leu Leu Thr Val
```

<210> SEQ ID NO 20
<211> LENGTH: 2259
<212> TYPE: DNA
<213> ORGANISM: Kaposi's sarcoma-associated herpesvirus

<400> SEQUENCE: 20

```
atggcagcgc tcgagggccc cctactactg ccaccgagcg cctccctgac gacgagtccg      60
cagaccacgt gttatcaagc gacttgggaa tcacagctgg aaatattctg ctgtctggcc     120
accaactcgc acctgcaggc agagctgacc ttagaaggtc ttgataagat gatgcagccc     180
gagcccacct ttttcgcctg cagagcgata cgcagactac tcctggggga acgcctccac     240
cctttatac atcaagaagg gactcttttg ggaaaagtgg gtcgacggta cagcggcgaa     300
ggtttaataa ttgacggtgg tggagtgttt acgcgcggac agatagacac cgacaactac     360
ctacctgcgg tgggatcatg gaacttacc gatgattgtg ataaaccctg cgaattcagg      420
gagctacgct cgctgtatct tcccgcgcta ctaacgtgca ccatatgtta caaagccatg     480
ttcaggatag tgtgcaggta cctggagttc tgggagttcg aacagtgttt tcatgcgttt     540
ctggcggtgt tgccccatag tctacaaccc acaatctatc aaaattattt tgcactcctg     600
gagagcctga agcatctctc gttttcaata atgccaccg catccccaga cgcacagcta      660
catttttaa agtttaacat cagcagcttc atggccacgt gggggtggca cggagagctg     720
gtctcgctgc gccgtgccat cgctcacaac gtagagcgac tgcccaccgt gctgaagaac     780
ctgtcgaaac agagtaagca ccaggacgtc aaggttaacg acgggatct ggtgggcttt      840
cagctggctc taaccagct cgtgtcccgt ctgcacgtaa aaatccaacg caaggacccc     900
ggaccaaagc catacagggt ggtcgtcagt accccagatt gtacctacta tctagtgtat     960
ccgggcacac cggccatcta cagactcgtc atgtgtatgg cagtggcaga ctgcatcggc    1020
cactcgtgca gcggactgca ccctgcgca aacttttag gcacccacga cacccgcgt      1080
ctcctggcgg cgacgctttc aagaatccgg tacgcgccga agaccggcg agcagccatg    1140
aaaggaaatt tgcaggcgtg cttccaacga tacgcggcca cggacgcgcg gactctgggc    1200
agctctacag tgtcagacat gctggaaccc acaaaacacg tcagtttgga aaacttcaag    1260
```

-continued

```
atcaccatat tcaacaccaa catggtgatt aacactaaga taagctgcca cgttcctaac    1320
accctgcaaa agactatttt aaacatcccc agattgacca acaatttgt tatacgaaag     1380 tactccgtaa aggaaccttc ttttaccata agcgtgtttt tttccgacaa catgtgtcaa    1440
ggcaccgcaa taaacatcaa catcagtggg gacatgctgc actttctctt cgcaatgggt    1500
acgctgaaat gctttctgcc aatcaggcac atatttcctg tatcgatagc aaattggaac    1560
tccacgttgg acctgcacgg actggaaaac cagtacatgg tgagaatggg gcgaaaaaac    1620
gtattttgga ccacaaactt tccatctgtg gtctccagca aggatgggct aaacgtgtcc    1680
tggtttaagg ccgcgacagc cacgatttct aaagtgtacg ggcagcctct tgtggaacag    1740
attcgccacg agctggcgcc cattctcacg gaccagcacg cgcgcatcga cggaaacaaa    1800
aatagaatat tctccctact tgagcacaga accgttccc aaatacagac gctacacaaa     1860
aggttcctgg agtgtctggt ggaatgctgt tcgtttctca ggcttgacgt ggcttgcatt    1920
aggcgagccg ccgcccgggg cctgtttgac ttctcaaaga agataatcag tcacactaaa    1980
agcaaacacg agtgcgcagt actgggatat aaaaagtgta acctaatccc gaaaatctat    2040
gcccgaaaca agaagaccag gctagacgag ttgggccgca atgcaaactt catttcgttc    2100
gtcgccacca cgggtcatcg gttcgccgct ctaaagccac aaattgtccg tcacgccatt    2160
cgcaaactag gcctgcactg gcgccaccga acggccgcgt ccaacgagca gacaccgcca    2220
gccgatcccc gcgtacgttg cgtccgtccg ctggtctaa                            2259
```

<210> SEQ ID NO 21
<211> LENGTH: 752
<212> TYPE: PRT
<213> ORGANISM: Kaposi's sarcoma-associated herpesvirus

<400> SEQUENCE: 21

```
Met Ala Ala Leu Glu Gly Pro Leu Leu Pro Pro Ser Ala Ser Leu
  1               5                  10                  15

Thr Thr Ser Pro Gln Thr Thr Cys Tyr Gln Ala Thr Trp Glu Ser Gln
                 20                  25                  30

Leu Glu Ile Phe Cys Cys Leu Ala Thr Asn Ser His Leu Gln Ala Glu
             35                  40                  45

Leu Thr Leu Glu Gly Leu Asp Lys Met Met Gln Pro Glu Pro Thr Phe
         50                  55                  60

Phe Ala Cys Arg Ala Ile Arg Arg Leu Leu Leu Gly Glu Arg Leu His
 65                  70                  75                  80

Pro Phe Ile His Gln Glu Gly Thr Leu Leu Gly Lys Val Gly Arg Arg
                 85                  90                  95

Tyr Ser Gly Glu Gly Leu Ile Ile Asp Gly Gly Val Phe Thr Arg
            100                 105                 110

Gly Gln Ile Asp Thr Asp Asn Tyr Leu Pro Ala Val Gly Ser Trp Glu
        115                 120                 125

Leu Thr Asp Asp Cys Asp Lys Pro Cys Glu Phe Arg Glu Leu Arg Ser
    130                 135                 140

Leu Tyr Leu Pro Ala Leu Leu Thr Cys Thr Ile Cys Tyr Lys Ala Met
145                 150                 155                 160

Phe Arg Ile Val Cys Arg Tyr Leu Glu Phe Trp Glu Phe Glu Gln Cys
                165                 170                 175

Phe His Ala Phe Leu Ala Val Leu Pro His Ser Leu Gln Pro Thr Ile
            180                 185                 190
```

-continued

```
Tyr Gln Asn Tyr Phe Ala Leu Leu Glu Ser Leu Lys His Leu Ser Phe
        195                 200                 205

Ser Ile Met Pro Pro Ala Ser Pro Asp Ala Gln Leu His Phe Leu Lys
    210                 215                 220

Phe Asn Ile Ser Ser Phe Met Ala Thr Trp Gly Trp His Gly Glu Leu
225                 230                 235                 240

Val Ser Leu Arg Arg Ala Ile Ala His Asn Val Glu Arg Leu Pro Thr
                245                 250                 255

Val Leu Lys Asn Leu Ser Lys Gln Ser Lys His Gln Asp Val Lys Val
            260                 265                 270

Asn Gly Arg Asp Leu Val Gly Phe Gln Leu Ala Leu Asn Gln Leu Val
        275                 280                 285

Ser Arg Leu His Val Lys Ile Gln Arg Lys Asp Pro Gly Pro Lys Pro
    290                 295                 300

Tyr Arg Val Val Val Ser Thr Pro Asp Cys Thr Tyr Tyr Leu Val Tyr
305                 310                 315                 320

Pro Gly Thr Pro Ala Ile Tyr Arg Leu Val Met Cys Met Ala Val Ala
                325                 330                 335

Asp Cys Ile Gly His Ser Cys Ser Gly Leu His Pro Cys Ala Asn Phe
            340                 345                 350

Leu Gly Thr His Glu Thr Pro Arg Leu Leu Ala Ala Thr Leu Ser Arg
        355                 360                 365

Ile Arg Tyr Ala Pro Lys Asp Arg Arg Ala Ala Met Lys Gly Asn Leu
    370                 375                 380

Gln Ala Cys Phe Gln Arg Tyr Ala Ala Thr Asp Ala Arg Thr Leu Gly
385                 390                 395                 400

Ser Ser Thr Val Ser Asp Met Leu Glu Pro Thr Lys His Val Ser Leu
                405                 410                 415

Glu Asn Phe Lys Ile Thr Ile Phe Asn Thr Asn Met Val Ile Asn Thr
            420                 425                 430

Lys Ile Ser Cys His Val Pro Asn Thr Leu Gln Lys Thr Ile Leu Asn
        435                 440                 445

Ile Pro Arg Leu Thr Asn Asn Phe Val Ile Arg Lys Tyr Ser Val Lys
    450                 455                 460

Glu Pro Ser Phe Thr Ile Ser Val Phe Phe Ser Asp Asn Met Cys Gln
465                 470                 475                 480

Gly Thr Ala Ile Asn Ile Asn Ile Ser Gly Asp Met Leu His Phe Leu
                485                 490                 495

Phe Ala Met Gly Thr Leu Lys Cys Phe Leu Pro Ile Arg His Ile Phe
            500                 505                 510

Pro Val Ser Ile Ala Asn Trp Asn Ser Thr Leu Asp Leu His Gly Leu
        515                 520                 525

Glu Asn Gln Tyr Met Val Arg Met Gly Arg Lys Asn Val Phe Trp Thr
    530                 535                 540

Thr Asn Phe Pro Ser Val Val Ser Ser Lys Asp Gly Leu Asn Val Ser
545                 550                 555                 560

Trp Phe Lys Ala Ala Thr Ala Thr Ile Ser Lys Val Tyr Gly Gln Pro
                565                 570                 575

Leu Val Glu Gln Ile Arg His Glu Leu Ala Pro Ile Leu Thr Asp Gln
            580                 585                 590

His Ala Arg Ile Asp Gly Asn Lys Asn Arg Ile Phe Ser Leu Leu Glu
        595                 600                 605

His Arg Asn Arg Ser Gln Ile Gln Thr Leu His Lys Arg Phe Leu Glu
```

```
       610                 615                 620
Cys Leu Val Glu Cys Cys Ser Phe Leu Arg Leu Asp Val Ala Cys Ile
625                 630                 635                 640

Arg Arg Ala Ala Ala Arg Gly Leu Phe Asp Phe Ser Lys Lys Ile Ile
                645                 650                 655

Ser His Thr Lys Ser Lys His Glu Cys Ala Val Leu Gly Tyr Lys Lys
                660                 665                 670

Cys Asn Leu Ile Pro Lys Ile Tyr Ala Arg Asn Lys Lys Thr Arg Leu
                675                 680                 685

Asp Glu Leu Gly Arg Asn Ala Asn Phe Ile Ser Phe Val Ala Thr Thr
                690                 695                 700

Gly His Arg Phe Ala Ala Leu Lys Pro Gln Ile Val Arg His Ala Ile
705                 710                 715                 720

Arg Lys Leu Gly Leu His Trp Arg His Arg Thr Ala Ala Ser Asn Glu
                725                 730                 735

Gln Thr Pro Pro Ala Asp Pro Arg Val Arg Cys Val Arg Pro Leu Val
                740                 745                 750

<210> SEQ ID NO 22
<211> LENGTH: 364
<212> TYPE: DNA
<213> ORGANISM: Kaposi's sarcoma-associated herpesvirus

<400> SEQUENCE: 22
atggtacgtc caaccgaggc cgaggttaag aaatccctga gcaggcttcc agcagcacgc      60
aaaagagcag gtaaccgggc ccacctggcc acctaccgcc ggctcctcaa gtactccacc     120
ctgcccgatc tatggcggtt tctaagtagc cggccccaga accctcccct ggacaccac     180 agattattct ttgaggtgac tctagggcac agaattgccg actgcgtaat tctggtatcg     240
ggtgggcatc agcccgtatg ttacgttgta gagctcaaga cttgtctgag tcaccagctg     300
atcccaacca acaccgtgag aacgtcacag cgagctcaag gcctgtgcca actctccgac     360
tcga                                                                  364

<210> SEQ ID NO 23
<211> LENGTH: 121
<212> TYPE: PRT
<213> ORGANISM: Kaposi's sarcoma-associated herpesvirus

<400> SEQUENCE: 23

Met Val Arg Pro Thr Glu Ala Glu Val Lys Lys Ser Leu Ser Arg Leu
 1               5                  10                  15

Pro Ala Ala Arg Lys Arg Ala Gly Asn Arg Ala His Leu Ala Thr Tyr
                20                  25                  30

Arg Arg Leu Leu Lys Tyr Ser Thr Leu Pro Asp Leu Trp Arg Phe Leu
            35                  40                  45

Ser Ser Arg Pro Gln Asn Pro Pro Leu Gly His His Arg Leu Phe Phe
    50                  55                  60

Glu Val Thr Leu Gly His Arg Ile Ala Asp Cys Val Ile Leu Val Ser
65                  70                  75                  80

Gly Gly His Gln Pro Val Cys Tyr Val Val Glu Leu Lys Thr Cys Leu
                85                  90                  95

Ser His Gln Leu Ile Pro Thr Asn Thr Val Arg Thr Ser Gln Arg Ala
                100                 105                 110

Gln Gly Leu Cys Gln Leu Ser Asp Ser
            115                 120
```

<210> SEQ ID NO 24
<211> LENGTH: 918
<212> TYPE: DNA
<213> ORGANISM: Kaposi's sarcoma-associated herpesvirus

<400> SEQUENCE: 24

```
atggcactcg acaagagtat agtggttaac ttcacctcca gactcttcgc tgatgaactg      60
gccgccttc  agtcaaaaat agggagcgta ctgccgctcg agattgcca  ccgtttacaa     120
aatatacagg cattgggcct ggggtgcgta tgctcacgtg agacatctcc ggactacatc     180
caaattatgc agtatctatc caagtgcaca ctcgctgtcc tggaggaggt tcgcccggac     240
agcctgcgcc taacgcggat ggatccctct gacaaccttc agataaaaaa cgtatatgcc     300
ccctttttc  agtgggacag caacacccag ctagcagtgc taccccatt  ttttagccga     360
aaggattcca ccattgtgct cgaatccaac ggatttgacc ccgtgttccc catggtcgtg     420
ccgcagcaac tggggcacgc tattctgcag cagctgttgg tgtaccacat ctactccaaa     480
atatcggccg ggccccgga  tgatgtaaat atggcggaac ttgatctata taccaccaat     540
gtgtcattta tggggcgcac atatcgtctg acgtagaca  acacggatcc acgtactgcc     600
ctgcgagtgc ttgacgatct gtccatgtac ctttgtatcc tatcagcctt ggttcccagg     660
gggtgtctcc gtctgctcac ggcgctcgtg cggcacgaca ggcatcctct gacagaggtg     720
tttgaggggg tggtgccaga tgaggtgacc aggatagatc tcgaccagtt gagcgtccca     780
gatgacatca ccaggatgcg cgtcatgttc tcctatcttc agagtctcag ttctatattt     840
aatcttggcc ccagactgca cgtgtatgcc tactcggcag agactttggc ggcctcctgt     900
tggtattccc cacgctaa                                                    918
```

<210> SEQ ID NO 25
<211> LENGTH: 305
<212> TYPE: PRT
<213> ORGANISM: Kaposi's sarcoma-associated herpesvirus

<400> SEQUENCE: 25

```
Met Ala Leu Asp Lys Ser Ile Val Val Asn Phe Thr Ser Arg Leu Phe
  1               5                  10                  15

Ala Asp Glu Leu Ala Ala Leu Gln Ser Lys Ile Gly Ser Val Leu Pro
             20                  25                  30

Leu Gly Asp Cys His Arg Leu Gln Asn Ile Gln Ala Leu Gly Leu Gly
         35                  40                  45

Cys Val Cys Ser Arg Glu Thr Ser Pro Asp Tyr Ile Gln Ile Met Gln
     50                  55                  60

Tyr Leu Ser Lys Cys Thr Leu Ala Val Leu Glu Glu Val Arg Pro Asp
 65                  70                  75                  80

Ser Leu Arg Leu Thr Arg Met Asp Pro Ser Asp Asn Leu Gln Ile Lys
                 85                  90                  95

Asn Val Tyr Ala Pro Phe Phe Gln Trp Asp Ser Asn Thr Gln Leu Ala
            100                 105                 110

Val Leu Pro Pro Phe Phe Ser Arg Lys Asp Ser Thr Ile Val Leu Glu
        115                 120                 125

Ser Asn Gly Phe Asp Pro Val Phe Pro Met Val Val Pro Gln Gln Leu
    130                 135                 140

Gly His Ala Ile Leu Gln Gln Leu Leu Val Tyr His Ile Tyr Ser Lys
145                 150                 155                 160
```

```
Ile Ser Ala Gly Ala Pro Asp Asp Val Asn Met Ala Glu Leu Asp Leu
            165                 170                 175

Tyr Thr Thr Asn Val Ser Phe Met Gly Arg Thr Tyr Arg Leu Asp Val
            180                 185                 190

Asp Asn Thr Asp Pro Arg Thr Ala Leu Arg Val Leu Asp Asp Leu Ser
            195                 200                 205

Met Tyr Leu Cys Ile Leu Ser Ala Leu Val Pro Arg Gly Cys Leu Arg
        210                 215                 220

Leu Leu Thr Ala Leu Val Arg His Asp Arg His Pro Leu Thr Glu Val
225                 230                 235                 240

Phe Glu Gly Val Val Pro Asp Glu Val Thr Arg Ile Asp Leu Asp Gln
            245                 250                 255

Leu Ser Val Pro Asp Asp Ile Thr Arg Met Arg Val Met Phe Ser Tyr
            260                 265                 270

Leu Gln Ser Leu Ser Ser Ile Phe Asn Leu Gly Pro Arg Leu His Val
        275                 280                 285

Tyr Ala Tyr Ser Ala Glu Thr Leu Ala Ala Ser Cys Trp Tyr Ser Pro
    290                 295                 300

Arg
305

<210> SEQ ID NO 26
<211> LENGTH: 873
<212> TYPE: DNA
<213> ORGANISM: Kaposi's sarcoma-associated herpesvirus

<400> SEQUENCE: 26
atggcgtcat ctgatattct gtcggttgca aggacggatg acggctccgt ctgtgaagtc      60
tccctgcgtg gaggtaggaa aaaaactacc gtctacctgc cggacactga accctgggtg     120
gtagagaccg acgccatcaa agacgccttc ctcagcgacg ggatcgtgga tatggctcga     180
aagcttcatc gtggtgccct gccctcaaat tctcacaacg gcttgaggat ggtgcttttt     240
tgttattgtt acttgcaaaa ttgtgtgtac ctagccctgt ttctgtgccc ccttaatcct     300
tacttggtaa ctccctcaag cattgagttt gccgagcccg ttgtggcacc tgaggtgctc     360
ttcccacacc cggctgagat gtctcgcggt tgcgatgacg cgattttctg taaactgccc     420
tataccgtgc ctataatcaa caccacgttt ggacgcattt acccgaactc tacacgcgag     480
ccggacggca ggcctacgga ttactccatg gcccttagaa gggcttttgc agttatggtt     540
aacacgtcat gtgcaggagt gacattgtgc cgcggagaaa ctcagaccgc atcccgtaac     600
cacactgagt gggaaaatct gctggctatg ttttctgtga ttatctatgc cttagatcac     660
aactgtcacc cggaagcact gtctatcgcg agcggcatct tgacgagcg tgactatgga     720 ttattcatct ctcagccccg gagcgtgccc tcgcctaccc cttgcgacgt gtcgtgggaa     780
gatatctaca acgggactta cctagctcgg cctggaaact gtgaccctg gcccaatcta     840 tccaccctc ccttgattct aaattttaaa taa                                    873

<210> SEQ ID NO 27
<211> LENGTH: 290
<212> TYPE: PRT
<213> ORGANISM: Kaposi's sarcoma-associated herpesvirus

<400> SEQUENCE: 27

Met Ala Ser Ser Asp Ile Leu Ser Val Ala Arg Thr Asp Asp Gly Ser
  1               5                  10                  15
```

-continued

```
Val Cys Glu Val Ser Leu Arg Gly Gly Arg Lys Lys Thr Thr Val Tyr
             20                  25                  30

Leu Pro Asp Thr Glu Pro Trp Val Val Glu Thr Asp Ala Ile Lys Asp
         35                  40                  45

Ala Phe Leu Ser Asp Gly Ile Val Asp Met Ala Arg Lys Leu His Arg
     50                  55                  60

Gly Ala Leu Pro Ser Asn Ser His Asn Gly Leu Arg Met Val Leu Phe
 65                  70                  75                  80

Cys Tyr Cys Tyr Leu Gln Asn Cys Val Tyr Leu Ala Leu Phe Leu Cys
                 85                  90                  95

Pro Leu Asn Pro Tyr Leu Val Thr Pro Ser Ser Ile Glu Phe Ala Glu
            100                 105                 110

Pro Val Val Ala Pro Glu Val Leu Phe Pro His Pro Ala Glu Met Ser
        115                 120                 125

Arg Gly Cys Asp Asp Ala Ile Phe Cys Lys Leu Pro Tyr Thr Val Pro
    130                 135                 140

Ile Ile Asn Thr Thr Phe Gly Arg Ile Tyr Pro Asn Ser Thr Arg Glu
145                 150                 155                 160

Pro Asp Gly Arg Pro Thr Asp Tyr Ser Met Ala Leu Arg Arg Ala Phe
                165                 170                 175

Ala Val Met Val Asn Thr Ser Cys Ala Gly Val Thr Leu Cys Arg Gly
            180                 185                 190

Glu Thr Gln Thr Ala Ser Arg Asn His Thr Glu Trp Glu Asn Leu Leu
        195                 200                 205

Ala Met Phe Ser Val Ile Ile Tyr Ala Leu Asp His Asn Cys His Pro
    210                 215                 220

Glu Ala Leu Ser Ile Ala Ser Gly Ile Phe Asp Glu Arg Asp Tyr Gly
225                 230                 235                 240

Leu Phe Ile Ser Gln Pro Arg Ser Val Pro Ser Pro Thr Pro Cys Asp
                245                 250                 255

Val Ser Trp Glu Asp Ile Tyr Asn Gly Thr Tyr Leu Ala Arg Pro Gly
            260                 265                 270

Asn Cys Asp Pro Trp Pro Asn Leu Ser Thr Pro Pro Leu Ile Leu Asn
        275                 280                 285

Phe Lys
    290

<210> SEQ ID NO 28
<211> LENGTH: 363
<212> TYPE: DNA
<213> ORGANISM: Kaposi's sarcoma-associated herpesvirus

<400> SEQUENCE: 28
atgagcatga ctttccccgt ctccagtcac cggaggaatg gtggacggct ccgtcctggt    60
gcgaatggcc accaagcctc ccgtgattgg tcttataaca gtgctcttcc tcctagtcat   120
aggcgcctgc gtctactgct gcattcgcgt gttcctggcg gctcgactgt ggcgcgccac   180
cccactaggc agggccaccg tggcgtatca ggtccttcgc accctgggac gcaggccgg    240 gtcacatgca ccgccgacgg tgggcatagc tacccaggag ccctaccgta caatatacat   300
gccagattag aacgggtgt gtgctataat ggatggctat ggggggggc tgtagataat     360 tga                                                                 363

<210> SEQ ID NO 29
<211> LENGTH: 120
```

<212> TYPE: PRT
<213> ORGANISM: Kaposi's sarcoma-associated herpesvirus

<400> SEQUENCE: 29

```
Met Ser Met Thr Phe Pro Val Ser Ser His Arg Arg Asn Gly Gly Arg
  1               5                  10                  15

Leu Arg Pro Gly Ala Asn Gly His Gln Ala Ser Arg Asp Trp Ser Tyr
                 20                  25                  30

Asn Ser Ala Leu Pro Pro Ser His Arg Arg Leu Arg Leu Leu Leu His
             35                  40                  45

Ser Arg Val Pro Gly Gly Ser Thr Val Ala Arg His Pro Thr Arg Gln
         50                  55                  60

Gly His Arg Gly Val Ser Gly Pro Ser His Pro Gly Thr Ala Gly Arg
 65                  70                  75                  80

Val Thr Cys Thr Ala Asp Gly Gly His Ser Tyr Pro Gly Ala Leu Pro
                 85                  90                  95

Tyr Asn Ile His Ala Arg Leu Glu Arg Gly Val Cys Tyr Asn Gly Trp
                100                 105                 110

Leu Trp Gly Gly Ala Val Asp Asn
            115                 120
```

<210> SEQ ID NO 30
<211> LENGTH: 921
<212> TYPE: DNA
<213> ORGANISM: Kaposi's sarcoma-associated herpesvirus

<400> SEQUENCE: 30

```
atgctgctca gccgtcacag ggagcgcctt gccgccaacc tggaggagac cgccaaagac      60
gccggagaga ggtgggaact gagtgccccg acattcacgc gacactgtcc caaacggca     120
cggatggcgc acccttttat tggcgtggtg cacagaataa actcatacag ttcggtcctg    180
gaaacatact gcacacggca ccatcccgcc acgcccacgt cagcaaatcc cgacgtggga    240
accccagac cgtccgagga caacgtcccc gcaaagccgc gcctattgga gtccctatca     300
acatacttgc agatgcggtg tgtgcgcgag gacgcgcacg tctccacggc cgatcaactg    360
gtcgagtacc aggcgggcag aaaaacacac gactccctgc acgcctgctc tgtctaccgc    420
gaacttcagg cttttctggt taacctttcg tcctttctga acggctgtta cgttcccggg    480
gtgcactggc tggagccctt ccaacagcag ctagtaatgc acactttttt ctttttggtt    540
tcaatcaagg ccccacaaaa gacgcaccag ttgtttggat tgtttaagca gtacttcggt    600
ttatttgaaa ctccaaacag tgttttacag acgtttaagc aaaaggcaag cgtattccta    660
ataccaagga gacacggaaa gacatggata gtggtggcga tcatcagcat gctactggca    720
tccgtagaga acattaacat tgggtacgta gcccaccaaa agcacgtagc caactccgtg    780
ttcgcggaaa tcataaagac gctttgtcgg tggttccccc ccaaaaattt aaacatcaag    840
aaggagaacg gaaccataat ctacacgcga cccggaggac ggtccagctc gctgatgtgc    900
gcaacatgct tcaataagaa c                                                921
```

<210> SEQ ID NO 31
<211> LENGTH: 307
<212> TYPE: PRT
<213> ORGANISM: Kaposi's sarcoma-associated herpesvirus

<400> SEQUENCE: 31

```
Met Leu Leu Ser Arg His Arg Glu Arg Leu Ala Ala Asn Leu Glu Glu
  1               5                  10                  15
```

```
Thr Ala Lys Asp Ala Gly Glu Arg Trp Glu Leu Ser Ala Pro Thr Phe
         20                  25                  30
Thr Arg His Cys Pro Lys Thr Ala Arg Met Ala His Pro Phe Ile Gly
         35                  40                  45
Val Val His Arg Ile Asn Ser Tyr Ser Val Leu Glu Thr Tyr Cys
 50                  55                  60
Thr Arg His His Pro Ala Thr Pro Thr Ser Ala Asn Pro Asp Val Gly
 65                  70                  75                  80
Thr Pro Arg Pro Ser Glu Asp Asn Val Pro Ala Lys Pro Arg Leu Leu
                 85                  90                  95
Glu Ser Leu Ser Thr Tyr Leu Gln Met Arg Cys Val Arg Glu Asp Ala
                100                 105                 110
His Val Ser Thr Ala Asp Gln Leu Val Glu Tyr Gln Ala Gly Arg Lys
            115                 120                 125
Thr His Asp Ser Leu His Ala Cys Ser Val Tyr Arg Glu Leu Gln Ala
130                 135                 140
Phe Leu Val Asn Leu Ser Ser Phe Leu Asn Gly Cys Tyr Val Pro Gly
145                 150                 155                 160
Val His Trp Leu Glu Pro Phe Gln Gln Gln Leu Val Met His Thr Phe
                165                 170                 175
Phe Phe Leu Val Ser Ile Lys Ala Pro Gln Lys Thr His Gln Leu Phe
                180                 185                 190
Gly Leu Phe Lys Gln Tyr Phe Gly Leu Phe Glu Thr Pro Asn Ser Val
            195                 200                 205
Leu Gln Thr Phe Lys Gln Lys Ala Ser Val Phe Leu Ile Pro Arg Arg
210                 215                 220
His Gly Lys Thr Trp Ile Val Val Ala Ile Ile Ser Met Leu Leu Ala
225                 230                 235                 240
Ser Val Glu Asn Ile Asn Ile Gly Tyr Val Ala His Gln Lys His Val
                245                 250                 255
Ala Asn Ser Val Phe Ala Glu Ile Ile Lys Thr Leu Cys Arg Trp Phe
            260                 265                 270
Pro Pro Lys Asn Leu Asn Ile Lys Lys Glu Asn Gly Thr Ile Ile Tyr
        275                 280                 285
Thr Arg Pro Gly Gly Arg Ser Ser Ser Leu Met Cys Ala Thr Cys Phe
290                 295                 300
Asn Lys Asn
305

<210> SEQ ID NO 32
<211> LENGTH: 1365
<212> TYPE: DNA
<213> ORGANISM: Kaposi's sarcoma-associated herpesvirus

<400> SEQUENCE: 32
atggatgcgc atgctatcaa cgaaagatac gtaggtcctc gctgccaccg tttggcccac      60
gtggtgctgc ctaggacctt tctgctgcat cacgccatac ccctggagcc cgagatcatc     120
ttttccacct acacccggtt cagccggtcg ccagggtcat cccgccggtt ggtggtgtgt     180
gggaaacgtg tcctgccagg ggaggaaaac caacttgcgt cttcaccttc tggtttggcg     240
cttagcctgc ctctgttttc ccacgatggg aactttcatc catttgacat ctcggtactg     300
cgcatttcct gccctggttc taatcttagt cttactgtca gatttctcta tctatctctg     360
gtggtggcta tgggggcggg acggaataat gcgcggagtc cgaccgttga cggggtatcg     420
```

```
ccgccagagg gcgccgtagc ccacccttg gaggaactgc agaggctggc gcgtgctacg      480
ccggacccgg cactcacccg tggaccgttg caggtcctga ccggccttct ccgcgcaggg      540
tcagacggag accgcgccac tcaccacatg gcgctcgagg ctccgggaac cgtgcgtgga      600
gaaagcctag acccgcctgt ttcacagaag gggccagcgc gcacacgcca caggccaccc      660
cccgtgcgac tgagcttcaa ccccgtcaat gccgatgtac ccgctacctg gcgagacgcc      720
actaacgtgt actcgggtgc tccctactat gtgtgtgttt acgaacgcgg tggccgtcag      780
gaagacgact ggctgccgat accactgagc ttcccagaag agcccgtgcc ccgccaccg       840 ggcttagtgt tcatggacga cttgttcatt aacacgaagc agtgcgactt tgtggacacg      900
ctagaggccg cctgtcgcac gcaaggctac acgttgagac agcgcgtgcc tgtcgccatt      960
cctcgcgacg cggaaatcgc agacgcagtt aaatcgcact ttttagaggc gtgcctagtg     1020 ttacggggc tggcttcgga ggctagtgcc tggataagac tgccacgtc cccgcccctt      1080 ggccgccacg cctgctggat ggacgtgtta ggattatggg aaagccgccc ccacactcta     1140
ggtttggagt tacgcggcgt aaactgtggc ggcacggacg tgactggtt agagatttta     1200 aaacagcccg atgtgcaaaa gacagtcagc gggagtcttg tggcatgcgt gatcgtcaca     1260
cccgcattgg aagcctggct tgtgttacct gggggttttg ctattaaagc ccgctatagg     1320
gcgtcgaagg aggatctggt gttcattcga ggccgctatg gctag                     1365
```

<210> SEQ ID NO 33
<211> LENGTH: 454
<212> TYPE: PRT
<213> ORGANISM: Kaposi's sarcoma-associated herpesvirus

<400> SEQUENCE: 33

```
Met Asp Ala His Ala Ile Asn Glu Arg Tyr Val Gly Pro Arg Cys His
  1               5                  10                  15

Arg Leu Ala His Val Val Leu Pro Arg Thr Phe Leu Leu His His Ala
                 20                  25                  30

Ile Pro Leu Glu Pro Glu Ile Ile Phe Ser Thr Tyr Thr Arg Phe Ser
             35                  40                  45

Arg Ser Pro Gly Ser Ser Arg Arg Leu Val Val Cys Gly Lys Arg Val
         50                  55                  60

Leu Pro Gly Glu Glu Asn Gln Leu Ala Ser Ser Pro Ser Gly Leu Ala
 65                  70                  75                  80

Leu Ser Leu Pro Leu Phe Ser His Asp Gly Asn Phe His Pro Phe Asp
                 85                  90                  95

Ile Ser Val Leu Arg Ile Ser Cys Pro Gly Ser Asn Leu Ser Leu Thr
            100                 105                 110

Val Arg Phe Leu Tyr Leu Ser Leu Val Val Ala Met Gly Ala Gly Arg
        115                 120                 125

Asn Asn Ala Arg Ser Pro Thr Val Asp Gly Val Ser Pro Glu Gly
    130                 135                 140

Ala Val Ala His Pro Leu Glu Glu Leu Gln Leu Ala Arg Ala Thr
145                 150                 155                 160

Pro Asp Pro Ala Leu Thr Arg Gly Pro Leu Gln Val Leu Thr Gly Leu
                165                 170                 175

Leu Arg Ala Gly Ser Asp Gly Asp Arg Ala Thr His His Met Ala Leu
            180                 185                 190

Glu Ala Pro Gly Thr Val Arg Gly Glu Ser Leu Asp Pro Pro Val Ser
        195                 200                 205
```

-continued

```
Gln Lys Gly Pro Ala Arg Thr Arg His Arg Pro Pro Val Arg Leu
    210                 215                 220

Ser Phe Asn Pro Val Asn Ala Asp Val Pro Ala Thr Trp Arg Asp Ala
225                 230                 235                 240

Thr Asn Val Tyr Ser Gly Ala Pro Tyr Tyr Val Cys Val Tyr Glu Arg
                245                 250                 255

Gly Gly Arg Gln Glu Asp Asp Trp Leu Pro Ile Pro Leu Ser Phe Pro
            260                 265                 270

Glu Glu Pro Val Pro Pro Pro Gly Leu Val Phe Met Asp Asp Leu
            275                 280                 285

Phe Ile Asn Thr Lys Gln Cys Asp Phe Val Asp Thr Leu Glu Ala Ala
    290                 295                 300

Cys Arg Thr Gln Gly Tyr Thr Leu Arg Gln Arg Val Pro Val Ala Ile
305                 310                 315                 320

Pro Arg Asp Ala Glu Ile Ala Asp Ala Val Lys Ser His Phe Leu Glu
                325                 330                 335

Ala Cys Leu Val Leu Arg Gly Leu Ala Ser Glu Ala Ser Ala Trp Ile
            340                 345                 350

Arg Ala Ala Thr Ser Pro Pro Leu Gly Arg His Ala Cys Trp Met Asp
            355                 360                 365

Val Leu Gly Leu Trp Glu Ser Arg Pro His Thr Leu Gly Leu Glu Leu
    370                 375                 380

Arg Gly Val Asn Cys Gly Gly Thr Asp Gly Asp Trp Leu Glu Ile Leu
385                 390                 395                 400

Lys Gln Pro Asp Val Gln Lys Thr Val Ser Gly Ser Leu Val Ala Cys
                405                 410                 415

Val Ile Val Thr Pro Ala Leu Glu Ala Trp Leu Val Leu Pro Gly Gly
            420                 425                 430

Phe Ala Ile Lys Ala Arg Tyr Arg Ala Ser Lys Glu Asp Leu Val Phe
            435                 440                 445

Ile Arg Gly Arg Tyr Gly
    450
```

<210> SEQ ID NO 34
<211> LENGTH: 984
<212> TYPE: DNA
<213> ORGANISM: Kaposi's sarcoma-associated herpesvirus

<400> SEQUENCE: 34

```
atgtttgctt tgagctcgct cgtgtccgag ggtgacccgg aggtgaccag taggtacgtc      60
aagggcgtac aacttgccct ggaccttagc gagaacacac ctggacaatt taagttgata     120
gaaactcccc tgaacagctt cctcttggtt tccaacgtga tgcccgaggt ccagccaatc     180
tgcagtggcc ggccggcctt gcggccagac tttagtaatc tccacttgcc tagactggag     240
aagctccaga gagtcctcgg gcagggtttc ggggcggcgg gtgaggaaat cgcactggac     300
ccgtctcacg tagaaacaca cgaaaagggc caggtgttct acaaccacta tgctaccgag     360
gagtggacgt gggctttgac tctgaataag gatgcgctcc ttcgggaggc tgtagatggc     420
ctgtgtgacc ccggaacttg gaagggtctt cttcctgacg accccttcc gttgctatgg      480 ctgctgttca acggacccgc ctcttttgt cgggccgact gttgcctgta caagcagcac      540
tgcggttacc cggcccggt gctacttcca ggtcacatgt acgctcccaa acgggatctt      600
ttgtcgttcg ttaatcatgc cctgaagtac accaagtttc tatacggaga tttttccggg     660
```

-continued

```
acatgggcgg cggcttgccg cccgccattc gctacttctc ggatacaaag ggtagtgagt     720
cagatgaaaa tcatagatgc ttccgacact tacatttccc acacctgcct cttgtgtcac     780
atatatcagc aaaatagcat aattgcgggt caggggaccc acgtgggtgg aatcctactg     840
ttgagtggaa aagggaccca gtatataaca ggcaatgttc agacccaaag gtgtccaact     900 acggcgact  atctaatcat cccatcgtat gacataccgg cgatcatcac catgatcaag     960
gagaatggac tcaaccaact ctaa                                            984
```

<210> SEQ ID NO 35
<211> LENGTH: 327
<212> TYPE: PRT
<213> ORGANISM: Kaposi's sarcoma-associated herpesvirus

<400> SEQUENCE: 35

```
Met Phe Ala Leu Ser Ser Leu Val Ser Glu Gly Asp Pro Glu Val Thr
  1               5                  10                  15

Ser Arg Tyr Val Lys Gly Val Gln Leu Ala Leu Asp Leu Ser Glu Asn
             20                  25                  30

Thr Pro Gly Gln Phe Lys Leu Ile Glu Thr Pro Leu Asn Ser Phe Leu
         35                  40                  45

Leu Val Ser Asn Val Met Pro Glu Val Gln Pro Ile Cys Ser Gly Arg
     50                  55                  60

Pro Ala Leu Arg Pro Asp Phe Ser Asn Leu His Leu Pro Arg Leu Glu
 65                  70                  75                  80

Lys Leu Gln Arg Val Leu Gly Gln Gly Phe Gly Ala Ala Gly Glu Glu
                 85                  90                  95

Ile Ala Leu Asp Pro Ser His Val Glu Thr His Glu Lys Gly Gln Val
            100                 105                 110

Phe Tyr Asn His Tyr Ala Thr Glu Glu Trp Thr Trp Ala Leu Thr Leu
        115                 120                 125

Asn Lys Asp Ala Leu Leu Arg Glu Ala Val Asp Gly Leu Cys Asp Pro
    130                 135                 140

Gly Thr Trp Lys Gly Leu Leu Pro Asp Asp Pro Leu Pro Leu Leu Trp
145                 150                 155                 160

Leu Leu Phe Asn Gly Pro Ala Ser Phe Cys Arg Ala Asp Cys Cys Leu
                165                 170                 175

Tyr Lys Gln His Cys Gly Tyr Pro Gly Pro Val Leu Leu Pro Gly His
            180                 185                 190

Met Tyr Ala Pro Lys Arg Asp Leu Leu Ser Phe Val Asn His Ala Leu
        195                 200                 205

Lys Tyr Thr Lys Phe Leu Tyr Gly Asp Phe Ser Gly Thr Trp Ala Ala
    210                 215                 220

Ala Cys Arg Pro Pro Phe Ala Thr Ser Arg Ile Gln Arg Val Val Ser
225                 230                 235                 240

Gln Met Lys Ile Ile Asp Ala Ser Asp Thr Tyr Ile Ser His Thr Cys
                245                 250                 255

Leu Leu Cys His Ile Tyr Gln Gln Asn Ser Ile Ile Ala Gly Gln Gly
            260                 265                 270

Thr His Val Gly Gly Ile Leu Leu Ser Gly Lys Gly Thr Gln Tyr
        275                 280                 285

Ile Thr Gly Asn Val Gln Thr Gln Arg Cys Pro Thr Thr Gly Asp Tyr
    290                 295                 300

Leu Ile Ile Pro Ser Tyr Asp Ile Pro Ala Ile Ile Thr Met Ile Lys
305                 310                 315                 320
```

Glu Asn Gly Leu Asn Gln Leu
           325

<210> SEQ ID NO 36
<211> LENGTH: 330
<212> TYPE: DNA
<213> ORGANISM: Kaposi's sarcoma-associated herpesvirus

<400> SEQUENCE: 36
ggatccctct gacaaccttc agataaaaaa cgtatatgcc ccctttttc agtgggacag      60 caacacccag ctagcagtgc taccccatt ttttagccga aaggattcca ccattgtgct     120
cgaatccaac ggatttgacc ccgtgttccc catggtcgtg ccgcagcaac tggggcacgc    180
tattctgcag cagctgttgg tgtaccacat ctactccaaa atatcggccg ggccccgga    240 tgatgtaaat atggcggaac ttgatctata taccaccaat gtgtcattta tggggcgcac    300
atatcgtctg gacgtagaca acacggatcc                                      330

<210> SEQ ID NO 37
<211> LENGTH: 627
<212> TYPE: DNA
<213> ORGANISM: Kaposi's sarcoma-associated herpesvirus

<400> SEQUENCE: 37
ggatccgctg gcaggtgggc gcgcacctcg tcgggtagct tggagacaaa cagctccagg     60
ccagtccgcg ccgtagcgcc tgcaggtgcc tcaccaccgg ggccgggtca tgcgatctgt    120
ttagtccgga aagataggg cccttgggaa gccgctgaac cagctccagg gtctccaaga    180
tgcgcaccgg ttgtcggagc tgtcgcgata gaggttaggg taggtgtccg gtccgtccgt    240
gggctcaaac ctgcccagac acaccactgt ctgctggggg atcatccttc tcagggagat    300
gcattctttg gaagtagtgg tagagatgga gcagactgcc agggcgttgc aggagtggtg    360
gcgatggtgc gcaccgtttt taagaaaccc ccagggtgg ggactcccgc tccctgcagc    420
atctcggcct gctgtacgtc cttggcgaat atgcgacgaa atcggctgtg cgcacggggt    480
cccagggccg gtccggtggc atacaggccg gtgagggccc cctgggtctg tccgcctgga    540
aacagggtgc tgtgaaacaa caggttgcaa ggccgcgaat accctctgc acgctgctgt    600 ggacgtgggt gtatgctccg tggatcc                                         627

<210> SEQ ID NO 38
<211> LENGTH: 233
<212> TYPE: DNA
<213> ORGANISM: Artificial Sequence
<220> FEATURE:
<223> OTHER INFORMATION: Description of Artificial Sequence: probe

<400> SEQUENCE: 38
agccgaaagg attccaccat tgtgctcgaa tccaacggat ttgaccccgt gttccccatg     60
gtcgtgccgc agcaactggg gcacgctatt ctgcagcagc tgttggtgta ccacatctac    120
tccaaaatat cggccgggc cccggatgat gtaaatatgg cggaacttga tctatatacc    180
accaatgtgt catttatggg gcgcacatat cgtctggacg tagacaacac gga           233

<210> SEQ ID NO 39
<211> LENGTH: 328
<212> TYPE: DNA
<213> ORGANISM: Artificial Sequence
<220> FEATURE:
<223> OTHER INFORMATION: Description of Artificial Sequence: probe

<400> SEQUENCE: 39

```
gaaattaccc acgagatcgc ttccctgcac accgcacttg ctactcatc agtcatcgcc      60
ccggcccacg tggccgccat aactacagac atgggagtac attgtcagga cctctttatg    120
attttcccag gggacgcgta tcaggaccgc cagctgcatg actatatcaa aatgaaagcg    180
ggcgtgcaaa ccggctcacc gggaaacaga atggatcacg tgggatacac tgctggggtt    240
cctcgctgcg agaacctgcc cggtttgagt catggtcagc tggcaacctg cgagataatt    300
cccacgccgg tcacatctga cgttgcct                                        328
```

<210> SEQ ID NO 40
<211> LENGTH: 132
<212> TYPE: DNA
<213> ORGANISM: Artificial Sequence
<220> FEATURE:
<223> OTHER INFORMATION: Description of Artificial Sequence: probe

<400> SEQUENCE: 40

```
aacacgtcat gtgcaggagt gacattgtgc cgcggagaaa ctcagaccgc atcccgtaac     60
cacactgagt gggaaaatct gctggctatg ttttctgtga ttatctatgc cttagatcac    120
aactgtcacc cg                                                         132
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 41

```
agccgaaagg attccaccat                                                  20
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 42

```
gaaattaccc acgagatcgc                                                  20
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 43

```
aacacgtcat gtgcaggagt gac                                              23
```

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 44

```
acagggctgg ttgcccaggg t                                                21
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 45
agttgcaaac cagacctcag                                                                        20

<210> SEQ ID NO 46
<211> LENGTH: 304
<212> TYPE: PRT
<213> ORGANISM: Kaposi's sarcoma-associated herpesvirus

<400> SEQUENCE: 46

```
Met Leu Thr Asp Lys Thr Ile Ile Val Ser Leu Thr Ser Arg Leu Phe
 1               5                  10                  15

Ala Asp Glu Ile Thr Lys Leu Gln Lys Lys Ile Gly Ser Ile Leu Pro
             20                  25                  30

Leu Gln Asp Pro His Lys Leu Gln Ser Leu Asp Thr Leu Gly Leu Asn
         35                  40                  45

Ala Val Cys Ser Arg Asp Val Phe Pro Asp Tyr Val His Met Phe Ser
     50                  55                  60

Tyr Leu Ser Lys Cys Thr Leu Ala Ile Leu Glu Glu Val Asn Pro Asp
 65                  70                  75                  80

Asn Leu Ile Leu Thr Arg Leu Asp Pro Ser Glu Thr Tyr Gln Ile Lys
                 85                  90                  95

Asn Val Tyr Glu Pro Met Phe Gln Trp Asp Gly Phe Ser Asn Leu Thr
            100                 105                 110

Val Ile Pro Pro Val Phe Gly Arg Gln Gln Ala Thr Val Thr Leu Glu
        115                 120                 125

Ser Asn Gly Phe Asp Leu Val Phe Pro Ser Val Val Pro Ser Asp Leu
    130                 135                 140

Ala Gln Ala Ile Ile Gly Lys Leu Leu Leu Tyr Asn Leu Tyr Ser Arg
145                 150                 155                 160

Leu Val Glu Ser Asp Pro Glu Ile Asn Ile Glu Glu Val Asn Met Tyr
                165                 170                 175

Thr Thr Asn Val Thr His Met Gly Arg His Tyr Val Leu Asp Ile Asn
            180                 185                 190

His Asn Asn Pro Asn Glu Ala Leu Lys Ser Leu Asp Asp Leu Ala Val
        195                 200                 205

Tyr Thr Lys Ile Leu Ser Ala Leu Ile Pro Arg Ala Lys Leu Arg Val
    210                 215                 220

Leu Thr Ile Leu Met Arg His Asp Gln His Glu Leu Leu Asp Val Phe
225                 230                 235                 240

Arg Gly Ile Val Pro Arg Glu Val Tyr Glu Ile Asp Ala Asn Ala Leu
                245                 250                 255

Ser Ile Gly Asp Asp Ile Thr Arg Met Thr Thr Phe Ile Thr Tyr Leu
            260                 265                 270

Gln Ser Leu Ser Ser Ile Phe Asn Leu Gly Ala Lys Leu His Leu Ser
        275                 280                 285

Ser Tyr Ala Ser Glu Thr Gln Thr Ala Thr Cys Trp Ile Ser Tyr Cys
    290                 295                 300
```

<210> SEQ ID NO 47

```
<211> LENGTH: 301
<212> TYPE: PRT
<213> ORGANISM: Epstein Barr Virus

<400> SEQUENCE: 47

Met Asp Leu Lys Val Val Ser Leu Ser Ser Arg Leu Tyr Thr Asp
 1               5                  10                  15

Glu Ile Ala Lys Met Gln Gln Arg Ile Gly Cys Ile Leu Pro Leu Ala
                 20                  25                  30

Ser Thr His Gly Thr Gln Asn Val Gln Gly Leu Gly Leu Gly Gln Val
             35                  40                  45

Tyr Ser Leu Glu Thr Val Pro Asp Tyr Val Ser Met Tyr Asn Tyr Leu
         50                  55                  60

Ser Asp Cys Thr Leu Ala Val Leu Asp Glu Val Ser Val Asp Ser Leu
 65                  70                  75                  80

Ile Leu Thr Lys Ile Val Pro Gly Gln Thr Tyr Ala Ile Lys Asn Lys
                 85                  90                  95

Tyr Gln Pro Phe Phe Gln Trp His Gly Thr Gly Ser Lys Ser Val Met
                100                 105                 110

Pro Pro Val Phe Gly Arg Glu His Ala Thr Val Lys Leu Glu Ser Asn
            115                 120                 125

Asp Val Asp Ile Val Phe Pro Met Val Leu Pro Thr Pro Ile Ala Glu
130                 135                 140

Glu Val Leu Gln Lys Ile Leu Leu Phe Asn Val Tyr Ser Arg Val Val
145                 150                 155                 160

Met Gln Ala Pro Gly Asn Ala Asp Met Leu Asp Val His Met His Leu
                165                 170                 175

Gly Ser Val Ser Tyr Leu Gly His His Tyr Glu Leu Ala Leu Pro Glu
            180                 185                 190

Val Pro Gly Pro Leu Gly Leu Ala Leu Leu Asp Asn Leu Ser Leu Tyr
        195                 200                 205

Phe Cys Ile Met Val Thr Leu Leu Pro Arg Ala Ser Met Arg Leu Val
210                 215                 220

Arg Gly Leu Ile Arg His Glu His His Asp Leu Leu Asn Leu Phe Gln
225                 230                 235                 240

Glu Met Val Pro Asp Glu Ile Ala Arg Ile Arg Leu Asp Asp Leu Ser
                245                 250                 255

Val Ala Asp Asp Leu Ser Arg Met Arg Val Met Met Thr Tyr Leu Gln
            260                 265                 270

Ser Leu Ala Ser Leu Phe Asn Leu Gly Pro Arg Leu Ala Thr Ala Ala
        275                 280                 285

Tyr Ser Gln Glu Thr Leu Thr Ala Thr Cys Trp Leu Arg
    290                 295                 300

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 48
tccgtgttgt ctacgtccag                                         20

<210> SEQ ID NO 49
<211> LENGTH: 18
<212> TYPE: DNA
```

<213> ORGANISM: Artificial Sequence
<220> FEATURE:
<223> OTHER INFORMATION: Description of Artificial Sequence: primer

<400> SEQUENCE: 49
aggcaacgtc agatgtga                                           18

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 50
cgggtgacag ttgtgatcta agg                                     23

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 51
agcactcgca gggcagtacg                                         20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 52
gactcttcgc tgatgaaact gg                                      22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 53
tccgtgttgt ctacgtccag                                         20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 54
aggcaacgtc agatgtgac                                          19

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 55
catgggagta cattgtcagg acctc                                   25

```
<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 56
ggaattatct cgcaggttgc c                                          21

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 57
ggcgacattc atcaacctca ggg                                        23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 58
atatcatcct gtgcgttcac gac                                        23
```